(12) United States Patent
Link et al.

(10) Patent No.: US 10,808,279 B2
(45) Date of Patent: *Oct. 20, 2020

(54) DIGITAL ANALYTE ANALYSIS

(71) Applicant: Bio-Rad Laboratories, Inc., Hercules, CA (US)

(72) Inventors: Darren Roy Link, Lexington, MA (US); Benjamin J. Miller, Littleton, MA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/460,247

(22) Filed: Jul. 2, 2019

(65) Prior Publication Data

US 2019/0330683 A1    Oct. 31, 2019

Related U.S. Application Data

(63) Continuation of application No. 13/866,111, filed on Apr. 19, 2013, now Pat. No. 10,351,905, which is a continuation-in-part of application No. 13/460,762, filed on Apr. 30, 2012, now Pat. No. 9,399,797, which is a continuation-in-part of application No. 13/026,120, filed on Feb. 11, 2011, now Pat. No. 9,074,242, said application No. 13/866,111 is a continuation-in-part of application No. 13/026,120, filed on Feb. 11, 2011, now Pat. No. 9,074,242.

(60) Provisional application No. 61/388,937, filed on Oct. 1, 2010, provisional application No. 61/347,158, filed on May 21, 2010, provisional application No. 61/331,490, filed on May 5, 2010, provisional application No. 61/304,163, filed on Feb. 12, 2010, provisional application No. 61/636,217, filed on Apr. 20, 2012.

(51) Int. Cl.
*C12Q 1/68* (2018.01)
*C12Q 1/686* (2018.01)

(52) U.S. Cl.
CPC .................................. *C12Q 1/686* (2013.01)

(58) Field of Classification Search
None
See application file for complete search history.

(56) References Cited

U.S. PATENT DOCUMENTS

| | | |
|---|---|---|
| 2,097,692 A | 11/1937 | Fiegel |
| 2,164,172 A | 6/1939 | Dalton |
| 2,636,855 A | 4/1953 | Schwartz |

(Continued)

FOREIGN PATENT DOCUMENTS

| | | |
|---|---|---|
| AT | 140025 T | 7/1996 |
| AT | 140880 T | 8/1996 |

(Continued)

OTHER PUBLICATIONS

Bernath et al., Directed evolution of protein inhibitors of DNA-nucleases by in vitro compartmentalization (IVC) and nano-droplet delivery, J. Mol. Biol 345(5):1015-26 (2005).

(Continued)

*Primary Examiner* — Aaron A Priest
(74) *Attorney, Agent, or Firm* — Brown Rudnick LLP; Thomas C. Meyers

(57) ABSTRACT

The invention generally relates to detecting target molecules.

9 Claims, 51 Drawing Sheets

Specification includes a Sequence Listing.

(56) References Cited

U.S. PATENT DOCUMENTS

| | | |
|---|---|---|
| 2,656,508 A | 10/1953 | Coulter |
| 2,692,800 A | 10/1954 | Nichols et al. |
| 2,797,149 A | 6/1957 | Skeggs |
| 2,879,141 A | 3/1959 | Skeggs |
| 2,971,700 A | 2/1961 | Peeps |
| 3,479,141 A | 11/1969 | Smythe et al. |
| 3,608,821 A | 9/1971 | Simm et al. |
| 3,698,635 A | 10/1972 | Sickles |
| 3,784,471 A | 1/1974 | Kaiser |
| 3,816,331 A | 6/1974 | Brown, Jr. et al. |
| 3,930,061 A | 12/1975 | Scharfenberger |
| 3,960,187 A | 6/1976 | Stock et al. |
| 3,980,541 A | 9/1976 | Aine |
| 3,982,541 A | 9/1976 | L'Esperance, Jr. |
| 4,014,469 A | 3/1977 | Sato |
| 4,022,575 A | 5/1977 | Hansen et al. |
| 4,034,966 A | 7/1977 | Suh et al. |
| 4,059,552 A | 11/1977 | Zweigle et al. |
| 4,091,042 A | 5/1978 | Alexanderson et al. |
| 4,117,550 A | 9/1978 | Folland et al. |
| 4,130,394 A | 12/1978 | Negersmith |
| 4,210,809 A | 7/1980 | Pelavin |
| 4,253,846 A | 3/1981 | Smythe et al. |
| 4,266,721 A | 5/1981 | Sickles |
| 4,279,345 A | 7/1981 | Allred |
| 4,297,345 A | 10/1981 | Howarth |
| 4,315,754 A | 2/1982 | Ruzicka et al. |
| 4,378,957 A | 4/1983 | Malkin et al. |
| 4,383,767 A | 5/1983 | Jido |
| 4,439,980 A | 4/1984 | Biblarz et al. |
| 4,508,265 A | 4/1985 | Jido |
| 4,533,634 A | 8/1985 | Maldonado et al. |
| 4,585,209 A | 4/1986 | Aine et al. |
| 4,618,476 A | 10/1986 | Columbus |
| 4,675,285 A | 6/1987 | Clark et al. |
| 4,676,274 A | 6/1987 | Brown |
| 4,683,195 A | 7/1987 | Mullis et al. |
| 4,683,202 A | 7/1987 | Mullis |
| 4,739,044 A | 4/1988 | Stabinsky |
| 4,757,141 A | 7/1988 | Fung et al. |
| 4,767,515 A | 8/1988 | Scott et al. |
| 4,767,929 A | 8/1988 | Valentine |
| 4,779,805 A | 10/1988 | Jackson et al. |
| 4,795,330 A | 1/1989 | Noakes et al. |
| 4,801,086 A | 1/1989 | Noakes |
| 4,801,529 A | 1/1989 | Perlman |
| 4,829,996 A | 5/1989 | Noakes et al. |
| 4,853,336 A | 8/1989 | Saros et al. |
| 4,856,363 A | 8/1989 | LaRocca et al. |
| 4,859,363 A | 8/1989 | Davis et al. |
| 4,865,444 A | 9/1989 | Green et al. |
| 4,883,750 A | 11/1989 | Whiteley et al. |
| 4,908,112 A | 3/1990 | Pace |
| 4,931,225 A | 6/1990 | Cheng |
| 4,941,959 A | 7/1990 | Scott |
| 4,962,885 A | 10/1990 | Coffee |
| 4,963,498 A | 10/1990 | Hillman et al. |
| 4,981,580 A | 1/1991 | Auer |
| 4,996,004 A | 2/1991 | Bucheler et al. |
| 5,091,652 A | 2/1992 | Mathies et al. |
| 5,096,615 A | 3/1992 | Prescott et al. |
| 5,104,813 A | 4/1992 | Besemer et al. |
| 5,122,360 A | 6/1992 | Harris et al. |
| 5,149,625 A | 9/1992 | Church et al. |
| 5,180,662 A | 1/1993 | Sitkovsky |
| 5,185,099 A | 2/1993 | Delpuech et al. |
| 5,188,290 A | 2/1993 | Gebauer et al. |
| 5,188,291 A | 2/1993 | Cross |
| 5,192,659 A | 3/1993 | Simons |
| 5,204,112 A | 4/1993 | Hope et al. |
| 5,207,973 A | 5/1993 | Harris et al. |
| 5,241,159 A | 8/1993 | Chatteriee et al. |
| 5,260,466 A | 11/1993 | McGibbon |
| 5,262,027 A | 11/1993 | Scott |
| 5,270,163 A | 12/1993 | Gold et al. |
| 5,296,375 A | 3/1994 | Kricka et al. |
| 5,304,487 A | 4/1994 | Wilding et al. |
| 5,310,653 A | 5/1994 | Hanausek-Walaszek et al. |
| 5,313,009 A | 5/1994 | Guenkel et al. |
| 5,333,675 A | 8/1994 | Mullis et al. |
| 5,344,594 A | 9/1994 | Sheridon |
| 5,376,252 A | 12/1994 | Ekstrom et al. |
| 5,378,957 A | 1/1995 | Kelly |
| 5,397,605 A | 3/1995 | Barbieri et al. |
| 5,399,461 A | 3/1995 | Van et al. |
| 5,399,491 A | 3/1995 | Kacian et al. |
| 5,403,617 A | 4/1995 | Haaland |
| 5,413,924 A | 5/1995 | Kosak et al. |
| 5,417,235 A | 5/1995 | Wise et al. |
| 5,427,946 A | 6/1995 | Kricka et al. |
| 5,445,934 A | 8/1995 | Fodor et al. |
| 5,452,878 A | 9/1995 | Gravesen et al. |
| 5,452,955 A | 9/1995 | Lundstrom |
| 5,454,472 A | 10/1995 | Benecke et al. |
| 5,460,945 A | 10/1995 | Springer et al. |
| 5,468,613 A | 11/1995 | Erlich et al. |
| 5,475,096 A | 12/1995 | Gold et al. |
| 5,475,610 A | 12/1995 | Atwood et al. |
| 5,480,614 A | 1/1996 | Kamahori |
| 5,486,335 A | 1/1996 | Wilding et al. |
| 5,498,392 A | 3/1996 | Wilding et al. |
| 5,500,415 A | 3/1996 | Dollat et al. |
| 5,503,851 A | 4/1996 | Mank et al. |
| 5,512,131 A | 4/1996 | Kumar et al. |
| 5,516,635 A | 5/1996 | Ekins et al. |
| 5,518,709 A | 5/1996 | Sutton et al. |
| 5,523,162 A | 6/1996 | Franz et al. |
| 5,587,128 A | 12/1996 | Wilding et al. |
| 5,589,136 A | 12/1996 | Northrup et al. |
| 5,602,756 A | 2/1997 | Atwood et al. |
| 5,604,097 A | 2/1997 | Brenner |
| 5,610,016 A | 3/1997 | Sato et al. |
| 5,612,188 A | 3/1997 | Shuler et al. |
| 5,616,478 A | 4/1997 | Chetverin et al. |
| 5,617,997 A | 4/1997 | Kobayashi et al. |
| 5,635,358 A | 6/1997 | Wilding et al. |
| 5,636,400 A | 6/1997 | Young |
| 5,641,658 A | 6/1997 | Adams et al. |
| 5,643,729 A | 7/1997 | Taniguchi et al. |
| 5,655,517 A | 8/1997 | Coffee |
| 5,656,155 A | 8/1997 | Norcross et al. |
| 5,656,493 A | 8/1997 | Mullis et al. |
| 5,661,222 A | 8/1997 | Hare |
| 5,662,874 A | 9/1997 | David |
| 5,670,325 A | 9/1997 | Lapidus et al. |
| 5,681,600 A | 10/1997 | Antinone et al. |
| 5,695,934 A | 12/1997 | Brenner |
| 5,726,026 A | 3/1998 | Wilding et al. |
| 5,726,404 A | 3/1998 | Brody |
| 5,733,526 A | 3/1998 | Trevino et al. |
| 5,739,036 A | 4/1998 | Parris |
| 5,744,366 A | 4/1998 | Kricka et al. |
| 5,750,988 A | 5/1998 | Apffel et al. |
| 5,762,775 A | 6/1998 | DePaoli |
| 5,779,868 A | 7/1998 | Parce et al. |
| 5,783,431 A | 7/1998 | Peterson et al. |
| 5,840,506 A | 11/1998 | Giordano |
| 5,846,719 A | 12/1998 | Brenner et al. |
| 5,849,491 A | 12/1998 | Radomski et al. |
| 5,851,769 A | 12/1998 | Gray et al. |
| 5,858,187 A | 1/1999 | Ramsey et al. |
| 5,858,655 A | 1/1999 | Arnold |
| 5,858,670 A | 1/1999 | Lam et al. |
| 5,863,722 A | 1/1999 | Brenner |
| 5,868,322 A | 2/1999 | Loucks |
| 5,872,010 A | 2/1999 | Karger et al. |
| 5,876,771 A | 3/1999 | Sizer et al. |
| 5,880,071 A | 3/1999 | Parce et al. |
| 5,882,680 A | 3/1999 | Suzuki et al. |
| 5,882,856 A | 3/1999 | Shuber |
| 5,884,846 A | 3/1999 | Tan |
| 5,887,755 A | 3/1999 | Hood, III |
| 5,888,746 A | 3/1999 | Tabiti et al. |
| 5,888,778 A | 3/1999 | Shuber |

(56) References Cited

U.S. PATENT DOCUMENTS

| | | |
|---|---|---|
| 5,904,933 A | 5/1999 | Riess et al. |
| 5,921,678 A | 7/1999 | Desai et al. |
| 5,927,852 A | 7/1999 | Serafin |
| 5,928,870 A | 7/1999 | Lapidus et al. |
| 5,932,100 A | 8/1999 | Yager et al. |
| 5,935,331 A | 8/1999 | Naka et al. |
| 5,942,056 A | 8/1999 | Singh |
| 5,942,443 A | 8/1999 | Parce et al. |
| 5,958,203 A | 9/1999 | Parce et al. |
| 5,972,187 A | 10/1999 | Parce et al. |
| 5,980,936 A | 11/1999 | Krafft et al. |
| 5,989,815 A | 11/1999 | Skolnick et al. |
| 5,989,892 A | 11/1999 | Nishimaki et al. |
| 5,995,341 A | 11/1999 | Tanaka et al. |
| 5,997,636 A | 12/1999 | Gamarnik et al. |
| 6,008,003 A | 12/1999 | Haak-Frendscho et al. |
| 6,023,540 A | 2/2000 | Walt et al. |
| 6,028,066 A | 2/2000 | Unger |
| 6,042,709 A | 3/2000 | Parce et al. |
| 6,045,755 A | 4/2000 | Lebl et al. |
| 6,046,056 A | 4/2000 | Parce et al. |
| 6,048,551 A | 4/2000 | Hilfinger et al. |
| 6,048,690 A | 4/2000 | Heller et al. |
| 6,068,199 A | 5/2000 | Coffee |
| 6,074,879 A | 6/2000 | Zelmanovic et al. |
| 6,080,295 A | 6/2000 | Parce et al. |
| 6,086,740 A | 7/2000 | Kennedy |
| 6,096,495 A | 8/2000 | Kasai et al. |
| 6,103,537 A | 8/2000 | Ullman et al. |
| 6,105,571 A | 8/2000 | Coffee |
| 6,105,877 A | 8/2000 | Coffee |
| 6,107,059 A | 8/2000 | Hart |
| 6,116,516 A | 9/2000 | Ganan-Calvo |
| 6,118,849 A | 9/2000 | Tanimori et al. |
| 6,119,953 A | 9/2000 | Ganan-Calvo et al. |
| 6,120,666 A | 9/2000 | Jacobson et al. |
| 6,124,388 A | 9/2000 | Takai et al. |
| 6,124,439 A | 9/2000 | Friedman et al. |
| 6,130,052 A | 10/2000 | Van Baren et al. |
| 6,130,098 A | 10/2000 | Handique et al. |
| 6,137,214 A | 10/2000 | Raina |
| 6,138,077 A | 10/2000 | Brenner |
| 6,139,303 A | 10/2000 | Reed et al. |
| 6,140,053 A | 10/2000 | Koster |
| 6,143,496 A | 11/2000 | Brown et al. |
| 6,146,828 A | 11/2000 | Lapidus et al. |
| 6,149,789 A | 11/2000 | Benecke et al. |
| 6,150,180 A | 11/2000 | Parce et al. |
| 6,150,516 A | 11/2000 | Brenner et al. |
| 6,165,778 A | 12/2000 | Kedar |
| 6,171,796 B1 | 1/2001 | An et al. |
| 6,171,850 B1 | 1/2001 | Nagle et al. |
| 6,172,214 B1 | 1/2001 | Brenner |
| 6,172,218 B1 | 1/2001 | Brenner |
| 6,174,160 B1 | 1/2001 | Lee et al. |
| 6,174,469 B1 | 1/2001 | Gañan-Calvo |
| 6,177,479 B1 | 1/2001 | Nakajima |
| 6,180,372 B1 | 1/2001 | Franzen |
| 6,184,012 B1 | 2/2001 | Neri et al. |
| 6,187,214 B1 | 2/2001 | Ganan-Calvo |
| 6,189,803 B1 | 2/2001 | Ganan-Calvo |
| 6,196,525 B1 | 3/2001 | Ganan-Calvo |
| 6,197,335 B1 | 3/2001 | Sherman |
| 6,197,835 B1 | 3/2001 | Ganan-Calvo |
| 6,203,993 B1 | 3/2001 | Shuber et al. |
| 6,207,372 B1 | 3/2001 | Shuber |
| 6,207,397 B1 | 3/2001 | Lynch et al. |
| 6,210,396 B1 | 4/2001 | MacDonald et al. |
| 6,210,891 B1 | 4/2001 | Nyren et al. |
| 6,210,896 B1 | 4/2001 | Chan |
| 6,214,558 B1 | 4/2001 | Shuber et al. |
| 6,221,654 B1 | 4/2001 | Quake et al. |
| 6,227,466 B1 | 5/2001 | Hartman et al. |
| 6,234,402 B1 | 5/2001 | Ganan-Calvo |
| 6,235,383 B1 | 5/2001 | Hong et al. |
| 6,235,475 B1 | 5/2001 | Brenner et al. |
| 6,241,159 B1 | 6/2001 | Ganan-Calvo et al. |
| 6,243,373 B1 | 6/2001 | Turock |
| 6,248,378 B1 | 6/2001 | Ganan-Calvo |
| 6,251,661 B1 | 6/2001 | Urabe et al. |
| 6,252,129 B1 | 6/2001 | Coffee |
| 6,258,568 B1 | 7/2001 | Nyren |
| 6,258,858 B1 | 7/2001 | Nakajima et al. |
| 6,263,222 B1 | 7/2001 | Diab et al. |
| 6,266,459 B1 | 7/2001 | Walt et al. |
| 6,267,353 B1 | 7/2001 | Friedline et al. |
| 6,267,858 B1 | 7/2001 | Parce et al. |
| 6,268,152 B1 | 7/2001 | Fodor et al. |
| 6,268,165 B1 | 7/2001 | O'Brien |
| 6,268,222 B1 | 7/2001 | Chandler et al. |
| 6,274,320 B1 | 8/2001 | Rothberg et al. |
| 6,274,337 B1 | 8/2001 | Parce et al. |
| 6,280,948 B1 | 8/2001 | Guilfoyle et al. |
| 6,292,756 B1 | 9/2001 | Lievois et al. |
| 6,294,344 B1 | 9/2001 | O'Brien |
| 6,296,020 B1 | 10/2001 | McNeely et al. |
| 6,296,673 B1 | 10/2001 | Santarsiero et al. |
| 6,299,145 B1 | 10/2001 | Ganan-Calvo |
| 6,301,055 B1 | 10/2001 | Legrand et al. |
| 6,306,659 B1 | 10/2001 | Parce et al. |
| 6,310,354 B1 | 10/2001 | Hanninen et al. |
| 6,310,653 B1 | 10/2001 | Malcolm, Jr. et al. |
| 6,316,208 B1 | 11/2001 | Roberts et al. |
| 6,316,213 B1 | 11/2001 | O'Brien |
| 6,318,640 B1 | 11/2001 | Coffee |
| 6,326,145 B1 | 12/2001 | Whitcombe et al. |
| 6,336,463 B1 | 1/2002 | Ohta |
| 6,344,325 B1 | 2/2002 | Quake et al. |
| 6,352,828 B1 | 3/2002 | Brenner |
| 6,355,193 B1 | 3/2002 | Stott |
| 6,355,198 B1 | 3/2002 | Kim et al. |
| 6,357,670 B2 | 3/2002 | Ganan-Calvo |
| 6,386,463 B1 | 5/2002 | Ganan-Calvo |
| 6,391,559 B1 | 5/2002 | Brown et al. |
| 6,394,429 B2 | 5/2002 | Ganan-Calvo |
| 6,399,339 B1 | 6/2002 | Wolberg et al. |
| 6,399,389 B1 | 6/2002 | Parce et al. |
| 6,403,373 B1 | 6/2002 | Scanlan et al. |
| 6,405,936 B1 | 6/2002 | Ganan-Calvo |
| 6,408,878 B2 | 6/2002 | Unger et al. |
| 6,409,832 B2 | 6/2002 | Weigl et al. |
| 6,429,025 B1 | 8/2002 | Parce et al. |
| 6,429,148 B1 | 8/2002 | Chu et al. |
| 6,432,143 B2 | 8/2002 | Kubiak et al. |
| 6,432,148 B1 | 8/2002 | Ganan-Calvo |
| 6,432,630 B1 | 8/2002 | Blankenstein |
| 6,439,103 B1 | 8/2002 | Miller |
| 6,440,706 B1 | 8/2002 | Vogelstein et al. |
| 6,440,760 B1 | 8/2002 | Cho et al. |
| 6,450,139 B1 | 9/2002 | Watanabe |
| 6,450,189 B1 | 9/2002 | Ganan-Calvo |
| 6,454,193 B1 | 9/2002 | Busick et al. |
| 6,464,336 B1 | 10/2002 | Sharma |
| 6,464,886 B2 | 10/2002 | Ganan-Calvo |
| 6,475,441 B1 | 11/2002 | Parce et al. |
| 6,481,648 B1 | 11/2002 | Zimmermann |
| 6,489,103 B1 | 12/2002 | Griffiths et al. |
| 6,503,933 B1 | 1/2003 | Moloney et al. |
| 6,506,609 B1 | 1/2003 | Wada et al. |
| 6,508,988 B1 | 1/2003 | Van Dam et al. |
| 6,520,425 B1 | 2/2003 | Reneker |
| 6,524,456 B1 | 2/2003 | Ramsey et al. |
| 6,540,395 B2 | 4/2003 | Muhlbauer et al. |
| 6,540,895 B1 | 4/2003 | Spence et al. |
| 6,551,836 B1 | 4/2003 | Chow et al. |
| 6,553,944 B1 | 4/2003 | Allen et al. |
| 6,553,960 B1 | 4/2003 | Yoshikawa et al. |
| 6,554,202 B2 | 4/2003 | Ganan-Calvo |
| 6,557,334 B2 | 5/2003 | Jager |
| 6,557,834 B2 | 5/2003 | Ganan-Calvo |
| 6,558,944 B1 | 5/2003 | Parce et al. |
| 6,558,960 B1 | 5/2003 | Parce et al. |
| 6,560,030 B2 | 5/2003 | Legrand et al. |
| 6,565,010 B2 | 5/2003 | Anderson et al. |

(56) References Cited

U.S. PATENT DOCUMENTS

| | | |
|---|---|---|
| 6,569,631 B1 | 5/2003 | Pantoliano et al. |
| 6,576,420 B1 | 6/2003 | Carson et al. |
| 6,591,852 B1 | 7/2003 | McNeely et al. |
| 6,592,321 B2 | 7/2003 | Bonker et al. |
| 6,592,821 B1 | 7/2003 | Wada et al. |
| 6,601,613 B2 | 8/2003 | McNeely et al. |
| 6,608,726 B2 | 8/2003 | Legrand et al. |
| 6,610,499 B1 | 8/2003 | Fulwyler et al. |
| 6,614,598 B1 | 9/2003 | Quake et al. |
| 6,627,603 B1 | 9/2003 | Bibette et al. |
| 6,630,006 B2 | 10/2003 | Santarsiero et al. |
| 6,630,353 B1 | 10/2003 | Parce et al. |
| 6,632,619 B1 | 10/2003 | Harrison et al. |
| 6,637,463 B1 | 10/2003 | Lei et al. |
| 6,638,749 B1 | 10/2003 | Beckman et al. |
| 6,645,432 B1 | 11/2003 | Anderson et al. |
| 6,646,253 B1 | 11/2003 | Rohwer et al. |
| 6,653,626 B2 | 11/2003 | Fischer et al. |
| 6,656,267 B2 | 12/2003 | Newman |
| 6,659,370 B1 | 12/2003 | Inoue |
| 6,660,252 B2 | 12/2003 | Matathia et al. |
| 6,670,142 B2 | 12/2003 | Lau et al. |
| 6,679,441 B1 | 1/2004 | Borra et al. |
| 6,680,178 B2 | 1/2004 | Harris et al. |
| 6,682,890 B2 | 1/2004 | Mack et al. |
| 6,717,136 B2 | 4/2004 | Andersson et al. |
| 6,729,561 B2 | 5/2004 | Hirae et al. |
| 6,738,502 B1 | 5/2004 | Coleman et al. |
| 6,739,036 B2 | 5/2004 | Koike et al. |
| 6,744,046 B2 | 6/2004 | Valaskovic et al. |
| 6,752,922 B2 | 6/2004 | Huang et al. |
| 6,753,147 B2 | 6/2004 | Vogelstein et al. |
| 6,766,817 B2 | 7/2004 | da Silva |
| 6,767,194 B2 | 7/2004 | Jeon et al. |
| 6,767,704 B2 | 7/2004 | Waldman et al. |
| 6,790,328 B2 | 9/2004 | Jacobson et al. |
| 6,793,753 B2 | 9/2004 | Unger et al. |
| 6,797,056 B2 | 9/2004 | David |
| 6,800,849 B2 | 10/2004 | Staats |
| 6,806,058 B2 | 10/2004 | Jesperson et al. |
| 6,808,382 B2 | 10/2004 | Lanfranchi |
| 6,808,882 B2 | 10/2004 | Griffiths et al. |
| 6,814,980 B2 | 11/2004 | Levy et al. |
| 6,818,395 B1 | 11/2004 | Quake et al. |
| 6,832,787 B1 | 12/2004 | Renzi |
| 6,833,242 B2 | 12/2004 | Quake et al. |
| 6,841,350 B2 | 1/2005 | Ogden et al. |
| 6,872,250 B2 | 3/2005 | David et al. |
| 6,890,487 B1 | 5/2005 | Sklar et al. |
| 6,897,018 B1 | 5/2005 | Yuan et al. |
| 6,905,844 B2 | 6/2005 | Kim |
| 6,918,404 B2 | 7/2005 | Dias da Silva |
| 6,926,313 B1 | 8/2005 | Renzi |
| 6,935,768 B2 | 8/2005 | Lowe et al. |
| 6,936,417 B2 | 8/2005 | Omtoft |
| 6,942,978 B1 | 9/2005 | O'Brien |
| 6,949,342 B2 | 9/2005 | Golub et al. |
| 6,960,437 B2 | 11/2005 | Enzelberger et al. |
| 6,974,667 B2 | 12/2005 | Horne et al. |
| 6,998,232 B1 | 2/2006 | Feinstein et al. |
| 7,022,472 B2 | 4/2006 | Robbins et al. |
| 7,041,481 B2 | 5/2006 | Anderson et al. |
| 7,049,072 B2 | 5/2006 | Seshi |
| 7,056,674 B2 | 6/2006 | Baker et al. |
| 7,057,026 B2 | 6/2006 | Barnes et al. |
| 7,066,586 B2 | 6/2006 | da Silva |
| 7,068,874 B2 | 6/2006 | Wang et al. |
| 7,078,180 B2 | 7/2006 | Genetta |
| 7,081,192 B1 | 7/2006 | Wang et al. |
| 7,081,340 B2 | 7/2006 | Baker et al. |
| 7,090,983 B1 | 8/2006 | Muramatsu et al. |
| 7,115,230 B2 | 10/2006 | Sundararajan |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,153,700 B1 | 12/2006 | Pardee et al. |
| 7,156,917 B2 | 1/2007 | Moriyama et al. |
| 7,163,801 B2 | 1/2007 | Reed |
| 7,169,560 B2 | 1/2007 | Lapidus et al. |
| 7,171,311 B2 | 1/2007 | Dai et al. |
| 7,198,899 B2 | 4/2007 | Schleyer et al. |
| 7,204,431 B2 | 4/2007 | Li et al. |
| 7,229,770 B1 | 6/2007 | Price et al. |
| 7,252,943 B2 | 8/2007 | Griffiths et al. |
| 7,267,938 B2 | 9/2007 | Anderson et al. |
| 7,268,167 B2 | 9/2007 | Higuchi et al. |
| 7,282,337 B1 | 10/2007 | Harris |
| 7,291,462 B2 | 11/2007 | O'Brien et al. |
| 7,294,503 B2 | 11/2007 | Quake et al. |
| 7,300,765 B2 | 11/2007 | Patel |
| 7,308,364 B2 | 12/2007 | Shaughnessy et al. |
| 7,314,721 B2 | 1/2008 | Gure et al. |
| 7,316,906 B2 | 1/2008 | Chiorazzi et al. |
| 7,326,529 B2 | 2/2008 | Ali et al. |
| 7,332,280 B2 | 2/2008 | Levy et al. |
| 7,332,590 B2 | 2/2008 | Nacht et al. |
| 7,341,211 B2 | 3/2008 | Ganan Calvo et al. |
| 7,348,142 B2 | 3/2008 | Wang |
| 7,358,231 B1 | 4/2008 | McCaffey et al. |
| 7,361,474 B2 | 4/2008 | Siegler |
| 7,364,862 B2 | 4/2008 | Ali et al. |
| 7,368,255 B2 | 5/2008 | Bae et al. |
| 7,378,233 B2 | 5/2008 | Sidransky et al. |
| 7,378,280 B2 | 5/2008 | Quake et al. |
| 7,390,463 B2 | 6/2008 | He et al. |
| 7,393,634 B1 | 7/2008 | Ahuja et al. |
| 7,393,665 B2 | 7/2008 | Brenner |
| 7,416,851 B2 | 8/2008 | Davi et al. |
| 7,429,467 B2 | 9/2008 | Holliger et al. |
| 7,432,064 B2 | 10/2008 | Salceda et al. |
| 7,442,507 B2 | 10/2008 | Polsky et al. |
| 7,449,303 B2 | 11/2008 | Coignet |
| 7,468,271 B2 | 12/2008 | Golovchenko et al. |
| 7,473,530 B2 | 1/2009 | Huttemann |
| 7,473,531 B1 | 1/2009 | Domon et al. |
| 7,476,506 B2 | 1/2009 | Schleyer et al. |
| 7,479,370 B2 | 1/2009 | Coignet |
| 7,479,371 B2 | 1/2009 | Ando et al. |
| 7,479,376 B2 | 1/2009 | Waldman et al. |
| 7,482,129 B2 | 1/2009 | Soyupak et al. |
| 7,501,244 B2 | 3/2009 | Reinhard et al. |
| 7,504,214 B2 | 3/2009 | Erlander et al. |
| 7,507,532 B2 | 3/2009 | Chang et al. |
| 7,507,541 B2 | 3/2009 | Raitano et al. |
| 7,510,707 B2 | 3/2009 | Platica et al. |
| 7,510,842 B2 | 3/2009 | Podust et al. |
| 7,514,209 B2 | 4/2009 | Dai et al. |
| 7,514,210 B2 | 4/2009 | Holliger et al. |
| 7,524,633 B2 | 4/2009 | Sidransky |
| 7,527,933 B2 | 5/2009 | Sahin et al. |
| 7,537,897 B2 | 5/2009 | Brenner et al. |
| 7,541,383 B2 | 6/2009 | Fu et al. |
| 7,544,473 B2 | 6/2009 | Brenner |
| 7,556,776 B2 | 7/2009 | Fraden et al. |
| 7,582,446 B2 | 9/2009 | Griffiths et al. |
| 7,604,938 B2 | 10/2009 | Takahashi et al. |
| 7,622,081 B2 | 11/2009 | Chou et al. |
| 7,632,562 B2 | 12/2009 | Nair et al. |
| 7,635,562 B2 | 12/2009 | Harris et al. |
| 7,638,276 B2 | 12/2009 | Griffiths et al. |
| 7,655,435 B2 | 2/2010 | Holliger et al. |
| 7,655,470 B2 | 2/2010 | Ismagilov et al. |
| 7,666,593 B2 | 2/2010 | Lapidus |
| 7,691,576 B2 | 4/2010 | Holliger et al. |
| 7,698,287 B2 | 4/2010 | Becker et al. |
| 7,708,949 B2 | 5/2010 | Stone et al. |
| 7,718,578 B2 | 5/2010 | Griffiths et al. |
| 7,736,890 B2 | 6/2010 | Sia et al. |
| 7,741,130 B2 | 6/2010 | Lee, Jr. et al. |
| RE41,780 E | 9/2010 | Anderson et al. |
| 7,814,175 B1 | 10/2010 | Chang et al. |
| 7,824,889 B2 | 11/2010 | Vogelstein et al. |
| 7,888,017 B2 | 2/2011 | Quake et al. |
| 7,897,044 B2 | 3/2011 | Hoyos et al. |

(56) References Cited

U.S. PATENT DOCUMENTS

| | | |
|---|---|---|
| 7,897,341 B2 | 3/2011 | Griffiths et al. |
| 7,901,939 B2 | 3/2011 | Ismagliov et al. |
| 7,915,015 B2 | 3/2011 | Vogelstein et al. |
| 7,968,287 B2 | 6/2011 | Griffiths et al. |
| 7,990,525 B2 | 8/2011 | Kanda |
| 8,012,382 B2 | 9/2011 | Kim et al. |
| 8,067,159 B2 | 11/2011 | Brown et al. |
| 8,153,402 B2 | 4/2012 | Holliger et al. |
| 8,257,925 B2 | 9/2012 | Brown et al. |
| 8,278,071 B2 | 10/2012 | Brown et al. |
| 8,278,711 B2 | 10/2012 | Rao et al. |
| 8,318,434 B2 | 11/2012 | Cuppens |
| 8,337,778 B2 | 12/2012 | Stone et al. |
| 8,436,993 B2 | 5/2013 | Kaduchak et al. |
| 8,528,589 B2 | 9/2013 | Miller et al. |
| 8,535,889 B2 | 9/2013 | Larson et al. |
| 8,592,221 B2 | 11/2013 | Fraden et al. |
| 8,673,595 B2 | 3/2014 | Nakamura et al. |
| 8,765,485 B2 | 7/2014 | Link et al. |
| 8,772,046 B2 | 7/2014 | Fraden et al. |
| 9,186,643 B2 | 11/2015 | Griffiths et al. |
| 2001/0010338 A1 | 8/2001 | Ganan-Calvo |
| 2001/0020011 A1 | 9/2001 | Mathiowitz et al. |
| 2001/0023078 A1 | 9/2001 | Bawendi et al. |
| 2001/0029983 A1 | 10/2001 | Unger et al. |
| 2001/0034025 A1 | 10/2001 | Modlin et al. |
| 2001/0034031 A1 | 10/2001 | Short et al. |
| 2001/0041343 A1 | 11/2001 | Pankowsky |
| 2001/0041344 A1 | 11/2001 | Sepetov et al. |
| 2001/0041357 A1 | 11/2001 | Fouillet et al. |
| 2001/0042793 A1 | 11/2001 | Ganan-Calvo |
| 2001/0048900 A1 | 12/2001 | Bardell et al. |
| 2001/0050881 A1 | 12/2001 | Depaoli et al. |
| 2002/0004532 A1 | 1/2002 | Matathia et al. |
| 2002/0005354 A1 | 1/2002 | Spence et al. |
| 2002/0008028 A1 | 1/2002 | Jacobson et al. |
| 2002/0012971 A1 | 1/2002 | Mehta |
| 2002/0022038 A1 | 2/2002 | Biatry et al. |
| 2002/0022261 A1 | 2/2002 | Anderson et al. |
| 2002/0033422 A1 | 3/2002 | Ganan-Calvo |
| 2002/0036018 A1 | 3/2002 | McNeely et al. |
| 2002/0036139 A1 | 3/2002 | Becker et al. |
| 2002/0041378 A1 | 4/2002 | Peltie et al. |
| 2002/0058332 A1 | 5/2002 | Quake et al. |
| 2002/0067800 A1 | 6/2002 | Newman et al. |
| 2002/0085961 A1 | 7/2002 | Morin et al. |
| 2002/0090720 A1* | 7/2002 | Mutz .................. B41J 2/14008 435/325 |
| 2002/0106667 A1 | 8/2002 | Yamamoto et al. |
| 2002/0119459 A1 | 8/2002 | Griffiths |
| 2002/0127591 A1 | 9/2002 | Wada et al. |
| 2002/0143437 A1 | 10/2002 | Handique et al. |
| 2002/0155080 A1 | 10/2002 | Glenn et al. |
| 2002/0158027 A1 | 10/2002 | Moon et al. |
| 2002/0164271 A1 | 11/2002 | Ho |
| 2002/0164629 A1 | 11/2002 | Quake et al. |
| 2002/0166582 A1 | 11/2002 | O'Connor et al. |
| 2003/0008308 A1 | 1/2003 | Enzelberger et al. |
| 2003/0012586 A1 | 1/2003 | Iwata et al. |
| 2003/0015425 A1 | 1/2003 | Bohm et al. |
| 2003/0017305 A1 | 1/2003 | Roitman et al. |
| 2003/0017579 A1 | 1/2003 | Corn et al. |
| 2003/0039169 A1 | 2/2003 | Ehrfeld et al. |
| 2003/0059764 A1 | 3/2003 | Ravkin et al. |
| 2003/0061687 A1 | 4/2003 | Hansen et al. |
| 2003/0064414 A1 | 4/2003 | Benecky et al. |
| 2003/0082795 A1 | 5/2003 | Shuler et al. |
| 2003/0104372 A1 | 6/2003 | Ahmadian et al. |
| 2003/0124586 A1 | 7/2003 | Griffiths et al. |
| 2003/0144260 A1 | 7/2003 | Gilon |
| 2003/0148544 A1 | 8/2003 | Nie et al. |
| 2003/0181574 A1 | 9/2003 | Adam et al. |
| 2003/0183525 A1 | 10/2003 | Elrod et al. |
| 2003/0207295 A1 | 11/2003 | Gunderson et al. |
| 2003/0219754 A1 | 11/2003 | Oleksy et al. |
| 2003/0224509 A1 | 12/2003 | Moon et al. |
| 2003/0229376 A1 | 12/2003 | Sandhu |
| 2003/0230486 A1 | 12/2003 | Chien et al. |
| 2003/0232356 A1 | 12/2003 | Dooley et al. |
| 2004/0005582 A1 | 1/2004 | Shipwash |
| 2004/0005594 A1 | 1/2004 | Holliger et al. |
| 2004/0018525 A1 | 1/2004 | Wirtz et al. |
| 2004/0027915 A1 | 2/2004 | Lowe et al. |
| 2004/0031688 A1 | 2/2004 | Shenderov |
| 2004/0037739 A1 | 2/2004 | McNeely et al. |
| 2004/0037813 A1 | 2/2004 | Simpson et al. |
| 2004/0041093 A1 | 3/2004 | Schultz et al. |
| 2004/0050946 A1 | 3/2004 | Wang et al. |
| 2004/0053247 A1 | 3/2004 | Cordon-Cardo et al. |
| 2004/0058450 A1 | 3/2004 | Pamula et al. |
| 2004/0068019 A1 | 4/2004 | Higuchi et al. |
| 2004/0071781 A1 | 4/2004 | Chattopadhyay et al. |
| 2004/0079881 A1 | 4/2004 | Fischer et al. |
| 2004/0086892 A1 | 5/2004 | Crothers et al. |
| 2004/0096515 A1 | 5/2004 | Bausch et al. |
| 2004/0134854 A1 | 7/2004 | Higuchi et al. |
| 2004/0136497 A1 | 7/2004 | Meldrum et al. |
| 2004/0142329 A1 | 7/2004 | Erikson et al. |
| 2004/0146921 A1 | 7/2004 | Eveleigh et al. |
| 2004/0159633 A1 | 8/2004 | Whitesides et al. |
| 2004/0181131 A1 | 9/2004 | Maynard et al. |
| 2004/0181343 A1 | 9/2004 | Wigstrom et al. |
| 2004/0182712 A1 | 9/2004 | Basol |
| 2004/0188254 A1 | 9/2004 | Spaid |
| 2004/0224419 A1 | 11/2004 | Zheng et al. |
| 2004/0229349 A1* | 11/2004 | Daridon .................. C12M 1/34 435/305.2 |
| 2004/0241693 A1 | 12/2004 | Ricoul et al. |
| 2004/0253731 A1 | 12/2004 | Holliger et al. |
| 2004/0258203 A1 | 12/2004 | Yamano et al. |
| 2004/0259083 A1 | 12/2004 | Oshima |
| 2005/0000970 A1 | 1/2005 | Kimbara et al. |
| 2005/0003380 A1 | 1/2005 | Cohen et al. |
| 2005/0019776 A1 | 1/2005 | Callow et al. |
| 2005/0032238 A1 | 2/2005 | Karp et al. |
| 2005/0032240 A1 | 2/2005 | Lee et al. |
| 2005/0037392 A1 | 2/2005 | Griffiths et al. |
| 2005/0042639 A1 | 2/2005 | Knapp et al. |
| 2005/0042648 A1 | 2/2005 | Griffiths et al. |
| 2005/0048467 A1 | 3/2005 | Sastry et al. |
| 2005/0064460 A1 | 3/2005 | Holliger et al. |
| 2005/0069920 A1 | 3/2005 | Griffiths et al. |
| 2005/0079501 A1 | 4/2005 | Koike et al. |
| 2005/0079510 A1 | 4/2005 | Berka et al. |
| 2005/0084923 A1 | 4/2005 | Mueller et al. |
| 2005/0087122 A1 | 4/2005 | Ismagliov et al. |
| 2005/0095611 A1 | 5/2005 | Chan et al. |
| 2005/0100895 A1 | 5/2005 | Waldman et al. |
| 2005/0103690 A1 | 5/2005 | Kawano et al. |
| 2005/0123937 A1 | 6/2005 | Thorp et al. |
| 2005/0129582 A1 | 6/2005 | Breidford et al. |
| 2005/0152908 A1 | 7/2005 | Liew et al. |
| 2005/0161669 A1 | 7/2005 | Jovanovich et al. |
| 2005/0164239 A1 | 7/2005 | Griffiths et al. |
| 2005/0169797 A1 | 8/2005 | Oshima |
| 2005/0170373 A1 | 8/2005 | Monforte |
| 2005/0170431 A1 | 8/2005 | Ibrahim et al. |
| 2005/0172476 A1 | 8/2005 | Stone et al. |
| 2005/0183995 A1 | 8/2005 | Deshpande et al. |
| 2005/0202489 A1 | 9/2005 | Cho et al. |
| 2005/0207940 A1 | 9/2005 | Butler et al. |
| 2005/0208495 A1 | 9/2005 | Joseph et al. |
| 2005/0214173 A1 | 9/2005 | Facer et al. |
| 2005/0221339 A1 | 10/2005 | Griffiths et al. |
| 2005/0221341 A1 | 10/2005 | Shimkets et al. |
| 2005/0226742 A1 | 10/2005 | Unger et al. |
| 2005/0227264 A1 | 10/2005 | Nobile et al. |
| 2005/0248066 A1 | 11/2005 | Esteban |
| 2005/0260566 A1 | 11/2005 | Fischer et al. |
| 2005/0272159 A1 | 12/2005 | Ismagilov et al. |
| 2006/0003347 A1 | 1/2006 | Griffiths et al. |
| 2006/0003429 A1 | 1/2006 | Frost et al. |
| 2006/0003439 A1 | 1/2006 | Ismagilov et al. |
| 2006/0008824 A1 | 1/2006 | Ronaghi et al. |

(56) References Cited

U.S. PATENT DOCUMENTS

| | | |
|---|---|---|
| 2006/0035386 A1 | 2/2006 | Hattori et al. |
| 2006/0036348 A1 | 2/2006 | Handique et al. |
| 2006/0040297 A1 | 2/2006 | Leamon et al. |
| 2006/0046257 A1 | 3/2006 | Pollock et al. |
| 2006/0051329 A1 | 3/2006 | Lee et al. |
| 2006/0068398 A1 | 3/2006 | McMillan |
| 2006/0078888 A1 | 4/2006 | Griffiths et al. |
| 2006/0078893 A1 | 4/2006 | Griffiths et al. |
| 2006/0094119 A1 | 5/2006 | Ismagilov et al. |
| 2006/0100788 A1 | 5/2006 | Carrino et al. |
| 2006/0108012 A1 | 5/2006 | Barrow et al. |
| 2006/0110759 A1 | 5/2006 | Paris et al. |
| 2006/0115821 A1 | 6/2006 | Einstein et al. |
| 2006/0147909 A1 | 7/2006 | Rarbach et al. |
| 2006/0153924 A1 | 7/2006 | Griffiths et al. |
| 2006/0154298 A1 | 7/2006 | Griffiths et al. |
| 2006/0160762 A1 | 7/2006 | Zetter et al. |
| 2006/0163385 A1 | 7/2006 | Link et al. |
| 2006/0169800 A1 | 8/2006 | Rosell et al. |
| 2006/0177832 A1 | 8/2006 | Brenner |
| 2006/0195269 A1 | 8/2006 | Yeatman et al. |
| 2006/0223127 A1 | 10/2006 | Yip et al. |
| 2006/0234254 A1 | 10/2006 | An et al. |
| 2006/0234259 A1 | 10/2006 | Rubin et al. |
| 2006/0246431 A1 | 11/2006 | Balachandran |
| 2006/0252057 A1 | 11/2006 | Raponi et al. |
| 2006/0257893 A1 | 11/2006 | Takahashi et al. |
| 2006/0258841 A1 | 11/2006 | Michl et al. |
| 2006/0263888 A1 | 11/2006 | Fritz et al. |
| 2006/0269558 A1 | 11/2006 | Murphy et al. |
| 2006/0269971 A1 | 11/2006 | Diamandis |
| 2006/0281089 A1 | 12/2006 | Gibson et al. |
| 2006/0281098 A1 | 12/2006 | Miao et al. |
| 2007/0003442 A1 | 1/2007 | Link et al. |
| 2007/0026439 A1 | 2/2007 | Faulstich et al. |
| 2007/0045117 A1 | 3/2007 | Pamula et al. |
| 2007/0048744 A1 | 3/2007 | Lapidus |
| 2007/0053896 A1 | 3/2007 | Ahmed et al. |
| 2007/0054119 A1 | 3/2007 | Garstecki et al. |
| 2007/0065823 A1 | 3/2007 | Dressman et al. |
| 2007/0077572 A1 | 4/2007 | Tawfik et al. |
| 2007/0077579 A1 | 4/2007 | Griffiths et al. |
| 2007/0092914 A1 | 4/2007 | Griffiths et al. |
| 2007/0111303 A1 | 5/2007 | Inoue et al. |
| 2007/0120899 A1 | 5/2007 | Ohnishi et al. |
| 2007/0141593 A1 | 6/2007 | Lee et al. |
| 2007/0154889 A1 | 7/2007 | Wang |
| 2007/0166705 A1 | 7/2007 | Milton et al. |
| 2007/0172873 A1 | 7/2007 | Brenner et al. |
| 2007/0184439 A1 | 8/2007 | Guilford et al. |
| 2007/0184489 A1 | 8/2007 | Griffiths et al. |
| 2007/0195127 A1 | 8/2007 | Ahn et al. |
| 2007/0202525 A1 | 8/2007 | Quake et al. |
| 2007/0213410 A1 | 9/2007 | Hastwell et al. |
| 2007/0241068 A1 | 10/2007 | Pamula et al. |
| 2007/0242105 A1 | 10/2007 | Srinivasan et al. |
| 2007/0243634 A1 | 10/2007 | Pamula et al. |
| 2007/0259351 A1 | 11/2007 | Chinitz et al. |
| 2007/0259368 A1 | 11/2007 | An et al. |
| 2007/0259374 A1 | 11/2007 | Griffiths et al. |
| 2007/0292869 A1 | 12/2007 | Becker et al. |
| 2008/0003142 A1* | 1/2008 | Link .................. B01F 3/0807 422/82.08 |
| 2008/0003571 A1 | 1/2008 | McKernan et al. |
| 2008/0004436 A1 | 1/2008 | Tawfik et al. |
| 2008/0009005 A1 | 1/2008 | Kruk |
| 2008/0014589 A1 | 1/2008 | Link et al. |
| 2008/0014590 A1 | 1/2008 | Dahary et al. |
| 2008/0020940 A1 | 1/2008 | Stedronsky et al. |
| 2008/0021330 A1 | 1/2008 | Hwang et al. |
| 2008/0023330 A1 | 1/2008 | Viovy et al. |
| 2008/0032413 A1 | 2/2008 | Kim et al. |
| 2008/0038754 A1 | 2/2008 | Farias-Eisner et al. |
| 2008/0044828 A1 | 2/2008 | Kwok |
| 2008/0050378 A1 | 2/2008 | Nakamura et al. |
| 2008/0050723 A1 | 2/2008 | Belacel et al. |
| 2008/0053205 A1 | 3/2008 | Pollack et al. |
| 2008/0057514 A1 | 3/2008 | Goldenring |
| 2008/0058432 A1 | 3/2008 | Wang et al. |
| 2008/0063227 A1 | 3/2008 | Rohrseitz |
| 2008/0064047 A1 | 3/2008 | Zetter et al. |
| 2008/0081330 A1 | 4/2008 | Kahvejian |
| 2008/0081333 A1 | 4/2008 | Mori et al. |
| 2008/0092973 A1 | 4/2008 | Lai |
| 2008/0113340 A1 | 5/2008 | Schlegel |
| 2008/0118462 A1 | 5/2008 | Alani et al. |
| 2008/0124726 A1* | 5/2008 | Monforte .......... B01L 3/502784 435/6.12 |
| 2008/0138806 A1 | 6/2008 | Chow et al. |
| 2008/0166772 A1 | 7/2008 | Hollinger et al. |
| 2008/0166793 A1 | 7/2008 | Beer et al. |
| 2008/0171078 A1 | 7/2008 | Gray |
| 2008/0176211 A1 | 7/2008 | Spence et al. |
| 2008/0176236 A1 | 7/2008 | Tsao et al. |
| 2008/0181850 A1 | 7/2008 | Thaxton et al. |
| 2008/0206756 A1 | 8/2008 | Lee et al. |
| 2008/0216563 A1* | 9/2008 | Reed ........................ G01N 1/18 73/61.71 |
| 2008/0220986 A1 | 9/2008 | Gormley et al. |
| 2008/0222741 A1 | 9/2008 | Chinnaiyan |
| 2008/0234138 A1 | 9/2008 | Shaughnessy et al. |
| 2008/0234139 A1 | 9/2008 | Shaughnessy et al. |
| 2008/0241830 A1 | 10/2008 | Vogelstein et al. |
| 2008/0261295 A1* | 10/2008 | Butler ............... B01L 3/502761 435/286.5 |
| 2008/0268473 A1 | 10/2008 | Moses et al. |
| 2008/0269157 A1 | 10/2008 | Srivastava et al. |
| 2008/0274513 A1 | 11/2008 | Shenderov et al. |
| 2008/0274908 A1 | 11/2008 | Chang |
| 2008/0280285 A1 | 11/2008 | Chen et al. |
| 2008/0280302 A1 | 11/2008 | Kebebew |
| 2008/0286199 A1 | 11/2008 | Livingston et al. |
| 2008/0286801 A1 | 11/2008 | Arjol et al. |
| 2008/0286811 A1 | 11/2008 | Moses et al. |
| 2008/0293578 A1 | 11/2008 | Shaugnessy et al. |
| 2008/0299565 A1 | 12/2008 | Schneider et al. |
| 2008/0311570 A1 | 12/2008 | Lai |
| 2008/0311604 A1 | 12/2008 | Elting et al. |
| 2009/0004687 A1 | 1/2009 | Mansfield et al. |
| 2009/0005254 A1 | 1/2009 | Griffiths et al. |
| 2009/0012187 A1 | 1/2009 | Chu et al. |
| 2009/0017463 A1 | 1/2009 | Bhowmick |
| 2009/0021728 A1 | 1/2009 | Heinz et al. |
| 2009/0023137 A1 | 1/2009 | Van Der Zee et al. |
| 2009/0026082 A1 | 1/2009 | Rothberg et al. |
| 2009/0029372 A1 | 1/2009 | Wewer |
| 2009/0042737 A1 | 2/2009 | Katz et al. |
| 2009/0053700 A1 | 2/2009 | Griffiths et al. |
| 2009/0053732 A1 | 2/2009 | Vermesh et al. |
| 2009/0060797 A1 | 3/2009 | Mathies et al. |
| 2009/0062144 A1 | 3/2009 | Guo |
| 2009/0068170 A1 | 3/2009 | Weitz et al. |
| 2009/0075265 A1 | 3/2009 | Budiman et al. |
| 2009/0075307 A1 | 3/2009 | Fischer et al. |
| 2009/0075311 A1 | 3/2009 | Karl |
| 2009/0081237 A1 | 3/2009 | D'Andrea et al. |
| 2009/0081685 A1 | 3/2009 | Beyer et al. |
| 2009/0087849 A1 | 4/2009 | Malinowski et al. |
| 2009/0092973 A1 | 4/2009 | Erlander et al. |
| 2009/0098542 A1 | 4/2009 | Budiman et al. |
| 2009/0098543 A1 | 4/2009 | Budiman et al. |
| 2009/0105959 A1 | 4/2009 | Braverman et al. |
| 2009/0118128 A1 | 5/2009 | Liu et al. |
| 2009/0124569 A1 | 5/2009 | Bergan et al. |
| 2009/0127454 A1 | 5/2009 | Ritchie et al. |
| 2009/0127589 A1 | 5/2009 | Rothberg et al. |
| 2009/0131353 A1 | 5/2009 | Insel et al. |
| 2009/0131543 A1 | 5/2009 | Weitz et al. |
| 2009/0191565 A1 | 7/2009 | Lapidus et al. |
| 2009/0197248 A1 | 8/2009 | Griffiths et al. |
| 2009/0197772 A1 | 8/2009 | Griffiths et al. |
| 2009/0226971 A1 | 9/2009 | Beer et al. |
| 2009/0226972 A1 | 9/2009 | Beer et al. |

(56) References Cited

U.S. PATENT DOCUMENTS

| | | |
|---|---|---|
| 2009/0233802 A1 | 9/2009 | Bignell et al. |
| 2009/0246788 A1 | 10/2009 | Albert et al. |
| 2009/0317798 A1 | 12/2009 | Heid et al. |
| 2009/0325217 A1* | 12/2009 | Luscher .............. G01N 15/1404 435/29 |
| 2009/0325236 A1 | 12/2009 | Griffiths et al. |
| 2010/0003687 A1 | 1/2010 | Simen et al. |
| 2010/0009353 A1 | 1/2010 | Barnes et al. |
| 2010/0022414 A1 | 1/2010 | Link et al. |
| 2010/0035252 A1 | 2/2010 | Rothberg et al. |
| 2010/0075436 A1 | 3/2010 | Urdea et al. |
| 2010/0105112 A1 | 4/2010 | Holtze et al. |
| 2010/0111768 A1 | 5/2010 | Banerjee et al. |
| 2010/0124759 A1 | 5/2010 | Wang et al. |
| 2010/0130369 A1 | 5/2010 | Shenderov et al. |
| 2010/0136544 A1 | 6/2010 | Agresti et al. |
| 2010/0137143 A1 | 6/2010 | Rothberg et al. |
| 2010/0137163 A1 | 6/2010 | Link et al. |
| 2010/0159592 A1 | 6/2010 | Holliger et al. |
| 2010/0172803 A1 | 7/2010 | Stone et al. |
| 2010/0173394 A1* | 7/2010 | Colston, Jr. ........... B01F 3/0807 435/287.2 |
| 2010/0188073 A1 | 7/2010 | Rothberg et al. |
| 2010/0197507 A1 | 8/2010 | Rothberg et al. |
| 2010/0210479 A1 | 8/2010 | Griffiths et al. |
| 2010/0213628 A1 | 8/2010 | Bausch et al. |
| 2010/0233026 A1 | 9/2010 | Ismagliov et al. |
| 2010/0273173 A1 | 10/2010 | Hirai et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0000560 A1 | 1/2011 | Miller et al. |
| 2011/0024455 A1 | 2/2011 | Bethuy et al. |
| 2011/0033854 A1 | 2/2011 | Drmanac et al. |
| 2011/0053151 A1 | 3/2011 | Hansen et al. |
| 2011/0142734 A1 | 6/2011 | Ismagilov et al. |
| 2011/0174622 A1 | 7/2011 | Ismagilov et al. |
| 2011/0176966 A1 | 7/2011 | Ismagilov et al. |
| 2011/0177494 A1 | 7/2011 | Ismagilov et al. |
| 2011/0177586 A1 | 7/2011 | Ismagilov et al. |
| 2011/0177609 A1 | 7/2011 | Ismagilov et al. |
| 2011/0188717 A1 | 8/2011 | Baudry et al. |
| 2011/0190146 A1 | 8/2011 | Boehm et al. |
| 2011/0244455 A1 | 10/2011 | Larson et al. |
| 2011/0250597 A1 | 10/2011 | Larson et al. |
| 2011/0267457 A1 | 11/2011 | Weitz et al. |
| 2011/0275063 A1 | 11/2011 | Weitz et al. |
| 2011/0311978 A1* | 12/2011 | Makarewicz, Jr. ... B01F 3/0807 435/6.12 |
| 2012/0010098 A1 | 1/2012 | Griffiths et al. |
| 2012/0015382 A1 | 1/2012 | Weitz et al. |
| 2012/0015822 A1 | 1/2012 | Weitz et al. |
| 2012/0127714 A1 | 5/2012 | Samuels et al. |
| 2012/0167142 A1 | 6/2012 | Hey |
| 2012/0190032 A1 | 7/2012 | Ness et al. |
| 2012/0220494 A1 | 8/2012 | Samuels et al. |
| 2012/0258516 A1 | 10/2012 | Schultz et al. |
| 2012/0288857 A1 | 11/2012 | Livak |
| 2012/0302448 A1 | 11/2012 | Hutchison et al. |
| 2013/0099018 A1 | 4/2013 | Miller et al. |
| 2013/0109577 A1 | 5/2013 | Korlach et al. |
| 2013/0157872 A1 | 6/2013 | Griffiths et al. |
| 2013/0178368 A1 | 7/2013 | Griffiths et al. |
| 2013/0178378 A1 | 7/2013 | Hatch et al. |
| 2013/0217601 A1 | 8/2013 | Griffiths et al. |
| 2013/0224751 A1 | 8/2013 | Olson et al. |
| 2013/0295567 A1 | 11/2013 | Link et al. |
| 2013/0295568 A1 | 11/2013 | Link |
| 2014/0065631 A1 | 3/2014 | Froehlich et al. |
| 2014/0274786 A1* | 9/2014 | McCoy ................ C12Q 1/6844 506/9 |
| 2014/0323317 A1 | 10/2014 | Link et al. |
| 2014/0329239 A1 | 11/2014 | Larson et al. |

FOREIGN PATENT DOCUMENTS

| | | |
|---|---|---|
| AT | 155711 T | 8/1997 |
| AT | 167816 T | 7/1998 |
| AU | 4032078 A | 4/1980 |
| AU | 6415380 A | 5/1981 |
| AU | 1045983 A | 6/1984 |
| AU | 2177292 A | 1/1993 |
| AU | 4222393 A | 11/1993 |
| AU | 4222593 A | 11/1993 |
| AU | 4222693 A | 11/1993 |
| AU | 4222793 A | 11/1993 |
| AU | 4223593 A | 11/1993 |
| AU | 677197 B2 | 4/1997 |
| AU | 677781 B2 | 5/1997 |
| AU | 680195 B2 | 7/1997 |
| AU | 2935197 A | 1/1998 |
| AU | 3499097 A | 1/1998 |
| AU | 3501297 A | 1/1998 |
| AU | 1276099 A | 6/1999 |
| AU | 4955799 A | 12/1999 |
| AU | 3961100 A | 10/2000 |
| AU | 4910300 A | 11/2000 |
| AU | 747464 B2 | 5/2002 |
| AU | 768399 B2 | 12/2003 |
| AU | 2004225691 B2 | 6/2010 |
| AU | 2010224352 A1 | 10/2010 |
| BR | 8200642 A | 12/1982 |
| BR | 9710052 A | 1/2000 |
| CA | 1093344 A1 | 1/1981 |
| CA | 2258481 A1 | 1/1998 |
| CA | 2520548 A1 | 10/2004 |
| CH | 563 087 A5 | 6/1975 |
| CH | 563807 A5 | 7/1975 |
| DE | 2100685 A1 | 7/1972 |
| DE | 3042915 A1 | 9/1981 |
| DE | 43 08 839 C2 | 4/1997 |
| DE | 69126763 T2 | 2/1998 |
| DE | 199 61 257 A1 | 7/2001 |
| DE | 100 15 109 A1 | 10/2001 |
| DE | 100 41 823 A1 | 3/2002 |
| EP | 0047130 B1 | 2/1985 |
| EP | 0402995 A2 | 12/1990 |
| EP | 0249007 A3 | 3/1991 |
| EP | 0418635 A1 | 3/1991 |
| EP | 0476178 A1 | 3/1992 |
| EP | 0618001 | 10/1994 |
| EP | 0637996 A1 | 2/1995 |
| EP | 0637997 A1 | 2/1995 |
| EP | 0718038 A2 | 6/1996 |
| EP | 0540281 B1 | 7/1996 |
| EP | 0528580 B1 | 12/1996 |
| EP | 0486351 B1 | 7/1997 |
| EP | 0895120 | 2/1999 |
| EP | 1362634 A1 | 11/2003 |
| EP | 04782399.2 | 5/2006 |
| EP | 1741482 | 1/2007 |
| EP | 2017910 A1 | 1/2009 |
| EP | 2127736 | 12/2009 |
| EP | 13165665.4 | 11/2013 |
| EP | 13165667.0 | 11/2013 |
| EP | 2363205 A3 | 6/2014 |
| ES | 2 095 413 T3 | 2/1997 |
| FR | 2 404 834 A1 | 4/1979 |
| FR | 2 451 579 A1 | 10/1980 |
| FR | 2 469 714 A1 | 5/1981 |
| FR | 2 470 385 A1 | 5/1981 |
| FR | 2 650 657 A1 | 2/1991 |
| FR | 2 669 028 A1 | 5/1992 |
| FR | 2 703 263 A1 | 10/1994 |
| GB | 1148543 | 4/1969 |
| GB | 1 446 998 | 8/1976 |
| GB | 2 005 224 | 4/1979 |
| GB | 2 047 880 | 12/1980 |
| GB | 2 062 225 | 5/1981 |
| GB | 2 064 114 | 6/1981 |
| GB | 2097692 A | 11/1982 |
| GB | 2 210 532 | 6/1989 |
| IE | 922432 A1 | 2/1993 |

(56) References Cited

FOREIGN PATENT DOCUMENTS

| | | |
|---|---|---|
| JP | S5372016 A | 6/1978 |
| JP | S5455495 A | 5/1979 |
| JP | 55125472 | 9/1980 |
| JP | S5636053 A | 4/1981 |
| JP | 56-124052 | 9/1981 |
| JP | 59-49832 A | 3/1984 |
| JP | 59-102163 | 6/1984 |
| JP | H0665609 A | 3/1994 |
| JP | 6-265447 A | 9/1994 |
| JP | 7-489 A | 1/1995 |
| JP | 8-153669 | 6/1996 |
| JP | 10-217477 | 8/1998 |
| JP | 3-232525 | 10/1998 |
| JP | 2000-271475 | 10/2000 |
| JP | 2001-301154 A | 10/2001 |
| JP | 2001-517353 A | 10/2001 |
| JP | 3232525 | 11/2001 |
| JP | 2002-085961 A | 3/2002 |
| JP | 2003-501257 A | 1/2003 |
| JP | 2003-502656 A | 1/2003 |
| JP | 2003-222633 A | 8/2003 |
| JP | 2005-037346 A | 2/2005 |
| JP | 2009-265751 A | 11/2009 |
| JP | 2010-198393 A | 9/2010 |
| JP | 2012-204765 A | 10/2012 |
| NZ | 264353 A | 5/1996 |
| WO | 84/02000 | 5/1984 |
| WO | 91/05058 A1 | 4/1991 |
| WO | 91/07772 | 5/1991 |
| WO | 91/16966 A1 | 11/1991 |
| WO | 92/03734 | 3/1992 |
| WO | 92/21746 | 12/1992 |
| WO | 93/03151 | 2/1993 |
| WO | 93/08278 | 4/1993 |
| WO | 93/22053 | 11/1993 |
| WO | 93/22054 | 11/1993 |
| WO | 93/22055 | 11/1993 |
| WO | 93/22058 | 11/1993 |
| WO | 93/22421 | 11/1993 |
| WO | 94/16332 | 7/1994 |
| WO | 94/23738 | 10/1994 |
| WO | 94/24314 | 10/1994 |
| WO | 94/26766 | 11/1994 |
| WO | 98/00705 | 1/1995 |
| WO | 95/11922 | 5/1995 |
| WO | 95/19922 | 7/1995 |
| WO | 95/24929 | 9/1995 |
| WO | 95/33447 | 12/1995 |
| WO | 96/34112 | 10/1996 |
| WO | 96/38730 | 12/1996 |
| WO | 96/40062 | 12/1996 |
| WO | 96/40723 | 12/1996 |
| WO | 97/00125 | 1/1997 |
| WO | 97/00442 | 1/1997 |
| WO | 97/01297 | 2/1997 |
| WO | 97/04748 | 2/1997 |
| WO | 97/23140 | 7/1997 |
| WO | 97/28556 | 8/1997 |
| WO | 97/39814 | 10/1997 |
| WO | 97/40141 | 10/1997 |
| WO | 97/45644 | 12/1997 |
| WO | 97/47763 A1 | 12/1997 |
| WO | 98/00231 | 1/1998 |
| WO | 98/02237 | 1/1998 |
| WO | 98/10267 | 3/1998 |
| WO | 98/13502 | 4/1998 |
| WO | 98/23733 | 6/1998 |
| WO | 98/31700 | 7/1998 |
| WO | 98/33001 | 7/1998 |
| WO | 98/34120 | 8/1998 |
| WO | 98/37186 | 8/1998 |
| WO | 98/41869 | 9/1998 |
| WO | 98/52691 | 11/1998 |
| WO | 98/58085 | 12/1998 |
| WO | 99/02671 | 1/1999 |
| WO | 99/22858 | 5/1999 |
| WO | 99/28020 | 6/1999 |
| WO | 99/31019 | 6/1999 |
| WO | 99/42539 A1 | 8/1999 |
| WO | 99/54730 | 10/1999 |
| WO | 99/61888 | 12/1999 |
| WO | 00/04139 A1 | 1/2000 |
| WO | 00/47322 | 2/2000 |
| WO | 00/52455 | 2/2000 |
| WO | 00/40712 | 6/2000 |
| WO | 00/54735 | 9/2000 |
| WO | 00/61275 | 10/2000 |
| WO | 00/70080 | 11/2000 |
| WO | 00/76673 | 12/2000 |
| WO | 00/078455 A1 | 12/2000 |
| WO | 01/12327 | 2/2001 |
| WO | 01/14589 | 3/2001 |
| WO | 01/18244 | 3/2001 |
| WO | 01/64332 | 9/2001 |
| WO | 01/68257 | 9/2001 |
| WO | 01/69289 | 9/2001 |
| WO | 01/72431 | 10/2001 |
| WO | 01/80283 | 10/2001 |
| WO | 01/89787 A2 | 11/2001 |
| WO | 01/89788 A2 | 11/2001 |
| WO | 01/94635 A2 | 12/2001 |
| WO | 02/16017 | 2/2002 |
| WO | 02/18949 | 3/2002 |
| WO | 02/22869 | 3/2002 |
| WO | 0223163 | 3/2002 |
| WO | 02/31203 | 4/2002 |
| WO | 02/47665 | 6/2002 |
| WO | 02/060275 | 8/2002 |
| WO | 02/060591 A1 | 8/2002 |
| WO | 02/068104 A1 | 9/2002 |
| WO | 02/078845 | 10/2002 |
| WO | 02/103011 | 12/2002 |
| WO | 02/103363 | 12/2002 |
| WO | 03/011443 | 2/2003 |
| WO | 03/026798 A1 | 4/2003 |
| WO | 03/037302 | 5/2003 |
| WO | 03/044187 | 5/2003 |
| WO | 03/078659 | 9/2003 |
| WO | 2003/003015 A3 | 10/2003 |
| WO | 03/099843 | 12/2003 |
| WO | 2004/002627 | 1/2004 |
| WO | 2004/018497 A2 | 3/2004 |
| WO | 2004/024917 | 3/2004 |
| WO | 2004/037374 A2 | 5/2004 |
| WO | 2004/038363 | 5/2004 |
| WO | 2004/069849 | 8/2004 |
| WO | 2004/071638 A2 | 8/2004 |
| WO | 2004/074504 | 9/2004 |
| WO | 2004/083443 | 9/2004 |
| WO | 2004/087308 | 10/2004 |
| WO | 2004/088314 | 10/2004 |
| WO | 2004/091763 | 10/2004 |
| WO | 2004/102204 | 11/2004 |
| WO | 2004/103565 | 12/2004 |
| WO | 2005/000970 | 1/2005 |
| WO | 2005/002730 | 1/2005 |
| WO | 2005/003375 A2 | 1/2005 |
| WO | 2005/11867 A2 | 2/2005 |
| WO | 2005/021151 | 3/2005 |
| WO | 2005/023427 A1 | 3/2005 |
| WO | 2005/049787 A2 | 6/2005 |
| WO | 2005/103106 | 11/2005 |
| WO | 2005/118138 | 12/2005 |
| WO | 2005/118867 A2 | 12/2005 |
| WO | 2006/002641 | 1/2006 |
| WO | 2006/009657 | 1/2006 |
| WO | 2006/027757 | 3/2006 |
| WO | 2006/038035 | 4/2006 |
| WO | 2006/040551 | 4/2006 |
| WO | 2006/040554 | 4/2006 |
| WO | 2006/078841 | 7/2006 |
| WO | 2006/096571 | 9/2006 |
| WO | 2006/101851 | 9/2006 |
| WO | 2007/021343 | 2/2007 |

(56) References Cited

FOREIGN PATENT DOCUMENTS

| | | |
|---|---|---|
| WO | 2007/030501 | 3/2007 |
| WO | 2007/081385 | 7/2007 |
| WO | 2007/081387 | 7/2007 |
| WO | 2007/089541 | 8/2007 |
| WO | 2007/114794 | 10/2007 |
| WO | 2007/123744 A2 | 11/2007 |
| WO | 2007/133710 | 11/2007 |
| WO | 2007/138178 | 12/2007 |
| WO | 2007/140015 A2 | 12/2007 |
| WO | 2008/021123 | 2/2008 |
| WO | 2008/063227 | 5/2008 |
| WO | 2008/097559 | 8/2008 |
| WO | 2008/115626 A2 | 9/2008 |
| WO | 2008/121342 | 10/2008 |
| WO | 2008/130623 | 10/2008 |
| WO | 2007/092473 A3 | 11/2008 |
| WO | 2008/134153 A1 | 11/2008 |
| WO | 2009/015296 A1 | 1/2009 |
| WO | 2009/029229 | 3/2009 |
| WO | 2009/049889 A1 | 4/2009 |
| WO | 2009/059430 A1 | 5/2009 |
| WO | 2009/085929 A1 | 7/2009 |
| WO | 2009/137606 A1 | 11/2009 |
| WO | 2010/056728 A1 | 5/2010 |
| WO | 2010/040006 | 8/2010 |
| WO | 2010/151776 | 12/2010 |
| WO | 2011/042564 | 4/2011 |
| WO | 2011/079176 | 6/2011 |
| WO | 2012/022976 A1 | 2/2012 |
| WO | 2012/048341 A1 | 4/2012 |
| WO | 2012/167142 A2 | 12/2012 |
| WO | 2013/14356 A2 | 1/2013 |

OTHER PUBLICATIONS

Betlach, L. et al., A restriction endonuclease analysis of the bacterial plasmid controlling the EcoRI restriction and modification of DNA. Federation Proceedings, 35:2037-2043 (1976).
Bibette et al., Emulsions: basic principles, Rep. Prog. Phys. 62:969-1033 (1999).
Bico, Jose et al., Rise of Liquids and Bubbles in Angular Capillary Tubes, Journal of Colloid and Interface Science, 247:162-166 (2002).
Bico, Jose et al., Self-Propelling Slugs, J. Fluid Mech., 467:101-127 (2002).
Binder et al., Mismatch and G-stack modulated probe signals on SNP microarrays, PLoS One. Nov. 17, 2009;4(11): e7862.
Blattner and Dahlberg, RNA synthesis startpoints in bacteriophage lambda: are the promoter and operator transcribed, Nature New Biol 237(77):227-32 (1972).
Boder et al., Yeast surface display for screening combinatorial polypeptide libraries, Nat Biotechnol 15(6):553-7 (1997).
Bougueleret, L. et al., Characterization of the gene coding for the EcoRV restriction and modification system of *Escherichia coli*, Nucleic Acids Res, 12(8):3659-76 (1984).
Boyum, A., Separation of leukocytes from blood and bone marrow. Introduction, Scand J Clin Lab Invest Suppl 97:7 (1968).
Branebjerg et al., Fast mixing by lamination, MEMS Proceedings 9th Ann Workshop, San Diego, Feb. 11-15, 1996, 9:441-446 (1996).
Braslavsky et al., Sequence information can be obtained from single DNA molecules, PNAS 100(7):3960-3964 (2003).
Bringer et al., Microfluidic Systems for Chemical Kinetics That Rely on Chaotic Mixing in Droplets, Philos Transact A Math Phys Eng Sci 362:1-18 (2004).
Brody et al., A self-assembled microlensing rotational probe, Applied Physics Letters, 74:144-46 (1999).
Brown et al., Chemical synthesis and cloning of a tyrosine tRNA gene, Methods Enzymol 68:109-151 (1979).
Bru, R. et al., Catalytic activity of elastase in reverse micelles, Biochem Mol Bio Int, 31(4):685-92 (1993).
Bru, R. et al., Product inhibition of alpha-chymotrypsin in reverse micelles. Eur J Biochem 199(1):95-103 (1991).
Brummelkamp et al., A system for stable expression of short interfering RNAs in mammalian cells, Science 296(5567):550-3 (2002).
Buckpitt et al.,Hepatic and pulmonary microsomal metabolism of naphthalene to glutathione adducts: factors affecting the relative rates of conjugate formation, J. Pharmacol. Exp. Ther. 231:291-300 (1984).
Buican et al., Automated single-cell manipulation and sorting by light trapping, Applied Optics 26(24):5311-5316 (1987).
Burbaum, J., Miniaturization technologies in HTS: how fast, how small, how soon Drug Discov Today 3:313-322 (1998).
Burns et al., Microfabricated structures for integrated DNA analysis, Proc. Natl. Acad. Sci. USA, 93:5556-5561(1996).
Burns, J.R. et al., The Intensification of Rapid Reactions in Multiphase Systems Using Slug Flow in Capillaries, Lab on a Chip, 1:10-15 (2001).
Burns, Mark et al., An Integrated Nanoliter DNA Analysis Device, Science, 282:484-487(1998).
Byrnes, P.J. et al., Sensitive fluorogenic substrates for the detection of trypsin-like proteases and pancreatic elastase, Anal Biochem, 126:447 (1982).
Cahill et al., Polymerase chain reaction and Q beta replicase amplification, Clin Chem 37(9):1482-5 (1991).
Caldwell, S.R. et al., Limits of diffusion in the hydrolysis of substrates by the phosphodiesterase from Pseudomonas diminuta, Biochemistry, 30: 7438-7444 (1991).
Calvert, P., Inkjet printing for materials and devices, Chem Mater 13: 3299-3305 (2001).
Caruthers, 1985, Gene synthesis machines: DNA chemistry and its uses, Science 230:281-285.
Chakrabarti, A.C. et al., Production of RNA by a polymerase protein encapsulated within phospholipid vesicles, J Mol Evol, 39(6):555-9 (1994).
Chamberlain and Ring, Characterization of T7-specific ribonucleic acid polymerase. 1. General properties of the enzymatic reaction and the template specificity of the enzyme, J Biol Chem 248:2235-44 (1973).
Chan, Emory M. et al., Size-Controlled Growth of CdSe Nanocrystals in Microfluidic Reactors, Nano Letters, 3(2):199-201(2003).
Chang and Su, Controlled double emulsification utilizing 3D PDMS microchannels, Journal of Micromechanics and Microengineering 18:1-8 (2008).
Chang, T.M., Recycling of NAD(P) by multienzyme systems immobilized by microencapsulation in artifical cells, Methods Enzymol, 136(67):67-82 (1987).
Chao et al., Control of Concentration and Volume Gradients in Microfluidic Droplet Arrays for Protein Crystallization Screening, 26th Annual International Conference of the IEEE Engineering in Medicine and Biology Society, San Francisco, California Sep. 1-5, 2004.
Chao et al., Droplet Arrays in Microfluidic Channels for Combinatorial Screening Assays, Hilton Head 2004: A Solid State Sensor, Actuator and Microsystems Workshop, Hilton Head Island, South Carolina, Jun. 6-10, 2004.
Chapman et al., In vitro selection of catalytic RNAs, Curr. op. Struct. Biol., 4:618-22 (1994).
Chayen, Crystallization with oils: a new dimension in macromolecular crystal growth Journal of Crystal Growth,196:434-441(1999).
Chen et al., Capturing a Photoexcited Molecular Structure Through Time-Domain X-ray Absorption Fine Structure, Science 292(5515):262-264 (2001).
Chen et al., Microfluidic Switch for Embryo and Cell Sorting The 12th International Conference on Solid State Sensors, Actuators, and Microsystems, Boston, MA Jun. 8-12, 2003 Transducers, 1: 659-662 (2003).
Chen-Goodspeed et al., Structural Determinants of the substrate and stereochemical specificity of phosphotriesterase, Biochemistry, 40(5):1325-31 (2001).
Chen-Goodspeed, M. et al., Enhancement, relaxation, and reversal of the stereoselectivity for phosphotriesterase by rational evolution of active site residues, Biochemistry, 40: 1332-1339 (2001b).

(56) References Cited

OTHER PUBLICATIONS

Cheng, Z., et al, Electro flow focusing in microfluidic devices, Microfluidics Poster, presented at DBAS, Frontiers in Nanoscience, presented Apr. 10, 2003.
Chetverin and Spirin, Replicable RNA vectors: prospects for cell-free gene amplification, expression, and cloning, Prog Nucleic Acid Res Mol Biol, 51:225-70 (1995).
Chiang, C.M. et al., Expression and purification of general transcription factors by FLAG epitope-tagging and peptide elution, Pept Res, 6:62-64 (1993).
Chiba et al., Controlled protein delivery from biodegradable tyrosino-containing poly(anhydride-co-imide) microspheres, Biomaterials, 18(13):893-901 (1997).
Chiou et al., A closed-cycle capillary polymerase chain reaction machine, Analytical Chemistry, American Chamical Society, 73:2018-21 (2001).
Chiu et al., Chemical transformations in individual ultrasmall biomimetic containers, Science, 283:1892-1895 (1999).
Chou et al., A microfabricated device for sizing and sorting DNA molecules 96:11-13(1998).
Clackson, T. et al., In vitro selection from protein and peptide libraries, Trends Biotechnol, 12:173-84 (1994).
Abstract of Sanchez et al., Breakup of Charged Capillary Jets, Bulletin of the American Physical Society Division of Fluid Dynamics 41:1768-1768 (1996).
Adang, A.E et al., The contribution of combinatorial chemistry to lead generation: an interim analysis, Curr Med Chem 8: 985-998 (2001).
Advisory Action dated Sep. 9, 2014 for U.S. Appl. No. 13/679,190.
Advisory Action for U.S. Appl. No. 11/360,845, dated Jun. 14, 2010.
Advisory Action for U.S. Appl. No. 11/698,298 dated May 20, 2011.
Affholter and F. Arnold, Engineering a Revolution, Chemistry in Britain, Apr. 1999, p. 48.
Agrawal, 1990, Site-specific functionalization of oligodeoxynucleotides for non-radioactive labelling, Tetrahedron Let 31:1543-1546.
Aharoni et al., High-Throughput screens and selections of enzyme-encoding genes, Curr Opin Chem Biol, 9(2): 210-6 (2005).
Ahn et al., Dielectrophoretic manipulation of drops for high-speed microluidic sorting devices, Applied Phys Lett 88, 024104 (2006).
Allen et al., High throughput fluorescence polarization: a homogeneous alternative to radioligand binding for cell surface receptors J Biomol Screen. 5(2):63-9 (2000).
Altman et al., Solid-state laser using a rhodamine-doped silica gel compound, IEEE Photonics technology letters 3(3):189-190 (1991).
Amplicon Sequencing, Application Note No. 5., Feb. 2007.
Amstutz, P. et al., In vitro display technologies: novel developments and applications. Curr Opin Biotechnol, 12, 400-405 (2001).
Anarbaev et al., Klenow fragment and DNA polymerase alpha-primase fromserva calf thymus in water-in-oil microemulsions, Biochim Biophy Acta 1384:315-324 (1998).
Anderson et al., Preparation of a cell-free protein-synthesizing system from wheat germ, Methods Enzymol 101:635-44 (1983).
Anderson, J.E., Restriction endonucleases and modification methylases, Curr. Op. Struct. Biol., 3:24-30 (1993).
Ando, S. et al., PLGA microspheres containing plasmid DNA: preservation of supercoiled DNA via cryopreparation and carbohydrate stabilization, J Pharm Sci, 88(1):126-130 (1999).
Angell et al., Silicon micromechanical devices, Scientific American 248:44-55 (1983).
Anhuf et al., Determination of SMN1 and SMN2 copy number using TaqMan technology, Hum Mutat 22(1):74-78 (2003).
Anna et al., Formation of dispersions using flow focusing in microchannels, Applied Physics Letters,82(3): 364-366 (2003).
Arkin, M.R. et al., Probing the importance of second sphere residues in an esterolytic antibody by phage display, J Mol Biol 284(4):1083-94 (1998).
Armstrong et al., Multiple-Component Condensation Strategies for Combinatorial Library Synthesis, Acc. Chem. Res. 29(3):123-131 (1996).

Ashkin and Dziedzic, Optical trapping and manipulation of viruses and bacteria, Science 235(4795):1517-20 (1987).
Ashkin et al., Optical trapping and manipulation of single cells using infrared laser beams, Nature 330:769-771 (1987).
Ashutosh Shastry et al, Directing Droplets Using Microstructured Surfaces.
Atwell, S. & Wells, J.A., Selection for Improved Subtiligases by Phage Display, PNAS 96: 9497-9502(1999).
Auroux, Pierre-Alain et al., Micro Total Analysis Systems. 2. Analytical Standard Operations and Applications, Analytical Chemistry, vol. 74, No. 12, 2002, pp. 2637-2652.
Baccarani et al., *Escherichia coli* dihydrofolate reductase: isolation and characterization of two isozymes, Biochemistry 16(16):3566-72 (1977).
Baez et al., Glutathione transferases catalyse the detoxication of oxidized metabolites (o-quinones) of catecholamines and may serve as an antioxidant system preventing degenerative cellular processes, Biochem. J 324:25-28 (1997).
Bagwe et al, Improved drug delivery using microemulsions: rationale, recent progress, and new horizons, Crit Rev Ther Drug Carr Sys 18(1):77-140 (2001).
Baker, M., Clever PCR: more genotyping, smaller volumes, Nature Methods 7:351-356 (2010).
Ball and Schwartz, CMATRIX: software for physiologically based pharmacokinetic modeling using a symbolic matrix representation system, Comput Biol Med 24(4):269-76 (1994).
Ballantyne and Nixon, Selective Area Metallization by Electron-Beam Controlled Direct Metallic Deposition, J. Vac. Sci. Technol. 10:1094 (1973).
Barany F., The ligase chain reaction in a PCR World, PCR Methods and Applications 1(1):5-16 (1991).
Barany, F. Genetic disease detection and DNA amplification using cloned thermostable ligase, PNAS 88(1): 189-93 (1991).
Baret et al., Fluorescence-activated droplet sorting (FADS): efficient microfluidic cell sorting based on enzymatic activity, Lab on a Chip 9:1850-1858 (2009).
Baret et al., Kinetic aspects of emulsion stabilization by surfactants: a microfluidic analysis, Langmuir 25:6088-6093 (2009).
Bass et al., Hormone Phage: An Enrichment Method for Variant Proteins With Altered Binding Properties, Proteins 8:309-314(1990).
Bauer, J., Advances in cell separation: recent developments in counterflow centrifugal elutriation and continuous flow cell separation, J Chromotography, 722:55-69 (1999).
Beebe et al., Functional hydrogel structures for autonomous flow control inside microfluidic channels, Nature 404:588-590 (2000).
Beer et al., 2008, On-chip single-copy real-time reverse transcription PCR in isolated picoliter droplets, Analytical Chemistry 80(6):1854-1858.
Beer et al., Anal. Chem., 2007, 79 (22), pp. 8471-8475.
Beer et al., On-Chip, Real-Time, Single-Copy Polymerase Chain Reaction in Picoliter Droplets, Anal. Chem., 79:847-8475 (2007).
Bein, Thomas, Efficient Assays for Combinatorial methods for the Discovery of Catalysts, Agnew. Chem. Int. Ed. 38:3, 323-26 (1999).
Benhar, I, et al., Highly efficient selection of phage antibodies mediated by display of antigen as Lpp-OmpA' fusions on live bacteria, Journal of Molecular Biology, 301 893-904 (2000).
Benichou et al., Double Emulsions Stabilized by New Molecular Recognition Hybrids of Natural Polymers, Polym. Adv. Tehcnol 13:1019-1031 (2002).
Benner, S.A., Expanding the genetic lexicon: incorporating non-standard amino acids into proteins by ribosome-based synthesis, Trends Biotechnol 12:158-63 (1994).
Benning, M.M. et al., The binding of substrate analogs to phosphotriesterase. J Biol Chem, 275:30556-30560 (2000).
Berman et al., An agarose gel electrophoresis assay for the detection of DNA-binding activities in yeast cell extracts, Methods Enzymol 155:528-37 (1987).
Bernath et al, In Vitro Compartmentalization by Double Emulsions: Sorting and Gene Enrichment by Fluorescence Activated Cell Sorting, Anal. Biochem 325:151-157 (2004).

(56) References Cited

OTHER PUBLICATIONS

Harrison et al., Micromachining a miniaturized capillary electrophoresis-based chemical analysis system on a chip, Science 261(5123):895-897 (1993).
Hasina et al., Plasminogen activator inhibitor-2: a molecular biomarker for head and neck cancer progression, Cancer Research 63:555-559 (2003).
Haynes Principles of Digital PCR and Measurement Issue Oct. 15, 2012.
Hayward et al., Dewetting Instability during the Formation of Polymersomes from BloceCopolymer-Stabilized Double Emulsions, Langmuir, 22(10): 4457-4461 (2006).
He et al., Selective encapsulation of single cells and subcellular organelles into picoliter- and femtoliter-volume droplets, Anal Chem 77(6):1539-1544 (2005).
Heim et al., Engineering Green Fluorescent Protein for Improved Brightness, Longer Wavelengths and Fluorescence Response Energy Transfer, Carr. Biol, 6(2): 178-182 (1996).
Hellman et al., Differential tissue-specific protein markers of vaginal carcinoma, Br J Cancer, 100(8): 1303-131 (2009).
Hergenrother et al., Small-Molecule Microarrays: Covalent Attachment and Screening of Alcohol-Containing Small Molecules on Glass Slides, J. Am. Chem. Soc, 122: 7849-7850 (2000).
Heyries, Kevin A, et al., Megapixel digital PCR, Nat. Methods 8, 649-651 (2011).
Hildebrand et al., Liquid-Liquid Solubility of Perfluoromethylcyclohexane with Benzene, Carbon Tetrachloride, Chlorobenzene, Chloroform and Toluene, J. Am. Chem. Soc, 71:22-25 (1949).
Hindson, Benjamin J., et al., High-Throughput Droplet Digital PCR System for Absolute Quantitation of DNA Copy Number, Anal. Chem., 83, 8604-8610 (2011).
Hjelmfelt et al, Pattern-Recognition in Coupled Chemical Kinetic Systems, Science, 260(5106):335-337 (1993).
Ho, S.N. et al., Site-directed mutageneiss by overlap extension using the polymerase chain reaction, Gene, 77(1):51-9 (1989).
Hoang, Physiologically based pharmacokinetic models: mathematical fundamentals and simulation implementations, Toxicol Lett 79(1-3):99-106 (1995).
Hochuli et al., New metal chelate adsorbent selective for proteins and peptides containing neighbouring histidine residues, J Chromatogr 411: 177-84 (1987).
Holmes et al., Reagents for Combinatorial Organic Synthesis: Development of a New O-Nitrobenzyl Photolabile Linder for Solid Phase Synthesis, J. OrgChem., 60: 2318-2319(1995).
Holtze, C., et al., Biocompatible surfactants for water-in-fluorocarbon emulsions, Lab Chip, 2008, 8, 1632-1639.
Hong, S.B. et al., Stereochemical constraints on the substrate specificity of phosphodiesterase, Biochemistry, 38: 1159-1165 (1999).
Hoogenboom et al., Multi-subunit proteins on the surface of filamentous phage: methodologies for displaying antibody (Fab) heavy and light chains, Nucl Acids Res., 91: 4133-4137 (1991).
Hoogenboom, H.R., Designing and optimizing library selection strategies for generating high-affinity antibodies, Trends Biotechnol, 15:62-70 (1997).
Hopfinger & Lasheras, Explosive Breakup of a Liquid Jet by a Swirling Coaxial Jet, Physics of Fluids 8(7):1696-1700 (1996).
Hopman et al., Rapid synthesis of biotin-, digoxigenin-, trinitrophenyl-, and fluorochrome-labeled tyramides and their application for in situ hybridization using CARD amplification, J of Histochem and Cytochem, 46(6):771-77 (1998).
Horton et al., Engineering hybrid genes without the use of restriction enzymes: gene splicing by overlap extension, Gene 77(1):61-8 (1989).
Hosokawa, Kazuo et al., Handling of Picoliter Liquid Samples in a Poly(dimethylsiloxane)-Based Microfluidic Device, Analytical Chemistry, 71(20):4781-4785 (1999).
How many species of bacteria are there(wisegeek.com; accessed Sep. 23, 2011).
Hsieh et al., 2009, Rapid label-free DNA analysis in picoliter microfluidic droplets using FRET probes, Microfluidics and nanofluidics 6(3):391-401.
Hsu et al., Comparison of process parameters for microencapsulation of plasmid DNA in poly(D, L-lactic-co-glycolic acid microspheres, J Drug Target, 7:313-23 (1999).
Hua et al., 2010, Multiplexed Real-Time Polymerase Chain Reaction on a Digital Microfluidic Platform, Analytical Chemistry 82(6):2310-2316.
Huang et al., Identification of 8 foodborne pathogens by multicolor combinational probe coding technology in a single real-time PCR, Clin Chem. Oct. 2007;53(10):1741-8.
Huang L. R. et al., Continuous particle separation through deterministic lateral displacement, Science 304(5673):987-990 (2004).
Huang, Z. et al., A sensitive competitive ELISA for 2,4-dinitrophenol using 3,6-fluorescein diphosphate as a fluorogenic substrate, J Immunol Meth, 149:261 (1992).
Huang, Z.J., Kinetic assay of fluorescein mono-beta-D-galactosidase hydrolysis by beta-galactosidase: a front-face measurement for strongly absorbing fluorogenic substrates, Biochemistry, 30:8530-4 (1991).
Hubert et al. Data Concordance from a Comparison between Filter Binding and Fluorescence Polarization Assay Formats for Identification of RUOCK-II Inhibitors, J biomol Screen 8(4):399-409 (2003).
Huebner, A. et al., Quantitative detection of protein expression in single cells using droplet microfluidics, Chem Com 12:1218-1220 (2007).
Hug et al. Measurement of the number of molecules of a single mRNA species in a complex mRNA preparation. J Theor Biol.; 221(4):615-24 (2003).
Hung et al., Optimization of Droplet Generation by controlling PDMS Surface Hydrophobicity, 2004 ASME International Mechanical Engineering Congress and RD&D Expo, Nov. 13-19, Anaheim, CA (2004).
Hung, et al, Controlled Droplet Fusion in Microfluidic Devices, MicroTAS 2004, Sep. 26-30, Malmo, Sweden (2004).
Hutchison et al., Cell-free cloning using Phi29 polymerase, PNAS 102(48):17332-17336 (2005).
Ibrahim, S.F. et al., High-speed cell sorting: fundamentals and recent advances, Curr Opin Biotchnol, 14(1):5-12 (2003).
Ikeda et al., Bioactivation of tegafur to 5-fluorouracil is catalyzed by cytochrome P-450 2A6 in human liver microsomes in vitro, Clin Cancer Res 6(11):4409-4415 (2000).
Inai et al., Immunohistochemical detection of an enamel protein-related epitope in rat bone at an early stage of osteogenesis, Histochemistry 99(5):335-362 (1993).
International Preliminary Report of Patentability for PCTUS2010061741 dated Sep. 16, 2011(4 pages).
International Preliminary Report on Patentability dated Sep. 20, 2007, for PCT/US2006/007772 (11 pages).
International Preliminary Report on Patentability PCT/US2004/027912 dated Jan. 26, 2005, 7 pages.
International Search Report and Written Opinion for PCT/US11/54353 dated Apr. 20, 2012 (34 pages).
International Search Report and Written Opinion for PCT/US12/024745 dated May 11, 2012 (21 pages).
International Search Report and Written Opinion for PCT/US12/24741 dated Jun. 12, 2012 (12 pages).
International Search Report and Written Opinion for PCT/US12/5499 dated May 29, 2012 (10 pages).
International Search Report and Written Opinion for PCT/US2009/050931 dated Nov. 26, 2009 (3 pages).
International Search Report and Written Opinion for PCT/US2013/037751 dated Aug. 22, 2013.
International Search Report and Written Opinion in PCT/EP2010/065188 dated Jan. 12, 2011 (7 pages).
International Search Report and Written Opinion in PCT/US11/24615 dated Jul. 25, 2011 (37 pages).
International Search Report and Written Opinion in PCT/US2004/010903 dated Dec. 20, 2004 (16 pages).
International Search Report and Written Opinion in PCT/US2006/021286 dated Sep. 14, 2007 (16 pages).

(56) References Cited

OTHER PUBLICATIONS

International Search Report and Written Opinion in PCT/US2007/002063 dated Nov. 15, 2007 (20 pages).
International Search Report and Written Opinion dated Apr. 23, 2015, for International Patent Application No. PCT/US14/34205, filed Apr. 15, 2014, 18 pages.
International Search Report and Written Opinion dated Nov. 25, 2014, for International Patent Application No. PCT/US14/34037, filed Apr. 14, 2014, 13 pages.
International Search Report and Written Opinion, dated Jun. 11, 2015, for PCT/US2014/032614, filed Apr. 2, 2014 (9 pages).
International Search Report for PCT/US2003/2052 dated Jun. 6, 2004.
International Search Report for PCT/US2006/001938 dated May 31, 2006, 5 pages.
International Search Report in PCT/US01/18400 dated Jan. 28, 2005 (37 pages).
Ismagilov, Integrated Microfluidic Systems, Angew. Chem. Int. Ed 42:4130-4132 (2003).
Janda, et al, Chemical selection for catalysis in combinatorial antibody libraries, Science, 275:945-948 (1997).
Jang et al., Controllable delivery of non-viral DNA from porous scaffold, J Controlled Release 86(1):157-168 (2003).
Japanese Notice of Reasons for Rejection for JP 2006-509830 dated Jun. 1, 2011 (4 pages).
Japanese Office Action for Application No. JP 2009-231040 dated Jul. 1, 2014.
Japanese Office Action for JP 2006-509830 dated Jun. 1, 2011 (4 pages).
Jermutus et al., Recent advances in producing and selecting functional proteins by using cell-free translation, Curr Opin Biotechnol 9(5): 534-48 (1998).
Jestin et al., A Method for the Selection of Catalytic Activity Using Phage Display and Proximity Coupling, Agnew. Chem. Int. Ed. Engl. 38(8):1124-1127 (1999).
Jo, et al, Encapsulation of Bovine Serum Albumin in Temperature-Programmed Shell-in-Shell Structures, Macromol. Rapid Comm 24:957-962 (2003).
Joerger et al., Analyte detection with DNA-labeled antibodies and polymerase chain reaction, Clin. Chem. 41(9):1371-7 (1995).
Johannsson et al., Amplification by Second Enzymes, In ELISA and Other Solid Phase Immunoassays, Kemeny et al (ed.), Chapter 4, pp. 85-106 John Wiley (1988).
Johannsson, A., Heterogeneous Enzyme Immunoassays, In Principles and Practice of Immunoassay, pp. 295-325 Stockton Press (1991).
Johnson, T.O. et al., Protein tyrosine phosphatase 1B inhibitors for diabetes, Nature Review Drug Discovery 1, 696-709(2002).
Jones et al. Glowing jellyfish, luminescence and a molecule called coelenterazine, Trends Biotechnol. 17(12):477-81 (1999).
Jones, L.J. et al., Quenched BODIPY dye-labeled casein substrates for the assay of protease activity by direct fluorescence measurement, Anal Biochem, 251:144 (1997).
Joo et al., Laboratory evolution of peroxide-mediated cytochrome P450 hydroxylaion, Nature 399:670 (1999).
Joos et al., Covalent attachment of hybridizable oligonucleotides to glass supports, Analytical Biochemistry 247:96-101 (1997).
Joyce, G.F., In vitro Evolution of Nucleic Acids, Curr. Opp. Structural Biol, 4: 331-336 (1994).
Kadir and Moore, Haem binding to horse spleen ferritin, Febs Lett, 276: 81-4 (1990).
Kallen, R.G. et al., The mechanism of the condensation of formaldehyde with tetrahydrofolic acid, J. Biol. Chem., 241:5851-63 (1966).
Kambara et al., Optimization of Parameters in a DNA Sequenator Using Fluorescence Detection, Nature Biotechnology 6:816-821 (1988).
Kamensky et al., Spectrophotometer: new instrument for ultrarapid cell analysis, Science 150(3696):630-631 (1965).

Kanouni et al., Preparation of a stable double emulsion (W1/0/W2): role of the interfacial films on the stability of the system, Adv. Collid. Interf. Sci., 99(3): 229-254 (2002).
Katanaev et al., Viral Q beta RNA as a high expression vector for mRNA translation in a cell-free system, Febs Lett, 359:89-92 (1995).
Katsura et al., Indirect micromanipulation of single molecules in water-in-oil emulsion, Electrophoresis, 22:289-93 (2001).
Kawakatsu et al., Regular-sized cell creation in microchannel emulsification by visual microprocessing method, Journal of the American Oil ChemistS Society, 74:317-21 (1997).
Keana J. & Cai, S. X., New reagents for photoaffinity labeling: synthesis and photolysis of functionalized pertluorophenyl azides, J. Org. Chem.55(11):3640-3647 (1990).
Keefe, A.D. et al., Functional proteins from a random-sequence library, Nature, 410: 715-718 (2001).
Keij et al., High-Speed Photodamage Cell Selection Using a Frequency-Doubled Argon Ion Laser, Cytometry, 19(3): 209-216 (1995).
Keij, J.F. et al., High-speed photodamage cell sorting: An evaluation of the ZAPPER prototype, Methods in cell biology, 42: 371-358 (1994).
Kelly et al., Miniaturizing chemistry and biology in microdroplets, Chem Commun 18:1773-1788 (2007).
Kerker, M., Elastic and inelastic light scattering in flow cytometry, Cytometry, 4:1-10 (1983).
Khandjian, UV crosslinking of RNA to nylon membrane enhances hybridization signals, Mol. Bio. Rep. 11: 107-115 (1986).
Kim et al., Comparative study on sustained release of human growth hormone from semi-crystalline poly(L-lactic acid) and amorphous poly(D,L-lactic-co-glycolic acid) microspheres: morphological effect on protein release, Journal of Controlled Release, 98(1):115-125 (2004).
Kim S. et al, Type ii quantum dots: CdTe/CdSe (core/shell) and CdSe/ZnTe (core/shell) heterostructures, J. Am Chem Soc. 125:11466-11467 (2003).
Kircher et al., High-throughput DNA sequencing-concepts and limitations, Bioessays 32(6):524-536 (2010).
Kiss et al., High-throughput quantitative polymerase chain reaction in picoliter droplets, Anal. Chem 80:8975-8981 (2008).
Kitagawa et al., Manipulation of a single cell with microcapillary tubing based on its electrophoretic mobility, Electrophoresis 16:1364-1368 (1995).
Klug and Famulok, All you wanted to know about selex, Molecular Biology Reports, 20:97-107 (1994).
Eggers, Jens et al., Coalescence of Liquid Drops, J. Fluid Mech., 401:293-310 (1999).
Ehrig, T. et al., Green-fluorescent protein mutants with altered fluorescence excitation spectra, Febs Lett, 367(2):163-66 (1995).
Eigen et al., Hypercycles and compartments: compartments assists—but does not replace—hypercyclic organization of early genetic information, J Theor Biol, 85:407-11 (1980).
Eigen et al., The hypercycle: coupling of RNA and protein biosynthesis in the infection cycle of an RNA bacteriophage, Biochemistry, 30:11005-18 (1991).
Eigen, Wie entsteht information Prinzipien der selbstorganisation in der biologie, Berichte der punsen-gesellschaft fur physikalische chemi, 80:1059-81 (1976).
Ellington and Szostak, In vitro selection of RNA molecules that bind specific ligands, Nature, 346:818-822 (1990).
Ellman et al., Biosynthetic method for introducing unnatural amino acids site-specifically into proteins, Methods Enzymol, 202:301-36 (1991).
Endo et al. Kinetic determination of trace cobalt by visual autocatalytic indication, Talanta 47:349-353 (1998).
Endo et al., Autocatalytic decomposition of cobalt complexes as an indicator system for the determination of trace amounts of cobalt and effectors, Analyst 121:391-394 (1996).
Engl, W. et al, Droplet Traffic at a Simple Junction at Low Capillary Numbers Physical Review Letters, 2005, vol. 95,208304.
Eow et al., Electrocoalesce-separators for the separation of aqueous drops from a flowing dielectric viscous liquid, Separation and Purification Tech 29:63-77 (2002).

(56) References Cited

OTHER PUBLICATIONS

Eow et al., Electrostatic enhancement of coalescence of water droplets in oil: a review of the technology, Chemical Engineeing Journal 85:357-368 (2002).
Eow et al., Motion, deformation and break-up of aqueous drops in oils under high electric field strengths, Chemical Eng Proc 42:259-272 (2003).
Eow et al., The behavior of a liquid-liquid interface and drop-interface coalescence under the influence of an electric field, Colloids and Surfaces A: Physiochem. Eng. Aspects 215:101-123 (2003).
Eow, et al. Electrostatic and hydrodynamic separation of aqueous drops in a flowing viscous oil, Chemical Eng Proc 41:649-657 (2002).
European Office Action dated Apr. 29, 2014 for EP 08165420.4.
European Search Report for EP 13165665.4 dated Nov. 22, 2013, 4 pages.
European Search Report for EP 13165667.0 dated Nov. 22, 2013, 4 pages.
European Search Report for EP Application No. 13165665 with the date of the completion of the search Nov. 15, 2013 (4 pages).
European Search Report for EP Application No. 13165667 with the date of the completion of the search Nov. 15, 2013 (4 pages).
Extended European Search Report for Application No. 11742907.6 dated Apr. 17, 2015 (18 pages).
Extended European Search Report for EP 10181911.8 dated Jun. 1, 2011 (7 pages).
Extended European Search Report for EP 10184514.7 dated Dec. 20, 2010 (5 pages).
Extended European Search Report for EP 10196179 dated May 2, 2014 (10 pages).
Extended European Search Report for EP 10196339 dated May 2, 2014 (9 pages).
Faca et al., A mouse to human search for plasma proteome changes associated with pancreatic tumor development, PLoS Med 5(6):e123 (2008).
Fahy et al., Self-sustained sequence replication (3SR): an isothermal transcription-based amplification system alternative to PCR, PCR Methods Appl 1:25-33 (1991).
Fan and Harrison, Micromachining of capillary electrophoresis injectors and separators on glass chips and evaluation of flow at capillary intersections, Anal Chem 66:177-184 (1994).
Fan et al., Detection of Aneuploidy with Digital PCR, available at https://arxiv.org/ftp/arxiv/papers /0705/0705.1 030.pdf, Dec. 31, 2007.
Fastrez, J., In vivo versus in vitro screening or selection for catalytic activity in enzymes and abzymes, Mol Biotechnol 7(1):37-55 (1997).
Fettinger et al., Stacked modules for micro flow systems in chemical analysis: concept and studies using an enlarged model, Sens Actuat B. 17:19-25 (1993).
Fiedler et al., Dielectrophoretic sorting of particles and cells in a microsystem, Anal Chem 70(9):1909-1915 (1998).
Field, J. et al., Purification of a RAS-responsive adenylyl cyclase complex from *Saccharomyces cervisiae* by use of an epitope addition method. Mol Cell Biol, 8: 2159-2165 (1988).
Fields, S. and Song, O., A novel genetic system to detect protein-protein interactions, Nature 340(6230):245-6 (1989).
Filella et al., TAG-72, CA 19.9 and CEA as tumor markers in gastric cancer, Acta Oncol. 33(7):747-751 (1994).
Finch, C.A., Encapsulation and controlled release, Spec Publ R Soc Chem, 138:35 (1993).
Finch, C.A., Industrial Microencapsulation: Polymers for Microcapsule Walls, 1-12 in Encapsulation and Controlled Release, Woodhead Publishing (1993).
Fire & Xu, Rolling replication of short DNA circles, PNAS 92(10):4641-5 (1995).
Firestine, S.M. et al., Using an AraC-based three hybrid system to detect biocatalysts in vivo, Nat Biotechnol 18: 544-547 (2000).

Fisch et al., A strategy of exon shuffling for making large peptide repertoires displayed on filamentous bacteriophage, PNAS 93:7761-6 (1996).
Fisher et al., Cell Encapsulation on a Microfluidic Platform, The Eighth International Conference on Miniaturised Systems for Chemistry and Life Scieces, MicroTAS Sep. 26-30, 2004, Malmo, Sweden.
Fletcher et al., Micro reactors: principles and applications in organic synthesis, Tetrahedron 58:4735-4757 (2002).
Fluri et al., Integrated capillary electrophoresis devices with an efficient postcolumn reactor in planar quartz and glass chips, Anal Chem 68:4285-4290 (1996).
Fornusek, L. et al., Polymeric microspheres as diagnostic tools for cell surface marker tracing, Crit Rev Ther Drug Carrier Syst, 2:137-74 (1986).
Fowler, Enhancement of Mixing by Droplet-Based Microfluidics, Int Conf MEMS 97-100 (2002).
Freese, E., The specific mutagenic effect of base analogues on Phage T4, J Mol Biol, 1: 87 (1959).
Frenz et al., Reliable microfluidic on-chip incubation of droplets in delay-lines, Lab on a Chip 9:1344-1348 (2008).
Fu et al., A microfabricated fluorescence-activated cell sorter, Nature Biotechnology, 17(11):1109-1111 (1999).
Fu et al., An Integrated Microfabricated Cell Sorter, Anal. Chem., 74: 2451-2457 (2002).
Fulton et al., Advanced multiplexed analysis with the FlowMetrix system, Clin Chem 43:1749-1756 (1997).
Fulwyler, Electronic Separation of Biological Cells by Volume, Science 150(3698):910-911 (1965).
Fungi (Wikipedia.com accessed Jun. 3, 2013).
Gallarate et al., On the stability of ascorbic acid in emulsified systems for topical and cosmetic use, Int J Pharm 188(2):233-241 (1999).
Ganan-Calvo, A.M., Perfectly Monodisperse Microbubbling by Capillary Flow Focusing, Phys Rev Lett 87(27): 274501-1-4 (2001).
Ganan-Calvo, Generation of Steady Liquid Microthreads and Micron-Sized Monodisperse Sprays and Gas Streams, Phys Rev Lett 80(2):285-288 (1998).
Garcia-Ruiz et al. A super-saturation wave of protein crystallization, J. Crystal Growth, 232:149-155(2001).
Garcia-Ruiz et al., Investigation on protein crystal growth by the gel acupuncture method, Acta, Cryst., 1994, D50, 99. pp. 484-490.
Garstecki, et al., Formation of monodisperse bubbles in a microfiuidic flow-focusing device, Appl Phys Lett 85(13):2649-2651 (2004).
Gasperlin et al., The structure elucidation of semisolid w/o emulsion systems containing silicone surfactant, Intl J Pharm, 107:51-6 (1994).
Gasperlin et al., Viscosity prediction of lipophillic semisolid emulsion systems by neural network modeling, Intl J Pharm, 196:37-50 (2000).
Georgiou et al., Display of heterologous proteins on the surface of microorganisms: from the screenign of combinatiorial libraires to live recombinant vaccines. Nat Biotechnol 15(1), 29-34 (1997).
Georgiou, G., Analysis of large libraries of protein mutants using flow cytometry, Adv Protein Chem, 55: 293-315 (2000).
Gerdts et al., A Synthetic Reaction NetWork: Chemical Amplification Using Nonequilibrium Autocatalytic Reactions Coupled in Time, J. Am. Chem. Soc 126:6327-6331 (2004).
Ghadessy et al., Directed Evolution of Polymerase Function by Compartmentalized Self-Replication, PNSAS 98(8): 4552-4557 (2001).
Gibbs et al., Detection of single DNA base differences by competitive oligonucleotide priming, Nucleic Acids Res. 17(7): 2437-48 (1989).
Gilliland, G., Analysis of cytokine mRNA and DNA: Detection and quantitation by competitive polymerase chain reaction, PNAS, 87(7):2725-9 (1990).
Giusti et al., Synthesis and characterization of 5' fluorescent dye labeled oligonucleotides, Genome Res 2:223-227 (1993).
Gold et al., Diversity of Oligonucleotide Functions Annu Rev Biochem, 64: 763-97 (1995).
Goodall, J. L. et al., Operation of Mixed-Culture Immobilized Cell Reactors for the Metabolism of Meta- and Para-Nitrobenzoate by

(56) References Cited

OTHER PUBLICATIONS

*Comamonas* Sp. JS46 and *Comamonas* Sp. JS47, Biotechnology and Bioengineering, 59 (1): 21-27 (1998).
Gordon and Balasubramanian, Solid phase synthesis—designer linkers for combinatorial chemistry: a review, J. Chem. Technol. Biotechnol., 74(9):835-851 (1999).
Grasland-Mongrain et al., Droplet coalescence in microfluidic devices, 30 pages (Jul. 2003) From internet: http://www.eleves.ens.fr/home/grasland/rapports/stage4.pdf.
Green, R. and Szostak, J.W., Selection of a Ribozyme That Functions as a Superior Template in a Self Copying Reaction, Science, 258: 1910-5 (1992).
Gregoriadis, G., Enzyme entrapment in liposomes, Methods Enzymol 44:218-227 (1976).
Griffiths et al., Directed evolution of an extremely fast phosphotriesterase by in vitro compartmentalization, EMBO J, 22:24-35 (2003).
Griffiths et al., Isolation of high affinity human antibodies directly from large synthetic repertoires, EMBO J 13(14):3245-60 (1994).
Griffiths et al., Man-made enzymes-from design to in vitro compartmentalisation, Curr Opin Biotechnol 11:338-353 (2000).
Griffiths, A., and Tawfik, D., Miniaturising the laboratory in emulsion droplets, Trend Biotech 24(9):395-402 (2006).
Griffiths, A.D. et al., Strategies for selection of antibodies by phage display, Curr Opin Biotechnol, 9:102-8 (1998).
Guatelli, J.C. et al., Isothermal, in vitro amplification of nucleic acids by a multienzyme reaction modeled after retroviral replication, PNAS, 87(5):1874-8 (1990).
Guixe et al., Ligand-Induced Conformational Transitions in *Escherichia coli* Phosphofructokinase 2: Evidence for an Allosteric Site for MgATP2n, Biochem., 37: 13269-12375 (1998).
Gupta, K.C., et al., A general method for the synthesis of 3'-sulfhydryl and phosphate group containing oligonucleotides, Nucl Acids Res 19 (11): 3019-3026 (1991).
Haber et al., Activity and spectroscopic properties of bovine liver catalase in sodium bis(2-ethylhexyl) sulfosuccinate/isooctane reverse micelles, Eur J Biochem 217(2): 567-73 (1993).
Habig and Jakoby, Assays for differentiation of glutathione S-transferases, Methods in Enzymology, 77: 398-405 (1981).
Hadd et al., Microchip Device for Performing Enzyme Assays, Anal. Chem 69(17): 3407-3412 (1997).
Haddad et al., A methodology for solving physiologically based pharmacokinetic models without the use of simulation software, Toxicol Lett. 85(2): 113-26 (1996).
Hagar and Spitzer, The effect of endotoxemia on concanavalin A induced alterations in cytoplasmic free calcium in rat spleen cells as determined with Fluo-3, Cell Calcium 13:123-130 (1992).
Hai et al., Investigation on the release of fluorescent markers from the w/o/w emulsions by fluorescence-activated cell sorter, J Control Release, 96(3): 393-402 (2004).
Haies et al., Morphometric study of rat lung cells. I. Numerical and dimensional characteristics of parenchymal cell population, Am. Rev. Respir. Dis. 123:533-54 (1981).
Hall, Experimental evolution of Ebg enzyme provides clues about the evolution of catalysis and to evolutionary potential, FEMS Microbiol Lett, 174(1):1-8 (1999).
Hall, The EBG system of *E. coli*: origin and evolution of a novel beta-galactosidase for the metabolism of lactose, Genetica 118(2-3):143-56 (2003).
Han et al., Quantum-dot-tagged Microbeads for Multiplexed Optical Coding of Biomolecules, Nat Biotech 19(7): 631-635(2001).
Handen, J.S., High-throughput screening—challenges for the future, Drug Discov World, 47-50 (2002).
Handique, K. et al., On-Chip Thermopneumatic Pressure for Discrete Drop Pumping, Analytical Chemistry, 73:1831-1838 (2001).
Hanes et al., Degradation of porous poly(anhydide-co-imide) microspheres and implication for controlled macromolecule delivery, Biomaterials, 19(1-3): 163-172(1998).
Hanes et al., In vitro selection and evolution of functional proteins by using ribosome display, PNAS 94:4937-42 (1997).
Hansen et al., A robust and scalable microlluidic metering method that allows protein crystal growth by free interface diffusion, PNAS 99(26):16531-16536 (2002).
Harada et al., Monoclonal antibody G6K12 specific for membrane-associated differentiation marker of human stratified squamous epithelia and squamous cell carcinoma, J. Oral Pathol. Med 22(4):145-152 (1993).
Harder, K.W. et al., Characterization and kinetic analysis of the intracellular domain of human protein tyrosine phosphatase beta (HPTP beta) using synthetic phosphopeptides, Biochem J 298 (Pt 2): 395-401 (1994).
Harries et al., A Numerical Model for Segmented Flow in a Microreactor, Int J of Heat and Mass Transfer, 46:3313-3322 (2006).
Harris et al., Single-molecule DNA sequencing of a viral genome, Science 320(5872):106-109 (2008).
Original and translated Notice of Reasons for Rejection dated Apr. 10, 2013 for Japanese Patent Application 2008-550290 (6 pages).
Oroskar et al., Detection of immobilized amplicons by ELISA-like techniques, Clin. Chem. 42:1547-1555 (1996).
Ostermeier, M. et al., A combinatorial approach to hybrid enzymes independent of DNA homology, Nat Biotechnol, 17(12):1205-9 (1999).
Ouelette, A new wave of microfluidic devices, Indust Physicist pp. 14-17 (2003).
Pabit et al., Laminar-Flow Fluid Mixer for Fast Fluorescence Kinetics Studies, Biophys J 83:2872-2878 (2002).
Paddison et al., Stable suppression of gene expression by RNAi in mammalian cells, PNAS 99(3):1443-1448 (2002).
Pannacci et al., Equilibrium and Nonequilibrium States in Microluidic Double Emulsions Physical Review Leters, 101(16):164502 (2008).
Park et al., Cylindrical compact thermal-cycling device for continuous-flow polymeras chain reaction, Anal Chem, ACS, 75:6029-33 (2003).
Park et al., Model of Formation of Monodispersed Colloids, J. Phys. Chem. B 105:11630-11635 (2001).
Parker et al., Development of high throughput screening assays using fluorescence polarization: nuclear receptor-ligand-binding and kinase/phosphatase assays, J Biomol Screen, 5(2): 77-88 (2000).
Parmley et al., Antibody-selectable filamentous fd phage vectors: affinity purification of target genes. Gene 73(2):305-18 (1988).
Pedersen et al., A method for directed evolution and functional cloning of enzymes, PNAS 95(18):10523-8 (1998).
Pekin et al., 2011, Quantitative and sensitive detection of rare mutations using droplet-based microfluidics, Lab on a Chip 11(13):2156.
Pelham and Jackson, An efficient mRNA-dependent translation system from reticulocyte lysates, Eur J Biochem 67:247-56 (1976).
Pelletier et al., An in vivo library-versus-library selection of optimized protein-protein interactions, Nature Biotechnology, 17:683-90 (1999).
Peng et al., Controlled Production of Emulsions Using a Crossflow Membrane, Particle & Particle Systems Characterization 15:21-25 (1998).
Perelson et al., Theorectical studies of clonal selection: minimal antibody repertoire size and relaibility of self-non-self discrimination. J Theor Biol 81(4):645-70 (1979).
Perez-Gilabert et al., Application of active-phase plot to the kinetic analysis of lipoxygenase in reverse micelles, Biochemistry J. 288:1011-1015 (1992).
Perrin, J., Polarisation de la lumiere de fluorescence vie moyenne des molecules dans letat excite, J. Phys. Rad. 1:390-401 (1926).
Petrounia, I.P. et al., Designed evolution of enzymatic properties, Curr Opin Biotechnol, 11:325-330 (2000).
Piemi et al., Transdermal delivery of glucose through hairless rat skin in vitro: effect of multiple and simple emulsions, Int J Pharm, 171:207-215 (1998).
Pirrung et al., A General Method for the Spatially Defined Immobilization of Biomolecules on Glass Surfaces Using Caged' Biotin, Bioconjug Chem 7: 317-321 (1996).
Plant (Wikipedia.com accessed Mar. 8, 2013).
Ploem, in Fluorescent and Luminescent Probes for Biological Activity Mason, T. G. Ed., Academic Press, Landon, pp. 1-11, 1993.

(56) References Cited

OTHER PUBLICATIONS

Pluckthun, A. et al., In vitro selection and evolution of proteins, Adv Protein Chem, 55: 367-403 (2000).
Pollack et al., Electrowetting-based actuation of droplets for integrated microfluidics, Lab Chip 2:96-101 (2002).
Pollack et al., Selective chemical catalysis by an antibody, Science 234(4783):1570-3 (1986).
Pons et al, Synthesis of Near-Infrared-Emitting, Water-Soluble CdTeSe/CdZnS Core/Shell Quantum Dots, Chemistry of Materials 21(8):1418-1424 (2009).
Posner et al., Engineering specificity for folate into dihydrofolate reductase from *Escherichia coli*, Biochemistry, 35: 1653-63 (1996).
Poulin and Theil, "A priori" prediction of tissue: plasma partition coefficients of drugs to facilitate the use of physiologically-based pharmokinetic models in drug discovery, J Pharm Sci 89(1):16-35 (2000).
Priest, et al. Generation of Monodisperse Gel Emulsions in a Microfluidic Device, Applied Physics Letters, 88:024106 (2006).
Qi et al., Acid Beta-Glucosidase: Intrinsic Fluorescence and Conformational Changes Induced by Phospholipids and Saposin C, Biochem., 37(33): 11544-11554 (1998).
Raghuraman et al., Emulston Liquid Membranes for Wastewater Treatment: Equillibrium Models for Some Typical Metal-Extractant Systems,Environ. Sci. Technol 28:1090-1098 (1994).
Ralhan, Discovery and Verification of Head-and-neck Cancer Biomarkers by Differential Protein Expression Analysis Using iTRAQ Labeling, Multidimensional Liquid Chromatography, and Tandem Mass Spectrometry, Mol Cell Proteomics 7(6):1162-1173 (2008).
Ramsey, J.M., The burgeoning power of the shrinking laboratory, Nat Biotechnol 17(11):1061-2 (1999).
Ramstrom and Lehn, Drug discovery by dynamic combinatorial libraries, Nat Rev Drug Discov 1:26-36 (2002).
Raushel, F.M. et al., Phosphotriesterase: an enzyme in search of its natural substrate, Adv Enzymol Relat Areas Mol Biol, 74: 51-93 (2000).
Rech et al., Introduction of a yeast artificial chromosome vector into Sarrachomyeces cervesia by electroporation, Nucleic Acids Res 18:1313 (1990).
Reyes et al., Micro Total Analysis Systems. 1. Introduction, Theory and Technology, Anal Chem 74(12):2623-2636 (2002).
Riess, J.S., Fluorous micro- and nanophases with a biomedical perspective, Tetrahedron 58(20):4113-4131 (2002).
Roach et al., Controlling nonspecific protein adsorption in a plug-based microfluidic system by controlling inteifacial chemistry using fluorous-phase surfactants, Anal. Chem. 77:785-796 (2005).
Roberts & Ja, In vitro selection of nucleic acids and proteins: What are we learning, Curr Opin Struct Biol 9(4): 521-9 (1999).
Roberts et al., Simian virus 40 DNA directs synthesis of authentic viral polypeptides in a linked transcription-translation cell-free system 72(5):1922-1926 (1975).
Roberts, et al., RNA-peptide fusion for the in vitro selection of peptides and proteins, PNAS 94:12297-302 (1997).
Roberts, J.W.,Termination factor for RNA synthesis, Nature, 224: 1168-74 (1969).
Roberts, R.W. Totally in vitro protein selection using mRNA-protein fusions and ribosome display. Curr Opin Chem Biol 3(3), 268-73 (1999).
Rodriguez-Antona et al., Quantitative RT-PCR measurement of human cytochrome P-450s: application to drug induction studies. Arch. Biochem. Biophys., 376:109-116 (2000).
Rolland et al., Fluorescence Polarization Assay by Flow Cytometry, J. Immunol. Meth., 76(1): 1-10 (1985).
Rosenberg et al.,Inhibition of Human Factor IX by Human Antithrombin, J Biol Chem, 250: 4755-64 (1975).
Rosenberg et al., Termination of transcription in bacteriophage lambda, J Biol Chem, 250: 4755-64 (1975).
Clausell-Tormos et al., Droplet-based microfluidic platforms for the encapsulation and screening of Mammalian cells and multicellular organisms, Chem Biol 15(5):427-437 (2008).

Cohen, S. et al., Controlled delivery systems for proteins based on poly(lactic/glycolic acid) microspheres, Pharm Res, 8(6):713-720 (1991).
Collins et al., Optimization of Shear Driven Droplet Generation in a Microluidic Device, ASME International Mechanical Engineering Congress and R&D Expo, Washington (2003).
Collins, J. et al., Microfluidic flow transducer based on the measurements of electrical admittance, Lab on a Chip, 4:7-10 (2004).
Compton, J., Nucleic acid sequence-based amplification, Nature, 350(6313):91-2 (1991).
Cormack, B.P. et al., FACS-optimized mutants of the green fluorescent protein (GFP), Gene 173(1):33-38 (1996).
Cortesi et al., Production of lipospheres as carriers for bioactive compounds, Biomateials, 23(11): 2283-2294 (2002).
Courrier et al., Reverse water-in-fluorocarbon emulsions and microemulsions obtained with a fluorinated surfactant, Colloids and Surfaces A: Physicochem. Eng. Aspects 244:141-148 (2004).
Craig, D. et al., Fluorescence-based enzymatic assay by capillary electrophoresis laser-induced fluoresence detection for the determinination of a few alpha-galactosidase molecules, Anal. Biochem. 226:147 (1995).
Creagh, A.L. et al., Structural and catalytic properties of enzymes in reverse micelles, Enzyme Microb Technol 15(5):383-92 (1993).
Crosland-Taylor, A Device for Counting Small Particles suspended in a Fluid through a Tube, Nature 171:37-38 (1953).
Crowley, J. M., Electrical breakdown of bimolecular lipid membranes as an electromechanical instability, Biophys J. 13(7):711-724 (1973).
Cull, M.G. et al., Screening for receptor ligands using large libraries of peptides linked to the C terminus of the lac repressor, PNAS 89:1865-9 (1992).
Curran, D.P., Strategy-level separations in organic synthesis: from planning to practice. Angew Chem Int Ed, 37:1174-11-96 (1998).
Czarnik, A.W., Encoding methods for combinatorial chemistry, Curr Opin Chem Biol 1:60-66 (1997).
Dankwardt et al., Combinatorial synthesis of small-molecule libraries using 3-amino-5-hydroxybenzoic acid, 1:113-120 (1995).
Davis, J.A. et al., Deterministic hydrodynamics: Taking blood apart, PNAS 103:14779-14784 (2006).
Davis, S.S. et al., Multiple emulsions as targetable delivery systems, Methods in Enzymology, 149:51-64 (1987).
De Gans, B.J. et al., Inkjet printing of polymers: state of the art and future developments, Advanced materials, 16: 203-213 (2004).
De Wildt, Ruud, et al., Isolation of receptor-ligand pairs by capture of long-lived multivalent interaction complexes, Proceedings of the National Academy of Sciences of the United States, 99, 8530-8535 (2002).
De-Bashan, L. E. et al., Removal of ammonium and phosphorus ions from synthetic wastewater by the microalgae Chlorella vulgaris coimmobilized in alginate beads with the microalgae growth-promoting bacterium Azospirillum brasilense, Water Research 36:2941-2948 (2002).
Delagrave, S. et al., Red-shifted excitation mutants of the green fluorescent protein, Biotechnology 13(2):151-4 (1995).
DelRaso, In vitro methodologies for enhanced toxicity testing, Toxicol. Lett. 68:91-99 (1993).
Demartis et al., A strategy for the isolation of catalytic activities from repertoires of enzymes displayed on phage, J. Mol. Biol 286:617-633 (1999).
Deng et al., Design and analysis of mismatch probes for long oligonucleotide microarrays, BMC Genomics. 2008; 9:491.
Dickinson, E., Emulsions and droplet size control, Wedlock, D.J., Ed., in Controlled Particle Droplet and Bubble Formulation, ButterWorth-Heine-mann, 191-257 (1994).
DiMatteo, et al., Genetic conversion of an SMN2 gene to SMN1: A novel approach to the treatment of spinal muscular atrophy, Exp Cell Res. 314(4):878-886 (2008).
Ding, Proc. Natl. Acad. Sci. USA, 2003, 100(33):7449-7453.
Dinsmore et al., Colioidosomes: Selectively Permeable Capsules Composed of Colloidal Particles, Science 298(5595):1006-1009. (2002).

(56) References Cited

OTHER PUBLICATIONS

Dittrich et al., A new embedded process for compartmentalized cell-free protein expression and on-line detection in microfluidic devices, Chembiochem 6(5):811-814 (2005).
Doi et al., In vitro selection of restriction endonucleases by in vitro compartmentilization, Nucleic Acids Res, 32(12): e95 (2004).
Doi, N. and Yanagawa, H. Stable: protein-DNA fusion system for screening of combinatorial protein libraries in vitro, FEBS Lett., 457: 227-230 (1999).
Doman, T.N. et al., Molecular docking and high-throughput screening for novel inhibitors of protein tyrosine phosphatase-1B, J Med Chem, 45: 2213-2221 (2002).
Domling A., Recent advances in isocyanide-based multicomponent chemistry, Curr Opin Chem Biol, 6(3):306-13 (2002).
Domling and Ugi, Multicomponent Reactions with Isocyanides, Angew Chem Int Ed 39(18):3168-3210 (2000).
Dove et al., In Brief, Nature Biotechnology 20:1213 (2002).
Dower et al., High efficiency transformation of E. coli by high voltage electroporation, Nucleic Acids Res 16:6127-6145 (1988).
Dressman et al., Transforming single DNA molecules into fluorescent magnetic particles for detection and enumeration of genetic variations, PNAS 100:8817-22 (2003).
Dreyfus et al., Ordered and disordered patterns in two phase flows in microchannels, Phys Rev Lett 90(14):144505-1-144505-4 (2003).
Drmanac, 1992, Sequencing by hybridization: towards an automated sequencing of one million M13 clones arrayed on membranes, Elctrophoresis 13:566-573.
Du, Wenbin, et al., SlipChip, Lab Chip, 2009, 9, 2286-2292.
Dubertret et al., In vivo imaging of quantum dots encapsulated in phospholipid micelles, Science, 298: 1759-1762 (2002).
Duffy et al., Rapid Protyping of Microfluidic Systems and Polydimethylsiloxane, Anal Chem 70:474-480 (1998).
Duggleby, R. G. Analysis of Enzyme Progress Curves by Nonlinear Regression, Pt D. Academic Press 249:61-90 (1995).
Dumas, D.P., Purification and properties of the phosphotriesterase from Psuedomonas diminuta, J Biol Chem 264: 19659-19665 (1989).
Eckert and Kunkel, DNA polymerase fidelity and the polymerase chain reaction, Genome Res 1:17-24 (1991).
Edd et al., Controlled encapsulation of single-cells into monodisperse picolitre drops, Lab Chip 8(8):1262-1264 (2008).
Edel, Joshua B. et al., Microfluidic Routes to the Controlled Production of Nanopaticles, Chemical Communications, 1136-1137 (2002).
Edris et al., Encapsulation of orange oil in a spray dried double emulsion, Nahrung/Food, 45(2):133-137 (2001).
Effenhauser et al., Glass chips for high-speed capillary electrophoresis separations with submicrometer plate heights, Anal Chem 65:2637-2642 (1993).
Stauber, et a., Rapid generation of monoclonal antibody-secreting hybridomas against African horse sickness virus by in vitro immunization and the fusion/cloning technique, J. Immunol. Meth 161(2):157-168 (1993).
Stemmer, W.P., DNA shuffling by random fragmentation and reassembly: in vitro recombination for molecular evolution. PNAS 91(22):10747-51(1994).
Stemmer, W.P., Rapid evolution of a protein in vitro by DNA shuffling, Nature 370(6488):389-91 (1994).
Stober et al., Controlled growth of monodisperse silica spheres in the micron size range, J Colloid and Interface Sci 26(1):62-69 (1968).
Stofko, H.R. et al., A single step purification for recombinant proteins. Characterization of microtube associated protein (MAP2) fragment which associates with the type II cAMP-dependent protein kinase, Febs Lett 302: 274-278 (1992).
Stone et al., Engineering flows in small devices: Microfluidics toward a lab-on-a-chip, Ann. Rev. Fluid Mech. 36:381-441 (2004).

Strizhkov et al., PCR amplification on a microarray of gel-immobilized oligonucleotides: Detection of bacterial toxin- and drug-resistant genes and their mutations, BioTechniques 29(4):844-857 (2000).
Stroock et al., Chaotic mixer for microchannels, Science 295(5555):647-651 (2002).
Studer et al., Fluorous Synthesis: A Fluorous-Phase Strategy for Improving Separation Efficiency in Organic Synthesis, Science 275: 823-826 (1997).
Sugiura et al., Effect of Channel Structure on MicroChannel Emuisification, Langmuir 18:5708-5712 (2002).
Sugiura et al., Interfacial tension driven monodispersed droplet formation from mtcrofabricated channel array Langmuir, 17: 5562-5566 (2001).
Sundberg et al., Spatially-Addressable Immobilisation of Macromolecules on Solid Supports, J. Am. Chem. Soc, 117:12050-12057 (1995).
Sung et al. Chip-based microfluidic devices coupled with electrospray ionization-mass spectrometry, Electrophoresis 26:1783-1791 (2005).
Supplementary European Search Report and European Search Opinion, dated Aug. 17, 2016, for EP 12745236.5 (5 pages).
Supplementary European Search Report and European Search Opinion, dated Feb. 15, 2017, for EP 14784827.9 (8 pages).
Supplementary European Search Report and European Search Opinion, dated Oct. 17, 2016, for EP 14778430.0 (8 pages).
Supplementary European Search Report and European Search Opinion, dated Sep. 20, 2018, for EP 18157363.5 (8 pages).
Suzuki et al., Random mutagenesis of thermus aquaticus DNA polmerase I: concordance of immutable sites in vivo with the crystal structure, PNAS USA, 93:96701-9675 (1996).
Tabatabai and Faghri, A New Two-Phase Flow Map and Transition Boundary Accounting for Surface Tension Effects in Horizontal Miniature and Micro Tubes, J Heat Transfer 123:958-968 (2001).
Tabatabai et al, Economic feasability study of polyelectrolyte-enhanced ultrafiltration (PEUF) for water softening, J Membrane Science 100(3):193-207 (1995).
Tabatabai et al., Reducing Surfactant Adsorption on Carbonate Reservoirs, SPE Resenroir Engineering 8(2):117-122 (1993).
Tabatabai, Water Softening Using polyelectrolyte-enhanced ultrafiltration, Separation Science Technology 30(2):211-224 (1995).
Takayama et al., Patterning Cells and Their Environments Using Multiple Laminar Fluid Flows in Capillary NetWO rks, PNAS 96:5545-5548 (1999).
Takeuchi et al., An Axisymmetric Flow-Focusing Microfluidic Device, Adv. Mater 17(8):1067-1072 (2005).
Taly et al., Droplets as Microreactors for High-Throughput Biology, Chembiochem 8(3):263-272 (2007).
Tan et al., Controlled Fission of Droplet Emulsions in Bifurcating Microfluidic Channels, Transducers Boston (2003).
Tan et al., Design of microluidic channel geometries for the control of droplet volume, chemical concentration, and sorting, Lab Chip, 4(4): 292-298 (2004).
Tan et al., Monodispersed microfluidic droplet generation by shear focusing microfluidic device, Sensors and Actuators 114:350-356 (2006).
Tan, Y.C., Microfluidic Liposome Generation from Monodisperse Droplet Emulsion-Towards the Realization of Artificial Cells, Summer Bioengineering Conference, Florida (2003).
Tan, Y.C., Monodisperse Droplet Emulsions in Co-Flow Microfluidic Channels, Micro TAS, Lake Tahoe (2003).
Tanaka et al., Ethanol Production from Starch by a Coimmobilized Mixed Culture System of Aspergillus awamori and Zymomonas mobilis, Biotechnol Bioeng XXVII:1761-1768 (1986).
Tang et al., A multi-color fast-switching microfluidic droplet dye laser, Lab Chip 9:2767-2771 (2009).
Taniguchi et al., Chemical Reactions in Microdroplets by Electrostatic Manipulation of Droplets in Liquid Media, Lab on a Chip 2:19-23 (2002).
Tawfik et al., catELISA: a facile general route to catalytic antibodies, PNAS 90(2):373-7 (1993).
Tawfik et al., Efficient and selective p-nitrophenyl-ester= hydrolyzing antibodies elicited by a p-nitrobenzyl phosphonate hapten, Eur J Biochem, 244:619-26 (1997).

(56) References Cited

OTHER PUBLICATIONS

Tawfik et al., Man-made cell-like compartments for molecular evolution, Nature Biotechnology, 7(16):652-56 (1998).
Tawfik, D.S. et al., 1,8-diabycyclo[5.4.0]undecane mediated transesterification of p-nitrophenyl phosphonates—a novel route to phosphono esters, Synthesis—Stuttgart, 10: 968-972 (1993).
Taylor et al., Characterization of chemisorbed monolayers by surface potential measurments, J. Phys. D. Appl. Phys. 24:1443 (1991).
Taylor, The formation of emulsions in definable field of flow, Proc R Soc London A 146(858):501-523 (1934).
Tchagang et al., Early detection of ovarian cancer using group biomarkers, Mol Cancer Ther 7:27-37 (2008).
Tencza et al., Development of a Fluorescence Polarization-Based Diagnostic Assay for Equine Infectious Anemia Virus, J Clinical Microbiol 38(5):1854-185 (2000).
Terray et al., Microfluidic Control Using Colloidal Devices,Science, 296(5574):1841-1844 (2002).
Terray, et al, Fabrication of linear colloidal structures for microfluidic applications, Applied Phys Lett 81(9):1555-1557 (2002).
Tewhey et al., Microdroplet-based PCR amplification for large scale targeted sequencing, Nat Biotechnol 27(11):1025-1031 (2009).
Theberge et al., Microdroplets in Microfluidics: An Evolving Platform for Discoveries in Chemistry and Biology, Angew. Chem. Int. Ed 49(34):5846-5868 (2010).
Thompson, L.F., Introduction to Lithography, ACS Symposium Series 219:1-13, (1983).
Thorsen et al., Dynamic pattern formation in a vesicle-generating microfluidic device, Phys Rev Lett 86(18):4163-4166 (2001).
Thorsen et al., Microfluidic Large-Scale Integration, Science 298:580-584 (2002).
Tice et al., Effects of viscosity on droplet formation and mixing in microfluidic channels, Analytica Chimica Acta 507:73-77 (2004).
Tice et al., Formation of droplets and mixing in multiphase microfluidics at low values of the reynolds and the capillary numbers, Langmuir 19:9127-9133 (2003).
Klug and Schwabe, Protein motifs 5. Zinc fingers, FASEB J 9(8):597-604 (1995).
Klug, A., Gene Regulatory Proteins and Their Interaction with DNA, Ann NY Acad Sci, 758: 143-60 (1995).
Knaak et al., Development of partition coefficients, Vmax and Km values, and allometric relationships, Toxicol Lett. 79(1-3):87-98 (1995).
Knight, James B., Hydrodynamic Focusing on a Silicon Chip: Mixing Nanoliters in Microseconds, Physical Review Lett 30(17):3863-3866 (1998).
Kojima et al. PCR amplification from single DNA molecules on magnetic beads in emulsion: application for high-throughput screening of transcription factor targets. Nucleic Acids Res. 33:e150 (2005).
Kolb et al., Cotranslational folding of proteins, Biochem Cell Biol, 73:1217-20 (1995).
Komatsu et al., Roles of cytochromes P450 1A2, 2A6, and 2C8 in 5-fluorouracil formation rom tegafur, an anticancer prodrug, in human liver microsomes. Drug Met. Disp., 28:1457-1463 (2001).
Kopp et al., Chemical amplification: continuous flow PCR on a chip, Science, 280:1046-48 (1998).
Koster et al., Drop-based microfluidic devices for encapsulation of single cells, Lab on a Chip 8:1110-1115 (2008).
Kowalczykowski et al., Biochemistry of homologous recombination in *Escherichia coli*, Microbiol Rev 58(3):401-65 (1994).
Krafft et al., Emulsions and microemulsions with a fluorocarbon phase, Colloid and Interface Science 8(3):251-258 (2003).
Krafft et al., Synthesis and preliminary data on the biocompatibility and emulsifying properties of perfluoroalkylated phosphoramidates as injectable surfactants, Eur. J. Med. Chem., 26:545-550 (1991).
Krafft, Fluorocarbons and fluorinated amphiphiles in drug delivery and biomedical research, Adv Rev Drug Disc 47:209-228 (2001).
Kralj et al., Surfactant-enhanced liquid-liquid extraction in microfluidic channels with inline electric-field enhanced coalescence, Lab Chip 5:531-535 (2005).

Krebber C, et al., Selectivity-infective phage (SIP): a mechanistic dissection of a novel in vivo selection for protein-ligand interactions, Journal of Molecular Biology, 268, 607-618 (1997).
Kricka and Wilding, Microchip PCR, Anal Bioanal Chem 377(5):820-825 (2003).
Kricka and Wilding, Micromachining: a new direction for clinical analyzers, Pure and Applied Chemistry 68(10):1831-1836 (1996).
Kritikou, Ekat, "It's cheaper in the Picolab," Nature, Sep., vol. 6, p. 668. (Year: 2005).
Krumdiek, C.L. et al., Solid-phase synthesis of pteroylpolyglutamates, Methods Enzymol, 524-29 (1980).
Kumar, A. et al., Activity and kinetic characteristics of glutathione reductase in vitro in reverse micellar waterpool, Biochem Biophys Acta, 996(1-2):1-6 (1989).
Lage et al., Whole genome analysis of genetic alterations in small DNA samples using hyperbranched strand displacement amplification and array-CGH. Genome Res. 13: 294-307 (2003).
Lamprecht et al., pH-sensitive microsphere delivery increases oral bioavailability of calcitonin, Journal of Controlled Release, 98(1): 1-9(2004).
Lancet, D. et al., Probability model for molecular recognition in biuological receptor repertoirs: significance to the olfactory system, PNAS, 90(8):3715-9 (1993).
Landergren et al., A ligase mediated gene detection technique. Science 241(4869):1077-80 (1988).
Langmuir, Directing Droplets Using Microstructured Surfaces, vol. 22 No. 14, Jun. 9, 2006 pp. 6161-6167.
Lasheras, et al., Breakup and Atomization of a Round Water Jet by a High Speed Annular Air Jet, J Fluid Mechanics 357:351-379 (1998).
Leary et al., Application of Advanced Cytometric and Molecular Technologies to Minimal Residual Disease Monitoring, Proceedings of SPIE 3913:36-44 (2000).
Lee et al, Investigating the target recognition of DNA cytosine-5 methyltransferase HhaI by library selection using in vitro compartmentalisation (IVC), Nucleic Acids Res 30:4937-4944 (2002).
Lee et al., Circulating flows inside a drop under time-periodic non-uniform electric fields, Phys Fuilds 12(8):1899-1910 (2000).
Lee, et al, Effective Formation of Silicone-in-Fluorocarbon-in-Water Double Emulsions: Studies on Droplet Morphology and Stability, Journal of Dispersion Sci Tech 23(4):491-497(2002).
Lee et al, Preparation of Silica Particles Encapsulating Retinol Using O/W/O Multiple Emulsions, Journal of Colloid and Interface Science, 240(1): 83-89 (2001).
Lemof, et al, An AC Magnetohydrodynamic Microfluidic Switch for Micro Total Analysis Systems, Biomedical Microdevices, 5(I):55-60 (2003).
Lesley et al., Use of in vitro protein synthesis from PCR-generated templates to study interaction of *E. coli* transcription factors with core RNA polymerase, J Biol Chem 266(4):2632-8 (1991).
Lesley, S.A., Preparation and use of *E. coli* S-30 extracts, Methods Mol Biol, 37:265-78 (1995).
Leung et al., A method for random mutagenesis of a defined DNA segment using a modified polymerase chain reaction. Technique 1:11-15 (1989).
Li and Harrison, Transport, Manipulation, and Reaction of Biological Cells On-Chip Using Electrokinetic Effects, Analytical Chemistry 69(8):1564-1568 (1997).
Li et al., Nanoliter microfluidic hybrid method for simultaneous screening and optimization validated with crystallization of membrane proteins, PNAS 103: 19243-19248 (2006).
Li et al., Single-step procedure for labeling DNA strand breaks with fllourescein-or BODIPY-conjugated deoxynucleotides: detection of apoptosis and bromodeoxyuridine incorporation. Cytometry 20:172-180 (1995).
Liao et al., Isolation of a thermostable enzyme variant by cloning and selection in a thermophile, PNAS 83:576-80 (1986).
Lim et al., Microencapsulated islets as bioartificial endocrine pancreas, Science 210(4472):908-10 (1980).
Lin et al., Self-Assembled Combinatorial Encoding Nanoarrays for Multiplexed Biosensing, Nanoletter, 2007, vol. No. 2 pp. 507-512.
Link et al, Geometrically Mediated Breakup of Drops in Microfluidic Devices, Phys. Rev. Lett., 92(5): 054503-1 thru 054503-4 (2004).

(56) References Cited

OTHER PUBLICATIONS

Link et al., Electric control droplets in microfluidic devices, Angew Chem Int Ed 45:2556-2560 (2006).
Lipinski et al., Experimental and Computational Approaches to Estimate Solubility and Permeability in Drug Discovery and Development Settings, Adv. Drug Deliv. Rev., 46:3-26 (2001).
Lipkin et al., Biomarkers of increased susceptibility to gastreointestinal cancer: new application to studies of cancer prevention in human subjects, Cancer Research 48:235-245 (1988).
Liu et al., Fabrication and characterization of hydrogel-based microvalves, Mecoelectromech. Syst.11:45-53 (2002).
Liu et al., Passive Mixing in a Three-Dimensional Serpentine MicroChannel, J MEMS 9(2):190-197 (2000).
Lizardi et al., Mutation detection and single-molecule counting using isothermal rolling-circle amplification. Nat Genet 19(3):225-32 (1998).
Loakes and Brown, 5-Nitroindole as a universal base analogue. Nucleic Acids Res 22: 4039-4043 (1994).
Loakes et al., Stability and structure of DNA oligonucleotides containing non-specific base analogues. J. Mol. Biol 270:426-435 (1997).
Rosenberry, T.L., Acetylcholinesterase, Adv Enzymol Relat Areas Mol Biol, 43: 103-218 (1975).
Rotman, Measurement of activities of single molecules of beta-galactosidase, PNAS, 47:1981-91 (1961).
Russon et al., Single-nucleotide polymorphism analysis by allele-specific extension of fluorescently labeled nucleotides in a microfluidic flow-through device, Electrophoresis, 24:158-61 (2003).
Sadtler et al., Achieving stable, reverse water-in-fluorocarbon emulsions. Angew Chem Int Ed 35:1976-1978 (1996).
Saiki, R.K, et al, Primer directed enzymatic amplification of DNA with a thermostable DNA polymerase. Science 239(4839):487-91 (1988).
Sakamoto, Rapid and simple quantification of bacterial cells by using a microfluidic device, Appl Env Microb. 71:2 (2005).
Sano, T. et al., Immuno-PCR-Very sensitive antigen-detection by means of sepcific antibody-DNA conjugates. Science 258(5079), 120-122 (1992).
SantaLucia, A unified view of polymer, dumbbell, and oligonucleotide DNA nearest-neighbor thermodynamics, PNAS 5(4):1460-5 (1998).
Santa et al., Fluorescence lifetime measurements to determine the core-shell nanostructure of FITC-doped silica nanoparticles: An optical approach to evaluate nanoparticle photostability, J Luminescence 117(1):75-82 (2006).
Schatz et al., Screening of peptide libraries linked to lac repressor, Methods Enzymol 267: 171-91 (1996).
Schneegass et al., Miniaturized flow-through PCR with different template types in a silicone chip thermocycler, Lab on a Chip, Royal Soc of Chem, 1:42-9 (2001).
Schubert et al., Designer Capsules, Nat Med 8:1362 (2002).
Schweitzer et al., Immunoassays with rolling circle DNA amplification: A versatile platform for ultrasensitive antigen detection, PNAS 97(18), 10113-10119 (2000).
Schweitzer, B. et al., Combining nucleic acid amplification and detection. Curr Opin Biotechnol 12(1):21-7 (2001).
Scott, R.L., The Solubility of Fluorocarbons, J. Am. Chem. Soc, 70: 4090-4093 (1948).
Seethala and Menzel, Homogeneous, Fluorescence Polarization Assay for Src-Family Tyrosine Kinases, Anal Biochem 253(2):210-218 (1997).
Seiler et al., Planar glass chips for capillary electrophoresis: repetitive sample injection, quantitation, and separation efficiency, Anal Chem 65(10):1481-1488 (1993).
Selwyn M. J., A simple test for inactivation of an enzyme during assay, Biochim Biophys Acta 105:193-195 (1965).
Seo et al., Microfluidic consecutive flow-focusing droplet generators, Soft Matter, 3:986-992 (2007).

Seong and Crooks, Efficient Mixing and Reactions Within Microfluidic Channels Using Microbead-Supported Catalysts, J Am Chem Soc 124(45):13360-1 (2002).
Seong et al., Fabrication of Microchambers Defined by Photopolymerized Hydrogels and Weirs Within Microfluidic Systems: Application to DNA Hybridization, Analytical Chem 74(14):3372-3377 (2002).
Sepp et al., Microbead display by in vitro compartmentalisation: selection for binding using flow cytometry, FEBS Letters 532:455-58 (2002).
Serpersu et al., Reversible and irreversible modification of erythrocyte membrane permeability by electric field, Biochim Biophys Acta 812(3):779-785 (1985).
Shapiro, H.M., Multistation multiparameter flow cytometry: a critical review and rationale, Cytometry 3: 227-243 (1983).
Shestopalov et al., Multi-Step Synthesis of Nanoparticles Performed on Millisecond Time Scale in a Microfluidic Droplet-Based System, The Royal Society of Chemistry 4:316-321(2004).
Shim, Jung-uk, et al., Using Microfluidics to Decoupled Nucleation and Growth of Protein Crystals, Cryst. Growth, Des. 2007; 7(11): 2192-2194.
Shtern V, and Hussain F., Hysteresis in swirling jets, J. Fluid Mech. 309:1-44 (1996).
Sia & Whitesides, Microfluidic devices fabricated in poly(dimethylsiloxane) for biological studies, Electrophoresis 24(21):3563-3576 (2003).
Sidhu, S.S., Phage display in pharmaceutical biotechnology, Curr Opin Biotech 11:610-616 (2000).
Siemering et al., Mutations that suppress the thermosensitivity of green fluorescent protein, Current Biology 6:1653-1663 (1996).
Silva-Cunha et al., W/O/W multiple emulsions of insulin containing a protease inhibitor and an absorption enhancer: biological activity after oral administration to normal and diabetic rats, Int J Pharm 169:33-44 (1998).
Sims et al., Immunopolymerase chain reaction using real-time polymerase chain reaction for detection, Anal. Biochem. 281(2):230-2 (2000).
Sista, R. (Doctoral Thesis (Mar. 2007) "Development of a Digital Microfluidic Lab-on-a-Chip for Automated Immunoassay with Magnetically Responsive Beads" Retrieved from the Florida State University Graduate School Digital Library).
Slappendel et al., Normal cations and abnormal membrane lipids in the red blood cells of dogs with familial stomatocytosis hypertrophic gastritis, Blood 84:904-909 (1994).
Slob et al., Structural identifiability of PBPK models: practical consequences for modeling strategies and study designs, Crit Rev Toxicol. 27(3):261-72 (1997).
Smith et al., Direct mechanical measurements of the elasticity of single DNA molecules by using magnetic beads, Science 258(5085):1122-1126 (1992).
Smith et al., Fluorescence detection in automated DNA sequence analysis, Nature 321:674-679 (1986).
Smith et al., Phage display, Chemical Reviews 97(2), 391-410 (1997).
Smith et al., The synthesis of oligonucleotides containing an aliphatic amino group at the 5' terminus: synthesis of fluorescent DNA primers for use in DNA sequence analysis, Nucl. Acid Res. 13:2399-2412 (1985).
Smith G.P., Filamentous fusion phage: novel expression vectors that display cloned antigens on the virion surface, Science 228(4705): 1315-7(1985).
Smyth et al., Markers of apoptosis: methods for elucidating the mechanism of apoptotic cell death from the nervous system, Biotechniques 32:648-665 (2000).
Sohn, et al, Capacitance cytometry: Measuring biological cells one by one, PNAS 97(20):10687-10690 (2000).
Somasundaram and Ramalingam, Gain studies of Rhodamine 6G dye doped polymer laser, J Photochem Photobiol 125(1-3):93-98 (1999).
Song et al., A microfluidic system for controlling reaction networks in time, Angew. Chem. Int. Ed. 42(7):768-772 (2003).
Song et al., Experimental Test of Scaling of Mixing by Chaotic Advection in Droplets Moving Through Microfluidic Channels, App Phy Lett 83(22):4664-4666 (2003).

(56) References Cited

OTHER PUBLICATIONS

Song, H. and Ismagilov, R.F., Millisecond kinetics on a microluidic chip using nanoliters of reagents, J Am Chem Soc. 125: 14613-14619 (2003).
Soni and Meller, Progress toward ultrafast DNA sequencing using solid-state nanopores, Clin Chem 53:1996-2001 (2007).
Soumillion et al., Novel concepts for the selection of catalytic activity. Curr Opin Biotechnol 12:387-394 (2001).
Soumillion et al., Selection of B-lactomase on filamentous bacteriophage by catalytic activity, J Mol Biol, 237:415-22 (1994).
Sproat et al., The synthesis of protected 5'-mercapto-2',5'-dideoxyribonucleoside-3'-0-phosphorainidites, uses of 5'-mercapto-oligodeoxyribonucleotides, Nucleic Acids Res 15:4837-4848 (1987).
Minshuil, J. and Stemmer, W.P., Protein evolution by molecular breeding, Curr Opin Chem Biol 3(3): 284-90 (1999).
Miroux and Walker, Over-production of proteins in *Escherichia coli*: mutant hosts that allow synthesis of some membrane proteins and globular proteins at high levels, J of Mol Biol 260(3):289-98 (1996).
Miyawaki et at., Fluorescent Indicators for Ca2+ Based on Green Fluorescent Proteins and Calmodulin, Nature, 388: 882-887 (1997).
Mize et al., Dual-enzyme cascade—an amplified method for the detection of alkaline phosphatase, Anal Biochem 179(2): 229-35 (1989).
Mock et al., A fluorometric assay for the biotin-avidin interaction based on displacement of the fluorescent probe 2-anilinonaphthalene-6-sulfonic acid, Anal Biochem, 151:178-81 (1985).
Moldavan, A., Photo-electric technique for the counting of microscopical cells, Science 80:188-189 (1934).
Montigiani, S. et al., Alanine substitutions in calmodulin-binding peptides result in unexpected affinity enhancement, J Mol Biol, 258:6-13 (1996).
Moore, M.J., Exploration by lamp light, Nature, 374:766-7 (1995).
Moudrianakis and Beer, Base sequence determination in nucelic acids with the electron microscope 3. Chemistry and microscopy of guanine-labeled DNA, PNAS 53:564-71 (1965).
Mueth et al., Origin of stratification in creaming emulsions, Physical Review Letters 77(3):578-581 (1996).
Mulbry, W.W. et al., Parathion hydrolase specified by the Flavobacterium opd gene: relationshio between the gene and protein. J Bacteriol, 171: 6740-6746 (1989).
Mulder et al., Characterization of two human monoclonal antibodies reactive with HLA-B12 and HLA-B60, respectively, raised by in vitro secondary immunization of peripheral blood lymphocytes, Hum. Immunol 36(3):186-192 (1993).
Murinae (Wikipedia.com accessed Mar. 18, 2013).
Nakano et al., High speed polymerase chain reaction in constant flow, Biosci Biotech and Biochem, 58:349-52 (1994).
Nakano et al., Single-molecule PCR using water-in-oil emulsion, J Biotech, 102:117-24 (2003).
Nakano et al., Single-molecule reverse transcription polymerase chain reaction using water-in-oil emulsion, J Biosci Bioeng 99:293-295 (2005).
Nametkin, S.N. et al., Cell-free translation in reversed micelles, FEB Letters, 309(3):330-32 (1992).
Narang et al, Improved phosphotriester method for the synthesis of gene fragments, Methods Enzymol, 68:90-98 (1979).
Nelson, P. S., et al., Bifunctional oligonucleotide probes synthesized using a novel CPG support are able to detect single base pair mutations, Nucl Acids Res 17(18): 7187-7194 (1989).
Nemoto et al., In vitro virus: bonding of mRNA bearing puromycin at the 3 terminal end to the C-terminal end of its encoded protein on the ribosome in vitro, Federation of European Biochemical Societies, 414:405-8 (1997).
Ness, J.E. et al., Molecular Breeding: the natural approach to protein design. Adv Protein Chem, 55: 261-292 (2000).
Ng et al., Protein crystallization by capillary counter-diffusion for applied crystallographic structure determination, J. Struct. Biol, 142:218-231(2003).

Ng, B.L. et al., Factors affecting flow karyotype resolution, Cytometry, Part A 69A: 1028-1036 (2006).
Nguyen et al., Optical detection for droplet size control in microfluidic droplet-based analysis systems, Sensors and Actuators B 117(2):431-436 (2006).
Nihant et al., Polylactide Microparticles Prepared by Double Emulsion/Evaporation Technique. I. Effect of Primary Emulsion Stability, Pharmaceutical Research, 11(10):1479-1484 (1994).
Nisisako et al., Controlled formulation of monodisperse double emulsions in a multiple-phase microluidic system, Sot Matter, 1:23-27 (2005).
Nisisako et al., Formation of droplets using branch channels in a microfluidic circuit, Proceedings of the SICE Annual conference. International Session Papers 1262-1264 (2002).
Nisisako et al., Microstructured Devices for Preparing Controlled Multiple Emulsions. Chem. Eng. Technol 31(8):1091-1098 (2008).
Nisisako, Takasi et al., Droplet Formation in a MicroChannel NetWork, Lab on a Chip, vol. 2, 2002, pp. 24-26.
Nissim, A. et al., Antibody fragments from a single pot phage display library as immunochemical reagents, Embo J, 13:692-8 (1994).
Nof and Shea, Drug-releasing scaffolds fabricated from drug-loaded microspheres, J. Biomed Mater Res 59:349-356 (2002).
Norman, A., Flow Cytometry, Med. Phys., 7(6):609-615 (1980).
Notice of Refusal for Application No. 04782399.2 dated Apr. 10, 2013 (10 pages).
Oberholzer et al., Enzymatic RNA replication in self-reproducing vesicles: an approach to a minimal cell, Biochem Biophys Res Commun 207(1):250-7 (1995).
Oberholzer et al., Polymerase chain reaction in liposomes, Chem. Biol. 2(10):677-82 (1995).
Obukowicz, M.G. et al., Secretion and export of IGF-1 in *Escerichia coli* strain JM101, Mol Gen Genet, 215:19-25 (1988).
Office Action for U.S. Appl. No. 11/360,845 dated Nov. 19, 2013, 16 pages.
Office Action for U.S. Appl. No. 13/679,190 dated Dec. 2, 2013, 13 pages.
Office Action for U.S. Appl. No. 11/246,911 dated Feb. 8, 2011.
Office Action for U.S. Appl. No. 11/360,845 dated Apr. 26, 2011.
Office Action for U.S. Appl. No. 11/360,845 dated Aug. 4, 2010.
Office Action for U.S. Appl. No. 11/698,298, dated Jun. 29, 2011.
Office Action dated Jun. 5, 2014 for U.S. Appl. No. 13/679,190.
Ogura, Y., Catalase activity at high concentrations of hydrogen peroxide, Archs Biochem Biophys, 57: 288-300 (1955).
Oh et al., Distribution of Macropores in Silica Particles Prepared by Using Multiple Emulsions, Journal of Colloid and Interface Science, 254(1): 79-86 (2002).
Oh et al., World-to-chip microfluidic interface with built-in valves for multichamber chip-based PCR assays, Lab Chip, 2005, 5, 845-850.
Okushima et al. Controlled production of monodisperse double emulsions by two-step droplet breakup in microfluidic devices, Langmuir 20(23): 9905-8 (2004).
Olsen et al., Function-based isolation of novel enzymes from a large library, Nat Bioteoltnol 13(10):1071-4 (2000).
Omburo, G.A. et al., Characterization of the zinc binding site of bacterial phosphotriesterase, J of Biological Chem, 267:13278-83 (1992).
Original and translated Notice of Final Rejection dated Nov. 19, 2013 for Japanese Patent Application 2008-550290 (5 pages).
Wittwer, Carl T., et al., Minimizing the Time Required for DNA Amplification by Efficient Heat Transfer to Small Samples, Anal. Biochem., 186, 328-331 (1990).
Wolff et al., Integrating advanced functionality in a microfabricated high-throughput fluorescent-activated cell sorter, Lab Chip, 3(1): 22-27 (2003).
Woolley, Adam T. and Mathies, Richard A., Ultra-high-speed DNA fragment separations using microfabricated capillary array electrophoresis chips, Proc. Natl. Acad. Sci. USA, 91, 11348-11352 (Nov. 1994).
Woolley, Adam T., et al., Functional Integration of PCR Amplification and Capillary Electrophoresis in a Microfabricated DNA Analysis Device, Anal. Chem. 68, 4081-4086 (Dec. 1, 1996).

(56) References Cited

OTHER PUBLICATIONS

Written Opinion for PCT/US2004/027912 dated Jan. 26, 2005, 6 pages.
Writtion Opinionfor PCT/US2006/001938 dated May 31, 2006, 8 pages.
Wronski et al., Two-color, fluorescence-based microplate assay for apoptosis detection. Biotechniques, 32:666-668 (2002).
Wu et al., The ligation amplification reaction (LAR)-amplification of specific DNA sequences using sequential rounds of template-dependent ligation, Genomics 4(4):560-9 (1989).
Wyatt et al., Synthesis and purification of large amounts of RNA oligonucleotides, Biotechniques 11(6):764-9 (1991).
Xia and Whitesides, Soft Lithography, Angew. Chem. Int. Ed. 37:550-575 (1998).
Xia and Whitesides, Soft Lithography, Ann. Rev. Mat. Sci. 28:153-184 (1998).
Xu et al., Design of 240, 000 orthogonal 25mer DNA barcode probes, PNAS, Feb. 17, 2009, 106(7) p. 2289-2294.
Xu, S. et al., Generation of monodisperse particles by using microfluidics: control over size, shape, and composition, Angew. Chem. Int. Ed. 44:724-728 (2005).
Yamagishi, J. et al., Mutational analysis of structure-activity relationships in human tumor necrosis factor-alpha, Protein Eng, 3:713-9 (1990).
Yamaguchi et al., Insulin-loaded biodegradable PLGA microcapsules: initial burst release controlled by hydrophilic additives, Journal of Controlled Release, 81(3): 235-249 (2002).
Yelamos, J. et al., Targeting of non-Ig sequences in place of the V segment by somatic hypermutation. Nature 376(6537):225-9 (1995).
Yershov et al., DNA analysis and diagnostics on oligonucleotide microchips, PNAS 93(10):4913-4918 (1996).
Yonezawa et al., DNA display for in vitro selection of diverse peptide libraries, Nucleic Acids Research, 31(19): e118 (2203).
Yu et al. Responsive biomimetic hydrogel valve for microfluidics. Appl. Phys. Lett 78:2589-2591 (2001).
Yu et al., Quantum dot and silica nanoparticle doped polymer optical fibers, Optics Express 15(16):9989-9994 (2007).
Yu et al., Specific inhibition of PCR by non-extendable oligonucleotides using a 5' to 3' exonuclease-deficient DNA polymerase, Biotechniques 23(4):714-6, 718-20 (1997).
Zaccolo, M. et al., An approach to random mutagenesis of DNA using mixtures of triphosphate derivatives of nucleoside analogues. J Mol Biol 255(4):589-603 (1996).
Zakrzewski, S.F., Preparation of tritiated dihydrofolic acid of high specific activity, Methods Enzymol, 539 (1980).
Zaug and Cech, The intervening sequence RNA of Tetrahymena is an enzyme, Science 231(4737):470-5 (1986).
Zaug and Cech, The Tetrahymena intervening sequence ribonucleic acid enzyme is a phosphotransferase and an acid phosphatase, Biochemistry 25(16):4478-82 (1986).
Zaug et al., The Tetrahymena ribozyme acts like an RNA restriction endonuclease, Nature 324(6096):429-33 (1986).
Zhang et al., A Simple Statistical Parameter for Use in Evaluation and Validation of High Throughput Screening Assays, Journal of Biomolecular Screening, 4(2): 67-73 (1999).
Zhang, Z.Y., Substrate specificity of the protein tyrosine phosphatases, PNAS 90: 4446-4450 (1993).
Zhao, B. et al., Control and Applications of Immiscible Liquids in Microchannels, J. Am. Chem. Soc, vol. 124:5284-5285 (2002).
Zhao, H. et al., Molecular evolution by staggered extension process (StEP) in vitro recombination. Nat Biotechnol 16(3):258-61 (1998).
Zheng et al., A Droplet-Based, Composite PDMS/Glass Capillary Microfluidic System for Evaluating Protein Crystallization Conditions by Microbatch and Vapor-Diffusion Methods with On-Chip X-Ray Diffraction, Angew. Chem., 116:1-4, (2004).
Zheng et al., A Microiuidic Approach for Screening Submicroliter Volumes against Multiple Reagents by Using Performed Arrays of Nanoliter Plugs in a Three-Phase Liquid/Liquid/Gas Flow, Angew. Chem. Int. Ed., 44(17): 2520-2523 (2005).
Zheng et al., Formation of Droplets of Alternating Composition in Microfluidic Channels and Applications to Indexing of Concentrations in Droplet-Based /Assays, Anal. Chem.,76: 4977-4982 (2004).
Zheng et al., Screening of Protein Crystallization Conditions on a Microfluidic Chip Using Nanoliter-Size Droplets, J Am Chem Soc 125(37):11170-11171 (2003).
Zhong et al., 2011, Multiplex digital PCR: breaking the one target per color barrier of quantitative PCR, Lab on a Chip 11(13):2167.
Zimmermann et al., Dielectric Breakdown of Cell Membranes, Biophys J 14(11):881-889 (1974).
Zimmermann et al., Microscale Production of Hybridomas by Hypo-Osmolar Electrofusion, Hum. Antibod. Hybridomas, 3(1): 14-18 (1992).
Zimmermann, Bernhard G., et al., Digital PCR: a powerful new tool for noninvasive prenatal diagnosis?, Prenat Diagn 28, 1087-1093 (2008).
Zubay, G., In vitro synthesis of protein in microbial systems, Annu Rev Genet, 7: 267-87 (1973).
Zubay, G., The isolation and properties of CAP, the catabolite gene activator, Methods Enzymol, 65: 856-77 (1980).
Zuckermann, R. et al., Efficient Methods for Attachment of Thiol-Specific Probes to the 3-end of Synthetic Oligodeoxyribonucleotides, Nucleic Acids Res. 15:5305-5321 (1987).
Loeker et al., Colloids and Surfaces A: Physicochem. Eng. Aspects 214:143-150, (2003).
Loeker et al., FTIR analysis of water in supercritical carbon dioxide microemulsions using monofunctional perfluoropolyether surfactants, Colloids and Surfaces A: Physicochem. Eng. Aspects 214:143-150, (2003).
Lopez-Herrera, et al, Coaxial jets generated from electrified Taylor cones. Scaling laws, Aerosol Science, 34:535-552 (2003).
Lopez-Herrera, et al, One-Dimensional Simulation of the Breakup of Capillary Jets of Conducting Liquids Application to E.H.D. Spraying, Aerosol. Set, 30 (7): 895-912 (1999).
Lopez-Herrera, et al, The electrospraying of viscous and non-viscous semi-insulating liquids. Scalilng laws, Bulletin of the American Physical Society,40 (12):2041(1995).
Lorenceau et al, Generation of Polymerosomes from Double-Emulsions, Langmuir, 21(20): 9183-9186 (2005).
Lorenz et al, Isolation and expression of a cDNA encoding Renilla reniformis luciferase, PNAS 88(10):4438-42 (1991).
Loscertales, et al, Micro/Nano Encapsulation via Electrified Coaxial Liquid Jets, Science, 295(5560): 1695-1698 (2002).
Low N.M. et al., Mimicking somatic hypermutaion: affinity maturation of antibodies displayed on bacteriophage using a bacterila mutator strain, J Mol Biol 260(3), 359-68 (1996).
Lowe, K.C., Perfluorochemical respiratory gas carriers: benefits to cell culture systems, J Fluorine Chem 118:19-26 (2002).
Lowman et al., Selecting high affinity binding proteins by monovalent phage display, Biochemistry 30(45):10832-8 (1991).
Lu et al., Robust fluorescein-doped silica nanoparticles via dense-liquid treatment, Colloids and Surfaces A Physicachemical and Engineering Aspects, 303(3):207-210 (2007).
Luisi et al, Activity and Conformation of Enzymes in Reverse Micellar Solutions, Meth. Enzymol 136:188-216 (1987).
Lund et al., Assesment of methods for covalent binding of nucleic acids to magnetic beads, Dynabeads, and the characteristics of the bound nucleic acids in hybridization reactions, Nucleic Acids Research, Oxford University Press, 16(22) (1998).
Lnderberg et al., Solid-phase technology: magnetic beads to improve nucleic acid detection and analysis, Biotechnology Annual Review, 1:373-401 (1995).
Lundstrom, et al, Breakthrough in cancer therapy: Encapsulation of drugs and viruses, www.currentdrugdiscovery.com, 19-23, Nov. 2002.
Lyne, P.D., Structure-Based Virtual Screening: An Overview, Drug Discov. Today, 7(20):1047-1055 (2002).
Ma, C. et al., In vitro protein engineering using synthetic tRNA(Ala) with different anticodons, Biochemistry 32 (31):7939-45 (1993).
Machine translation of JP 2002-282682 (26 pages).
Mackenzie et al., The application of flow microfluorimetry to biomedical research and diagnosis: a review, Dev Biol Stand 64:181-193 (1986).

(56) References Cited

OTHER PUBLICATIONS

Mackenzie, IABS Symposium on Reduction of Animal Usage in the Development and Control of Biological Products, London, UK, 1985.
Maclean, D. et al., Glossary of terms used in combinatorial chemistry, Pure Appl. Chem. 71(12):2349-2365 (1999).
Magdassi et al., Multiple Emulsions: HLB Shift Caused by Emulsifier Migration to External Interface, J. Colloid Interface Sci 97:374-379 (1984).
Mahajan et al., Bcl-2 and Bax Interactions in Mitochondria Probed with Green Florescent Protein and Fluorescence Resonance Energy Transfer, Nat. Biotechnol. 16(6): 547-552 (1998).
Mahjoob et al., Rapid microfluidic thermal cycler for polymerase chain reaction nucleic acid amplification. Int J HeatMass Transfer 2008;51:2109-22.
Malmborg, A, et al., Selective phage infection mediated by epitope expression on F pilus, Journal of Molecular Biology, 273, 544-551 (1997).
Mammal Wikipedia.com accessed Sep. 22, 2011).
Manley et al., In vitro transcription: whole cell extract, Methods Enzymol, 101:568-82 (1983).
Manz et al., Micromachining of monocrystalline silicon and glass for chemical analysis systems A look into next century's technology or just a fashionable craze, Trends in Analytical Chemistry 10(5):144-149 (1991).
Mao et al., Kinetic behaviour of alpha-chymotrypsin in reverse micelles: a stopped-flow study, Eur J Biochem 208 (1):165-70 (1992).
Mao, Q. et al., Substrate effects on the enzymatic activity of alphachymotrypsin in reverse micelles, Biochem Biophys Res Commun, 178(3):1105-12 (1991).
Mardis, E.R., The impact of next-generation sequencing technology on genetics, Trends Genet 24:133-141 (2008).
Margulies, M et al., Genome sequencing in microfabricated high-density picolitre reactors, Nature 437(7057):376-380 (2005).
Marques et al., Porous Flow within Concentric Cylinders, Bull Am Phys Soc Div Fluid Dyn 41:1768 (1996).
Mason, T.J. and Bibette, J. Shear Rupturing of Droplets in Complex Fluids, Langmuir, 13(17):4600-4613 (1997).
Mastrobattista et al., High-throughput screening of enzyme libraries: in vitro evolution of a beta-galactosidase by fluorescence-activated sorting of double emulsions, Chem. Biol. 12(12): 1291-1300 (2005).
Masui et ai., Probing of DNA-Binding Sites of *Escherichia coli* RecA Protein Utilizing 1-anilinonaphthalene-8-Sulfonic Acid, Biochem 37(35):12133-12143 (1998).
Matayoshi, E.D. et al., Novel fluorogenic substrates for assaying retroviral proteases by resonance energy transfer, Science 247:954 (1990).
Mattheakis et al., An in vitro polysome display system for identifying ligands from very large peptide libraries, PNAS 91:9022-6 (1994).
Mayr, L.M., and Fuerst, P., The Future of High-Throughput Screening, JBiomol Screen 13:443-448 (2008).
Mazutis et al., Droplet-Based Microfluidic Systems for High-Throughput Single DNA Molecule Isothermal Amplification and Analysis, Anal Chem 81(12):4813-4821 (2009).
Mazutis et al., Multi-step microfluidic droplet processing: kinetic analysis of an in vitro translated enzyme, Lab Chip 9:2902-2908 (2009).
McCafferty et al., Phage antibodies: filamentous phage displaying antibody variable domains,Nature, 348: 552-4 (1990).
McDonald and Whitesides, Poly(dimethylsiloxane) as a material for fabricating microfluidic devices, Account Chem. Res. 35:491-499 (2002).
McDonald et al. Fabrication of microfluidic systems in poly(dimethylsiloxane), Electrophoresis 21(1):27-40 (2000).
Melton et al., Efficient in vitro synthesis of biologically active RNA and RNA hybridization probes from plasmids containing a bacteriophage SP6 promoter, Nucl. Acids Res. 12(18):7035-7056 (1984).

Mendel, D. et al., Site-Directed Mutagenesis with an Expanded Genetic Code, Annu Rev Biophys Biomol Struct, 24:435-62 (1995).
Menger and Yamada, Enzyme catalysis in water pools, J. Am. Chem. Soc., 101:6731-4 (1979).
Meylan and Howard, Atom/fragment contribution method for estimating octanol-water partition coefficients, J Pharm Sci. 84(1):83-92 (1995).
Miele et al., Autocatalytic replication of a recombinant RNA, J Mol Biol, 171:281-95 (1983).
Titomanlio et al., Capillary experiments of flow induced crystallization of HOPE, AlChe Journal, 36(1):13-18(1990).
Tleugabulova et al., Evaluating formation and growth mechanisms of silica particles using fluorescence anisotropy decay analysis, Langmuir 20(14):5924-5932 (2004).
Tokatlidis et al., Nascent chains: folding and chaperone intraction during elongation on ribosomes, Philos Trans R Soc Lond B Biol Sci, 348:89-95 (1995).
Tokeshi et al., Continuous-Flow Chemical Processing on a Microchip by Combining Microunit Operations and a Multiphase Flow NetWork, Anal Chem 74(7):1565-1571 (2002).
Tokumitsu, H. et al., Preparation of gadopentetic acid-loaded chitosan micropartides for gadolinium neutron-capture therapy of cancer by a novel emulsion-droplet coalescence technique, Chem and Pharm Bull 47(6):838-842 (1999).
Tramontano, A., Catalytic antibodies, Science 234(4783):1566-70 (1986).
Trindade, T., Nanocrystalline semiconductors: synthesis, properties, and perspectives, Chem. Mat 13:3843-3858 (2001).
Tripet, B. et al., Engineering a de novo-designed coiled-coil heterodimerization domain off the rapid detection, purification and characterization of recombinantly expressed peptides and proteins, Protein Engng., 9:1029-42 (1996).
Tuerk, C. and Gold, L., Systematic Evolution of Ligands by Exponentid Enrichment: RNA Ligands to Bacteriophage T4 DNA Polymerase, Science, 249:505-10 (1990).
Umbanhowar et al., Monodisperse Emulsion Generation via Drop Break Off in a Coflowing Stream, Langmuir 16(2):347-351 (2000).
Unger et al., Monolithic microfabricated valves and pumps by multylayer soft lithography, Science 288(5463):113-116 (2000).
Utada, A. et al., Monodisperse double emulsions generated from a microcapillary device, Science, 308:537-541 (2005).
Vainshtein et al., Peptide rescue of an N-terminal truncation of the stoffel fragment of Taq DNA polymerase, Protein Science, 5:1785-92 (1996).
Van Bockstaele et al., Prognostic markers in chronic lymphocytic leukemia: a comprehensive review, Blood Rev 23(1):25-47 (2009).
Van Dilla et al., Cell Microfluorometry: A Method for Rapid Fluorescence Measurement, Science 163(3872):1213-1214 (1969).
Van Dilla et al., The fluorescent cell photometer: a new method for the rapid measurement of biological cells stained with fluorescent dyes, Annual Report of the Los Alamos Scientific Laboratory of the University of California (Los Alamos, NM), Biological and Medical Research Groupp (H-4) of the Health Division, Compiled by D. G. Ott, pp. 100-105, distributed Jan. 23, 1968.
Vanhooke et al., Three-dimensional structure of the zinc-containing phosphotrieesterase with the bound substrate analog diethy 4-methylbenzylphosphonate, Biochemistry 35:6020-6025 (1996).
Varga, J.M. et al., Mechanism of allergic cross-reactions-I. Multispecific binding of ligands to a mouse monoclonal anti-DNP IgE antibody. Mol Immunol 28(6), 641-54 (1991).
Vary, A homogeneous nucleic acid hybridization assay based on strand displacement, Nucl Acids Res 15(17):6883-6897 (1987).
Venkateswaran et al., Production of Anti-Fibroblast Growth Factor Receptor Monoclonal Antibodies by In Vitro Immunization, Hybirdoma, 11(6):729-739 (1992).
Venter et al., The sequence of the human genome, Science 291(5507):1304-51 (2001).
Viruses (Wikipedia.com, accessed Nov. 24, 2012).
Vogelstein et al., Digital PCR, PNAS 96(16):9236-9241 (1999).
Voss, E.W., Kinetic measurements of molecular interactions by spectrofluorometry, J Mol Recognit, 6:51-58 (1993).
Wahler, D. et al., Novel methods for biocatalyst screening. Curr Opin Chem Biol, 5: 152-158 (2001).

(56) References Cited

OTHER PUBLICATIONS

Walde, P. et al., Oparin's reactions revisited: enzymatic synthesis of poly(adenylic acid) in micelles and self-reproducing vesicles. J Am Chem Soc, 116: 7541-7547 (1994).

Walde, P. et al., Spectroscopic and kinetic studies of lipases solubilized in reverse micelles, Biochemistry, 32(15):4029-34 (1993).

Walde, P. et al., Structure and activity of trypsin in reverse micelles, Eur J Biochem, 173(2):401-9 (1988).

Walker et al., Isothermal in vitro amplification of DNA by a restriction enzyme/DNA polymerase system, PNAS 89(1):392-6 (1992).

Walker et al., Strand displacement amplification—an isothermal, in vitro DNA amplification technique, Nucleic Acid Res, 20(7):1691-6 (1992).

Wang et al., DEP actuated nanoliter droplet dispensing using feedback control, Lab on a Chip 9:901-909 (2008).

Wang et al., Preparation of Titania Particles Utilizing the Insoluble Phase Interface in a MicroChannel Reactor, Chemical Communications 14:1462-1463 (2002).

Wang, A.M. et al., Quantitation of mRNA by the polymerase chain reaction. Proc natl Acad Sci USA 86(24), 9717-21 (1989).

Wang, G.T. et al., Design and synthesis of new fluorogenic HIV protease substrates based on resonance energy transfer, Tetrahedron Lett., 31:6493 (1990).

Wang, Jun, et al., Quantifying EGFR Alterations in the Lung Cancer Genome with Nanofluidic Digital PCR Arrays, Clinical Chemistry 56:4 (2010).

Warburton, B., Microcapsules for Multiple Emulsions, Encapsulation and Controlled Release, Spec Publ R Soc Chem, 35-51 (1993).

Wasserman et al., Structure and reactivity of allyl-siloxane monolayers formed by reaction of allcyltrichlorosilanes on silicon substrates, Langmuir 5:1074-1087 (1989).

Weaver, Suzanne, et al., Taking qPCR to a higher level: Analysis of CNV reveals the power of high throughput qPCR to enhance quantitative resolution, Methods 50, 271-276 (2010).

Weil et al., Selective and accurate initiation of transcription at the Ad2 major late promotor in a soluble system dependent on purified RNA polymerase II and DNA, Cell, 18(2):469-84 (1979).

Werle et al., Convenient single-step, one tube purification of PCR products for direct sequencing, Nucl Acids Res 22(20):4354-4355 (1994).

Wetmur et al., Molecular haplotyping by linking emulsion PCR: analysis of paraoxonase 1 haplotypes and phenotypes, Nucleic Acids Res 33(8):2615-2619 (2005).

Wick et al., Enzyme-containing liposomes can endogenously produce membrane-constituting lipids, Chem Biol 3(4):277-85 (1996).

Widersten and Mannervik, Glutathione Transferases with Novel Active Sites Isolated by Phage Display from a Library of Random Mutants, J Mol Biol 250(2):115-22 (1995).

Wiggins et al., Foundations of chaotic mixing, Philos Transact A Math Phys Eng Sci 362(1818):937-70 (2004).

Williams et al., Amplification of complex gene libraries by emulsion PCR, Nature Methods 3(7):545-550 (2006).

Williams et al., Methotrexate, a high-affinity pseudosubstrate of dihydrofolate reductase, Biochemistry, 18(12):2567-73 (1979).

Wilson, D.S. and Szostak, J.W., In vitro selection of functional nucleic acids, Ann. Rev. Biochem. 68: 611-647 (1999).

Winter et al., Making antibodies by phage display technology, Annu Rev Immunol 12:433-55 (1994).

Wittrup, K.D., Protein engineering by cell-surface display. Curr Opin Biotechnology, 12: 395-399 (2001).

Wittwer, C.T., et al., Automated polymerase chain reaction in capillary tubes with hot air, Nucleic Acids Res., 17(11) 4353-4357 (1989).

Michalatos-Beloin, 1996, Molecular haplotyping of genetic markers 10 kb apart by allele-specific long-range PCR, Nucl Acids Res 24(23):4841-4843

\* cited by examiner

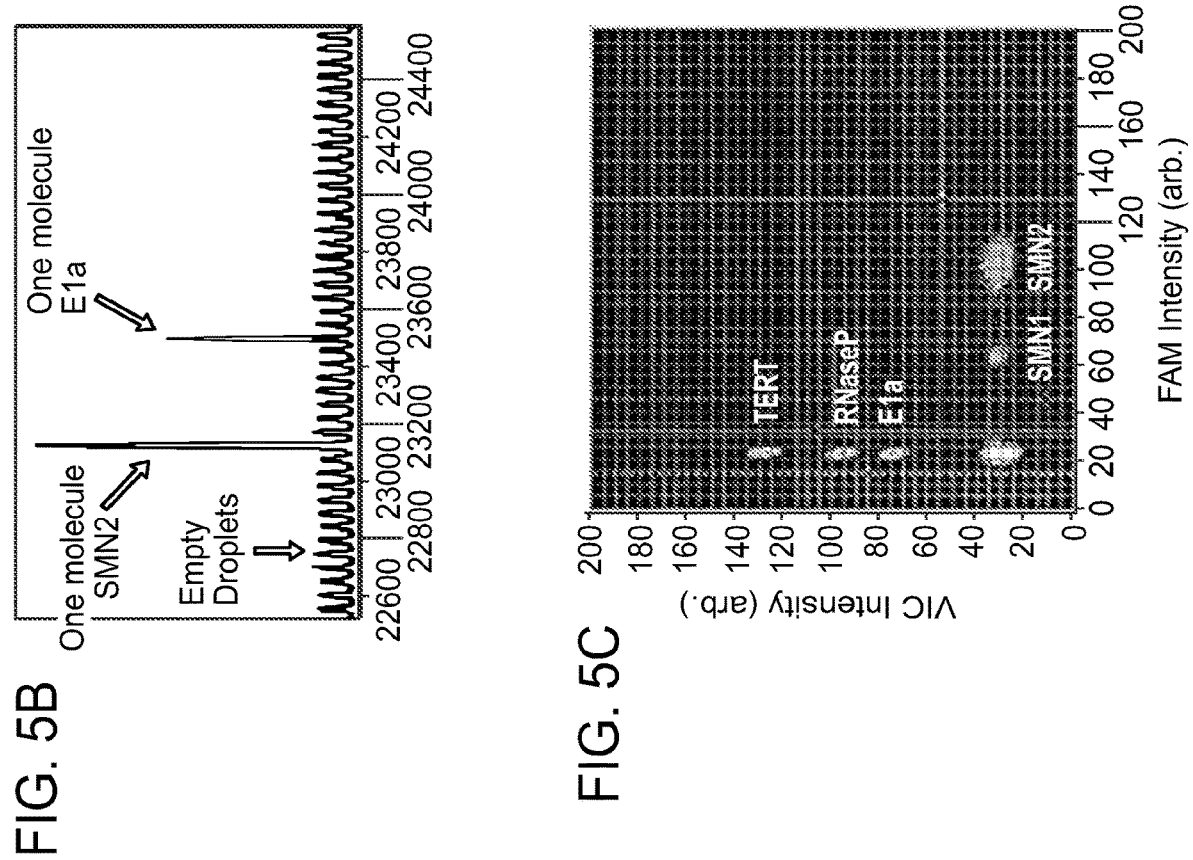

One Color One Target

Single molecule amplification produces of fluorescence burst of a quantized intensity.

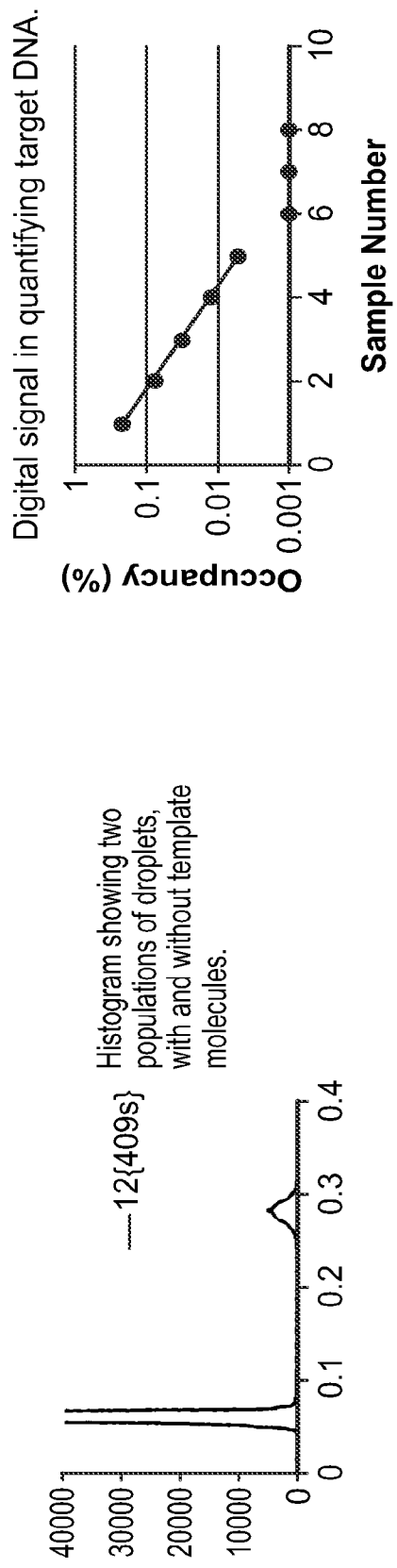
FIG. 7D
FIG. 7E
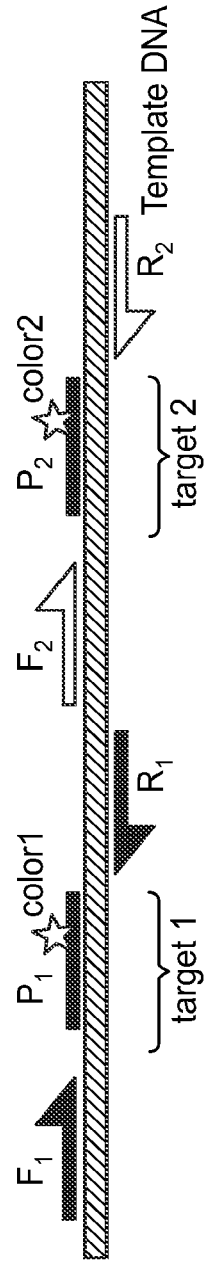
Two Colors Two Targets
FIG. 8A

Two Colors THREE Targets

Histogram showing four populations of droplets: with target1, with target2, with target3 and without any of the three targets.

FIG. 12A

Tuning the Intensity of Target 2

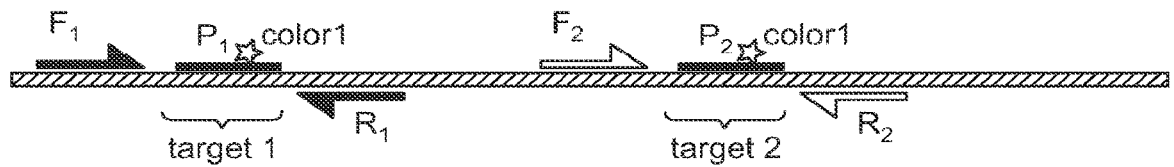

Probe 2 has a single base missmatch to target two and will produce a digital read-out of lower signal intensity

FIG. 12B

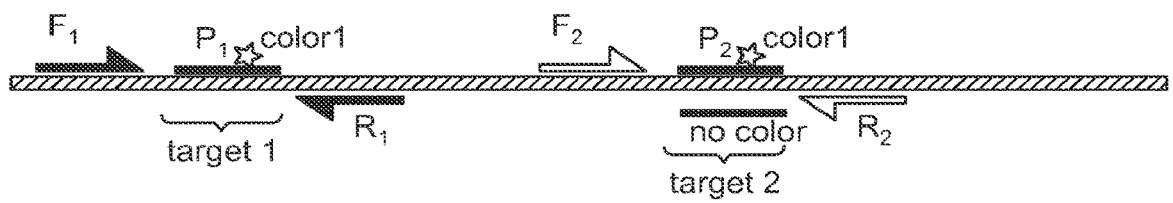

Probe 2 is a blend of identical probes doth with and without a fluorophore to reduce the overall intensity of the fluorescent signal

FIG. 12C

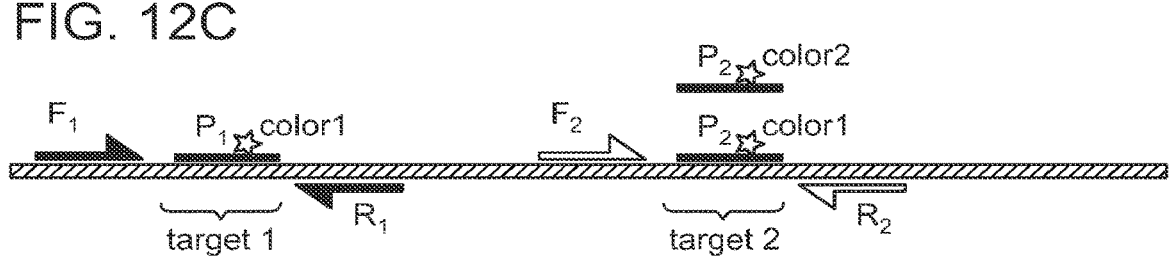

Probe 2 is a blend of identical probes each with a different color fluorophore to produce a multi-color fluorescent burst.

Figure 32A
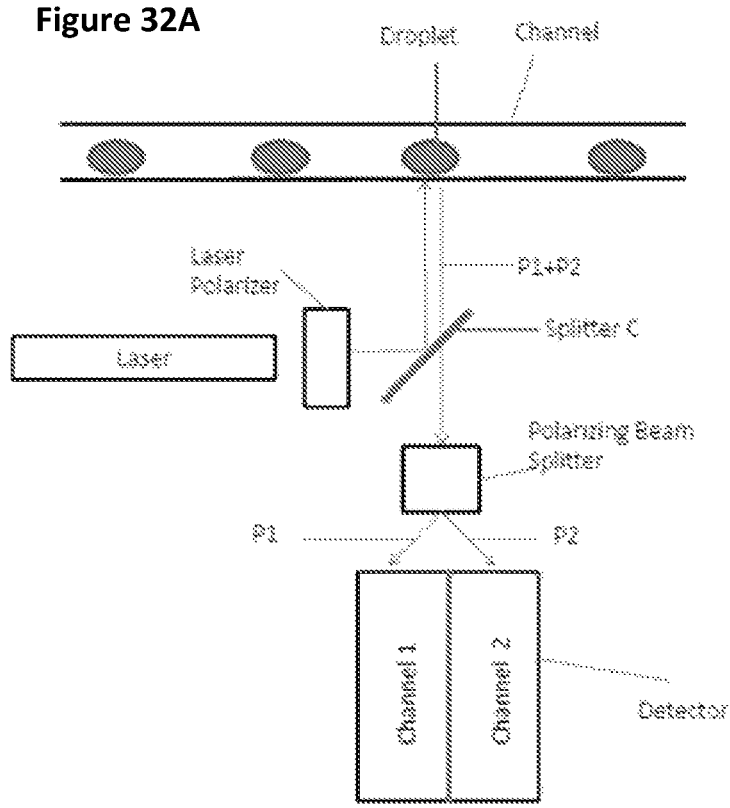
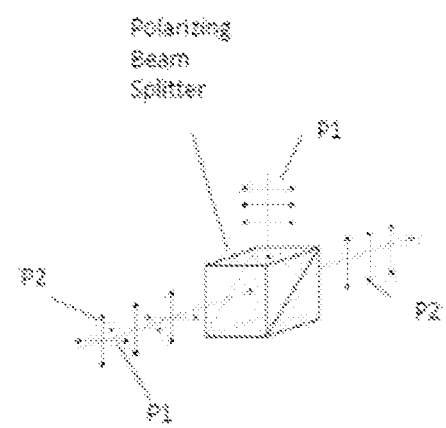
Figure 32B

SEQUENCE LISTING

<160> NUMBER OF SEQ ID NOS: 14

<210> SEQ ID NO 1
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 1
aatgcttttt aacatccata taaagct                                      27

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 2
ccttaattta aggaatgtga gcacc                                        25

<210> SEQ ID NO 3
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 3
cagggtttca gacaaa                                                  16

<210> SEQ ID NO 4
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 4
aatgcttttt aacatccata taaagct                                      27

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 5
ccttaattta aggaatgtga gcacc                                        25

<210> SEQ ID NO 6
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 6
tgattttgtc taaaaccc                                                18

<210> SEQ ID NO 7
<211> LENGTH: 24
<212> TYPE: DNA
<213> ORGANISM: Artificial Sequence

```
<220> FEATURE:
<223> OTHER INFORMATION: Synthetic oligonucleotide

<400> SEQUENCE: 7
caacctactc ttctcagacg tgta                                          24

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 8
tcgaagtgat ccagtgggta gtg                                           23

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
caggagatgc ccgcccagct c                                             21

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 10
tgctgatgct ttgggaagta tgtta                                         25

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 11
catgagtggc tatcatac                                                 18

<210> SEQ ID NO 12
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 12
tgtcaggaaa agatgctgag tgatt                                         25

<210> SEQ ID NO 13
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 13
atgagtggct gtcatac                                                  17
```

```
<210> SEQ ID NO 14
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 14
catgagtggc tgtcatac                                                    18
```

DIGITAL ANALYTE ANALYSIS

REFERENCE TO RELATED APPLICATIONS

This application is a continuation of U.S. application Ser. No. 13/866,111, filed Apr. 19, 2013, which is a continuation-in-part of U.S. application Ser. No. 13/026,120, filed Feb. 11, 2011, which claims priority to U.S. provisional application Ser. No. 61/388,937, filed Oct. 1, 2010; U.S. provisional application Ser. No. 61/347,158, filed May 21, 2010; U.S. provisional application Ser. No. 61/331,490, filed May 5, 2010; and U.S. provisional application Ser. No. 61/304,163, filed Feb. 12, 2010.

U.S. application Ser. No. 13/866,111 is also a continuation-in-part of U.S. application Ser. No. 13/460,762, filed Apr. 30, 2012, which is a continuation-in-part of Ser. No. 13/026,120, filed Feb. 11, 2011, which claims priority to U.S. provisional application Ser. No. 61/388,937, filed Oct. 1, 2010; U.S. provisional application Ser. No. 61/347,158, filed May 21, 2010; U.S. provisional application Ser. No. 61/331,490, filed May 5, 2010; and U.S. provisional application Ser. No. 61/304,163, filed Feb. 12, 2010.

U.S. application Ser. No. 13/866,111 also claims the benefit of and priority to U.S. provisional application Ser. No. 61/636,217, filed Apr. 20, 2012.

The content of each application is incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on Jul. 1, 2019, is named RDT-548-US20-Sequence.txt and is 3,321 bytes in size.

FIELD OF THE INVENTION

The invention generally relates to droplet based digital PCR and methods for analyzing a target nucleic acid using the same.

BACKGROUND

Assays have been developed that rely on analyzing nucleic acid molecules from bodily fluids for the presence of mutations, thus leading to early diagnosis of certain diseases such as cancer. In a typical bodily fluid sample however, any abnormal nucleic acids containing mutations of interest are often present in small amounts (e.g., less than 1%) relative to a total amount of nucleic acid in the bodily fluid sample. This can result in a failure to detect the small amount of abnormal nucleic acid due to stochastic sampling bias.

The advent of PCR and real-time PCR methodologies has greatly improved the analysis of nucleic acids from both throughput and quantitative perspectives. While traditional PCR techniques typically rely on end-point, and sometimes semi-quantitative, analysis of amplified DNA targets via agarose gel electrophoresis, real-time PCR (or qPCR) methods are geared toward accurately quantifying exponential amplification as the reaction progresses. qPCR reactions are monitored either using a variety of highly sequence specific fluorescent probe technologies, or by using non-specific DNA intercalating fluorogenic dyes.

As the need for higher throughput in analyzing multiple targets in parallel continues to escalate in the fields of genomics and genetics, and as the need for more efficient use of sample grows in medically related fields such as diagnostics, the ability to perform and quantify multiple amplifications simultaneously within the same reaction volume (multiplexing) is paramount for both PCR and qPCR. While end-point PCR can support a high level of amplicon multiplexing, such ample capacity for multiplexing probe-based qPCR reactions remains elusive for a number of reasons. For example, most commercial real-time thermal cyclers only support up to four differently colored fluorophores for detection as a consequence of the limited spectral resolution of common fluorophores, translating into a multiplexing capacity of 4×. Additionally, while optimization of single target primer/probe reactions is now standard practice, combining primers and probes for multiple reactions changes the thermodynamic efficiencies and/or chemical kinetics, necessitating potentially extensive troubleshooting and optimization. Very high multiplexing of greater than 100× has been demonstrated in a "one of many" detection format for pathogen identification using "sloppy" molecular beacons and melting points as fingerprints, however the approach is restricted to applications with a slim likelihood of the presence of multiple simultaneous targets. A half-multiplexing method achieved 19$x$ in a two step reaction with general multiplexed preamplification in the first step, followed by separate single-plex quantitative PCR in the second step. However a general purpose single-pot solution to qPCR multiplexing does not yet exist.

Digital PCR (dPCR) is an alternative quantitation method in which dilute samples are divided into many separate reactions. See for example, Brown et al. (U.S. Pat. Nos. 6,143,496 and 6,391,559) and Vogelstein et al. (U.S. Pat. Nos. 6,440,706, 6,753,147, and 7,824,889), the content of each of which is incorporated by reference herein in its entirety. The distribution from background of target DNA molecules among the reactions follows Poisson statistics, and at so called "terminal dilution" the vast majority of reactions contain either one or zero target DNA molecules for practical intents and purposes. In another case, at so called "limiting dilution" some reactions contain zero DNA molecules, some reactions contain one molecule, and frequently some other reactions contain multiple molecules, following the Poisson distribution. It is understood that terminal dilution and limiting dilution are useful concepts for describing DNA loading in reaction vessels, but they have no formal mathematical definition, nor are they necessarily mutually exclusive. Ideally, at terminal dilution, the number of PCR positive reactions (PCR(+)) equals the number of template molecules originally present. At limiting dilution, Poisson statistics are used to uncover the underlying amount of DNA. The principle advantage of digital compared to qPCR is that it avoids any need to interpret the time dependence of fluorescence intensity—an analog signal—along with the main underlying uncertainty of non-exponential amplification during early cycles.

SUMMARY

The invention generally relates to the manipulation of nucleic acid in droplets, and in particular, nucleic acid amplification and detection. In one aspect, the invention provides a droplet that contains a single nucleic acid template and a plurality of primer pairs specific for multiple target sites on the template. The single nucleic acid template can be DNA (e.g., genomic DNA, cDNA, etc.) or RNA. The template is amplified in the droplet for detection; and may preferably be amplified using a plurality of primer pairs as described herein.

The ability to amplify and detect single nucleic acids in droplets enables digital PCR, detection, counting, and differentiation among nucleic acids, especially those present in heterogeneous samples. Thus, the invention applies to digital amplification techniques and, in specific embodiments enables multiplex PCR in droplets. For example, multiplexing primers in droplets enables the simultaneous increase in the number of PCR droplets while keeping the amount of input DNA the same or lower and generate the same or greater amplicon yield. This results in an overall increase in the amount of PCR positive droplets and amplicon yield without the consumption of more DNA. Even though the number of PCR primer pairs per droplet is greater than one, there is only one template molecule per droplet, and thus, in some implementations, there is only one primer pair per droplet that is being utilized at one time. As such, the advantages of droplet PCR for eliminating bias from either allele specific PCR or competition between different amplicons is maintained. However, as described below in relation to detection of haplotypes, other implementations advantageously allow detection of multiple loci on a single template using multiple primer pairs, preferably designed to minimize bias.

In further aspects of the invention, a plurality of primer pairs encompassed within a droplet each include a bridge section flanked by a first targeting arm and a second targeting arm. Each primer pair is specific for a different target site on a single template nucleic acid also disposed within the droplet. The first targeting arm hybridizes to a first region of the target site and the second targeting arm hybridizes to a second targeting site. The bridge section is not complementary to the single template nucleic acid within the droplet. The droplet also includes a plurality of probes in which each member of the plurality of probes corresponds to a primer and is designed to hybridize to a complement of the bridge region of the corresponding primer. Preferably, the bridge section of each primer of a primer pair is the same, and thus corresponds to the same probe for detection. According to certain embodiments, each member of the plurality of probes designed to hybridize to a bridge region includes a detectable label. The plurality of probes may include one or more groups of probes at varying concentrations. Members of the one or more groups of probes may each have the same detectable label. Alternatively, each member of the plurality of probes includes a unique detectable label. Typically, the detectable label is a fluorescent label.

Microfluidic droplets for multiplex analysis according to the invention contain a plurality of probes that hybridize to amplicons produced in the droplets. Preferably, the droplet contains two or more probes, e.g., 2, 3, 4, 5, 6, 7, 8, 9, 10, 12, 14, 16, 18, 20, 25, 30, 35, 40, 45, 50, 55, 60, 65, 60, 75, 80, 85, 90, 95, 100, 110, 120, 130, 140, 150, 160, 170, 180, 190, 200, 500, or more probes. Certain members of the plurality of probes include a detectable label. Members of the plurality of probes can each include the same detectable label, or a different detectable label. The detectable label is preferably a fluorescent label. The plurality of probes can include one or more groups of probes at varying concentrations. The one or more groups of probes can include the same detectable label which will vary in intensity upon detection, due to the varying probe concentrations. The droplets of the invention can further contain one or more reagents for conducting a polymerase chain reaction, such as a DNA or RNA polymerase, and/or dNTPs.

The present invention additionally relates to a method for detecting a plurality of targets in a biological sample using digital PCR in microfluidic droplets. The sample may be a human tissue or body fluid. Exemplary body fluids pus, sputum, semen, urine, blood, saliva, and cerebrospinal fluid.

One or more droplets are formed, each containing a single nucleic acid template and a heterogeneous mixture of primer pairs and probes, each specific for multiple target sites on the template. For example, a first fluid (either continuous, or discontinuous as in droplets) containing a single nucleic acid template (DNA or RNA) is merged with a second fluid (also either continuous, or discontinuous as in droplets) containing a plurality of primer pairs and a plurality of probes, each specific for multiple targets sites on the nucleic acid template to form a droplet containing the single nucleic acid template and a heterogeneous mixture of primer pairs and probes. The second fluid can also contain reagents for conducting a PCR reaction, such as a polymerase and dNTPs.

Certain members of the plurality of probes include a detectable label. Members of the plurality of probes can each include the same detectable label, or a different detectable label. The detectable label is preferably a fluorescent label. The plurality of probes can include one or more groups of probes at varying concentrations. The one or more groups of probes can include the same detectable label which varies in intensity upon detection, due to the varying probe concentrations.

The first and second fluids can each be in droplet form. Any technique known in the art for forming droplets may be used with methods of the invention. An exemplary method involves flowing a stream of the sample fluid containing the nucleic acid template such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets containing the first fluid. The carrier fluid may be any fluid that is immiscible with the sample fluid. An exemplary carrier fluid is oil. In certain embodiments, the carrier fluid includes a surfactant, such as a fluorosurfactant. The same method may be applied to create individual droplets from the second fluid containing the primer pairs (and, in some implementations, the amplification reagents). Either the droplets containing the first fluid, the droplets containing the second fluid, or both, may be formed and then stored in a library for later merging, aspects of certain implementations of which are described in U.S. patent application Ser. No. 12/504,764, hereby incorporated herein in its entirety for all purposes. Once formed, droplets containing the first and second fluids can be merged to form single droplets containing the single nucleic acid template and heterogeneous mixture of primer pairs and probes. Merging can be accomplished, for example, in the presence of an electric field. Moreover, it is not required that both fluids be in the form of droplets when merging takes places. One exemplary method for merging of fluid portions with droplets is taught, for example, in co-pending U.S. Patent Application No. 61/441,985, filed on Feb. 11, 2011.

The nucleic acid template in each of the merged/formed droplets is amplified, e.g., by thermocycling the droplets under temperatures/conditions sufficient to conduct a PCR reaction. The resulting amplicons in the droplets can then be analyzed. For example, the presence of absence of the plurality of targets in the one or more droplets is detected optically, e.g., by the detectable label on the plurality of probes.

The invention further relates to methods for analyzing a target nucleic acid. More particularly, methods of the invention are able to detect polymerase errors that occur during a PCR reaction and are able to exclude from analysis amplification products that are a result of a polymerase error. Methods of the invention are particularly useful in digital PCR where a polymerase error may result in a partitioned section of sample being incorrectly identified as containing a mutant allele, i.e., a false positive. Such false positives greatly impact the validity and precision of digital PCR results. Methods of the invention are able to uniquely detect multiple targets with the same optical color. Methods of the invention are particularly useful in digital PCR where it is desirable to identify multiple different target molecules that may be present in the starting test fluid.

Methods of the invention involve forming sample droplets containing target nucleic acid. Ideally, methods of the invention comprise forming droplets for digital PCR. Preferred digital PCR droplets contain one copy of a nucleic acid to be amplified, although they may contain multiple copies of the same nucleic acid sequence. Any technique known in the art for forming sample droplets may be used with methods of the invention. One exemplary method involves flowing a stream of sample fluid including nucleic acids such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets. The carrier fluid may be any fluid that is immiscible with the sample fluid. An exemplary carrier fluid is oil. In certain embodiments, the carrier fluid includes a surfactant, such as a fluorosurfactant.

The targets are then amplified in the droplets. Any method known in the art may be used to amplify the target nucleic acids either linearly or exponentially. A preferred method is the polymerase chain reaction (PCR). For purposes of the invention, any amplification technique commonly known in the art may be implemented such as rolling circle amplification, isothermal amplification, or any combination of amplification methods using loci specific primers, nested-primers, or random primers (such primers, and/or primers used for PCR, are included in the term "amplification reagents"). Once amplified, droplets containing amplicon from the target and amplicon from a variant of the target are excluded. One method to exclude droplets that contain a heterogeneous population of amplicons from droplets that contain a homogeneous population of amplicons includes hybridizing detectably-labeled probes to the amplicons, flowing the droplets through a microfluidic channel, and excluding those droplets in which both amplicon from the target and amplicon from a variant of the target are detected.

Once droplets containing a heterogeneous population of amplicons are excluded, droplets that contain a homogeneous population of amplicons are analyzed. Any analytical technique known in the art may be used. In certain embodiments, analyzing the droplets involves determining a number of droplets that contain only wild-type target, and determining a number of droplets that contain only a variant of the target. Generally, the presence of droplets containing only the variant is indicative of a disease, such as cancer. The variant may be an allelic variant. An exemplary allelic variant is a single nucleotide polymorphism. The variant may also be a specific haplotype. Haplotypes refer to the presence of two or more variants on the same nucleic acid strand. Haplotypes can be more informative or predictive than genotypes when used to determine such things as the presence or severity of disease, response to drug therapy or drug resistance of bacterial or viral infections. Because each droplet contains only one template strand it is an ideal vessel for the determination of haplotypes. The detection of two or more variants in a single droplet that contains a single intact nucleic acid strand identifies the haplotype of the variants on that strand. The presence of two or more markers in the same droplet can be identified by such methods as the presence of dyes of multiple colors or the increase in the intensity of a single dye or a combination of both. Any method that allows the identification of multiple variants in a single droplet enables the determination of a samples haplotype.

In accordance with some implementations of the invention, a method is provided for analyzing a target nucleic acid that includes compartmentalizing a first fluid into portions, each portion containing a single target nucleic acid; amplifying the target in the portions; excluding portions containing amplicon from the target and amplicon from a variant of the target; and analyzing target amplicons.

In other aspects, the invention generally provides methods for detecting a recurrence of a cancer in a patient. Those methods may involve forming sample droplets containing a single target nucleic acid derived from a patient sample, flowing the sample droplets through a channel, amplifying the target in the droplets, detecting amplified target in the droplets, excluding droplets including a heterogeneous population of amplicons, and analyzing non-excluded droplets to determine the presence of mutant alleles indicative of recurrence. In certain embodiments, the analyzing step includes capturing amplicon obtained from the droplets using labeled capture probes. The sample may be a human tissue or body fluid. Exemplary body fluids are pus, sputum, semen, urine, blood, saliva, stool, and cerebrospinal fluid. In other aspects of the invention generally provide a method for forensic identification of low levels of target nucleic acid in an environment having multiple other sources of nucleic acid. Such methods may also be practiced using fluids compartmentalized in containers other than or in addition to droplets.

As described, aspects of the invention require determining whether a droplet contains an amplifiable product. One technique for determining whether a droplet contains amplifiable product includes flowing droplets in a mono-dispersed fashion past a detector (e.g. one droplet passing the detector at a time), and detecting the signals of each droplet separately. Droplets having signals above background are droplets that include amplifiable product. A problem with this mono-dispersed detection technique is that it requires a large data file because the signal from every droplet is obtained and recorded. In addition, the mono-disperse flow of droplets past the detector takes time and is inefficient. In order to solve the problems associated with mono-dispersed detection, methods of the invention provide a non-mono-dispersed technique for determining whether a droplet contains amplifiable product. In this alternative technique, a plurality of droplets is simultaneously flowed past the detector, in which the plurality of droplets is not mono-dispersed within a portion of the channel. The detector is configured to only obtain and record signals above background noise. As a result, only droplets having amplifiable product are counted and detected as they pass the detector.

According to one embodiment, the invention provides a method for counting droplets. The method includes providing a plurality of droplets, in which a subset of droplets includes nucleic acid from a sample. The nucleic acid is then amplified within the droplets. A signal above background is detected for only droplets containing amplified nucleic acid. From the detected droplets having signals above background, a ratio of normal to abnormal nucleic acid is determined. This ratio is indicative of a condition. In certain embodiments, at least one of the plurality of droplets includes a first detectable target and at least one other droplet includes a second detectable target. The first detectable target includes a normal nucleic acid and the second detectable target includes an abnormal nucleic acid. In certain embodiments, the ratio is determined by counting a number X of droplets containing the first detectable target and a number Y of droplets containing a second detectable target.

In further aspects of the invention, methods of determining the nucleic acid make-up of a sample are provided. More specifically, these methods can be used to detect contiguous, intact sequences of RNA or DNA within a sample as well as fragments of those sequences. For certain experiments, samples comprising a higher proportion of contiguous, intact sequences are better candidates for additional testing than samples comprising mostly fragmented sequences. These methods may include partitioning a nucleic acid sample of different lengths into a plurality of different portions, where each portion includes, on average, a single nucleic acid molecule. A first and second primer pairs and a first and second detectably labeled probes are also introduced into the partitioned portions, where the first and second primer pairs are specific for first and second locations on the nucleic acid. If the nucleic acid contains the first and second locations spaced apart from each other, when the first probe hybridizes to the first location and the second probe hybridizes to the second location, an amplicon is created spanning a length. Thus, by amplifying the nucleic acid in the partitioned portions and detecting amplicons in the partitioned portions, the presence of signal from both probes indicates the presence of a nucleic acid that is contiguous between the first and second locations. By making this measurement for the plurality of portions, it is possible to determine a nucleic acid make-up of the sample based on the detecting step. In certain embodiments, the determining step may include comparing relative amounts of contiguous nucleic acid to relative amounts of non-contiguous nucleic acid. In other embodiments, the determining step may include comparing relative amounts of contiguous nucleic acid or non-contiguous nucleic acid to a total amount of nucleic acid.

Methods in accordance with the invention also encompass the use of a single primer pair. The method includes providing a fluid comprising the sample nucleic acid and a plurality of one or more primer pairs, wherein each primer pair has at least one unique related probe and is selected to be complementary to one or more sequences of known length. The method also includes partitioning the fluid into a plurality of partitions, wherein at least a first portion of the partitions comprise one molecule of the nucleic acid sample having sequences complementary to one or more of the primer pairs, and at least one related probe, and a second portion of the partitions comprise no molecules of the sample nucleic acid having sequences complementary to one or more of the primer pairs. The method further includes conducting a PCR reaction in the partitions, thereby changing a fluorescent property of the first portion of the partitions, detecting the fluorescent property of each partition, and determining the number of occurrences in the sample nucleic acid of one or more sequences of known length based on the detecting step. In some aspects of the invention, the method further includes comparing a first number of occurrences of a first sequence of known length to a second number of occurrences of a second sequence of a second known length.

Additional embodiments of the invention may also contemplate the use of a single primer pair as well as rely on something other than a probe for detecting the amplified sequence. In certain embodiments, the method comprises partitioning a sample comprising nucleic acid of different lengths into a plurality of partitioned portions, wherein each portion comprises, on average a single nucleic acid molecule. The method further includes introducing at least one primer pair, in which each primer of the pair is specific for a first and second location on the nucleic acid, the first and second locations being spaced apart from each other. The method further includes amplifying the nucleic acid in the partitioned portions, detecting the amplicons in the partitioned portions, and determining a nucleic acid make-up of the sample based on the results of the detecting step.

Methods in accordance with the invention also encompass the analysis of cell-free nucleic acids in a biological sample. In some embodiments, the biological sample can be blood, saliva, sputum, urine, semen, transvaginal fluid, cerebrospinal fluid, sweat, breast milk, breast fluid (e.g., breast nipple aspirate), stool, a cell or a tissue biopsy.

The methods of the invention can also be used to evaluate the quality of cell-free nucleic acids, for example cell-free DNA or RNA, which can be obtained from a biological sample. The invention allows the cell-free nucleic acid to be evaluated for quality, e.g., continuity, prior to amplification and sequencing. Thus, a cell-free nucleic acid sample can be partitioned into samples comprising nucleic acids of different lengths, primer pairs can be introduced along with appropriate probes, the nucleic acids amplified, and the make-up, e.g., the continuity of the cell-free nucleic acid sample can be determined.

BRIEF DESCRIPTION OF THE DRAWINGS

FIG. 3A depicts the droplet generation chip; FIG. 3B depicts the droplet spacing for readout; and FIG. 3C depicts a cartoon of droplet readout by fluorescence.

FIG. 4A shows droplet fluorescence during readout for the most concentrated sample. Each discrete burst of fluorescence corresponded to an individual droplet. Two different groups of droplets were evident: PCR(+) droplets peaking at ~0.8 V and PCR(−) droplets at ~0.1 V; FIG. 4B shows a histogram of the peak fluorescence intensities of droplets from the complete data trace in (a). PCR(+) and PCR(−) droplets appeared as two very distinct populations centered at 0.78 and 0.10 V, respectively; FIG. 4C shows the serial dilution of template DNA. Open circles: measured occupancies; solid line: the best fit to Eqn 2 (A=0.15, f=4.8, $R^2$−0.9999).

FIG. 5A is a schematic representation of a droplet having 5 sets of primers for PCR amplification of a template sequence and 5 probes, each labeled with a fluorescent dye, that binds specifically to the amplified sequences; FIG. 5B is a time trace of fluorescence intensity detected from droplets after PCR amplification; FIG. 5C is a scatter plot showing clusters representing droplets that contain specific amplified sequences (TERT, RNaseP, E1a, SMN1 and SMN2). As shown in FIG. 5A, five Taqman assays are conducted in a droplet. This provides for expression analysis and precise quantification of copy number while only requiring 1/5 the DNA of 5 opti-plex reaction. Each reaction has a unique location in the 2D scatter plot shown in FIG. 5C.

In FIG. 6A, off-axis populations are generated by making blends of probes, which expands optical space available for multiplexing assays.

FIGS. 7A-E are a schematic depicting one-color detection of a genetic sequence with a microfluidic device.

FIGS. 8A-D are a schematic depicting two-color detection of two genetic sequences with a microfluidic device.

FIG. 11A depicts a histogram of droplet peak fluorescence intensities; FIG. 11B shows a comparison of gene copy numbers measured by monochromatic dPCR.

FIGS. 12A-12C are a schematic for tuning the intensity of a detectable label to a particular target with a microfluidic device. In FIGS. 12A-12C, relative intensity of signals from multiple targets of the same color can be generated in a variety of ways. Examples include: FIG. 12A) using a single base mismatch of the probe and target to distinguish different targets;

FIG. 12B) blend identical probes with and without fluorophores; and FIG. 12C) blend identical probes with two or more different color fluorophores.

FIG. 14A is a 2D histogram of droplet fluorescence intensities, shown as a heat map, for the 5-plex assay against the synthetic model chromosome for validation. The six well resolved droplet populations corresponded to the five individual assays plus the empty droplets; FIG. 14B shows the results of the SMA pilot study.

FIGS. 15A and 15B show 2-D histograms of droplet fluorescence intensity, shown as heat maps with hotter colors representing higher droplet counts, for the 9-plex assay against the synthetic model chromosome FIG. 15A=Before optimization; FIG. 15B=after optimization).

FIGS. 32A and 32B depict another configuration for detecting fluorescence polarization according to certain embodiments.

DETAILED DESCRIPTION

Figure 1:
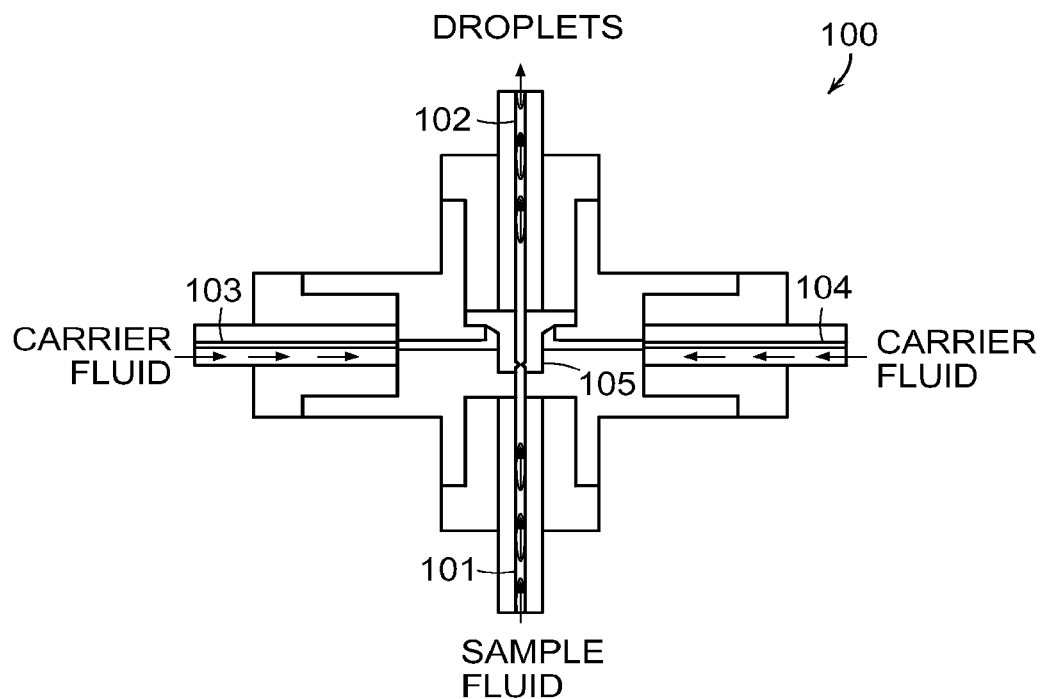
FIG. 1 depicts a droplet formation device.

The invention provides materials and methods for analysis of biomolecules. In one aspect, the invention provides for digital analysis in droplets, such as microfluidic droplets. The invention allows digital PCR to be conducted and provides for significantly reduced or eliminated errors.

Ideally, the sensitivity of digital PCR is limited only by the number of independent amplifications that can be analyzed, which has motivated the development of several ultra-high throughput miniaturized methods allowing millions of single molecule PCR reactions to be performed in parallel (discussed in detail elsewhere). In a preferred embodiment of the invention, digital PCR is performed in aqueous droplets separated by oil using a microfluidics system. In another preferred embodiment, the oil is a fluorinated oil such as the Fluorinert oils (3M). In a still more preferred embodiment the fluorinated oil contains a surfactant, such as PFPE-PEG-PFPE triblock copolymer, to stabilize the droplets against coalescence during the amplification step or at any point where they contact each other. Microfluidic approaches allow the rapid generation of large numbers (e.g. $10^6$ or greater) of very uniformly sized droplets that function as picoliter volume reaction vessels (see reviews of droplet-based microfluidics). But as will be described, the invention is not limited to dPCR performed in water-in-oil emulsions, but rather is general to all methods of reaction compartmentalization for dPCR. In the description that follows, the invention is described in terms of the use of droplets for compartmentalization, but it is understood that this choice of description is not limiting for the invention, and that all of the methods of the invention are compatible with all other methods of reaction compartmentalization for dPCR.

Methods of the invention involve novel strategies for performing multiple different amplification reactions on the same sample simultaneously to quantify the abundance of multiple different DNA targets, commonly known to those familiar with the art as "multiplexing". Methods of the invention for multiplexing dPCR assays promise greater plexity—the number of simultaneous reactions—than possible with existing qPCR or dPCR techniques. It is based on the singular nature of amplifications at terminal or limiting dilution that arises because most often only a single target allele is ever present in any one droplet even when multiple primers/probes targeting different alleles are present. This alleviates the complications that otherwise plague simultaneous competing reactions, such as varying arrival time into the exponential stage and unintended interactions between primers.

In one aspect, the invention provides materials and methods for improving amplicon yield while maintaining the sensitivity and specificity in droplet based digital PCR. More specifically, the invention provides droplets containing a single nucleic acid template and multiplexed PCR primers and methods for detecting a plurality of targets in a biological sample by forming such droplets and amplifying the nucleic acid templates using droplet based digital PCR.

Reactions within microfluidic droplets yield very uniform fluorescence intensity at the end point, and ultimately the intensity depends on the efficiency of probe hydrolysis. Thus, in another aspect of the methods of the invention, different reactions with different efficiencies can be discriminated on the basis of end point fluorescence intensity alone even if they have the same color. Furthermore, in another method of the invention, the efficiencies can be tuned simply by adjusting the probe concentration, resulting in an easy-to-use and general purpose method for multiplexing. In one demonstration of the invention, a 5-plex TaqMan® dPCR assay worked "right out of the box", in contrast to lengthy optimizations that typify qPCR multiplexing to this degree. In another aspect of the invention, adding multiple colors increases the number of possible reactions geometrically, rather than linearly as with qPCR, because individual reactions can be labeled with multiple fluorophores. As an example, two fluorophores (VIC and FAM) were used to distinguish five different reactions in one implementation of the invention.

Methods of the invention are able to detect polymerase errors that occur during an amplification reaction and are able to exclude from analysis those products that are a result of polymerase errors. In essence, methods of the invention increase the sensitivity of digital PCR by identifying amplification products that are false positives, and excluding those products from analysis.

Methods of the invention involve forming sample droplets containing a single target nucleic acid, amplifying the target in the droplets, excluding droplets containing amplicon from the target and amplicon from a variant of the target, and analyzing target amplicons.

Nucleic Acid Target Molecules

Nucleic acid target molecules include deoxyribonucleic acid (DNA) and/or ribonucleic acid (RNA). Nucleic acid molecules can be synthetic or derived from naturally occurring sources. In one embodiment, nucleic acid molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain embodiments, the nucleic acid molecules are obtained from a single cell. Biological samples for use in the present invention include viral particles or preparations. Nucleic acid molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA. In certain embodiments, the nucleic acid molecules are bound as to other target molecules such as proteins, enzymes, substrates, antibodies, binding agents, beads, small molecules, peptides, or any other molecule and serve as a surrogate for quantifying and/or detecting the target molecule.

Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Nucleic acid molecules may be single-stranded, double-stranded, or double-stranded with single-stranded regions (for example, stem- and loop-structures).

Droplet Formation

Methods of the invention involve forming sample droplets where some droplets contain zero target nucleic acid molecules, some droplets contain one target nucleic acid molecule, and some droplets may or may not contain multiple nucleic acid molecules (corresponding to limiting or terminal dilution, respectively, as defined above). In the preferred embodiment, the distribution of molecules within droplets obeys the Poisson distribution. However, methods for non-Poisson loading of droplets are known to those familiar with the art, and include but are not limited to active sorting of droplets, such as by laser-induced fluorescence, or by passive one-to-one loading. The description that follows assumes Poisson loading of droplets, but such description is not intended to exclude non-Poisson loading, as the invention is compatible with all distributions of DNA loading that conform to limiting or terminal dilution.

The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as U.S. Pat. No. RE41,780) and European publication number EP2047910 to Raindance Technologies Inc. The content of each of which is incorporated by reference herein in its entirety.

Figure 2:
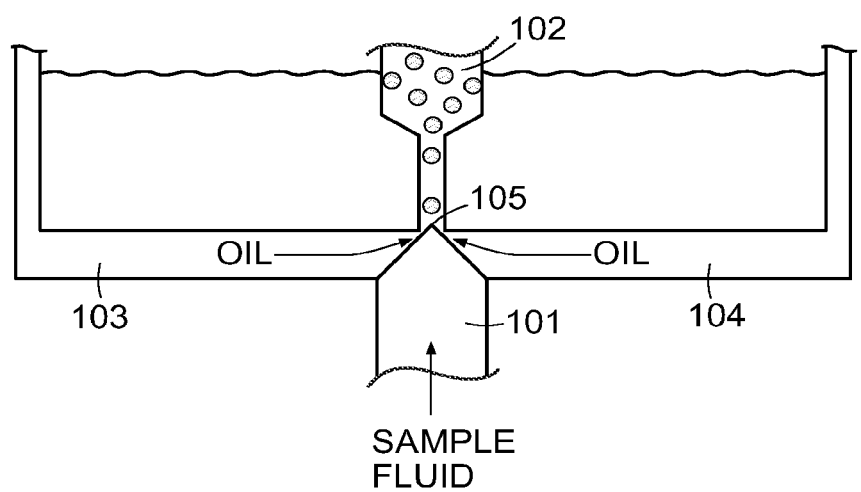
FIG. 2 depicts a portion of the droplet formation device of FIG. 1.

FIG. 1 shows an exemplary embodiment of a device 100 for droplet formation. Device 100 includes an inlet channel 101, and outlet channel 102, and two carrier fluid channels 103 and 104. Channels 101, 102, 103, and 104 meet at a junction 105. Inlet channel 101 flows sample fluid to the junction 105. Carrier fluid channels 103 and 104 flow a carrier fluid that is immiscible with the sample fluid to the junction 105. Inlet channel 101 narrows at its distal portion wherein it connects to junction 105 (See FIG. 2). Inlet channel 101 is oriented to be perpendicular to carrier fluid channels 103 and 104. Droplets are formed as sample fluid flows from inlet channel 101 to junction 105, where the sample fluid interacts with flowing carrier fluid provided to the junction 105 by carrier fluid channels 103 and 104. Outlet channel 102 receives the droplets of sample fluid surrounded by carrier fluid.

The sample fluid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with nucleic acid molecules can be used. The carrier fluid is one that is immiscible with the sample fluid. The carrier fluid can be a non-polar solvent, decane (e g., tetradecane or hexadecane), fluorocarbon oil, silicone oil or another oil (for example, mineral oil).

In certain embodiments, the carrier fluid contains one or more additives, such as agents which increase, reduce, or otherwise create non-Newtonian surface tensions (surfactants) and/or stabilize droplets against spontaneous coalescence on contact. Surfactants can include Tween, Span, fluorosurfactants, and other agents that are soluble in oil relative to water. In some applications, performance is improved by adding a second surfactant, or other agent, such as a polymer or other additive, to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be coated with a surfactant or a mixture of surfactants. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

In certain embodiments, the carrier fluid may be caused to flow through the outlet channel so that the surfactant in the carrier fluid coats the channel walls. In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Flourinert (3M)), which then serves as the carrier fluid.

One approach to merging sample fluids, using a device called a lambda injector, involves forming a droplet, and contacting the droplet with a fluid stream, in which a portion of the fluid stream integrates with the droplet to form a mixed droplet. In this approach, only one phase needs to reach a merge area in a form of a droplet. Further description of such method is shown in the co-owned and co-pending U.S. patent application to Yurkovetsky, et al. (U.S. patent application Ser. No. 61/441,985), the content of which is incorporated y reference herein in its entirety.

According to a method for operating the lambda injector, a droplet is formed as described above. After formation of the sample droplet from the first sample fluid, the droplet is contacted with a flow of a second sample fluid stream. Contact between the droplet and the fluid stream results in a portion of the fluid stream integrating with the droplet to form a mixed droplet.

The droplets of the first sample fluid flow through a first channel separated from each other by immiscible carrier fluid and suspended in the immiscible carrier fluid. The droplets are delivered to the merge area, i.e., junction of the first channel with the second channel, by a pressure-driven flow generated by a positive displacement pump. While droplet arrives at the merge area, a bolus of a second sample fluid is protruding from an opening of the second channel into the first channel. Preferably, the channels are oriented perpendicular to each other. However, any angle that results in an intersection of the channels may be used.

The bolus of the second sample fluid stream continues to increase in size due to pumping action of a positive displacement pump connected to channel, which outputs a steady stream of the second sample fluid into the merge area. The flowing droplet containing the first sample fluid eventually contacts the bolus of the second sample fluid that is protruding into the first channel. Contact between the two sample fluids results in a portion of the second sample fluid being segmented from the second sample fluid stream and joining with the first sample fluid droplet to form a mixed droplet. In certain embodiments, each incoming droplet of first sample fluid is merged with the same amount of second sample fluid.

In certain embodiments, an electric charge is applied to the first and second sample fluids. Description of applying electric charge to sample fluids is provided in Link et al. (U.S. patent application number 2007/0003442) and European Patent Number EP2004316 to Raindance Technologies Inc, the content of each of which is incorporated by reference herein in its entirety. Electric charge may be created in the first and second sample fluids within the carrier fluid using any suitable technique, for example, by placing the first and second sample fluids within an electric field (which may be AC, DC, etc.), and/or causing a reaction to occur that causes the first and second sample fluids to have an electric charge, for example, a chemical reaction, an ionic reaction, a photocatalyzed reaction, etc.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can be used.

The electric field facilitates rupture of the interface separating the second sample fluid and the droplet. Rupturing the interface facilitates merging of bolus of the second sample fluid and the first sample fluid droplet. The forming mixed droplet continues to increase in size until it a portion of the second sample fluid breaks free or segments from the second sample fluid stream prior to arrival and merging of the next droplet containing the first sample fluid. The segmenting of the portion of the second sample fluid from the second sample fluid stream occurs as soon as the shear force exerted on the forming mixed droplet by the immiscible carrier fluid overcomes the surface tension whose action is to keep the segmenting portion of the second sample fluid connected with the second sample fluid stream. The now fully formed mixed droplet continues to flow through the first channel.

In other embodiments, the rupture of the interface can be spontaneous, or the rupture can be facilitated by surface chemistry. The invention is not limited in regard to the method of rupture at the interface, as rupture can be brought about by any means.

In the context of PCR, in a preferred embodiment, the first sample fluid contains nucleic acid templates. Droplets of the first sample fluid are formed as described above. Those droplets will include the nucleic acid templates. In certain embodiments, the droplets will include only a single nucleic acid template, and thus digital PCR can be conducted. The second sample fluid contains reagents for the PCR reaction. Such reagents generally include Taq polymerase, deoxynucleotides of type A, C, G and T, magnesium chloride, and forward and reverse primers, all suspended within an aqueous buffer. The second fluid also includes detectably labeled probes for detection of the amplified target nucleic acid, the details of which are discussed below. A droplet containing the nucleic acid is then caused to merge with the PCR reagents in the second fluid as described above, producing a droplet that includes Taq polymerase, deoxynucleotides of type A, C, G and T, magnesium chloride, forward and reverse primers, detectably labeled probes, and the target nucleic acid. In another embodiment, the first fluid can contain the template DNA and PCR master mix (defined below), and the second fluid can contain the forward and reverse primers and the probe. The invention is not restricted in any way regarding the constituency of the first and second fluidics for PCR or digital PCR. For example, in some embodiments, the template DNA is contained in the second fluid inside droplets.

Target Amplification

Methods of the invention further involve amplifying the target nucleic acid in each droplet. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification, transcription based amplification system, nucleic acid sequence-based amplification, rolling circle amplification, and hyper-branched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

To effect amplification, primers are annealed to their complementary sequence within the target molecule. Following annealing, the primers are extended with a polymerase so as to form a new pair of complementary strands. The steps of denaturation, primer annealing and polymerase extension can be repeated many times (i.e., denaturation, annealing and extension constitute one cycle; there can be numerous cycles) to obtain a high concentration of an amplified segment of a desired target sequence. The length of the amplified segment of the desired target sequence is determined by relative positions of the primers with respect to each other and by cycling parameters, and therefore, this length is a controllable parameter.

Methods for performing PCR in droplets are shown for example in Link et al. (U.S. patent application numbers 2008/0014589, 2008/0003142, and 2010/0137163), Anderson et al. (U.S. Pat. No. 7,041,481 and which reissued as U.S. Pat. No. RE41,780) and European publication number EP2047910 to Raindance Technologies Inc. The content of each of which is incorporated by reference herein in its entirety.

The sample droplet may be pre-mixed with a primer or primers, or the primer or primers may be added to the droplet. In some embodiments, droplets created by segmenting the starting sample are merged with a second set of droplets including one or more primers for the target nucleic acid in order to produce final droplets. The merging of droplets can be accomplished using, for example, one or more droplet merging techniques described for example in Link et al. (U.S. patent application numbers 2008/0014589, 2008/0003142, and 2010/0137163) and European publication number EP2047910 to Raindance Technologies Inc.

In embodiments involving merging of droplets, two droplet formation modules are used. In one embodiment, a first droplet formation module produces the sample droplets consistent with limiting or terminal dilution of target nucleic acid. A second droplet formation or reinjection module inserts droplets that contain reagents for a PCR reaction. Such droplets generally include the "PCR master mix" (known to those in the art as a mixture containing at least Taq polymerase, deoxynucleotides of type A, C, G and T, and magnesium chloride) and forward and reverse primers (known to those in the art collectively as "primers"), all suspended within an aqueous buffer. The second droplet also includes detectably labeled probes for detection of the amplified target nucleic acid, the details of which are discussed below. Different arrangements of reagents between the two droplet types is envisioned. For example, in another embodiment, the template droplets also contain the PCR master mix, but the primers and probes remain in the second droplets. Any arrangement of reagents and template DNA can be used according to the invention.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule (Td=2(A+T)+4(G+C)). Another method for determining the melting temperature of primers is the nearest neighbor method Computer programs can also be used to design primers, including but not limited to Array Designer Software (Arrayit Inc.), Oligonucleotide Probe Sequence Design Software for Genetic Analysis (Olympus Optical Co.), NetPrimer, and DNAs is from Hitachi Software Engineering. The TM (melting or annealing temperature) of each primer is calculated using software programs such as Oligo Design, available from Invitrogen Corp.

According to certain aspects, primers suitable for use in methods of the invention each include a first targeting arm coupled to a second targeting arm via a bridge section (e.g. the first and second targeting arms flank the bridge section). The first and second targeting arms of a primer are designed to hybridize (at least partially) to different nucleic acids on a single nucleic acid template. That is, the first targeting arm targets a first region and the second targeting arm targets a second region. The first and second regions may be separated by one or more nucleotides. The bridge section includes a sequence that does not hybridize to any naturally occurring sequence. Accordingly, when bound, the bridge section of the primer do not hybridize to nucleic acid on the template nucleic acid. Each droplet includes primer pairs that hybridize to different nucleic acid templates. For example, a single droplet may include primer pairs in which a set of the primer hybridize to sites on chromosome 21, a set of the primer hybridize to sites on chromosome 10, a set of the primer hybridize to sites on chromosome 3, a set of the primer hybridize to sites on chromosome 2, etc. Any number of different sets of primer pairs may be put into droplets. For example, some droplets may include sets of primer pairs against two or more different chromosomes, three or more different chromosomes, five or more different chromosomes, ten or more different chromosomes, twenty or more different chromosomes, or all 24 chromosomes.

The target site may include a few nucleotides to about 100 or more nucleotides on the single nucleic acid template. For example, primers can be designed to capture targets having lengths in the range of up to 10, 20, 30, 40, 50, 60, 70, 80, 90, 100, or more bases (or base pairs). It should be appreciated that primers can be used to target single-stranded or double-stranded template nucleic acid. It is to be appreciated that the length of the target site of the template nucleic acid may be selected based upon multiple considerations (e.g. constraints on the droplet size). In one example, where analysis of the target involves sequencing, e.g., with a next-generation sequencer, the target length should typically match the sequencing read-length so that shotgun library construction is not necessary. However, it should be appreciated that captured nucleic acids may be sequenced using any suitable sequencing technique as aspects of the invention are not limited in this respect.

The targeting arms of primers according to certain aspects may be of the same length or of different lengths. The targeting arms may consist of any number of nucleotides (e.g., in the ranges of 1-200 bases) configured to hybridize to specific regions of the target template. The targeting arms of each primer of the plurality of primers within a droplet are either, for example, chromosome-specific or mutation-specific.

The bridge section (flanked by the first and second targeting arms) is formed from a nucleotide sequence that is not complementary to and does not hybridize to the single nucleic acid template. The bridge section may include one or more nucleotides, which may be the same or different from the number of nucleotides spanning between the first region and the second region of the target site. For multiplex reactions, the bridge section of a primer corresponds to a unique probe that is designed to hybridize to a complement of the bridge section. This allows a primer hybridized to a target site to be detected via the probe hybridized to a complement of the bridge section after the an amplification reaction. For primer pairs, the bridge section of each primer of a primer pair may be the same or different. Preferably, each primer of a primer pair has the same bridge section so that a corresponding probe will bind to either primer for detection of a target site specific to the primer pair.

Probes designed to hybridize to a complement of a primer bridge region allow the target template nucleic acid to be detected. Preferably, the droplet contains two or more probes, e.g., 2, 3, 4, 5, 6, 7, 8, 9, 10, 12, 14, 16, 18, 20, 25, 30, 35, 40, 45, 50, 55, 60, 65, 60, 75, 80, 85, 90, 95, 100, 110, 120, 130, 140, 150, 160, 170, 180, 190, 200, 500, or more probes, each being specific to a complement of a bridge region. A probe may be designed to hybridize to the complement of the bridge region or a portion thereof. Each probe (or member) of a plurality of probes in a droplet may include a detectable label. Probes of the plurality of probes may be grouped together and at varying concentrations within the droplet. Members (probes) of each group may include the same detectable label. Alternatively, each probe may include a unique detectable label. Types of detectable labels suitable for use with probes specific to bridge regions of a primer and other probes for use in methods of the invention are described hereinafter.

In one embodiment, the droplet formation modules are arranged and controlled to produce an interdigitation of sample droplets and PCR reagent droplets flowing through a channel. Such an arrangement is described for example in Link et al. (U.S. patent application numbers 2008/0014589, 2008/0003142, and 2010/0137163) and European publication number EP2047910 to Raindance Technologies Inc.

A sample droplet is then caused to merge with a PCR reagent droplet, producing a droplet that includes the PCR master mix, primers, detectably labeled probes, and the target nucleic acid. Droplets may be merged for example by: producing dielectrophoretic forces on the droplets using electric field gradients and then controlling the forces to cause the droplets to merge; producing droplets of different sizes that thus travel at different velocities, which causes the droplets to merge; and producing droplets having different viscosities that thus travel at different velocities, which causes the droplets to merge with each other. Each of those techniques is further described in Link et al. (U.S. patent application numbers 2008/0014589, 2008/0003142, and 2010/0137163) and European publication number EP2047910 to Raindance Technologies Inc. Further description of producing and controlling dielectrophoretic forces on droplets to cause the droplets to merge is described in Link et al. (U.S. patent application number 2007/0003442) and European Patent Number EP2004316 to Raindance Technologies Inc.

In another embodiment, called simple droplet generation, a single droplet formation module, or a plurality of droplet formation modules are arranged to produce droplets from a mixture already containing the template DNA, the PCR master mix, primers, and detectably labeled probes. In yet another embodiment, called co-flow, upstream from a single droplet formation module two channels intersect allowing two flow streams to converge. One flow stream contains one set of reagents and the template DNA, and the other contains the remaining reagents. In the preferred embodiment for co-flow, the template DNA and the PCR master mix are in one flow stream, and the primers and probes are in the other. However, the invention is not limited in regard to the constituency of either flow stream. For example, in another embodiment, one flow stream contains just the template DNA, and the other contains the PCR master mix, the primers, and the probes. On convergence of the flow streams in a fluidic intersection, the flow streams may or may not mix before the droplet generation nozzle. In either embodiment, some amount of fluid from the first stream, and some amount of fluid from the second stream are encapsulated within a single droplet. Following encapsulation, complete mixing occurs.

Once final droplets have been produced by any of the droplet forming embodiments above, or by any other embodiments, the droplets are thermal cycled, resulting in amplification of the target nucleic acid in each droplet. In certain embodiments, the droplets are collected off-chip as an emulsion in a PCR thermal cycling tube and then thermally cycled in a conventional thermal cycler. Temperature profiles for thermal cycling can be adjusted and optimized as with any conventional DNA amplification by PCR.

In certain embodiments, the droplets are flowed through a channel in a serpentine path between heating and cooling lines to amplify the nucleic acid in the droplet. The width and depth of the channel may be adjusted to set the residence time at each temperature, which can be controlled to anywhere between less than a second and minutes.

In certain embodiments, the three temperature zones are used for the amplification reaction. The three temperature zones are controlled to result in denaturation of double stranded nucleic acid (high temperature zone), annealing of primers (low temperature zones), and amplification of single stranded nucleic acid to produce double stranded nucleic acids (intermediate temperature zones). The temperatures within these zones fall within ranges well known in the art for conducting PCR reactions. See for example, Sambrook et al. (Molecular Cloning, A Laboratory Manual, $3^{rd}$ edition, Cold Spring Harbor Laboratory Press, Cold Spring Harbor, N.Y., 2001).

In certain embodiments, the three temperature zones are controlled to have temperatures as follows: 95° C. ($T_H$), 55° C. ($T_L$), 72° C. ($T_M$). The prepared sample droplets flow through the channel at a controlled rate. The sample droplets first pass the initial denaturation zone ($T_H$) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the high temperature zone, of approximately 95° C., where the sample is first separated into single stranded DNA in a process called denaturation. The sample then flows to the low temperature, of approximately 55° C., where the hybridization process takes place, during which the primers anneal to the complementary sequences of the sample. Finally, as the sample flows through the third medium temperature, of approximately 72° C., the polymerase process occurs when the primers are extended along the single strand of DNA with a thermostable enzyme. Methods for controlling the temperature in each zone may include but are not limited to electrical resistance, peltier junction, microwave radiation, and illumination with infrared radiation.

The nucleic acids undergo the same thermal cycling and chemical reaction as the droplets passes through each thermal cycle as they flow through the channel. The total number of cycles in the device is easily altered by an extension of thermal zones or by the creation of a continuous loop structure. The sample undergoes the same thermal cycling and chemical reaction as it passes through N amplification cycles of the complete thermal device.

In other embodiments, the temperature zones are controlled to achieve two individual temperature zones for a PCR reaction. In certain embodiments, the two temperature zones are controlled to have temperatures as follows: 95° C. ($T_H$) and 60° C. ($T_L$). The sample droplet optionally flows through an initial preheat zone before entering thermal cycling. The preheat zone may be important for some chemistry for activation and also to ensure that double stranded nucleic acid in the droplets are fully denatured before the thermal cycling reaction begins. In an exemplary embodiment, the preheat dwell length results in approximately 10 minutes preheat of the droplets at the higher temperature.

The sample droplet continues into the high temperature zone, of approximately 95° C., where the sample is first separated into single stranded DNA in a process called denaturation. The sample then flows through the device to the low temperature zone, of approximately 60° C., where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing.

In another embodiment the droplets are created and/or merged on chip followed by their storage either on the same chip or another chip or off chip in some type of storage vessel such as a PCR tube. The chip or storage vessel containing the droplets is then cycled in its entirety to achieve the desired PCR heating and cooling cycles.

In another embodiment the droplets are collected in a chamber where the density difference between the droplets and the surrounding oil allows for the oil to be rapidly exchanged without removing the droplets. The temperature of the droplets can then be rapidly changed by exchange of the oil in the vessel for oil of a different temperature. This technique is broadly useful with two and three step temperature cycling or any other sequence of temperatures.

The invention is not limited by the method used to thermocycle the droplets. Any method of thermocycling the droplets may be used.

Target Detection

After amplification, droplets are flowed to a detection module for detection of amplification products. For embodiments in which the droplets are thermally cycled off-chip, the droplets require re-injection into either a second fluidic circuit for read-out—that may or may not reside on the same chip as the fluidic circuit or circuits for droplet generation—or in certain embodiments the droplets may be reinjected for read-out back into the original fluidic circuit used for droplet generation. The droplets may be individually analyzed and detected using any methods known in the art, such as detecting the presence or amount of a reporter. Generally, the detection module is in communication with one or more detection apparatuses. The detection apparatuses can be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at a sorting module. Further description of detection modules and methods of detecting amplification products in droplets are shown in Link et al. (U.S. patent application numbers 2008/0014589, 2008/0003142, and 2010/0137163) and European publication number EP2047910 to Raindance Technologies Inc.

In certain embodiments, amplified target are detected using detectably labeled probes. In particular embodiments, the detectably labeled probes are optically labeled probes, such as fluorescently labeled probes. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. Preferred fluorescent labels are FAM and VIC™ (from Applied Bio systems). Labels other than fluorescent labels are contemplated by the invention, including other optically-detectable labels.

In certain aspects, the droplets of the invention contain a plurality of detectable probes that hybridize to amplicons produced in the droplets. Members of the plurality of probes can each include the same detectable label, or a different detectable label. The plurality of probes can also include one or more groups of probes at varying concentration. The groups of probes at varying concentrations can include the same detectable label which vary in intensity, due to varying probe concentrations. In some embodiments, the droplets of the invention contain a plurality of barcodes that hybridize to amplicons produced in the droplets or are incorporated into the amplicons. The barcodes may be used in lieu of fluorescent probes, to detect the presence of a target sequence, or the barcodes can be used in addition to fluorescent probes, to track a multitude of sample sources. A detectable barcode-type label can be any barcode-type label known in the art including, for example, barcoded magnetic beads (e.g., from Applied Biocode, Inc., Santa Fe Springs, Calif.), and nucleic acid sequences. Nucleic acid barcode sequences typically include a set of oligonucleotides ranging from about 4 to about 20 oligonucleotide bases (e.g., 8-10 oligonucleotide bases) and uniquely encode a discrete library member without containing significant homology to any sequence in the targeted sample.

The barcode sequence generally includes features useful in sequencing reactions. For example, the barcode sequences are designed to have minimal or no homopolymer regions, i.e., 2 or more of the same base in a row such as AA or CCC, within the barcode sequence. The barcode sequences are also designed so that they are at least one edit distance away from the base addition order when performing base-by-base sequencing, ensuring that the first and last base do not match the expected bases of the sequence. In certain embodiments, the barcode sequences are designed to be correlated to a particular subject, allowing subject samples to be distinguished. Designing barcodes is shown U.S. Pat. No. 6,235, 475, the contents of which are incorporated by reference herein in their entirety.

In some instances, the primers used in the invention (including, e.g, primers having targeting arms flanked with a bridge section) may include barcodes such that the barcodes will be incorporated into the amplified products. For example, the unique barcode sequence could be incorporated into the 5' end of the primer, or the barcode sequence could be incorporated into the 3' end of the primer. In some embodiments, the barcodes may be incorporated into the amplified products after amplification. For example, a suitable restriction enzyme (or other endonuclease) may be introduced to a sample, e.g., a droplet, where it will cut off an end of an amplification product so that a barcode can be added with a ligase.

Attaching barcode sequences to nucleic acids is shown in U.S. Pub. 2008/0081330 and PCT/US09/64001, the content of each of which is incorporated by reference herein in its entirety. Methods for designing sets of barcode sequences and other methods for attaching barcode sequences are shown in U.S. Pat. Nos. 6,138,077; 6,352,828; 5,636,400; 6,172,214; 6,235,475; 7,393,665; 7,544,473; 5,846,719; 5,695,934; 5,604,097; 6,150,516; RE39,793; 7,537,897; 6,172,218; and 5,863,722, the content of each of which is incorporated by reference herein in its entirety.

In a separate embodiment the detection can occur by the scanning of droplets confined to a monolayer in a storage device that is transparent to the wavelengths or method or detection. Droplets stored in this fashion can be scanned either by the movement of the storage device by the scanner or the movement of the scanner over the storage device.

The invention is not limited to the TaqMan assay, as described above, but rather the invention encompasses the use of all fluorogenic DNA hybridization probes, such as molecular beacons, Solaris probes, scorpion probes, and any other probes that function by sequence specific recognition of target DNA by hybridization and result in increased fluorescence on amplification of the target sequence.

Digital PCR Performance in Droplets

Digital PCR performance in the emulsion format was validated by measuring a serial dilution of a reference gene, branched chain keto acid dehydrogenase E1 (BCKDHA). Mixtures of the PCR master mix, 1× primers and probe for BCKDHA, and varying concentrations of a mixture of human genomic DNA (1:1 NA14091 and NA13705) were compartmentalized into over one million 5.3 pL droplets in a water-in-fluorinated oil emulsion using the droplet generation microfluidic chip. The emulsion was thermally cycled off-chip and afterwards the fluorescence of each droplet was analyzed by fluorescence in the readout chip (see FIGS. 3A-3C).

Figure 3A:
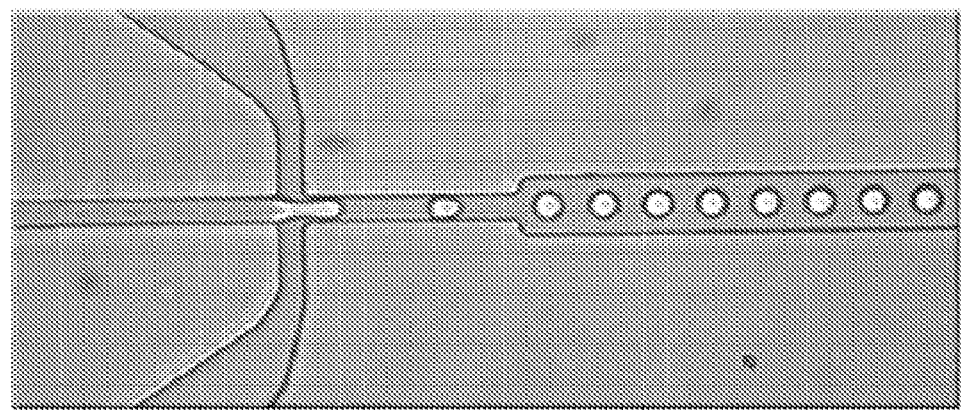
FIGS. 3A-3C depicts an exemplary microfluidic system for droplet generation and readout.
Figure 3B:
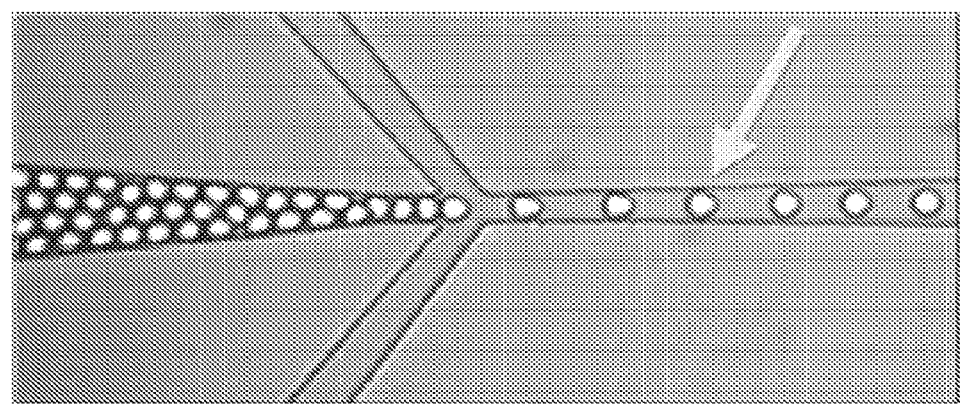
Figure 3C:
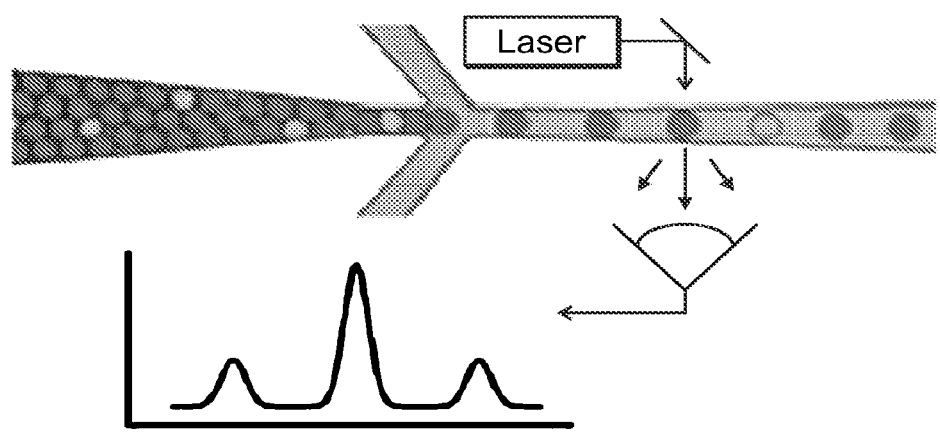

An exemplary microfluidic system for droplet generation and readout is depicted in FIGS. 3A-3C. The microfluidic system for droplet generation and readout. As shown in FIG. 3A (droplet generation chip), a continuous aqueous phase containing the PCR master mix, primers, and probes, and template DNA flowed into the fluidic intersection from the left, and the carrier oil entered from the top and bottom. An emerging bolus of aqueous liquid was imaged inside the intersection just prior to snapping off into a discrete 4 pL droplet as the fluidic strain began to exceed the surface tension of the aqueous liquid. The steady train of droplets leaving the intersection toward the right was collected off chip as a stable emulsion for thermal cycling. FIG. 3B depicts the droplet spacing for readout. Flows were arranged as in FIG. 3A, except instead of a continuos phase, the emulsion from (a) was injected from the left into the intersection after thermal cycling. The oil drained from the emulsion during off-chip handling, hence the emulsion appeared tightly packed in the image before the intersection. The oil introduced in the intersection separated the droplets and the fluorescence of each droplet was measured at the location marked by the arrow. FIG. 3C depicts a cartoon of droplet readout by fluorescence. The relatively infrequent PCR(+) droplets (light gray) flow along with the majority of PCR(−) droplets (dark gray) toward the detector. The droplets were interrogated sequentially by laser induced fluorescence while passing through the detection region.

In a serial dilution the average number of target DNA molecules per droplet—called the "occupancy" from this point forward—should decrease in direct proportion to the DNA concentration. The occupancy was calculated from Poisson statistics using the following equation well known to those experienced in the art:

$$\text{occupancy} = \ln\left(\frac{P+N}{N}\right), \quad (1)$$

where P and N are the numbers of PCR(+) and PCR(−) droplets respectively.

Figure 4A:
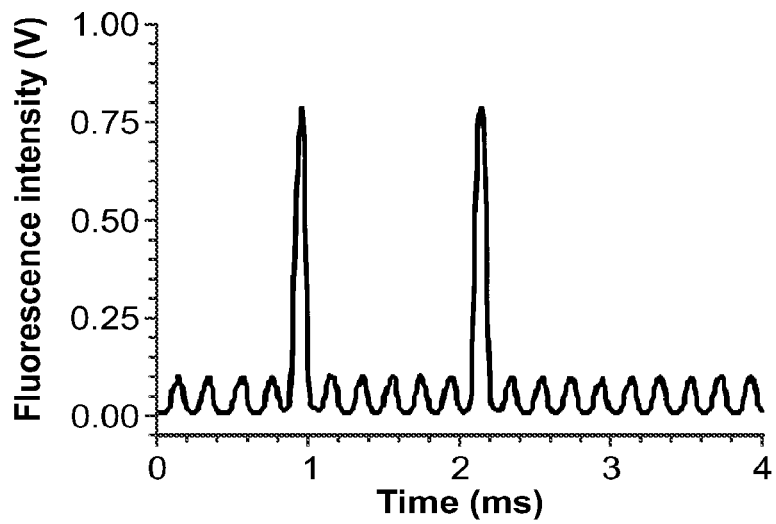
FIGS. 4A-4C depicts the serial dilution of template DNA quantified by dPCR.
Figure 4B:
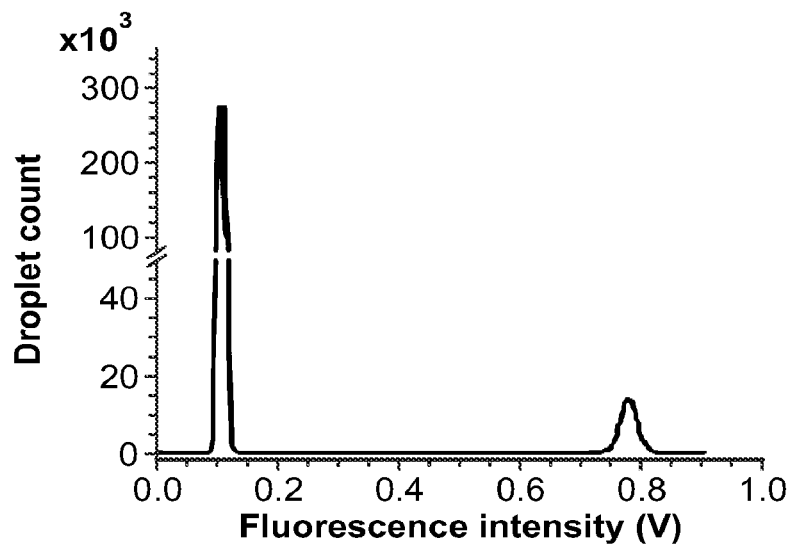
Figure 4C:
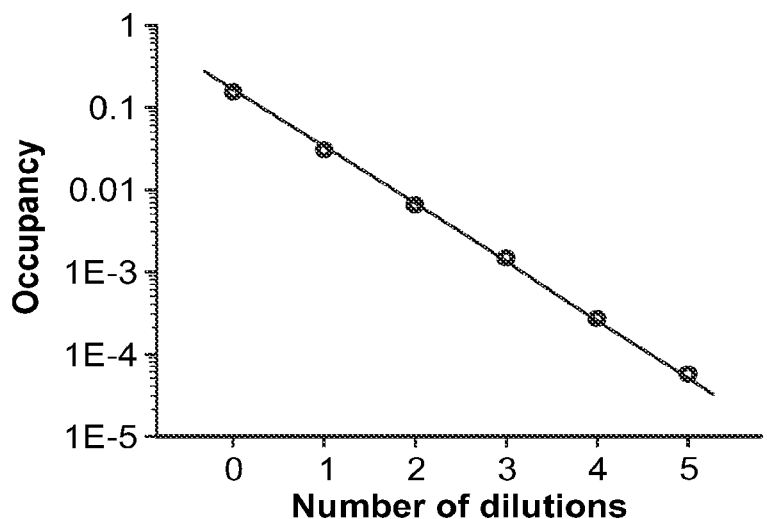

Droplets were analyzed by fluorescence while flowing through the readout chip to count the numbers of PCR(+) and PCR(−) droplets (see FIG. 3C). As each droplet passed the detection zone (marked with an arrow in FIG. 3B), a burst of fluorescence was observed. To account for small run-to-run differences in the fluorescence intensity that can occur due to different chip positioning, etc., each set of data was scaled such that the average fluorescence intensity of the empty droplets was 0.1 V. FIG. 4A shows a very short duration of a typical trace of fluorescence bursts from individual droplets for the sample with the highest DNA concentration in the series. PCR(+) and PCR(−) droplets were easily discriminated by fluorescence intensity. The two large bursts of fluorescence peaking at −0.8 V arose from the PCR(+) droplets, whereas the smaller bursts due to incomplete fluorescence quenching in the PCR(−) droplets peaked at −0.1 V. A histogram of peak intensities from the complete data set revealed two clear populations centered at 0.10 and 0.78 V (FIG. 4B), demonstrating that the trend evident in the short trace in FIG. 4A was stable over much longer periods of time. Integration over the two populations in FIG. 4B yielded a total of 197,507 PCR(+) and 1,240,126 PCR(−) droplets. Hence the occupancy was 0.15 for this sample by Eqn. 1, corresponding to the expected occupancy of 0.18 based on the measured DNA concentration of 110 ng/µL. The occupancy was measured for each sample in the serial dilution and fit to the dilution equation:

$$\text{occupancy}(n) = \frac{A}{f^n}, \quad (2)$$

where n is the number of dilutions, A is the occupancy at the starting concentration (n=0), and f is the dilution factor. The linear fit was in excellent agreement with the data, with an $R^2$ value of 0.9999 and the fitted dilution factor of 4.8 in close agreement with the expected value of 5.0.

Multiplexing Primers in a Digital PCR Reaction

Droplet based digital PCR technology, as described in Link et al. (U.S. patent application numbers 2008/0014589, 2008/0003142, and 2010/0137163), Anderson et al. (U.S. Pat. No. 7,041,481 and which reissued as U.S. Pat. No. RE41,780) and European publication number EP2047910 to Raindance Technologies Inc, (the contents of each of which are incorporated by reference herein in their entireties) utilizes a single primer pair per library droplet. This library droplet is merged with a template droplet which contains all the PCR reagents including genomic DNA except for the primers. After merging of the template and the primer library droplets the new droplet now contains all the reagents necessary to perform PCR. The droplet is then thermal cycled to produce amplicons. In one embodiment, the template DNA is diluted in the template mix such that on average there is less than one haploid genome per droplet.

Having only one haploid genome (i.e., one allele) per droplet gives droplet PCR advantages over standard singleplex or multiplex PCR in tubes or microwells. For example, in traditional PCR, both alleles are present in the reaction mix so if there is a difference in the PCR efficiency between alleles, the allele with the highest efficiency will be over represented. Additionally, there can be variances in the sequence to which the PCR primers hybridize, despite careful primer design. A variance in the primer hybridization sequence can cause that primer to have a lower efficiency for hybridization for the allele that has the variance compared to the allele that has the wild type sequence. This can also cause one allele to be amplified preferentially over the other allele if both alleles are present in the same reaction mix.

These issues are avoided in droplet based PCR because there is only one template molecule per droplet, and thus one allele per droplet. Thus, even if primer variance exists that reduces the PCR efficiency for one allele, there is no competition between alleles because the alleles are separated and thus uniformly amplified.

Optimization of traditional multiplexing of standard PCR primers in tubes or wells is known to be difficult. Multiple PCR amplicons being generated in the same reaction can lead to competition between amplicons that have differing efficiencies due to differences in sequence or length. This results in varying yields between competing amplicons which can result in non uniform amplicon yields. However, because droplet based digital PCR utilizes only one template molecule per droplet, even if there are multiple PCR primer pairs present in the droplet, only one primer pair will be active. Since only one amplicon is being generated per droplet, there is no competition between amplicons, resulting in a more uniform amplicon yield between different amplicons.

A certain amount of DNA is required to generate either a specific quantity of DNA and/or a specific number of PCR positive droplets to achieve sufficient sequencing coverage per base. Because only a percentage of the droplets are PCR positive, approximately 1 in 3 in the standard procedure, it takes more DNA to achieve the equivalent PCR yield per template DNA molecule. The number of PCR positive droplets and thus the amplicon yield can be increased by adding more genomic DNA. For instance, increasing the amount of genomic DNA twofold while maintaining the number of droplets constant will double the amplicon yield. However there is a limit to the amount of genomic DNA that can be added before there is a significant chance of having both alleles for a gene in the same droplet, thereby eliminating the advantage of droplet PCR for overcoming allele specific PCR and resulting in allelic dropout.

One way to allow the input of more genomic DNA is by generating more droplets to keep the haploid molecules per droplet ratio constant. For instance doubling the amount of DNA and doubling the amount of droplets increases the amplicon yield by 2× while maintaining the same haploid genome per droplet ratio. However, while doubling the number of droplets isn't problematic, increasing the amount of DNA can be challenging to users that have a limited amount of DNA.

The multiplexing of PCR primers in droplets enables the simultaneous increase in the number of PCR droplets while keeping the amount of input DNA the same or lower to generate an equal or greater amplicon yield. This results in an overall increase in the amount of PCR positive droplets and amplicon yield without the consumption of more DNA.

By way of example, if there is an average of 1 haploid genome per every 4 droplets or ¼ of the haploid genome per droplet and one PCR primer pair per droplet, the chances of the correct template being present for the PCR primer in the droplet is 1 out of 4. However, if there are 2 PCR primer pairs per droplet, then there is double the chance that there will be the correct template present in the droplet. This results in 1 out of 2 droplets being PCR positive which doubles the amplicon yield without doubling the input DNA. If the number of droplets containing the 2× multiplexed primers is doubled and the DNA kept constant, then the number of PCR positive droplets drops back to 1 in 4, but the total number of PCR droplets remains the same because the number of droplets have been doubled. If the multiplexing level in each droplet is increased to 4× and the input DNA is the same, the chance of the correct template molecule being present in each droplet doubles. This results in the number of PCR positive droplets being increased to 1 in 2 which doubles the amount of amplicon yield without increasing the amount of input DNA. Thus, by increasing the multiplexing of PCR primers in each droplet and by increasing the number of droplets overall, the amplicon yield can be increased by 4-fold without increasing the amount of input DNA.

Alternatively, if the amplicon yield is already sufficient, by increasing the multiplexing level for the PCR primers in each droplet, the amount of input genomic DNA can be dropped without sacrificing amplicon yield. For example if the multiplexing level of the PCR primers goes from 1× to 2×, the amount of input genomic DNA can be decreased by 2× while still maintaining the same overall amplicon yield.

Even though the number of PCR primer pairs per droplet is greater than one, there is still only one template molecule per droplet and thus there is only one primer pair per droplet that is being utilized at one time. This means that the advantages of droplet PCR for eliminating bias from either allele specific PCR or competition between different amplicons is maintained.

An example demonstration of droplet-based amplification and detection of multiple target sequences in a single droplet is shown here. Multiple copies of 5 sets of primers (primers for TERT, RNaseP, E1a, SMN1 and SMN2) were encapsulated in a single droplet at various concentrations along with the template DNA and the PCR master mix. Probes that specifically bind to TERT, RNaseP, E1a, SMN1 or SMN2 were also encapsulated in the droplets containing the primers. Probes for TERT, RNaseP and E1a were labeled with the VIC dye and probes for SMN1 and SMN2 were labeled with the FAM dye. The sequences for TERT RNaseP, E1a, SMN1 and SMN2 were amplified by PCR. The PCR was conducted with a standard thermal cycling setting. For example:

95° C. for 10 min
31 cycles
92° C. for 15 s
60° C. for 60 s

At the end of the PCR, the fluorescence emission from each droplet was determined and plotted on a scattered plot based on its wavelength and intensity. Six clusters, each representing droplets having the corresponding fluorescence wavelength and intensity were shown. The TERT, RNaseP and E1a clusters showed the fluorescence of the VIC dye at three distinct intensities and SMN1 and SMN1 clusters showed the fluorescence of the FAM dye at two distinct intensities (FIG. 5). The number of droplets, each having one or more sequences selected from TERT, RNaseP, E1a, SMN1 and SMN2, can be determined from the scattered plot.

In an another demonstration of droplet-based amplification and detection of multiple target sequences in a single droplet, 5 sets of primers (primers for TERT, RNaseP, E1a, 815A and 815G) were encapsulated in a single droplet at various concentrations along with the template DNA, the PCR master mix, and the probes. The five different probes TERT, RNaseP, E1a, 815A and 815G were also encapsulated in the droplets containing the primers. Probes for TERT and 815A were labeled with the VIC dye and probes for 815G were labeled with the FAM dye. For each of RNaseP and E1a, two probes, one labeled with the VIC dye and the other labeled with the FAM dye, were encapsulated.

The droplets containing both the primers and probes were fused with droplets containing the template. PCR reactions were conducted with the fused droplets to amply the sequences for TERT, RNaseP, E1a, 815A and 815G. The PCR was conducted with a standard thermal cycling setting.

Figure 6C:
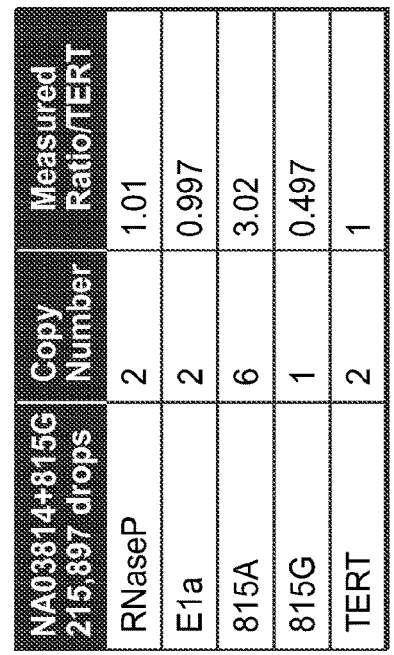
FIG. 6C is a table showing the copy number of specific sequences shown in FIG. 6B.
Figure 6B:
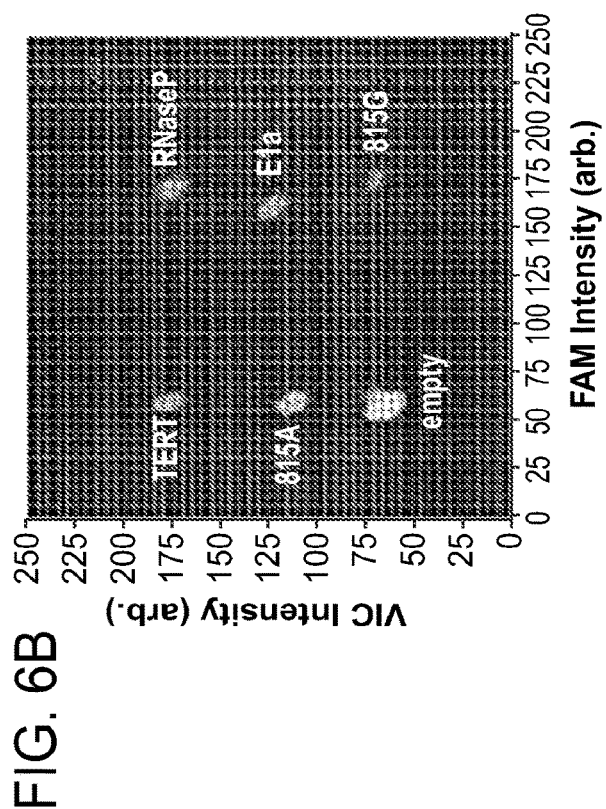
FIG. 6B is a scatter plot showing clusters representing droplets that contain specific amplified sequences (TERT, 815A, RNaseP, E1a, and 815G)
Figure 6A:
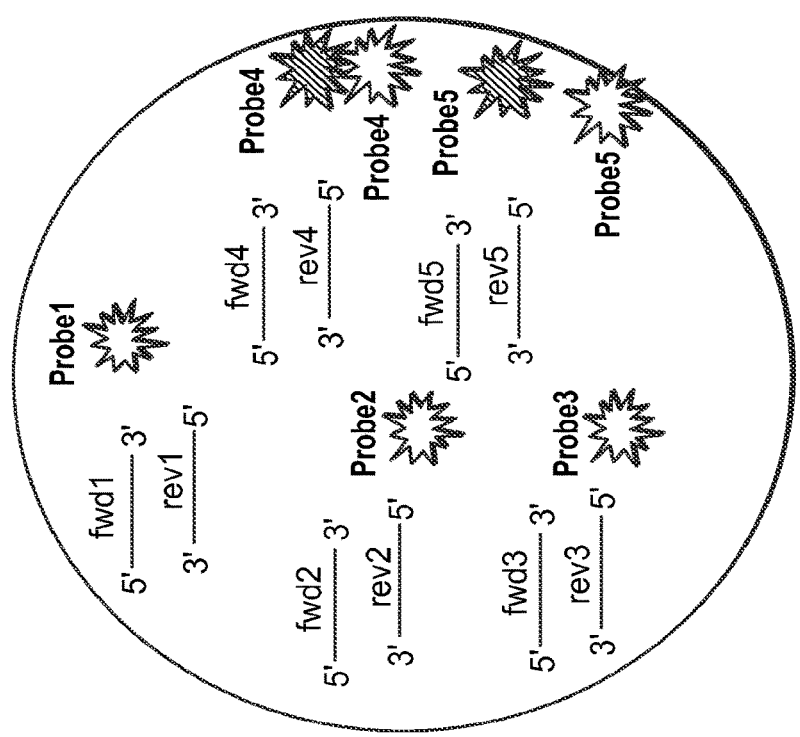
FIG. 6A is a schematic representation of a droplet having 5 sets of primers for PCR amplification of a template sequence and 5 probes, each labeled with a fluorescent dye, that binds specifically to the amplified sequences.

At the end of the PCR, the fluorescence emission from each fused droplet was determined and plotted on a scattered plot based on its wavelength and intensity. Six clusters, each representing droplets having the corresponding fluorescence wavelength and intensity were shown. The TERT and 815A clusters showed the fluorescence of the VIC dye at two distinct intensities; the 815G clusters showed the fluorescence of the FAM dye; and the RNaseP and E1a clusters showed the fluorescence of both the FAM and the VIC dye at distinct intensities (FIG. 6). The number of droplets, each having one or more sequences selected from TERT, RNaseP, E1a, 815A and 815G, can be determined from the scattered plot. The copy number of RNaseP, E1a, 815A and 815G in the template were determined by the ratio between the number of droplets having the RNaseP, E1a, 815A and/or 815G sequences and the number of droplets having the TERT sequence (FIG. 6).

In yet another exemplary demonstration of multiplexed primer pairs in a droplet-based digital PCR reaction, two droplet libraries were generated: droplet library A was generated where each droplet contained only one primer pair; and droplet library B was generated where the primer pairs were multiplexed at 5× level in each droplet. HapMap sample NA18858 was processed in duplicate with droplet libraries A or B using standard procedures. Two µg sample DNA was used for droplet library A and one µg sample DNA was used for the 5× multiplex droplet library B. After PCR amplification, both droplet libraries were broken and purified over a Qiagen MinElute column and then run on an Agilent Bioanalyzer. Samples were sequenced by Illumina on the Illumina GAII with 50 nucleotide reads and the sequencing results were analyzed using the standard sequencing metrics. The results from the 5× multiplexed droplet library B were compared to the singleplex droplet library A using standard metrics shown in the Table below.

The results obtained from the 5× multiplexed droplet library B were equivalent or better than what was obtained from droplet library A. The multiplexing of primers delivers the same sequencing results for base coverage, specificity and uniformity that the singleplexing does with the added advantage of reduced input DNA.

| Sample | Total reads | Mapped reads | Specificity | Mean base coverage | C1 | C20 | C100 | Base coverage (0.2× of mean) |
|---|---|---|---|---|---|---|---|---|
| Library A with sample 1 | 27431697 | 99.4% | 0.813 | 1394 | 99.5% | 99.0% | 98.2% | 92.8% |
| Library A with sample 2 | 15147288 | 99.4% | 0.862 | 819 | 99.1% | 98.2% | 87.6% | 78.0% |
| Library B with sample 1 | 27861378 | 99.5% | 0.847 | 1472 | 99.7% | 99.3% | 97.6% | 89.9% |

| Sample | Total reads | Mapped reads | Specificity | Mean base coverage | C1 | C20 | C100 | Base coverage (0.2x of mean) |
|---|---|---|---|---|---|---|---|---|
| Library B with sample 2 | 25758406 | 99.1% | 0.837 | 1321 | 99.8% | 99.4% | 97.9% | 91.3% |

Total reads: total number of sequencing read found within the provided sample data.
Mapped reads (%): percentage of total reads that mapped to the human genome.
Specificity: percentage of mapped reads that include the target. The target includes all amplicon sequences with primer sequences excluded.
Mean base coverage: average base coverage within the target. The target includes all amplicon sequences with primer sequences excluded.
C1: % of target that has at least 1x base coverage. Note: non-unique sequencing reads are mapped randomly.
C20: % of target that has at least 20x base coverage.
C100: % of target that has at least 100x base coverage.
Base coverage (0.2x of mean): % of target that has at least 20% of mean base coverage.

Monochromatic Gene Copy Number Assay

Figure 7A:
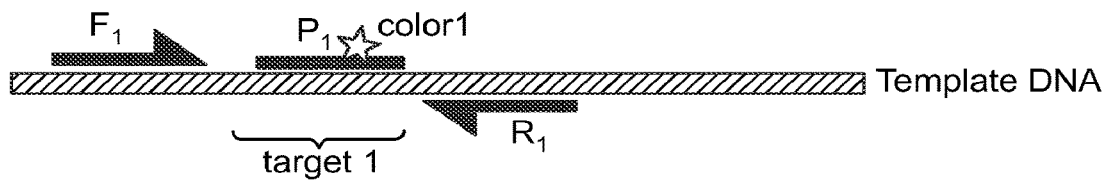
Figure 7B:
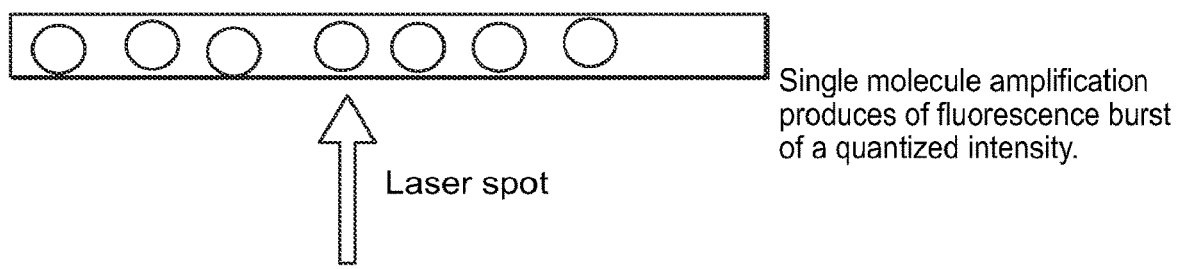
Figure 7C:
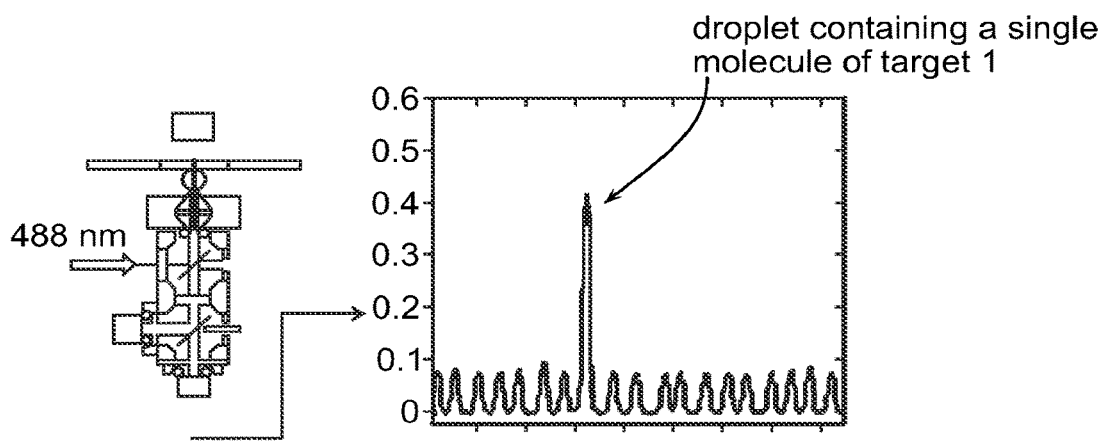

Traditional digital PCR methods involve the use of a single labeled probe specific for an individual target. FIG. 7 is a schematic depicting one-color detection of a target sequence using droplet based digital PCR. As shown in Panel A of FIG. 7, a template DNA is amplified with a forward primer (F1) and a reverse primer (R1). Probe (P1) labeled with a fluorophore of color 1 binds to the target genetic sequence (target 1). Microdroplets are made of diluted solution of template DNA under conditions of limiting or terminal dilution. Droplets containing the target sequence emit fluorescence and are detected by laser (Panels B and C). The number of microcapsules either containing or not containing the target sequence is shown in a histogram (D) and quantified (E).

Figure 8B:
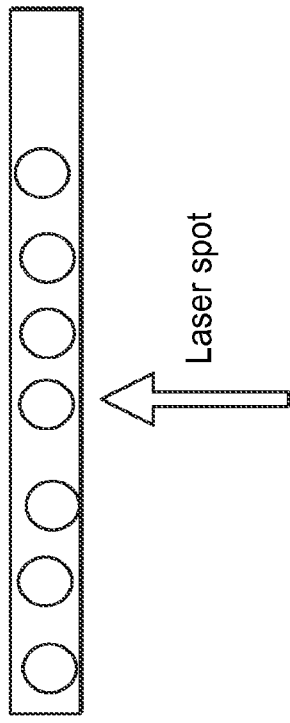
Figure 8C:
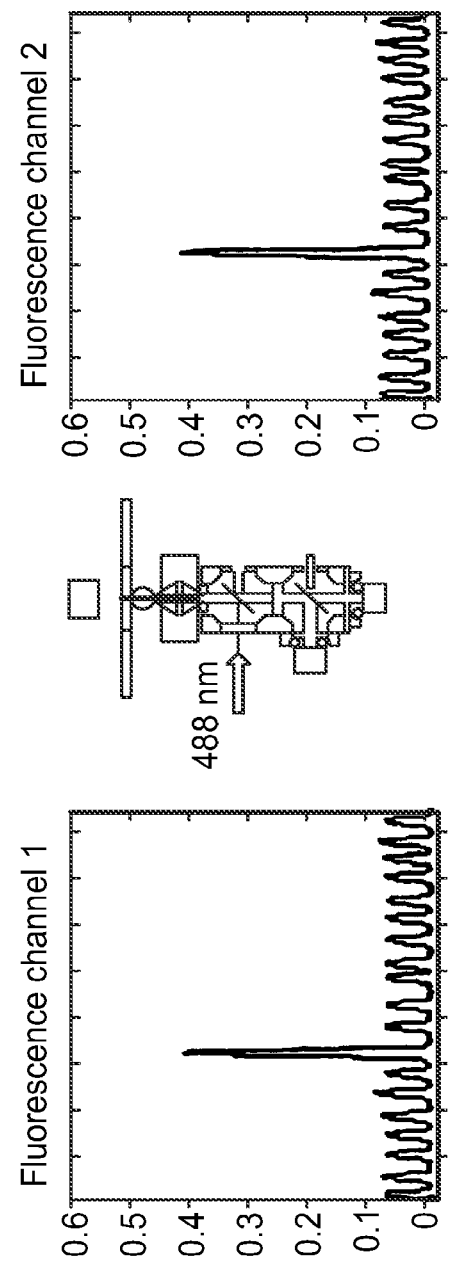
Figure 8D:
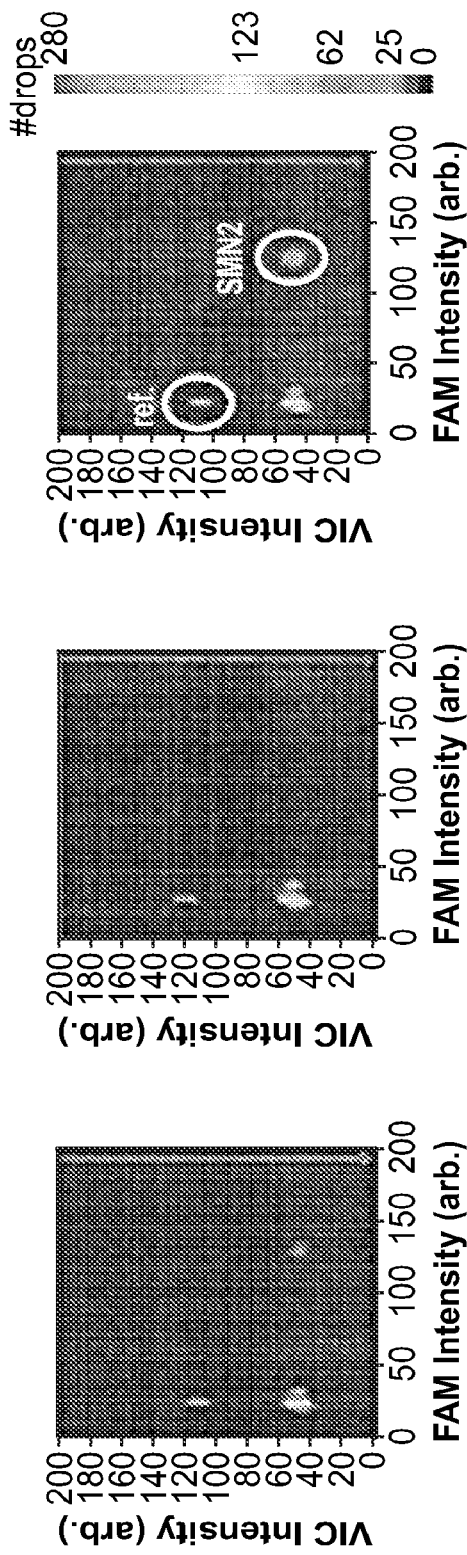
Figure 9A:
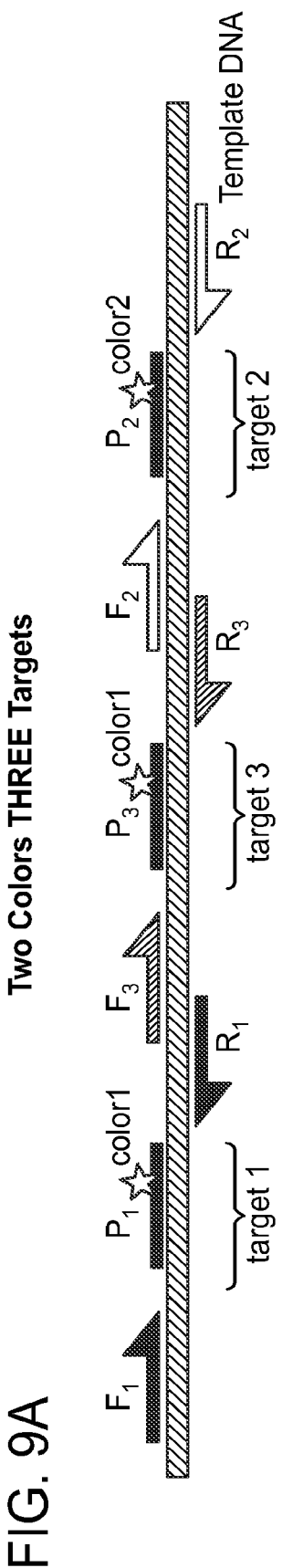
FIGS. 9A-D are a schematic depicting two-color detection of three genetic sequences with a microfluidic device.
Figure 9B:
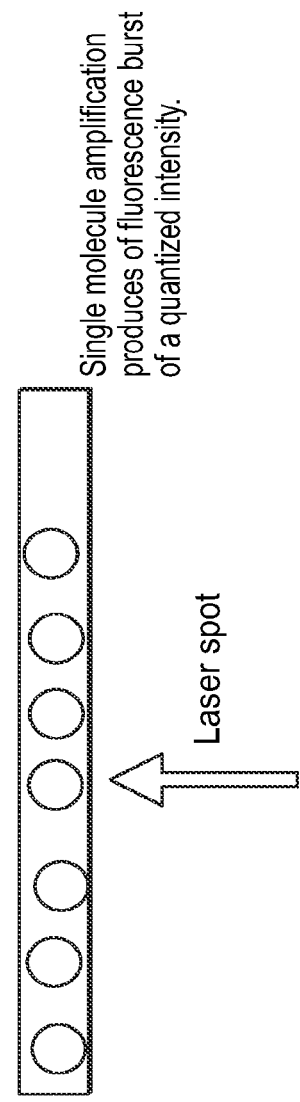
Figure 9C:
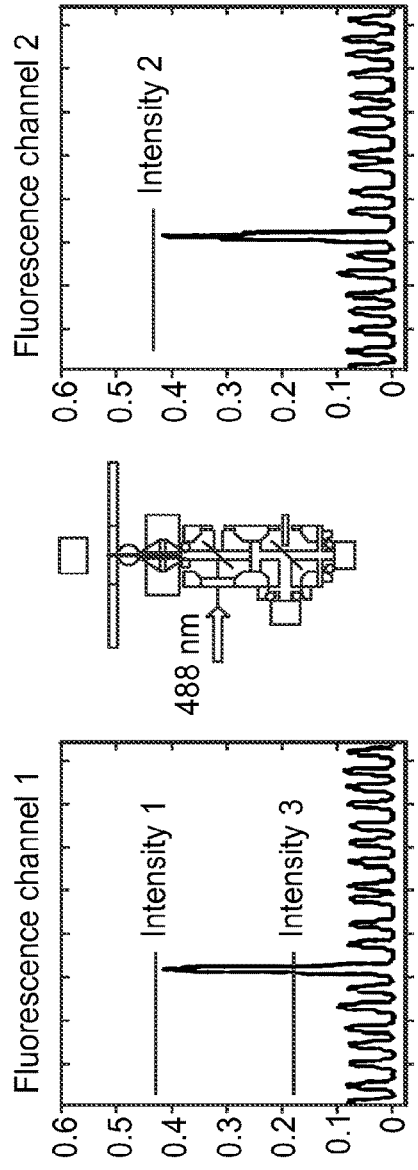
Figure 9D:
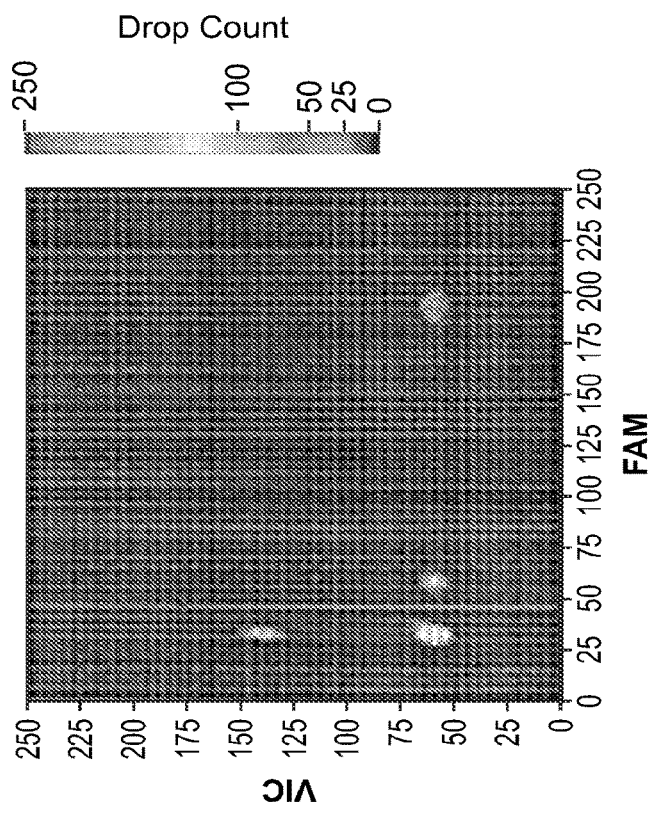

FIG. 8 is a schematic depicting two-color detection of two genetic sequences with a microfluidic device. As shown in Panel A of FIG. 8, a template DNA is amplified with two sets of primers: forward primer (F1) and a reverse primer (R1), and forward primer (F2) and a reverse primer (R2). Probe (P1) labeled with a fluorophore of color 1 binds to the target 1 and probe (P2) labeled with a fluorophore of color 2 binds to the target 2 (Panels B and C). Droplets are made of diluted solution of template DNA under conditions of limiting or terminal dilution. Droplets containing the target sequence 1 or 2 emit fluorescence of color 1 or 2 respectively and are optically detected by laser (Panels B and C). The number of microcapsules containing target 1 or 2 is shown by histogram in Panel D.

Methods of the invention involve performing accurate quantitation of multiple different DNA targets by dPCR using probes with the same fluorophore. FIG. 9 is a schematic depicting two-color detection of three genetic sequences with a microfluidic device. As shown in Panel A of FIG. 9, a template DNA is amplified with three sets of primers: forward primers (F1, F2 and F3) and reverse primers (R1, R2 and R3). Probes (P1, P2 and P3) are labeled with fluorophores (color 1, color 2 and color 1) and bind to the target genetic sequences (target 1, target 2 and target 3) (Panels B and C). Microdroplets are made of diluted solution of template DNA under conditions of limiting or terminal dilution. Microdroplets containing target sequence 1 or 3 emit fluorescence of color 1 at two different intensities; and microdroplets containing target sequence 2 emit fluorescence of color 2. The number of microdroplets containing target 1, 2 or 3 is shown by histogram in Panel D.

Recent results from the droplet digital PCR (dPCR) shows that multiple independent PCR reactions can be run and separately quantified using the same fluorophore. Specifically, an SMN2 assay yields an unexpected population of droplets with slightly elevated signal in the FAM detection channel.

Figure 10:
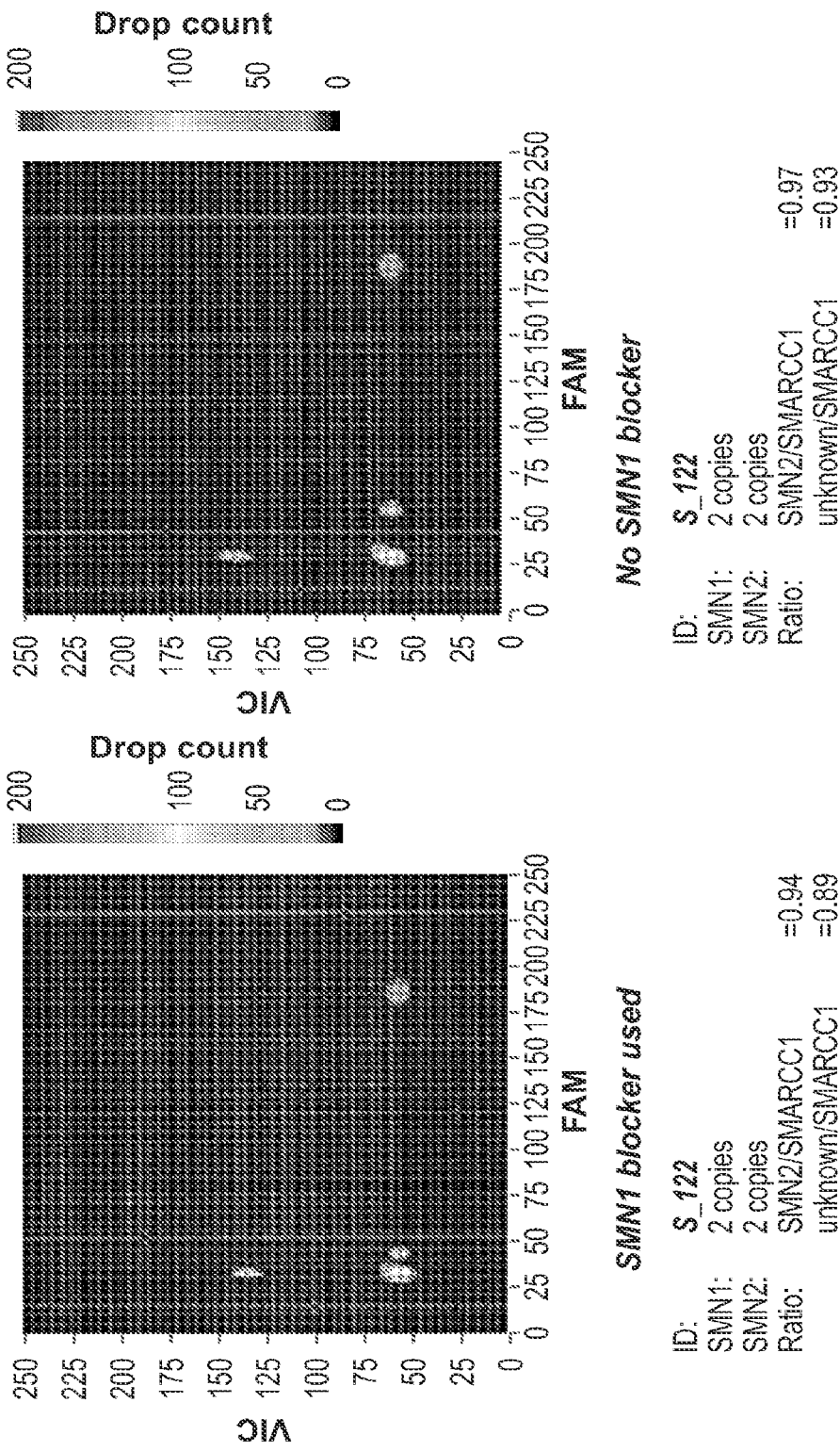
FIG. 10 shows two dot plots depicting clusters of genetic sequences detected through fluorescence intensity. Left panel is a dot plot showing four clusters. Block for SMN1 sequence was present. Top left: microdroplets containing the reference sequence (SMARCC1); bottom left: microdroplets not containing any sequence; bottom middle: microdroplets containing sequence for SMN1; and bottom right: microdroplets containing sequence for SMN2. Right panel is a dot plot showing four clusters. No block for SMN1 sequence was present. Top left: microdroplets containing the reference sequence (SMARCC1); bottom left: microdroplets not containing any sequence; bottom middle: microdroplets containing sequence for SMN1; and bottom right: microdroplets containing sequence for SMN2. The shift of the bottom middle cluster in right panel as compared to left panel confirms that fluorescence intensity provides a very sensitive measurement for the presence of a sequence.

The results are depicted in FIG. 10. The left-side dot plot in FIG. 10 depicts the effect of having the SMN1 blocker present in the reaction. The four clusters depicted in the left-side dot plot are as follows: the top left cluster includes microdroplets containing the reference sequence (SMARCC1); the bottom left cluster includes microdroplets not containing any sequence; the bottom middle cluster includes microdroplets containing sequence for SMN1; and the bottom right cluster includes microdroplets containing sequence for SMN2. The dot plot on the right-side of FIG. 10 depicts four clusters where no SMN1 blocker was present in the reaction: the top left cluster includes microdroplets containing the reference sequence (SMARCC1); the bottom left cluster includes microdroplets not containing any sequence; the bottom middle cluster includes microdroplets containing sequence for SMN1; and the bottom right cluster includes microdroplets containing sequence for SMN2. The shift of the bottom middle cluster in right panel as compared to left panel confirms that fluorescence intensity provides a very sensitive measurement for the presence of a sequence.

Without intending to be bound by any theory, the simplest explanation is that the cluster arises from weak association of the SMN2 probe to the SMN1 gene despite the presence of a blocker to that gene (a nonfluorescent complementary probe to the SMN1 gene).

One definitive confirmation of SMN1 as the source of the unexpected cluster was an observed dependence of the intensity of this feature on the presence of the SMN1 blocker. A clear shift toward higher FAM fluorescent intensities was observed in the absence of the blocker (FIG. 10). In another definitive confirmation the ratio of the SMN1 (putative) population size to the reference size of 0.96 in perfect agreement with expectation (two copies of each) (S_131 sample). Another sample, S_122, with the same number of SMN1 copies yielded a ratio of 0.88 in one run and 0.93 in another, also consistent with the proposed explanation of the unexpected cluster.

Without intending to be bound by any theory, these observations indicate that SMN2 probe binding to SMN1 DNA yields an elevated fluorescent signal. A simple kinetic model explaining this phenomenon assumes that the hybridization of the SMN2 probe to the SMN1 DNA achieves equilibrium at a faster rate than the polymerase fills in the complementary strand. The amount of probe fluorophore that is released in each thermal cycle is therefore proportional to (or even equal to) the number of bound probes.

Thus the lower the binding affinity the fewer the number of probe fluorophores that are released. Due to SMN1 sequence mismatch(es) with the SMN2 probe, the affinity of the probe is certainly expected to be lower to SMN1 than SMN2. This model also explains the signal dependence on the sMN1 blocker: the blocker competitively inhibits the SMN2 probe hydrolysis by the polymerase exonuclease activity.

It may also be, however, that the probe hybridization does not reach equilibrium before exonuclease activity. In this case, the association rates would play a more dominant role. Similar logic applies. The binding rate to the matching site is likely to be faster than to the mismatch site, and the blocker would act to decelerate probe binding to the mismatch site. The binding of SMN2 probe to SMN1 DNA might be detectable by conventional bulk qPCR, especially in absence of SMN2, but highly quantitative results like those shown here are very unlikely. Definitely, there is no report of qPCR or any other technique quantifying two different DNA sequence motifs with the same color fluorophore. Sequestration of the individual reactions by single molecule amplification within droplets eliminates any confusion regarding mixed contributions to the signal.

The advantage of quantifying DNA with multiple probes of the same color fluorophore extends beyond the example of two highly homologous sequences shown here. Rather, any plurality of sequences of any degree of similarity or dissimilarity can be quantified so long as the different probes have significantly different binding occupancies to their respective DNA binding sites.

Another advantage of the dPCR approach for multiplexed reactions is that the different reactions do not compete with each other for reagents as they would in a bulk qPCR assay. However, the possibility for unintended cross-reactivity remains. A multiplexes assay can require a more dilute sample. For instance, at 10% occupancy a duplex reaction would have double occupancy 1% of the time. Hence 1 in 10 PCR+ droplets would be doubles, resulting in a final intensity at least as high and possibly higher than the brighter of the two probes. For a simple duplex system the contribution from each probe could be recovered. In this example the total number of PCR+ droplets for probe 1 would be (Probe 1)+(Probe1+Probe2). Higher degrees of multiplexing would require greater dilution. For example, for a 4-plex at 1% occupancy the probability of one probe overlapping any of the other 3 is ~3%, and that error may be too high for some applications. The need for large dilutions strongly favors the large number of dPCR reactions.

In another example of the invention, a single fluorophore (FAM) was used in a gene copy number assay for both the reference and the target DNA. A model system was used with varying concentrations of plasmid DNA to represent a change in the target gene copy number, relative to a reference gene, equivalent to 0-16 copies of the target gene per cell. BCKDHA and SMN2 plasmid DNA served as the reference and target with 1× and 0.5× primers and probes respectively. With a starting ratio of 8:1 SMN2 to BCKDHA, the sample was diluted serially by 2× into a solution of BCKDHA at the same concentration to vary just the amount of SMN2. The resultant samples were emulsified, thermally cycled, and over $10^5$ droplets were analyzed for each sample as described in the previous section. The process was repeated in triplicate.

Figure 11A:
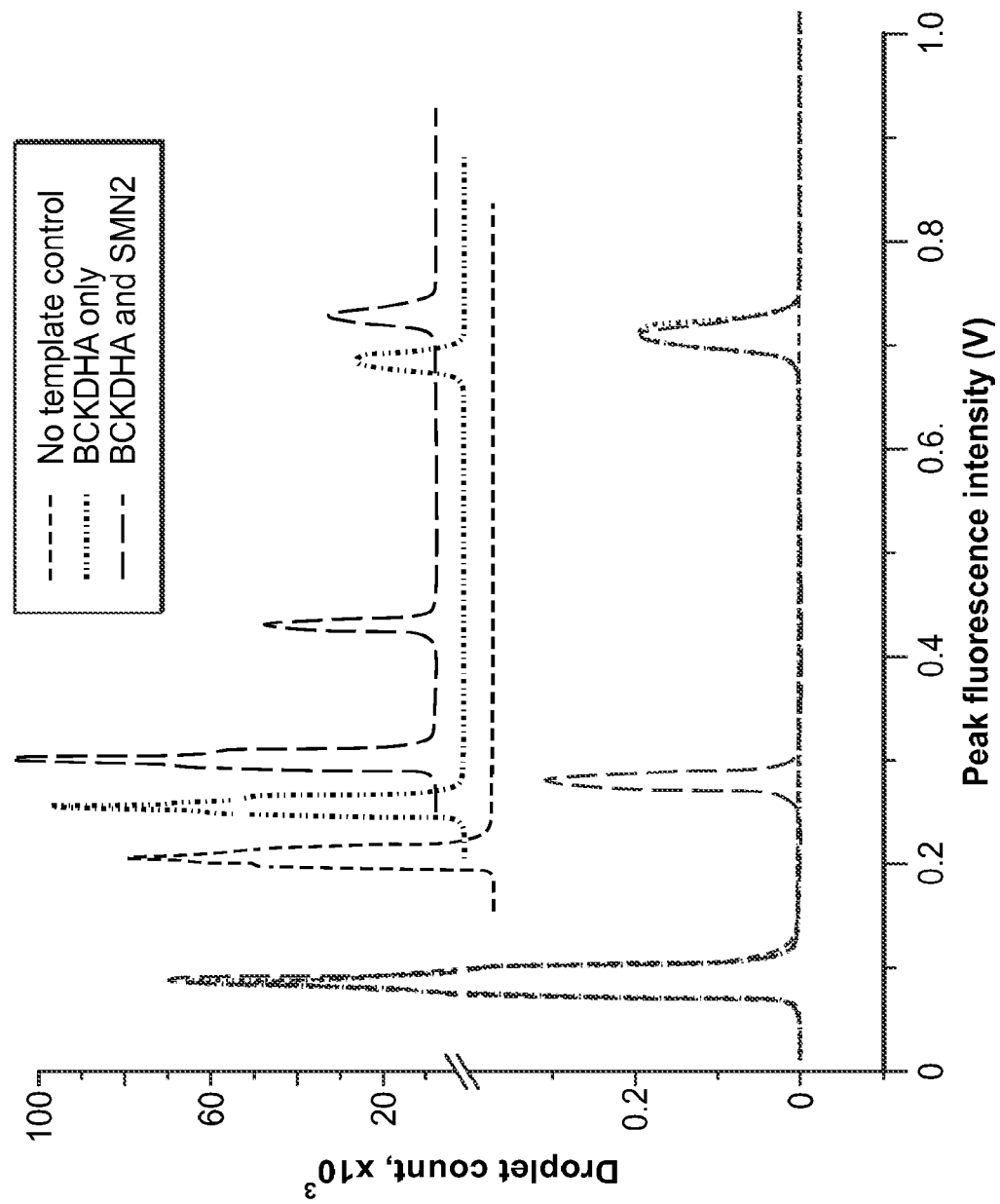
FIGS. 11A and 11B depict histograms of a duplex gene copy number assay using only one type of fluorophore by digital PCR.
Figure 11B:
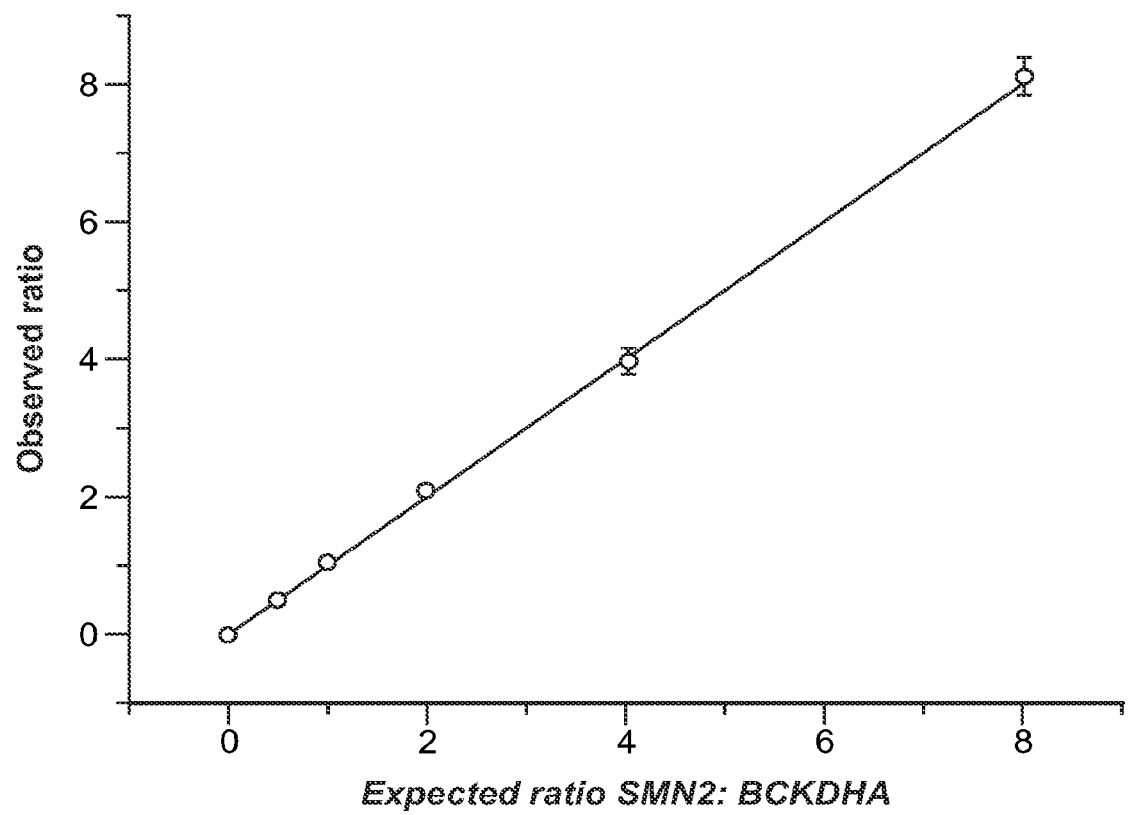

Methods of the invention also include analytical techniques for identification of fluorescence signatures unique to each probe. In this example of the invention, histograms of the droplet fluorescence intensities are shown in FIG. 11a for three different template DNA samples: a no template control (dotted line), BCKDHA only (solid line), and 1:1 BCKDHA to SMN2 (dashed line). For clarity, the histograms are shown both overlapped to highlight the similarity for certain peaks, and offset from each other to reveal all of the features. In the case of 1:1 BCKDHA to SMN2, three populations were readily apparent: a dominant feature appeared at 0.08 V, and two smaller peaks were evident at 0.27 and 0.71 V. The dominant feature at 0.08 V was assigned to PCR(−) droplets since both small peaks disappeared, but the large one remained, in the no template control. The peak at 0.71 V was assigned to BCKDHA since it was the sole feature arising with the addition of just BCKDHA, and the peak at 0.27 V appeared on subsequent addition of SMN2, completing the assignments. A very small peak appeared at −0.9 V, not visible on the scale of FIG. 11a, that corresponded to droplets occupied by both genes. As another method of the invention, once the different peaks are identified, droplets within each peak were counted corresponding to each possible state (PCR(+) for either BCKDHA or SMN2, or both, or PCR(−)), and the gene copy number was then determined from the ratio of occupancies. Gene copy numbers for each sample in the serial dilution are plotted in FIG. 11b against expected values (observed ratios of SMN2 to BCKDHA to expected ratios of SMN2 to BSKDHA), with an excellent linear fit (y=1.01x) across the full range ($R^2$=0.9997, slope=1.01), demonstrating accurate and precise measurement of the equivalent of 0 to 16 copies of SMN2 per cell.

Detection of Alternatively Spliced Transcripts

The same principle can be used to detect and count alternatively spliced transcripts. TaqMan assays can be designed that are specific for each of the exons in an RNA transcript. After the RNA is turned into cDNA it can be encapsulated into a droplet at 1 copy or less per droplet. The droplet would also contain the multiplexed TaqMan assay for each of the exons. Each of the TaqMan assays would contain a different probe but all the probes would have the same fluorescent dye attached. The droplets would be thermocycled to generate signal for each of the TaqMan assays. If there are multiple splice variants in the sample they each will contain a different number of exons depending on the splicing events. The fluorescent intensity of each droplet would be different depending on the number of exons present. By counting the number of droplets with different intensities it would be possible to identify the presence and abundance of different splice variants in a sample.

Copy Number Variants in a Heterogeneous Sample

It would be possible to determine if a heterogeneous sample contained components with different copy level numbers. If the copy number variants to be assayed were spaced close enough along the chromosome, the DNA from a sample could be fragmented and encapsulated in droplets at a level of one haploid genomic equivalent or less per droplet. The droplet would also contain a TaqMan assay specific for the copy number variant. The intensity of the signal in each droplet would depend on the number of copy number variants are present for the sample. Counting of the number of droplets of different intensities would indicate things like how many cells in a particular sample had what level of copy number variants.

Tuning TaqMan® Probe Fluorescence Intensity

Identifying probes by fluorescence intensity often requires adjusting the brightness of the probes, particularly for higher-plex assays with dense probe patterns. In the previous section the probes for the gene copy number assay yielded very well resolved peaks (FIG. 11a). Clearly room exists to accommodate one or multiple extra probes in the copy number assay within the resolution of the measurement, but a method for adjusting the fluorescence intensity of the new probes is required to avoid interference with the existing assay. One method of the invention involves varying the probe and primer concentrations together as a very simple technique to optimize relative intensities in higher-plex reactions.

FIG. 12 is a schematic for tuning the intensity of a detectable label to a particular target with a microfluidic device. As shown in FIG. 12A, a template DNA is amplified with two sets of primers: forward primers (F1 and F2) and reverse primers (R1 and R2). Probes (P1 and P2) are labeled with fluorophore of color 1 and bind to target 1 and target 2 respectively. Fluorescence from target 2 is lower in intensity than that from target 1 due to single base mismatch between P2 and target 2. As shown in-FIG. 12B, template DNA is amplified with two sets of primers: forward primers (F1 and F2) and reverse primers (R1 and R2) (FIG. 12B). Fluorescence from target 2 is lower in intensity than that from target 1 due to the presence of a competing probe 2 that is not labeled with the fluorophore. As shown in FIG. 12C, template DNA is amplified with two sets of primers: forward primers (F1 and F2) and reverse primers (R1 and R2). Probes (P1 and P2) are labeled with fluorophore of color 1 and bind to target 1 and target 2 respectively. Fluorescence from target 2 is lower in intensity than that from target 1 due to the presence of a competing probe 2 that is labeled with a different fluorophore.

Figure 13:
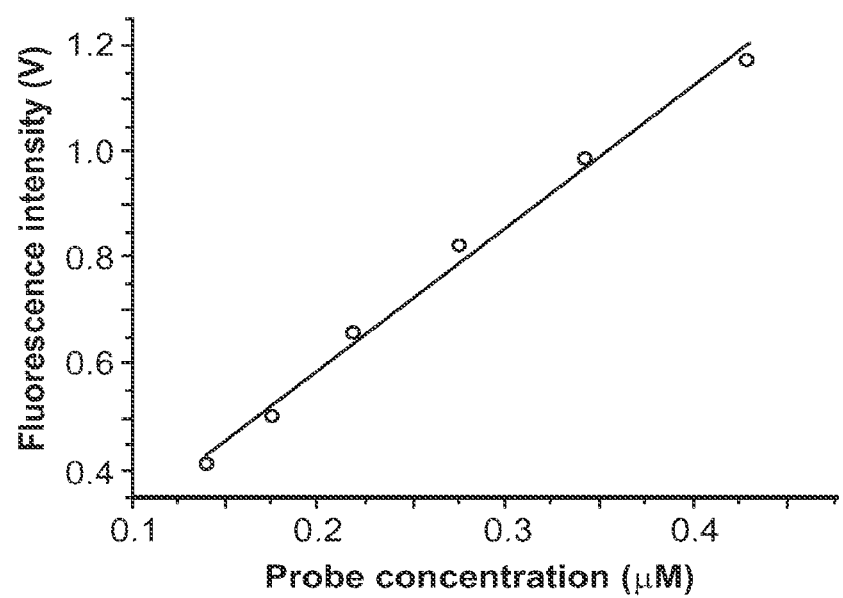
FIG. 13 is a line graph depicting the linear dependence of droplet fluorescence intensity on probe concentration (Line, best linear fit (y=−0.092x+0.082, $R^2$=0.995).

FIG. 13 shows probe fluorescence intensities throughout a serial dilution of the probes and primers for a different reference gene, ribonuclease P (RNaseP), against a constant amount of genomic DNA from the Coriell cell line NA3814 at an occupancy of 0.02 target DNA molecules per droplet. The probe fluorescent intensities varied in direct proportion to probe concentration over a narrow concentration range spanning ~0.15 to 0.4 µM ($R^2$=0.995)—roughly centered about the typical probe concentration of 0.2 µM—after compensation for dilution errors and other run-to-run differences such as optical realignments using the intensity of the PCR(−) droplets as a reference. In summary, probe intensities can be varied by dilution over a small but adequate range for the purpose of tuning multiplexed assays without affecting the amplification itself.

Although the example above for adjusting probe fluorescence intensities involves varying probe and primer concentrations together by the same factor, the invention is not limited to this method alone for varying probe intensity. Other methods known to those familiar with the art for varying probe intensities are also considered. Such methods include varying just the probe concentration; varying just the primer concentrations; varying just the forward primer concentration; varying just the reverse primer concentration; varying the probe, forward, and reverse primers concentrations in any way; varying the thermal cycling program; varying the PCR master mix; incorporating into the assay some fraction of probes that lack fluorophores; or incorporating into the assay any hybridization-based competitive inhibitors to probe binding, such as blocking oligomer nucleotides, peptide nucleic acids, and locked nucleic acids. The invention incorporates the use of these methods adjusting probe fluorescence intensity, or any other methods for adjusting probe fluorescence intensity, used either by themselves or in any combination.

Higher-Plex Reactions

One method of the invention involves performing higher-plex assays with a single probe color (i.e. fluorophore). As described above, probe fluorescent intensities can be adjusted by a variety of means such that each intensity level uniquely identifies a DNA target. For example, targets T1, T2, T3, and T4 might be uniquely identified by intensity levels I1, I2, I3, and I4. Not intending to be bound by theory, the maximum number of intensity levels possible for unique identification of targets is related to the resolution of the different intensity levels—that is the spread of intensities for each particular probe compared to the separation between the average intensities of the probes—and it is also related to the intensity of the empty droplets that tends to grow with increasing numbers of probes. The number of intensity levels can be 0, or 1, or 2, or 3, or 4, or up to 10, or up to 20, or up to 50, or up to 100. The number of intensity levels can be higher than 100. In the examples show below, as many as three intensity levels are demonstrated.

Another method of the invention involves performing higher-plex assays using multiple different probe colors (i.e. fluorophores). As above for the monochromatic multiplexing assay, for each color probe, multiple targets can be identified based on intensity. Additionally, multiple colors that are spectrally separable can be used simultaneously. For example, a single droplet might contain four different probes for measuring four different targets. Two probes might be of color A with different intensities (say, A1 and A2), and the other two probes of color B with different intensities (say B1 and B2). The corresponding targets are T1, T2, T3, and T4 for A1, A2, B1, and B2 respectively. If a droplet shows an increase in fluoresce in color A, the droplet therefore contained either targets T1 or T2. Then, based on the fluorescence intensity of color A, the target could be identified as T1 or the target could be identified as T2. If, however, a droplet shows an increase in fluorescence in color B, the droplet therefore contained either targets T3 or T4. Then, based on the fluorescence intensity of color B, the target could be identified as T3 or the target could be identified as T4. Not intending to be bound by theory, the maximum number of different colors possible is limited by spectral overlap between fluorescence emission of the different fluorophores. The maximum number of colors can be 1, or 2, or 3, or 4, or up to 10, or up to 20. The maximum number of colors can be higher than 20. In the demonstrations that follow, the largest number of colors is two.

Another method of the invention involves performing higher-plex assays using multiple different probe colors (i.e. fluorophores), however unlike the strategy above where each target is identified by single type of probe with a unique color and intensity, instead in this method a single target may be identified by multiple probes that constitute a unique signature of both colors and intensities. For example, a single droplet might contain four different probes for measuring three different targets (say, T1, T2, and T3). Two probes might be of color A (say, A1, and A2), and two probes might be of color B (say, B1 and B2). T1 is measured by probe A1, T2 is measured by probe B1, but T3 is measured by both probes A2 and B2. Thus, when a droplet contains T1 only increased fluorescence appears in color A. When a droplet contains T2 only increased fluorescence appears in color B. However when a droplet contains T3, increased fluorescence appears in both colors A and B.

Generally, without wishing to be constrained by theory, the above three methods for higher-plex dPCR are simplest to implement under conditions of terminal dilution, that is when the probability of multiple different target molecules co-occupying the same droplet is very low compared to the probability of any single target occupying a droplet. With multiple occupancy arises the complexity of simultaneous assays competing within the same reaction droplet, and also complexity of assigning the resulting fluorescence intensity that involves a combination of fluorescence from two different reaction products that may or may not be equal to the sum of the two fluorescence intensities of the individual reaction products. However, methods of the invention can accommodate these complications arising from multiple occupancy.

Methods of the invention for higher-plex reactions also include methods for primer and probe pairing. In the simplest case targets are unlikely to reside on the same DNA fragments, such as when targets are from different cells; or when targets are from different chromosomes within a single cell type; or when targets are distant from each other within a single chromosome such that they become physically separated during DNA fragmentation; or when targets are very close to each other within a chromosome, but nevertheless become separated by targeted cleavage of the DNA, such as by restriction enzyme digestion; or for any other reason. In such cases each probe can be paired with a single set of primers (forward and reverse). However, in other cases the target regions might frequently reside on the same DNA fragments, for example when targets reside within the same codon, or for any other reason. In such cases, a single set of primers might serve for multiple probes (for an example, see Pekin et al.).

Figure 22:
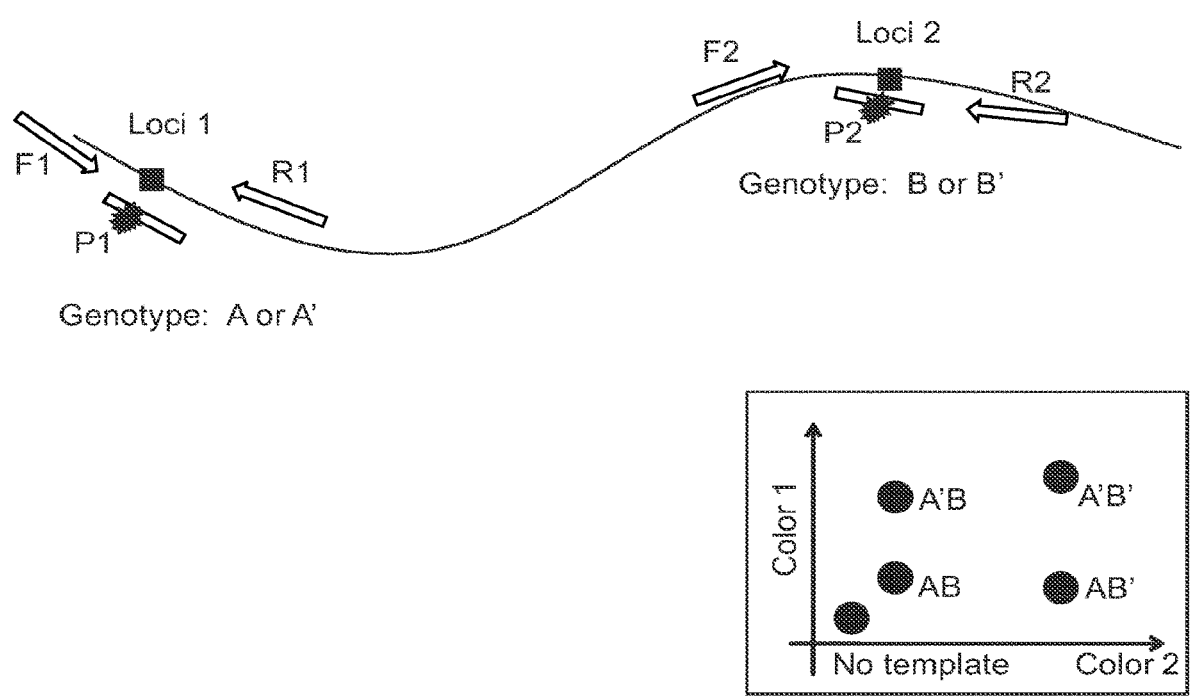
FIG. 22 is a schematic showing haplotype detection in droplets.

Higher multiplex reactions can be performed to distinguish the haplotypes of two SNPs. For example, assume that at position one there can be genotypes A or A' and at position two there can be genotypes of B or B'. In a diploid genome four unique haplotypes are possible (A,B; A,B'; A',B; and A',B'). If for example A' and B' represent drug resistant mutations for infection, it is often the case that A'B and AB' are less sever and treated differently than A'B' which represents a significant drug resistance that must be treated with extreme care. Digital PCR with intensity discrimination is ideally suited for identifying low prevalence of A'B' in a background of mixtures of the other three haplotypes. Haplotyping information is also important for construction of haplotypes in HLA. One way that the present example can be constructed is by assay design such that color one is used for A and is of high or low intensity indicative of allele A or A' respectively and color two is used for B and is of high or low intensity respectively indicative of B or B'. Populations of [color1,color2] corresponding to [Low, Low] would be a measure of an allele if AB and [high, low] allele A'B and an allele of [A'B'] will be readily distinguishable as [high, high] even in a background that is predominately a mixture of A'B and AB'. See FIG. 22. In some cases it will be advantageous to start by encapsulating into the droplets long single molecules of nucleic acid that contain both A and B SNP location and in other cases it will be desirable to start by encapsulating single cells, bacteria or other organism within the droplets prior to releasing the nucleic acid from the organism. In still other embodiments the multiplex intensity detection of multiple simultaneous targets can be used as surrogate markers for multiple types of binding interactions or labeling of target materials. This technique is also not limited to single molecule detection and can be used for haplotype detection in single cells (e.g., bacteria, somatic cells, etc.). In single cell analysis, a sorting step may be applied prior to haplotyping.

5-Plex Assay for Spinal Muscular Atrophy

An aspect of the invention was reduced to practice in an example demonstration of the quantitation of several genetic markers for spinal muscular atrophy (SMA). SMA was selected for one of the example demonstrations due to both its important clinical significance as well as its complicated genetics. It is the second-most prevalent fatal neurodegenerative disease and affects ~1 in 10,000 live births. SMA is most often caused by homozygous absence of exon 7 within the survival of motor neuron 1 gene (SMN1, reviewed by Wirth et al.), however the severity of the condition is modulated by the number of gene copies of SMN2 with prognosis ranging from lethal to asymptomatic over 1-5 copy numbers (reviewed by Elsheikh et al.). Hence accurate quantitation of SMN2 copy number is important for clinical prognosis and genetic counseling. Aside from large deletions of SMN1, a number of single point mutations or short deletions/duplications within the same gene also account for ~4% of cases of SMA. In a significant step toward a comprehensive SMA assay, the multiplexed dPCR assay demonstrated here contains both copy number assays (for SMN1 & 2) and an assay for one of the prevalent SNPs (c.815A>G).

One embodiment of the invention is a 5-plex assay for SMA diagnostics. The 5-plex assay quantifies common genetic variants impacting SMA including two copy number assays for the SMN1 and SMN2 genes with BCKDHA as a reference, and a SNP assay for the c.815A>G mutation. Two differently colored fluorophores, FAM and VIC, were used to uniquely identify each of the assays. The probes for SMN1 and SMN2 contained only FAM, and for c.815A only VIC. However, mixtures of VIC and FAM-labeled probes were used for BCKDHA and c.815G. The use of VIC and FAM fluorophores in this example does not limit the invention, rather the 5-plex assay can be used with any spectrally separable fluorophores compatible with the TaqMan assay, or any other fluorogenic hybridization-based probe chemistries. For validating the assay, a model chromosome was synthesized containing a single target region for each of the different primer/probe pairs. EcoRV restriction sites flanked each target, allowing separation of the fragments.

Figure 14A:
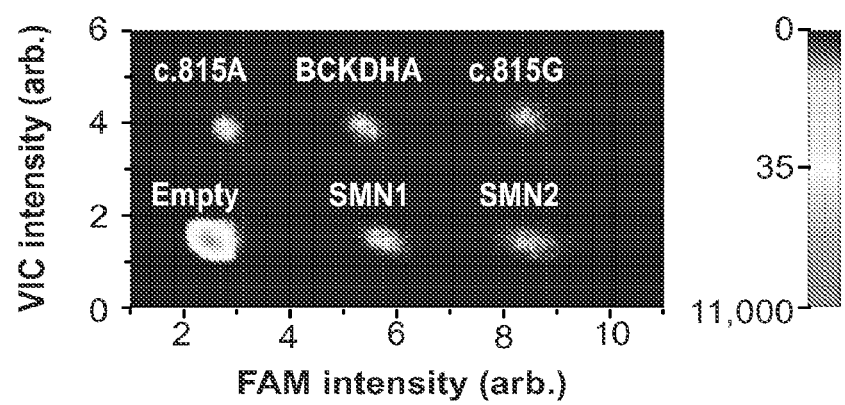
FIGS. 14A-B depict a 5-plex dPCR assay for spinal muscular atrophy with only two fluorophores.

As another method of the invention, histogram-based data presentation and analysis is incorporated into the invention for identifying and characterizing statistically similar populations of droplets that arise from one probe signature (color and intensity), and for discriminating one population of droplets from the others. FIG. 14a shows a 2-dimensional histogram of droplet fluorescence intensities as a contoured heat map, with hotter colors representing higher occurrences. Standard techniques were used to compensate for spectral overlap of the FAM and VIC signals. Samples were run at 0.006 occupancy per target. Six populations were clearly evident, five for the assay and one for PCR(−) droplets. As one method of the invention, the populations were assigned by selective exclusion of assay components. For example, excluding the SMN2 primers and probe eliminated the population at the bottom right in the histogram, but otherwise the distribution remained unchanged. Assignments are labeled in FIG. 14a. As we have found to be generally true for this method of multiplexing, the assay worked immediately with well resolved or at least distinguishable populations for each target. As another method of the invention, the relative positions of the different populations in the histogram were then adjusted into a regularly spaced rectangular array by tuning the probe concentration as described in the previous section. Usually no more than two iterations are required for optimization.

Figure 14B:
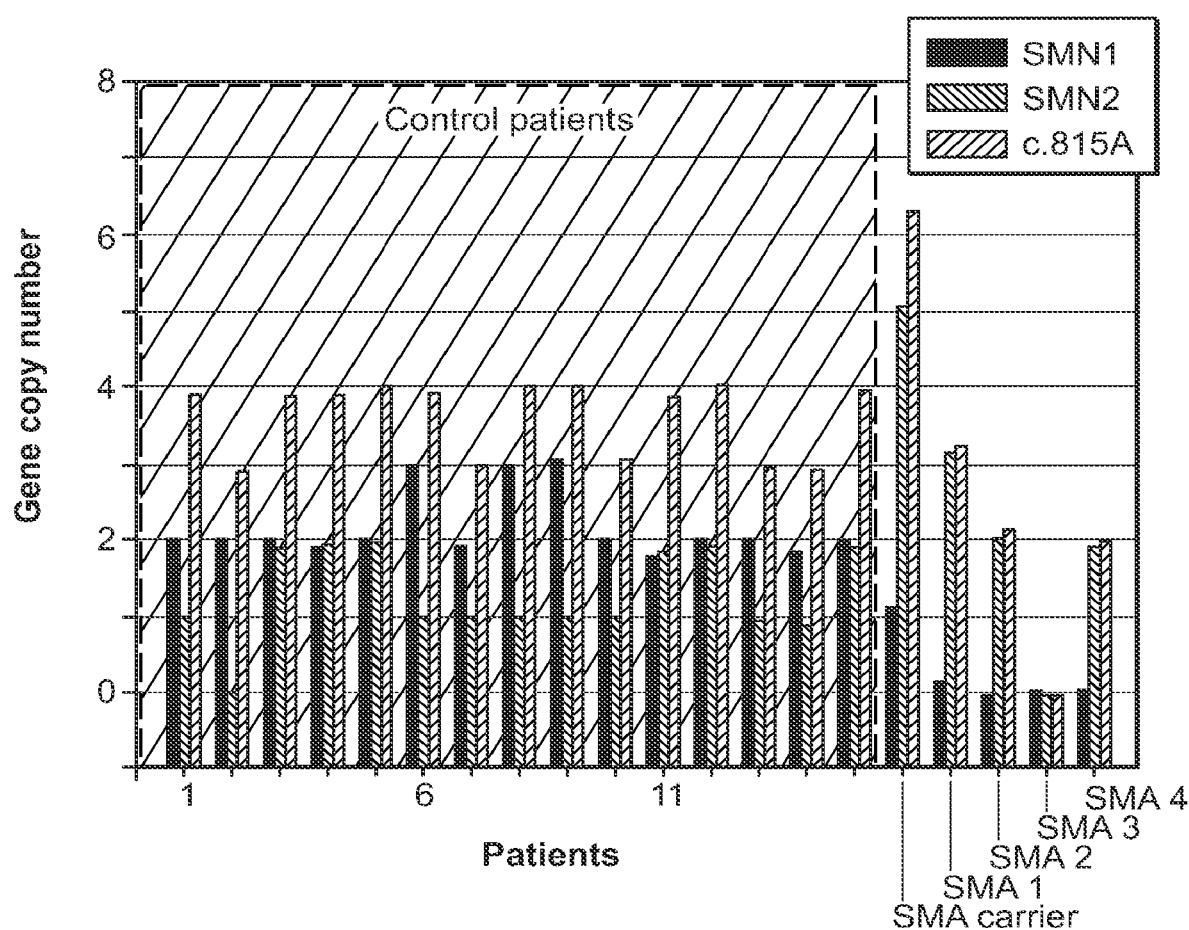

In another method of the invention, the different populations were sufficiently well resolved to allow droplets within each population to be counted by integration across rectangular boundaries. The boundaries were positioned at midsections between neighboring peaks. The methods of the invention are not constrained to rectangular boundaries, or to specific boundary locations between peaks. Rather, any closed or unclosed boundary condition can suffice. Boundary conditions do not need to be "binary" either, in the sense that weighted integrations can also be performed across the boundaries to arrive at droplet counts. The peak position of each cluster varied by no more than 2% from run to run after normalization to the intensity of the empty droplets to account for variations in detection efficiency (data not shown). Hence, once identified, the same boundaries for integration could be reused between samples. The methods of the invention are not limited to fixed boundary positions. Dynamic population identification and boundary selection in between samples or studies is anticipated. Twenty different patient samples from the Coriell cell repositories were analyzed with this assay: 4 afflicted with SMA, 1 SMA carrier, and 15 negative controls. Assay results are shown in FIG. 14b. Gene copy number was calculated as before, as the ratio of occupancies derived from the number of target droplets vs. reference droplets. Like the copy number measurement in FIG. 11, each assay yielded ratios very close to the expected integer values, but when all of the patient data was plotted as actual ratio vs. expected integer ratio a small systematic deviation from the ideal slope of 1 was observed. Measured slopes were 0.92, 0.92, and 0.99 for SMN1, SMN2, and c.815A respectively. For clarity, the data in FIG. 14b was scaled to the ideal slope of 1.

The measured genotypes of the different patients were consistent with their disease conditions (unafflicted, carrier, or afflicted). The patients afflicted with SMA each had zero copies of SMN1 (numbers SMA 1-4 in FIG. 14b), the carrier had just one copy, and the negative controls all had two or three copies (numbers 1-15). Three unrelated individuals (numbers 6, 8, and 9) had three copies of SMN1, occurring at a rate of 20% which is similar to a previous report for healthy individuals. Variability in SMN1 copy number is not surprising since it lies within an unstable region of chromosome 5q13. A larger variety of SMN2 copy numbers was observed. One to two copies were most common in the control group, although one individual had zero copies, a distribution consistent with expectations for normal individuals. The SMA carrier and afflicted patients had elevated copy numbers of SMN2 on average: 5 for the carrier, two afflicted with 3 copies, and the others with 2 copies. The afflicted patients were all diagnosed as SMA Type I, the most severe form, based on clinical observations according to the Coriell repository. The strong genotype/phenotype correlation between SMN2 copy number and disease severity suggests that the two individuals with three copies of SMN2 might have an improved Type II prognosis, especially for the patient SMA 1 who had survived to three years at the time of sampling, much beyond the typical maximum life expectancy for SMA Type I of 2 years. However there remains reluctance to predict disease outcome based on SMN2 copies alone since other less well characterized or unknown modifying genes may impact prognosis and because not all SMN2 copies may be complete genes. Furthermore some Type I patients have begun surviving longer in newer clinical settings. Hence, with little clinical information regarding the patients available to us, we can conclude that our SMN2 assay results were consistent with broad expectations for disease severity.

The SNP assay revealed that all patients carried the normal c.815A genotype and no instances of c.815G were observed. The mutation is relatively rare and hence was not expected to appear in a small patient panel. Of interest, however, was the presence of an apparent extra gene fragment in two unrelated individuals that was uncovered with the SNP assay. The c.815A>G assay does not discriminate between SMN1 and SMN2 due to their high sequence similarity, and hence the total copies of c.815A and G should equal the sum of the copies of SMN1 and SMN2. This was true for all patients except for healthy patients number 1 and 2, both of whom had one extra copy of c.815A. c.815 lies on exon 6, and the SNP that discriminates between the SMN1 and SMN2 genes lies on exon 7, hence the extra genes may be fragments of SMN1 lacking exon 7. This seems reasonable because the deletion of exon 7 is the common mutation causing 95% of cases of SMA (reviewed by Wirth et al.) and it is carried by 1/40 to 1/60 adults. Thus these patients might have been typical carriers of SMA but for the acquisition of at least one compensating healthy copy of SMN1 on the same chromosome.

9-Plex Assay for Spinal Muscular Atrophy

Figure 15A:
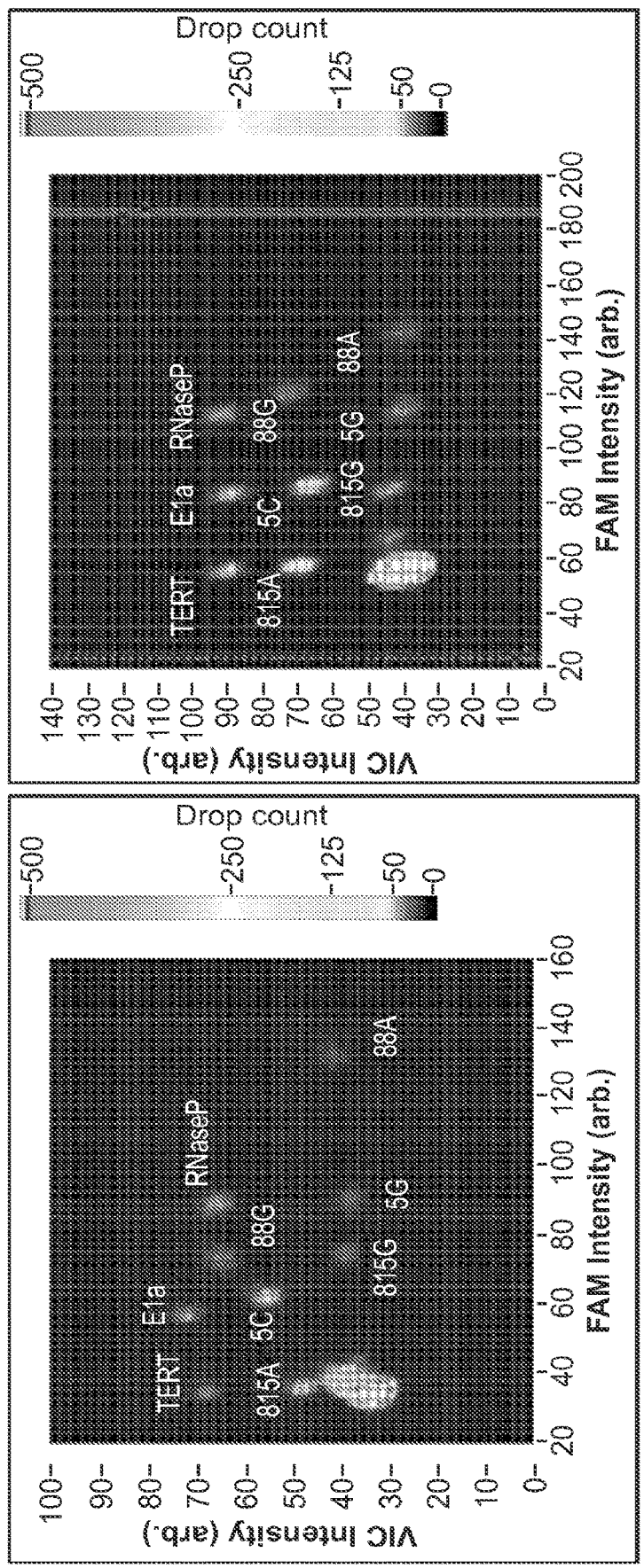
FIGS. 15A-B depict a 9-plex dPCR assay for spinal muscular atrophy with only two fluorophores, showing the process of optimizing droplet intensities.
Figure 15B:
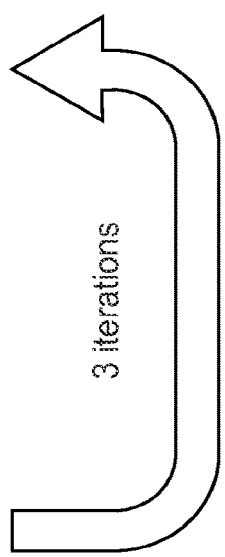

A 9-plex assay for certain SMA related targets was also demonstrated with just two colors (probes containing FAM and VIC fluorophores). Aside from the optimized primer and probe concentrations, assay conditions and experimental procedures were identical to the 5-plex assay above. FIG. 15a shows the various droplet populations in 2-D histograms before optimization of probe concentrations. The identity of the different targets is shown on the figure itself. As one method of the invention, the identification of the different populations was made as before, by selective exclusion and/or addition of one or more assays. Most of the populations were already well resolved, with the exception of the probe for the c.815A genotype that was in close proximity with the cluster corresponding to empty droplets. After three iterations of optimization of probe concentrations, all of the target populations were well resolved from each other, and well resolved from the empty droplets (FIG. 15b). Three methods of the invention were highlighted in this demonstration: (1) nine DNA targets were uniquely identified in a two-dimensional histogram, far beyond the capabilities of conventional qPCR; (2) target DNA molecules were distinguished on the basis of some combination of both color and intensity arising from one or multiple probes against the same target; and (3) the relative positions of the target molecules within the histogram were adjusted by varying the probe concentrations to optimize the pattern of colors and intensities for increased resolution amongst the various droplet populations.

As one method of the invention, different droplet populations were identified by selective addition or exclusion of assays in the examples above. However the invention is not limited to this method alone. Rather, any method for population assignments known to those in the art are considered. Methods of the invention include any method that can cause an identifiable displacement, appearance, or disappearance of one or more populations within the histograms including changing the probe and primer concentrations together, either by the same factor or by different factors; changing the probe concentration alone; changing the primer concentrations alone; changing the thermal cycling conditions; and changing the master mix composition. Another method of the invention takes advantage of prior knowledge of the position of an assay within a histogram to assist assignment.

Multiplexing Capacity

The level of multiplexing demonstrated in the preceding SMA example was 9×, significantly exceeding the maximum practicable number with qPCR. Without wishing to be constrained by theory, the two main limitations are the resolution between assays and the increasing fluorescence intensity of empty droplets with higher loading of probes. A method of the invention involves optimizing the pattern of colors and intensities of the different probes for maximum multiplexing while still achieving adequate specificity for each individual reaction. Although rectangular arrays of droplet populations were demonstrated for the 5- and 9-plex reactions, another desirable pattern is the tight-packed hexagonal array. However the invention is not constrained to any particular array strategy.

Adding extra colors would increase the capability even further, however with some diminishing returns because the fluorescence of the empty droplets would continue to rise. The capacity could be yet further increased with better probes yielding larger differential signals, such as hybrid 5'-nuclease/molecular beacon probes that reduce background by contact quenching yet exhibit the bright signals typical of free unquenched fluorophores. With such improvements multiplexing capacity exceeding 50× can be envisioned.

Combined Multiplexing with Optical Labeling

Using droplet-based microfluidics, multiple targets can also be measured simultaneously by a different method. According to the alternative method, primers and probes can be loaded individually into droplets along with an optical label to uniquely identify the assay. Typically the optical label is a fluorophore, or a combination of different fluorophores, that are spectrally distinct from the probe fluorophore. Various different types of droplets, each containing different assays that are uniquely identified by different optical labels, can be mixed into a "library" of droplets. Then, according to methods of the invention above, library droplets are merged one-to-one with droplets containing template DNA. After thermal cycling, some droplets that contain template DNA will exhibit brighter fluorescence at the emission wavelengths of the probes. The specific target DNA molecules giving rise to these PCR(+) signals are subsequently identified by the optical probes. In one study, the six common mutations in KRAS codon 12 were screened in parallel in a single experiment by one-to-one fusion of droplets containing genomic DNA with any one of seven different types of droplets (a seven-member library), each containing a TaqMan® probe specific for a different KRAS mutation, or wild-type KRAS, and an optical code.

In one method of the invention, optical labeling can be combined with the various methods for multiplexing dPCR already incorporated into this invention. For example, a single optical label might code for the entire 5-plex SMA assay, above, instead of just a single assay as in the KRAS example above. In this manner, other optical labels might code for different screening assays for newborn infants. According to other methods of the invention, above, a single DNA sample from an infant could then be analyzed with all of the assays simultaneously by merging droplets containing the DNA one-to-one with library droplets containing the optically encoded assays.

Figure 16:
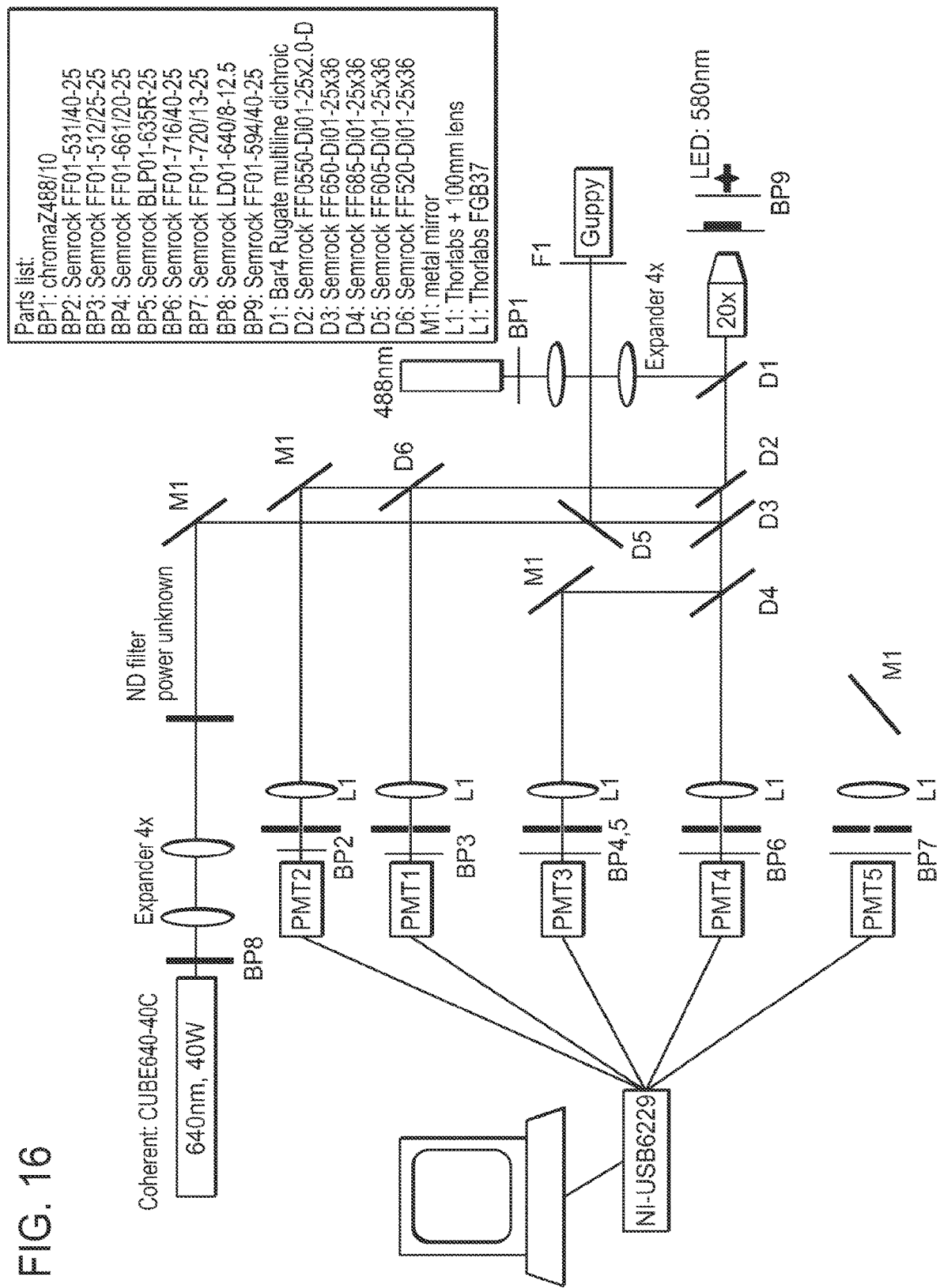
FIG. 16 depicts an optical schematic for combining optical labels with multiplexing.

As an example of combining multiplexing with optical labels, a so called 3×3×3 combination multiplex reaction with optical labeling was demonstrated (3×3 optical labeling with two fluorophores, each encoding a triplex assay, for a total of 27-plex). Two fluorophores were employed for optical labeling, Alexa633 and CF680 (excited by a 640 nm laser), with three intensity levels each producing nine total optical labels. As before with the 5- and 9-plex assays for SMA, TaqMan assays were used with FAM and VIC fluorophores (excited by a 488 nm laser). The fluorescence from the FAM and VIC fluorophores were recorded simultaneously with the fluorescence from the optical labels, requiring modifications to the optical layout of the instrumentation described for the SMA assay (the optical schematic for two-laser excitation and 4-color detection is shown in entirety in FIG. 16). Also, co-flow microfluidics were used in this example (the use of co-flow based microfluidics for this application is one of the methods of the invention described above). In this case, the template DNA was introduced into the chip in one flow, and the PCR master mix, the primers and probes for one triplex assay, and the unique composition of fluorophores for the optical label were introduced into the chip in another flow simultaneously. The two flow streams converged in a fluidic intersection upstream from the droplet forming module, and thus each droplet formed contained the contents of both flow streams. Methods to implement co-flow microfluidics are well known to those in the art. The droplets were collected, and then the procedure was repeated with the next triplex assay and optical label. The procedure was repeated a total of nine times, once for each pair of assays and optical labels. All of the droplets were collected into a single PCR tube and thermally cycled off chip. The mixture of thermally cycled droplets was reinjected into the same read-out chip as used for the SMA assay, above, and the fluorescence intensities of the assays from all four fluorophores was recorded.

Figure 17:
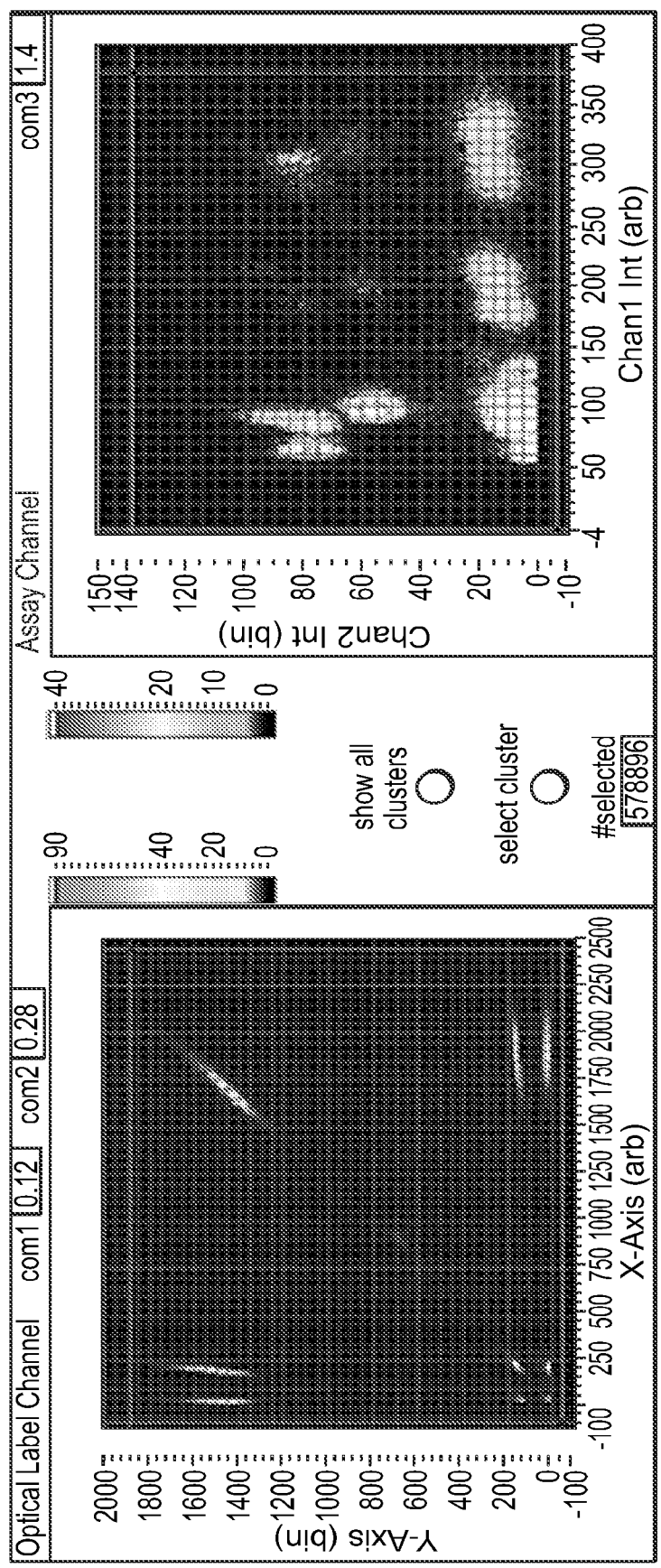
FIG. 17 depicts a dPCR assay combining multiplexing with optical labels using co-flow microfluidics. The contributions from all droplets are shown, that is, from three different triplex assays. (Both panels) 2-D histograms shown as heat maps with hotter colors representing higher droplet counts. (Left panel) histogram of optical labels, i.e. fluorescence intensities of droplets measured at wavelengths for the two fluorophores comprising the optical labels. (Right panel) assay histogram, i.e. fluorescence intensities of droplets measured at wavelengths suitable for FAM detection (x-axis), and VIC detection (y-axis). Both histograms were compensated for spectral overlap by standard techniques.

FIG. 17 shows the cumulative results from all droplets in the 3×3×3 assay using co-flow microfluidics. The figure shows two 2-D histograms of droplet fluorescence intensities, the histogram on the left from all of the optical labels, and the histogram on the right from the assays. Standard methods were used to compensate for spectral overlap. The histograms are shown as a heat maps, with hotter colors designating larger numbers of droplets. Nine different clusters of droplets were clearly evident in the histogram of the optical labels, corresponding to each of the nine different optical labels: there is a small group of four clusters at the bottom left corner of the histogram, corresponding to optical labels with the lowest fluorescent intensities; and there are five clusters appearing as linear streaks at the higher intensities. The droplet clusters were less distinct in the histogram for the assay, but this was as expected because the droplets shown contained all of the triplex assays. The individual assays became clearly distinct once a single type of assay was selected by using the optical labels, as follows.

Methods of the invention involve selecting individual populations of droplets all containing the same optical labels, or groups of optical labels. In some methods of the invention, boundaries of fluorescence intensity were used to specify populations. In the example shown here, a rectangular boundary was used specifying the minimum and maximum fluorescence intensities for each fluorophore. However the methods of the invention are not restricted to rectangular boundaries. Any boundary, closed or unclosed, can be employed. Furthermore, according to methods of the invention, selections of droplet populations can be made by any method, and is not restricted to threshold-based methods such as boundary selection.

Figure 18A:
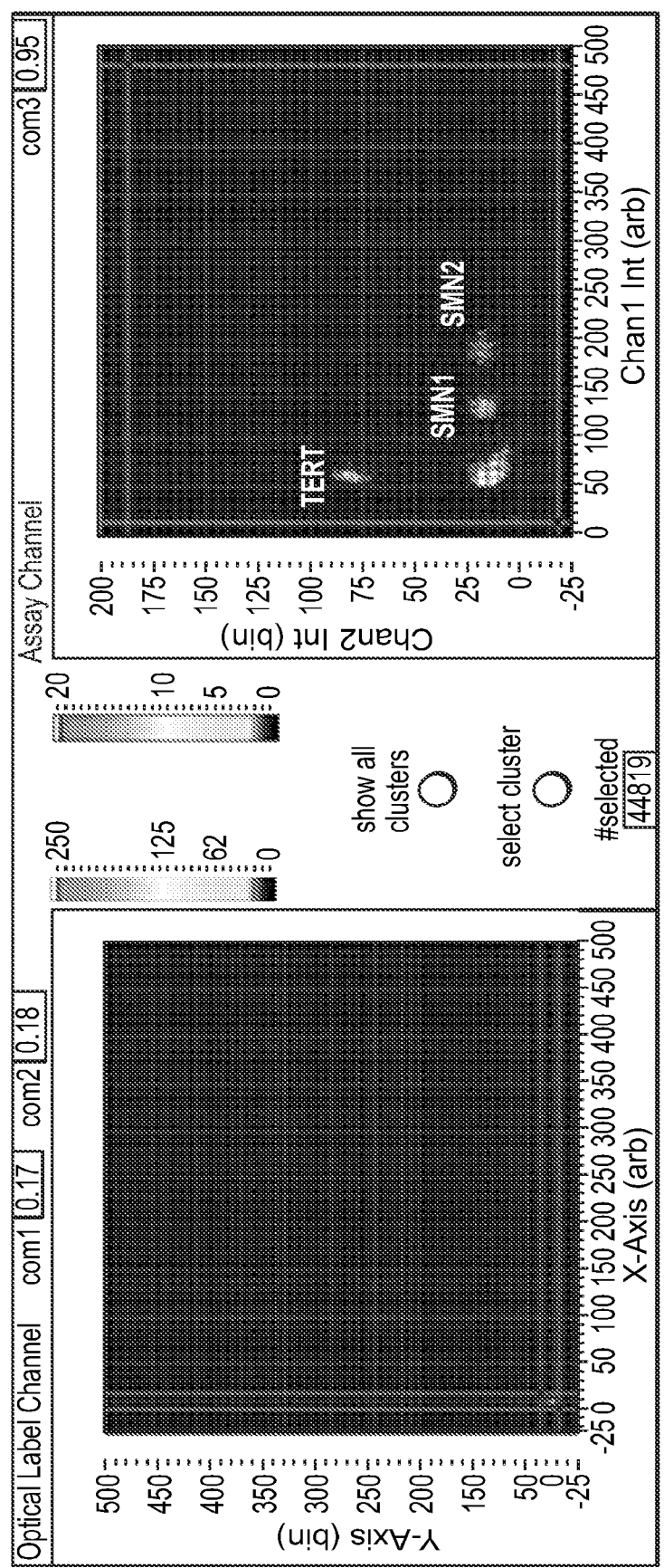
FIGS. 18A-C show single assay selections using optical labels. Selections were taken from all of the droplets from FIG. 17. Each of the three different selections in Figures A-C were for optical labels encoding the same assay (TERT, SMN1, and SMN2). Histograms are as described in FIG. 17. (Left histograms, optical labels) Superimposed lines demark the bounding box for selecting a single optical label. (Right histograms, assay) Only droplets containing the selected optical label are displayed.
Figure 18B:
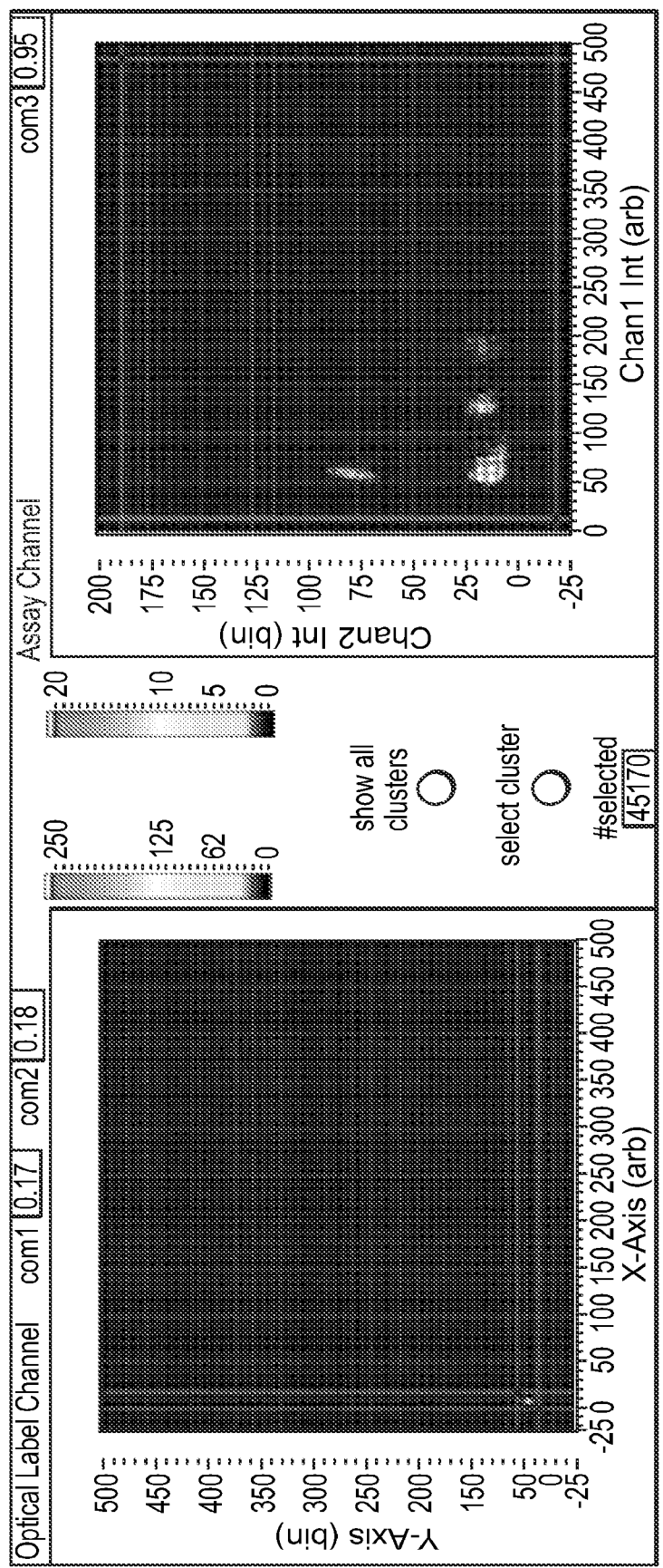
Figure 18C:
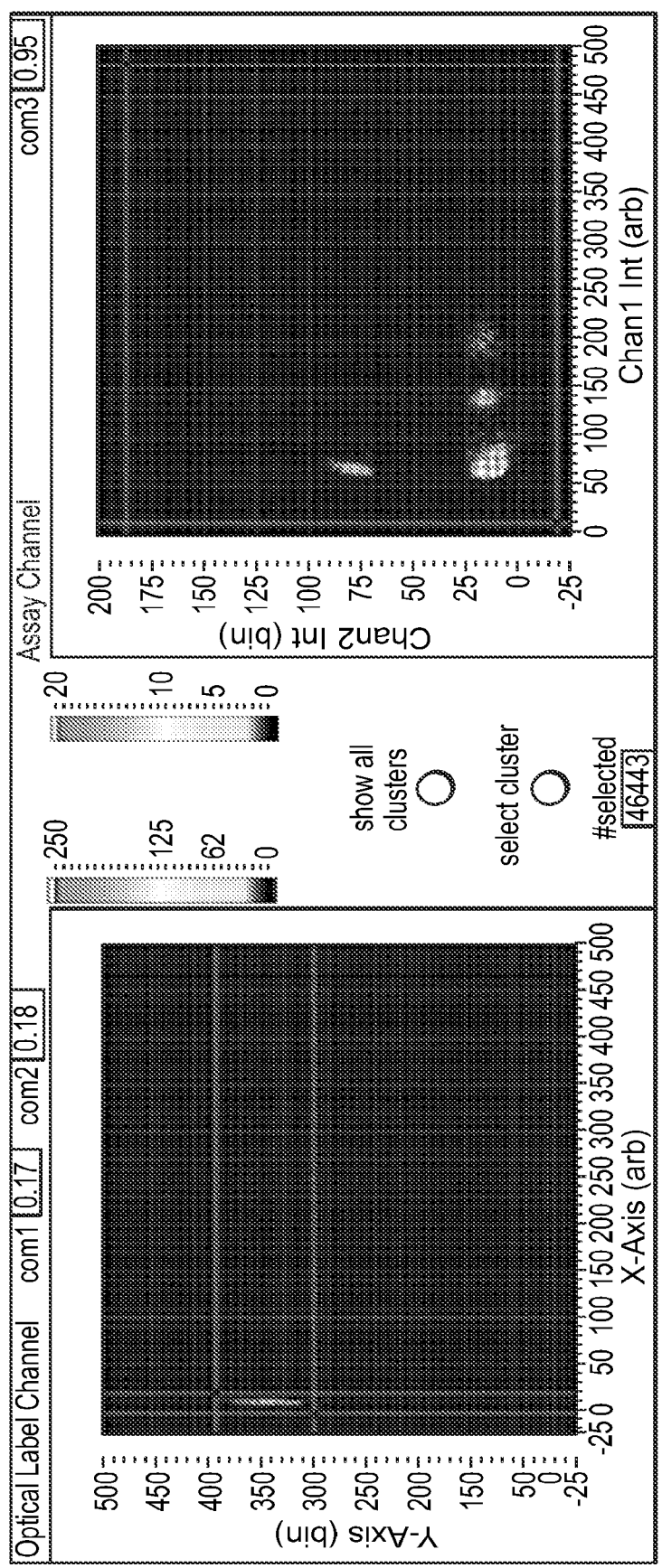

FIG. 18A shows the droplet fluorescence intensities for the assay (right histogram) when only one optical label was selected (left histogram). The lines overlaid on the histogram of the optical labels identify the rectangular boundary used to select just the optical label with the lowest fluorescence for both fluorophores. Both histograms showed only the droplets that were selected. After selection, four distinct clusters of droplets appeared in the assay histogram, three for the different assays (in this case, assays for SMN1, SMN2, and TERT, where TERT is another common reference gene) and one for the empty droplets. The copy numbers for SMN1 and SMN2 were measured by the same methods of the invention as described above for the 5-plex SMA assay, with values of 1.8 and 0.94 close to the expected values of 2 and 1, respectively. The same assay was encoded with two other optical labels, and their selections are shown in FIGS. 18B and C. Similar results were achieved, with an overall measurement of 1.9±0.1 and 0.9±0.1 copies of SMN1 and SMN2 respectively, showing the measurement to be accurate within experimental uncertainty.

Figure 19A:
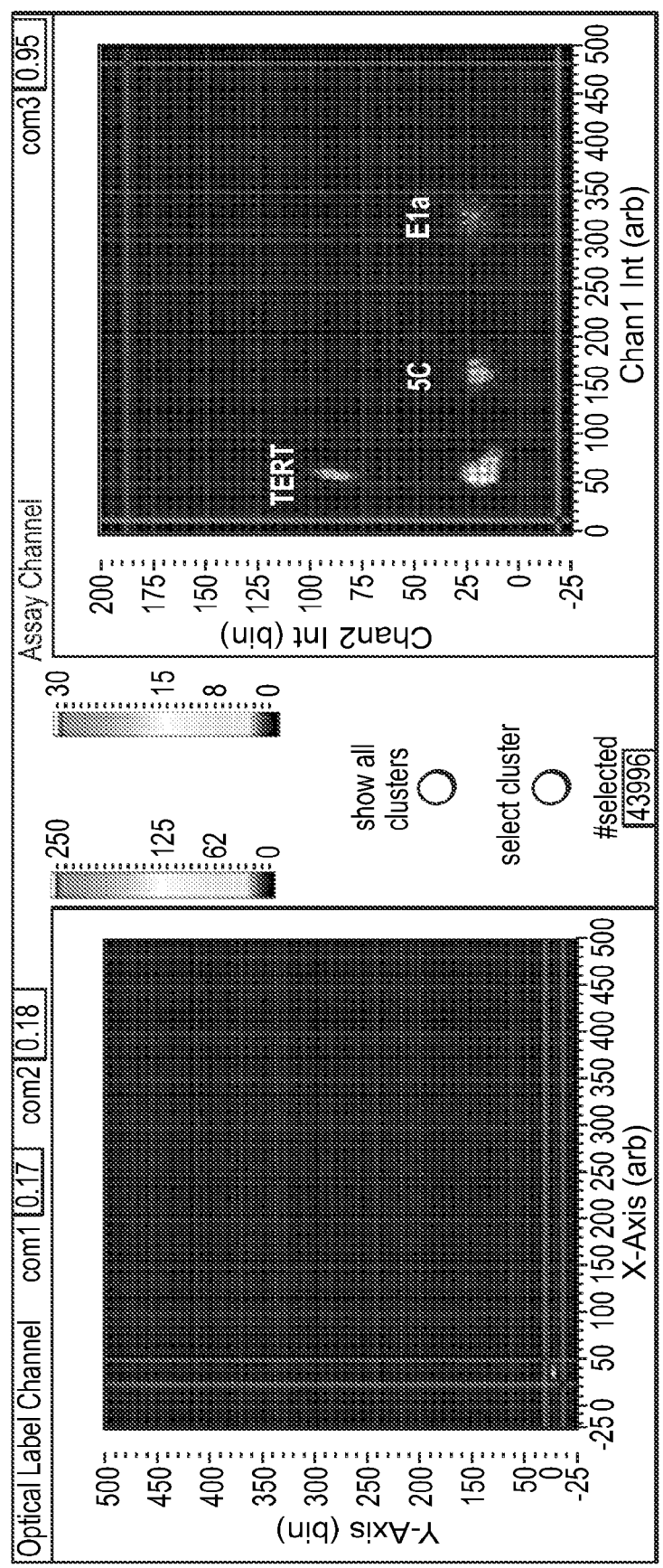
FIGS. 19A-C show single assay selections using optical labels. Selections were taken from all of the droplets from FIG. 17. Each of the three different selections in Figures A-C was for optical labels encoding the same assay (TERT, c.5C from SMN1, and BCKDHA). Histograms are as described in FIG. 17. (Left histograms, optical labels) Superimposed lines demark the bounding box for selecting a single optical label. (Right histograms, assay) Only droplets containing the selected optical label are displayed.
Figure 19B:
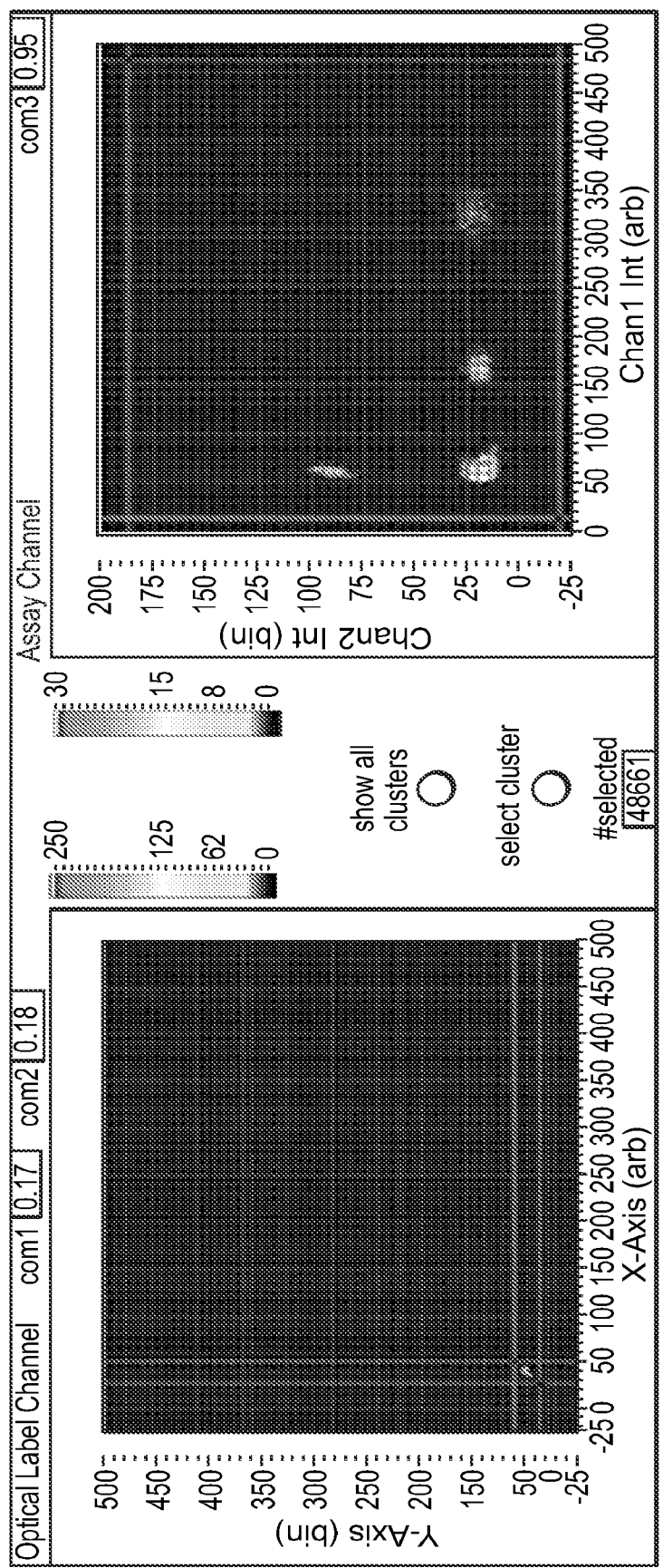
Figure 19C:
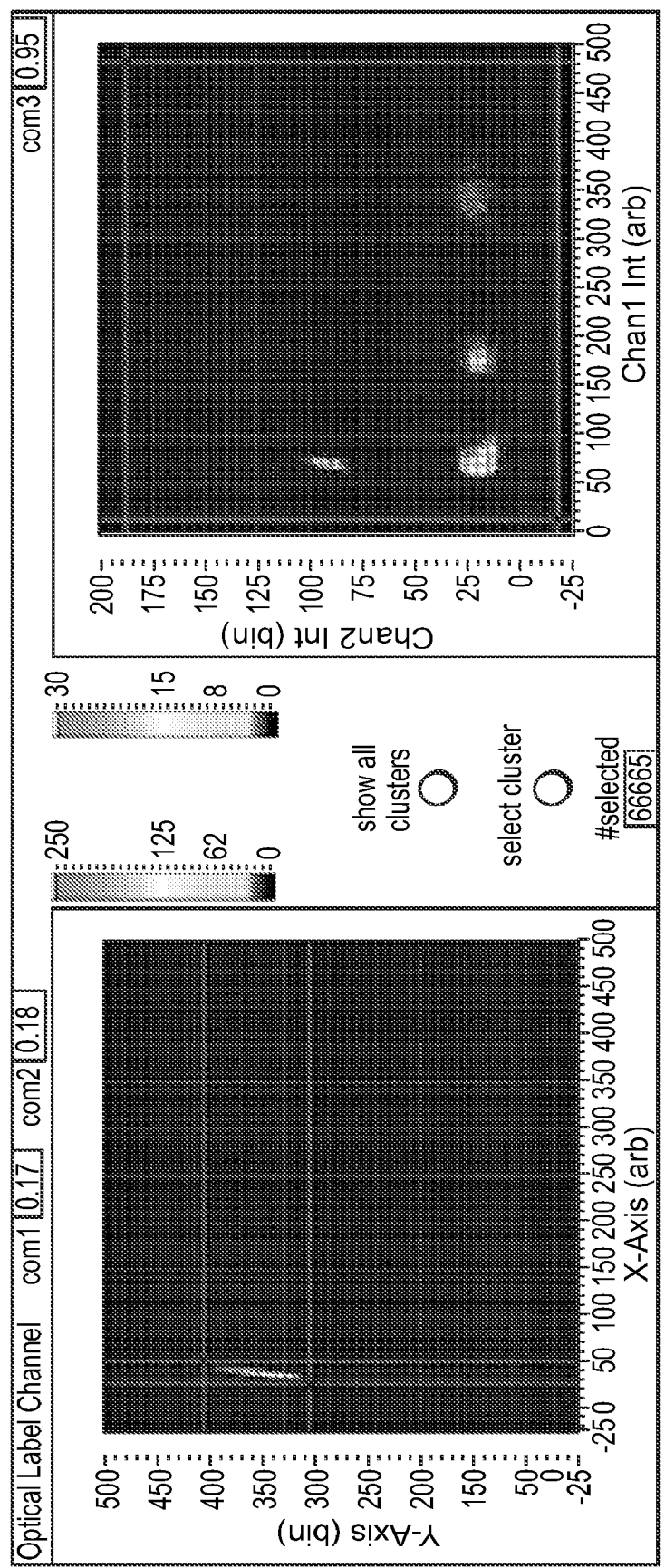
Figure 20A:
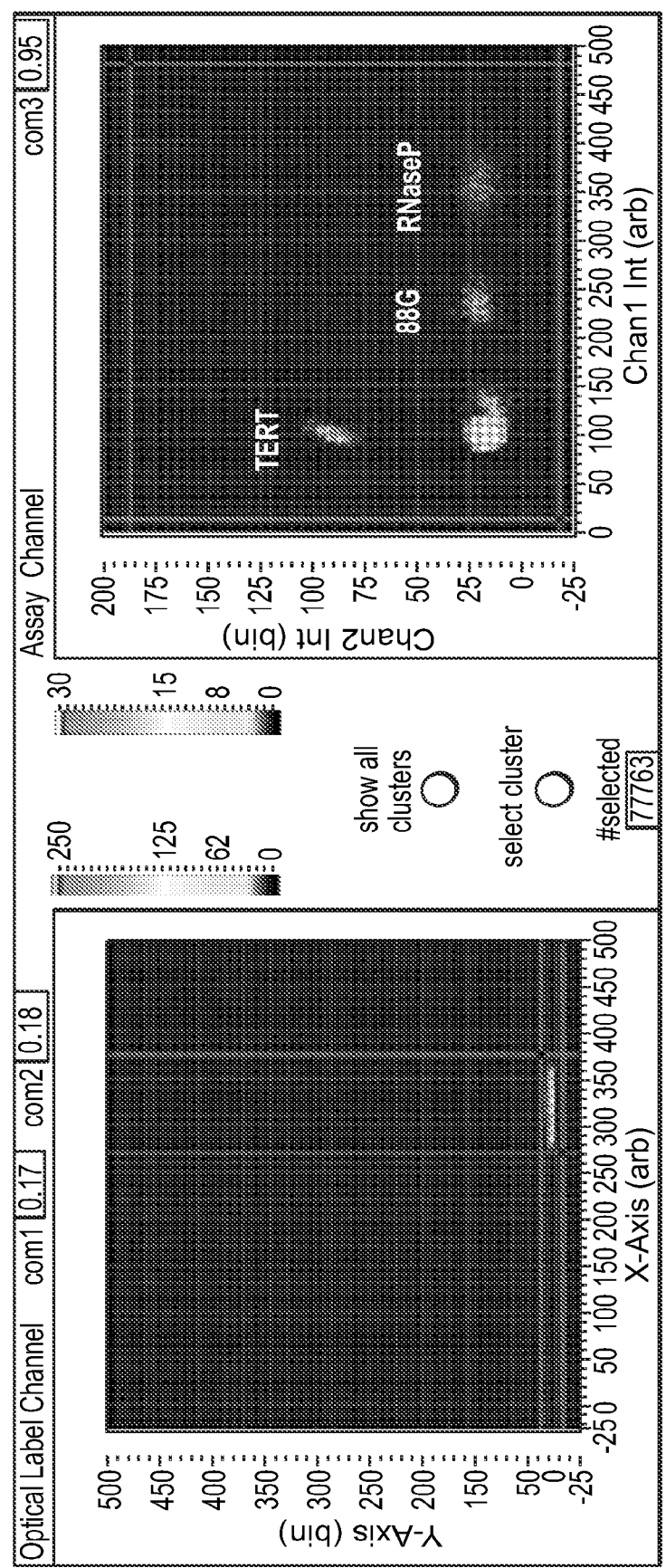
FIGS. 20A-C show single assay selections using optical labels. Selections were taken from all of the droplets from FIG. 17. Each of the three different selections in FIGS. 20A-C was for optical labels encoding the same assay (TERT, c.88G from SMN1, and RNaseP). Histograms are as described in FIG. 17. (Left histograms, optical labels) Superimposed lines demark the bounding box for selecting a single optical label. (Right histograms, assay) Only droplets containing the selected optical label are displayed.
Figure 20B:
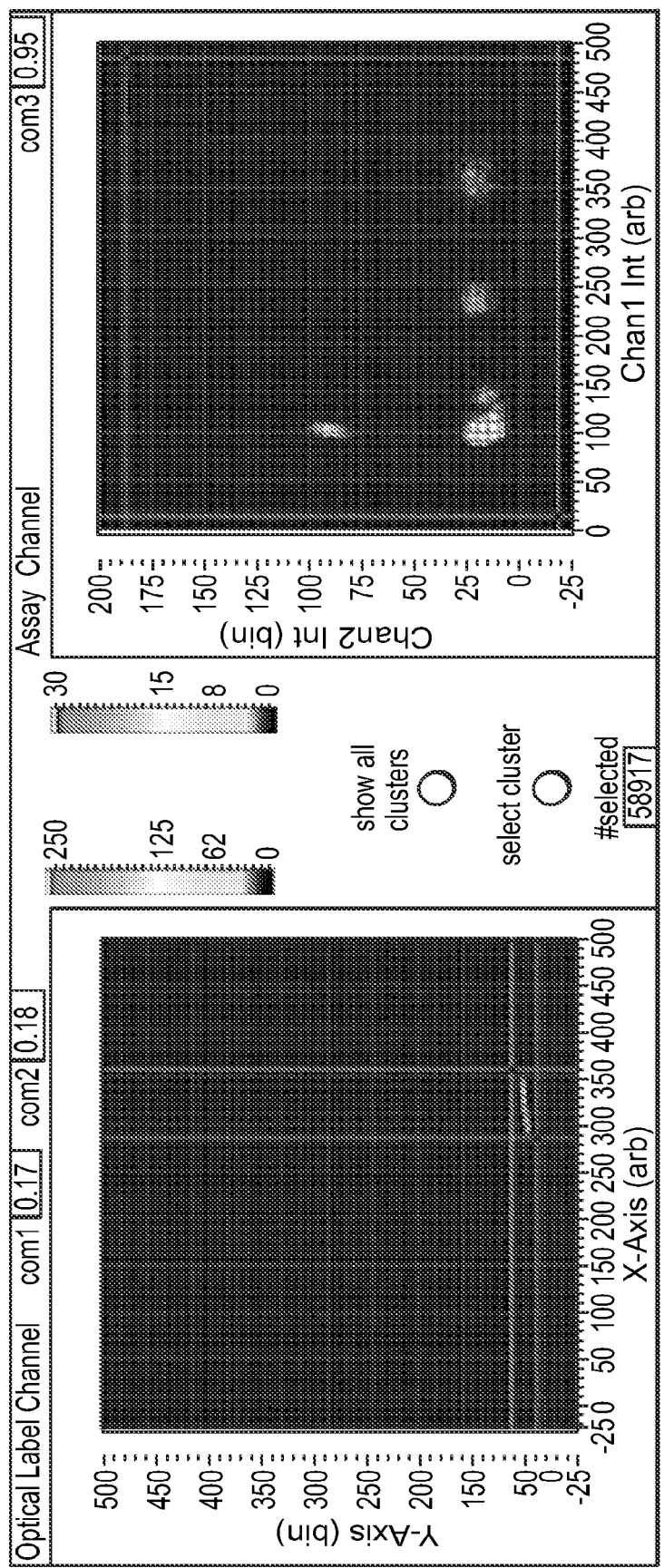
Figure 20C:
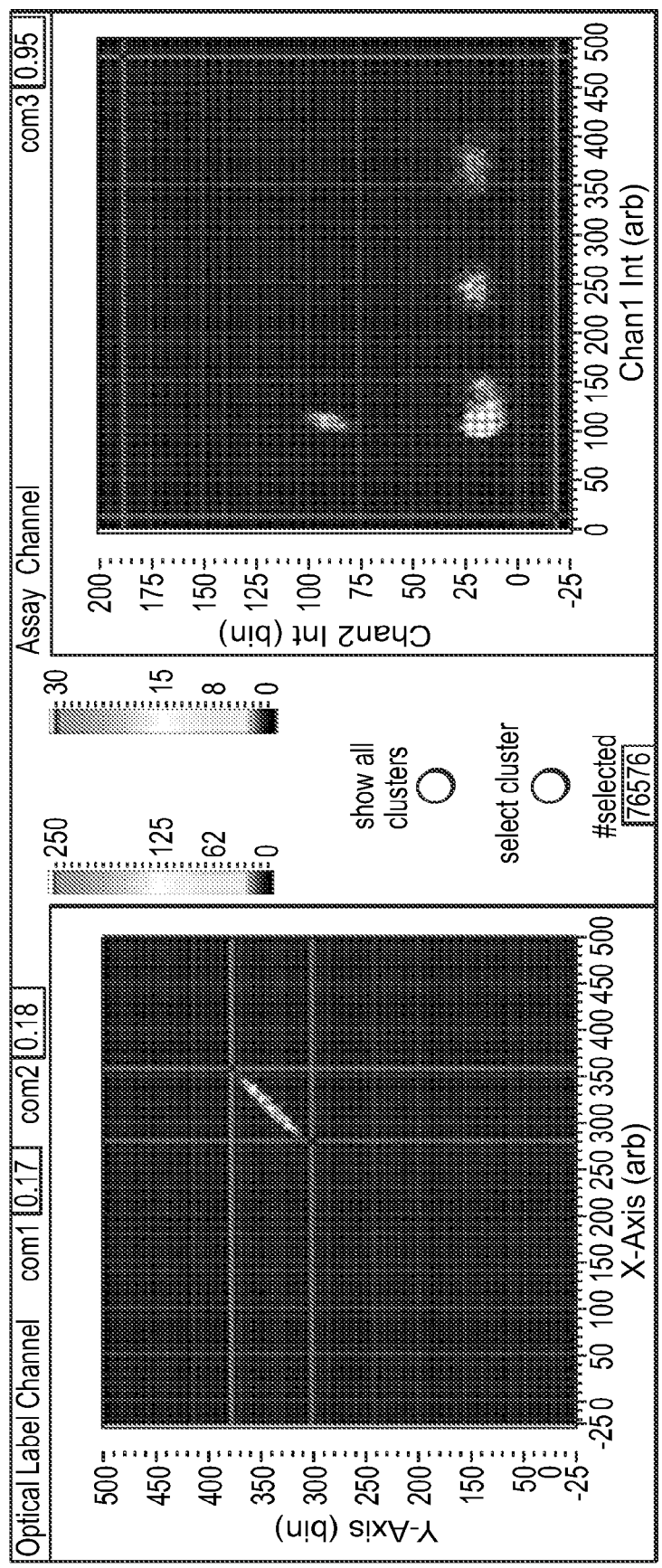
Figure 21A:
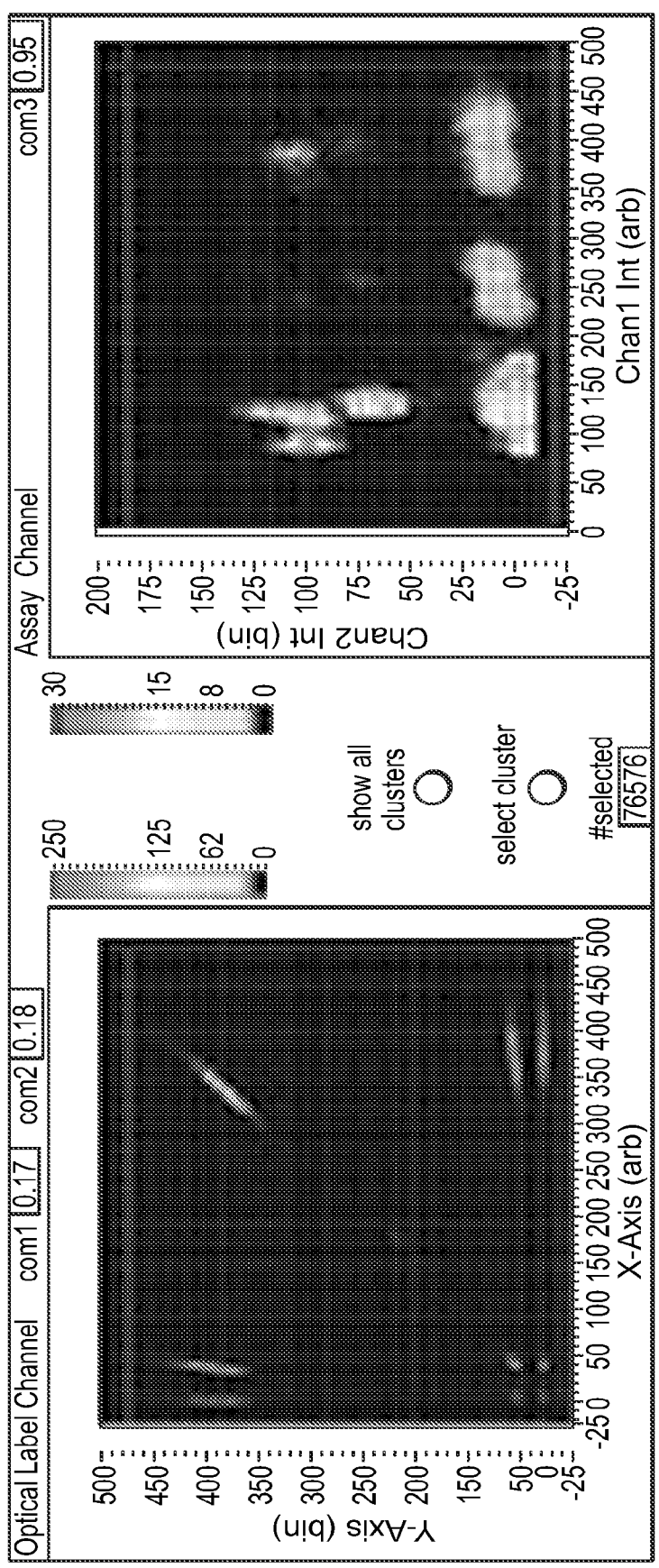
FIGS. 21A-J depict a dPCR assay combining multiplexing with optical labels using droplet merging.
Figure 21B:
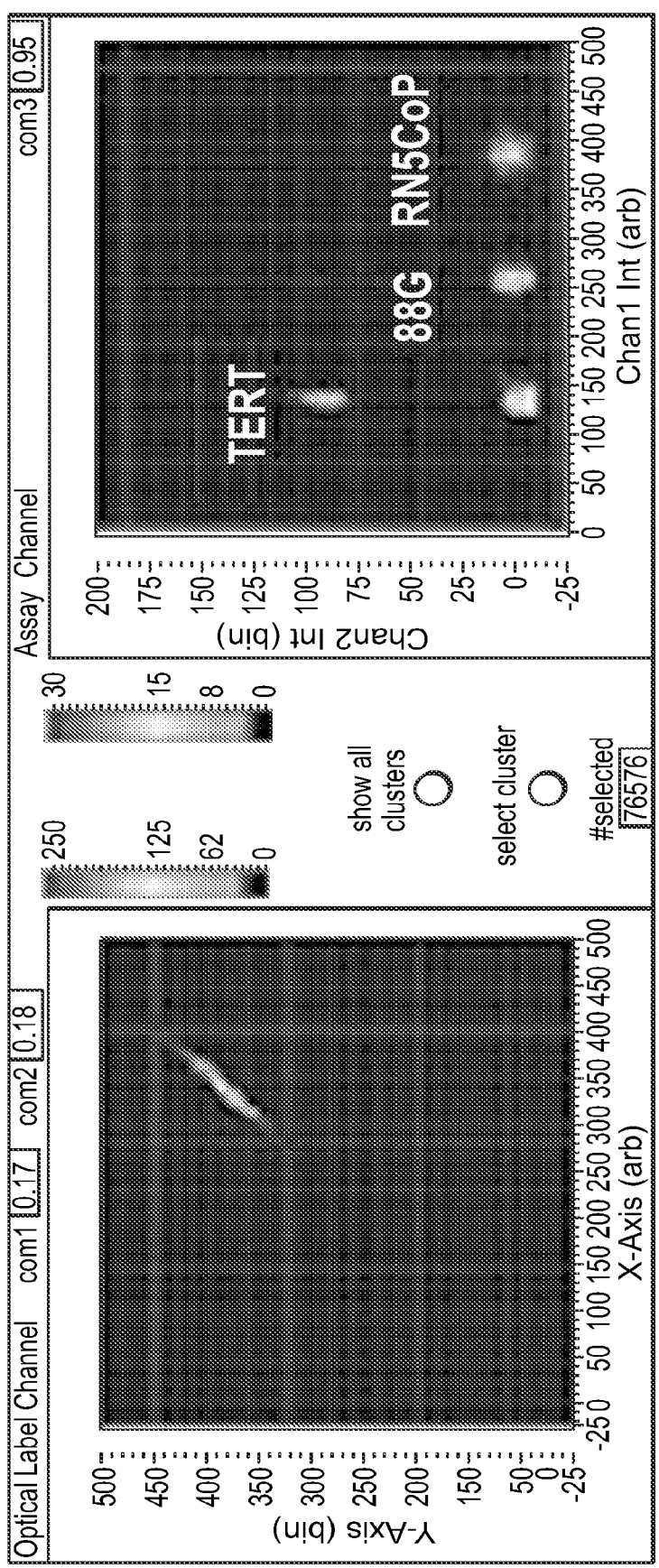
Figure 21C:
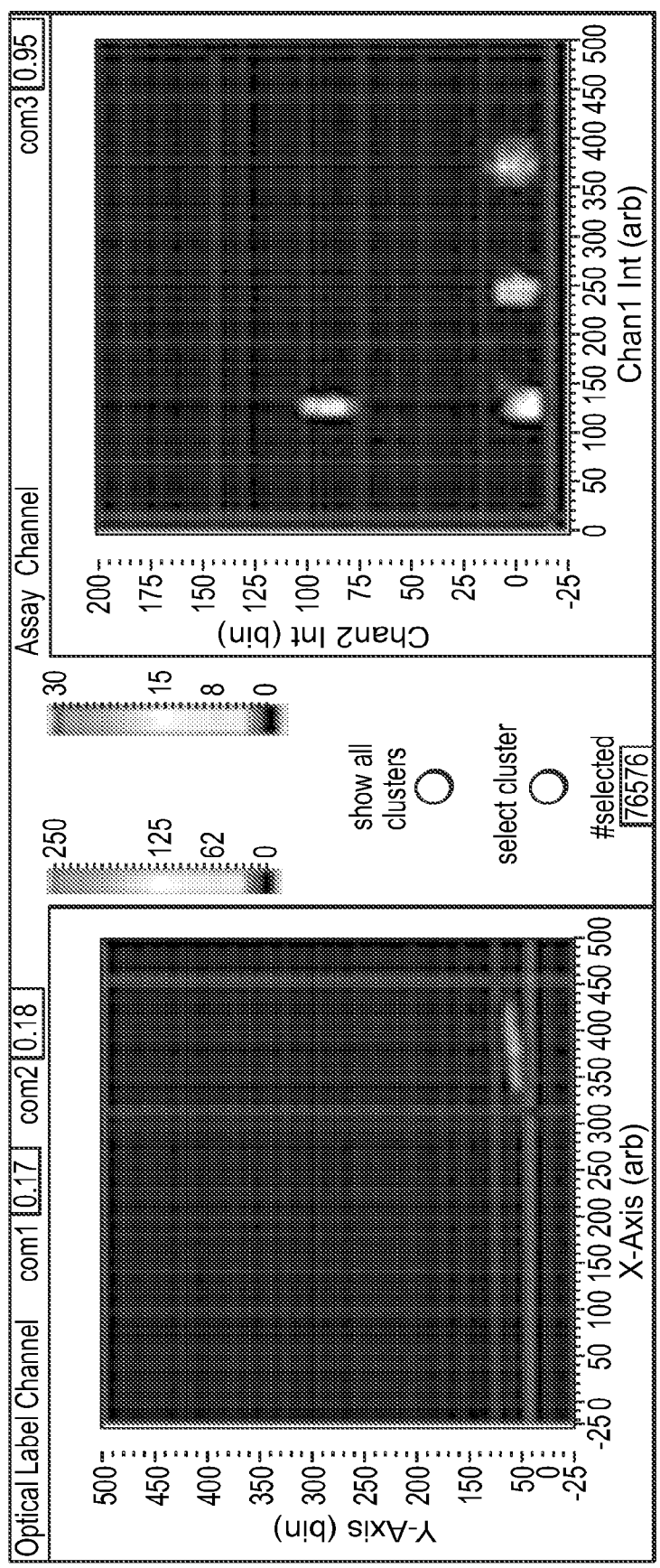
Figure 21D:
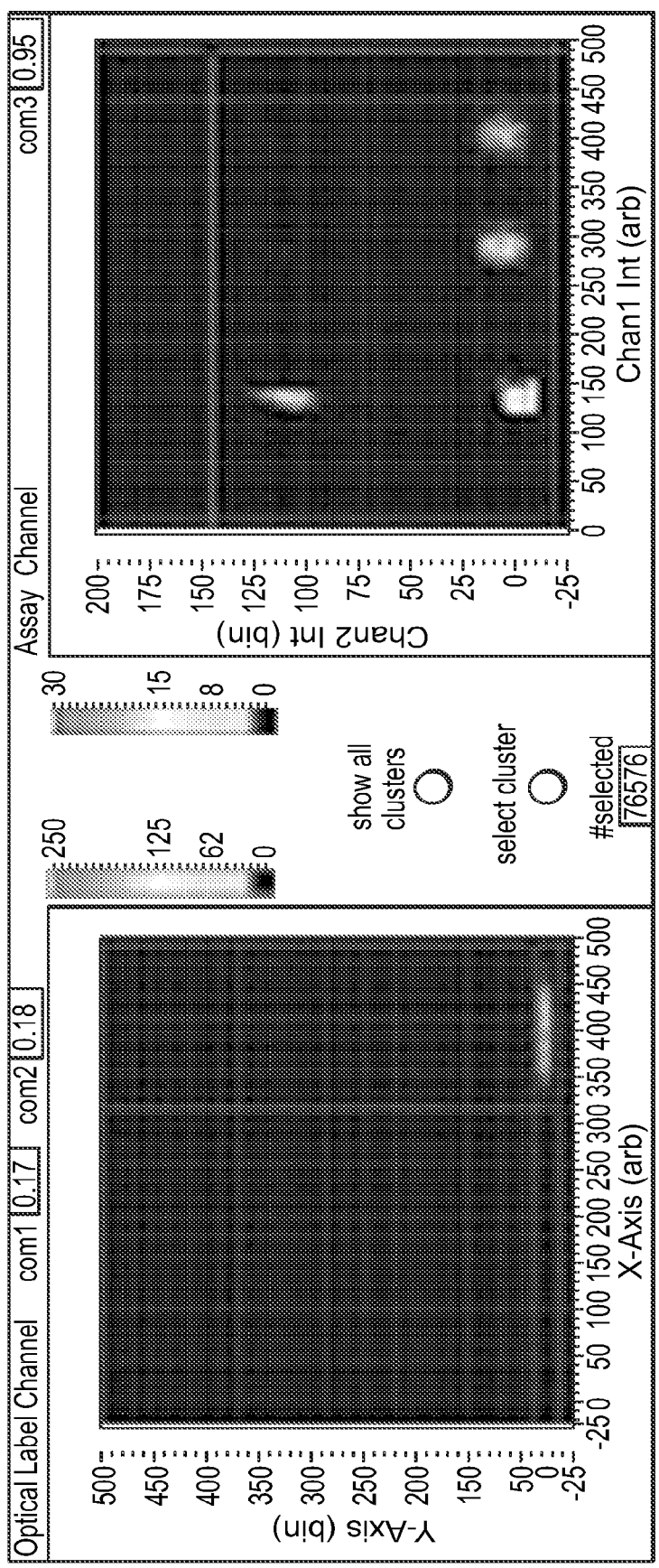
Figure 21E:
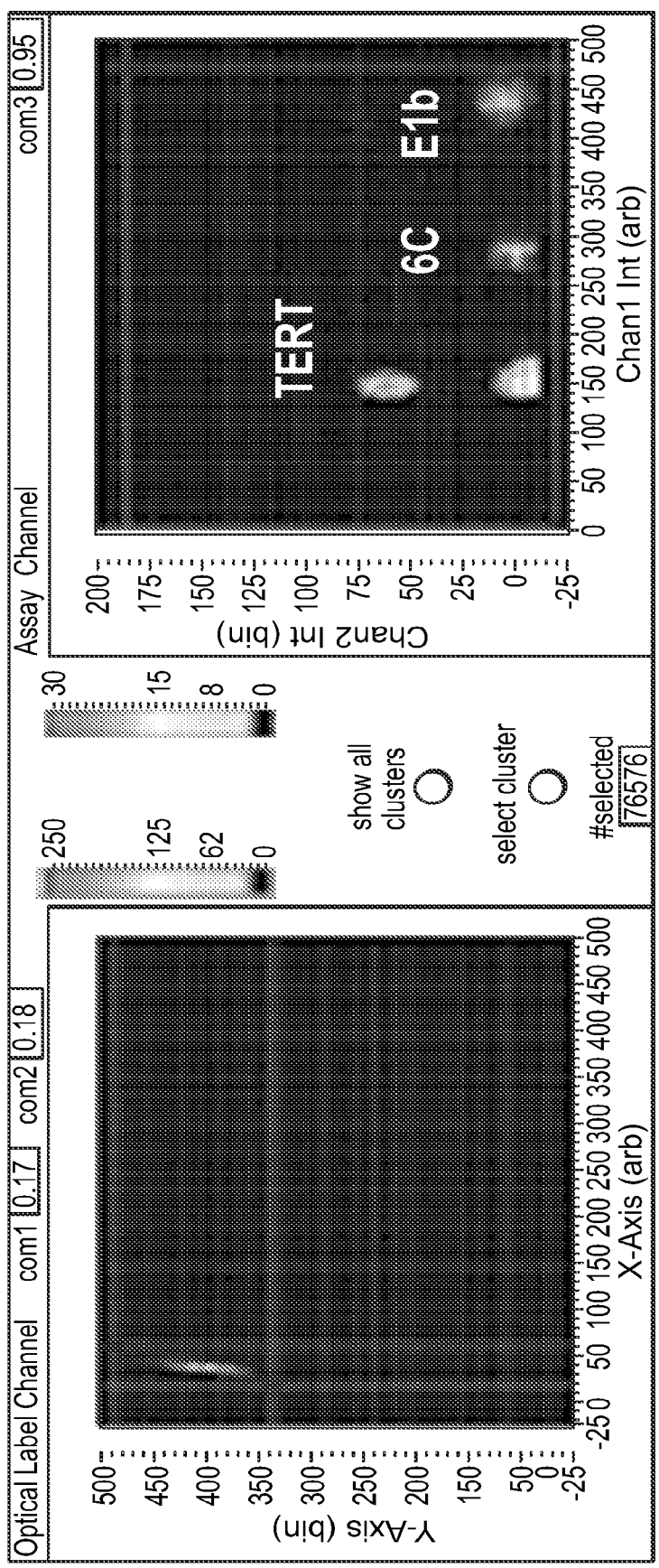
Figure 21F:
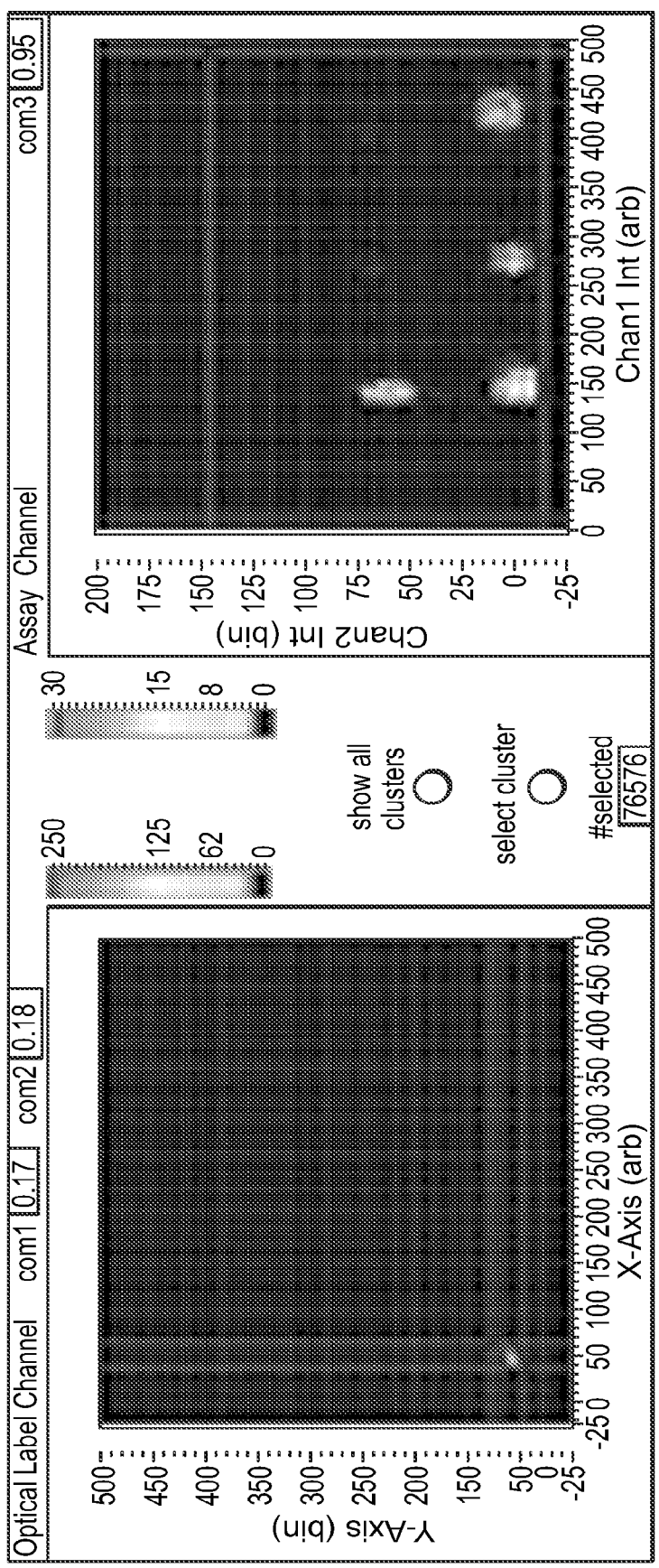
Figure 21G:
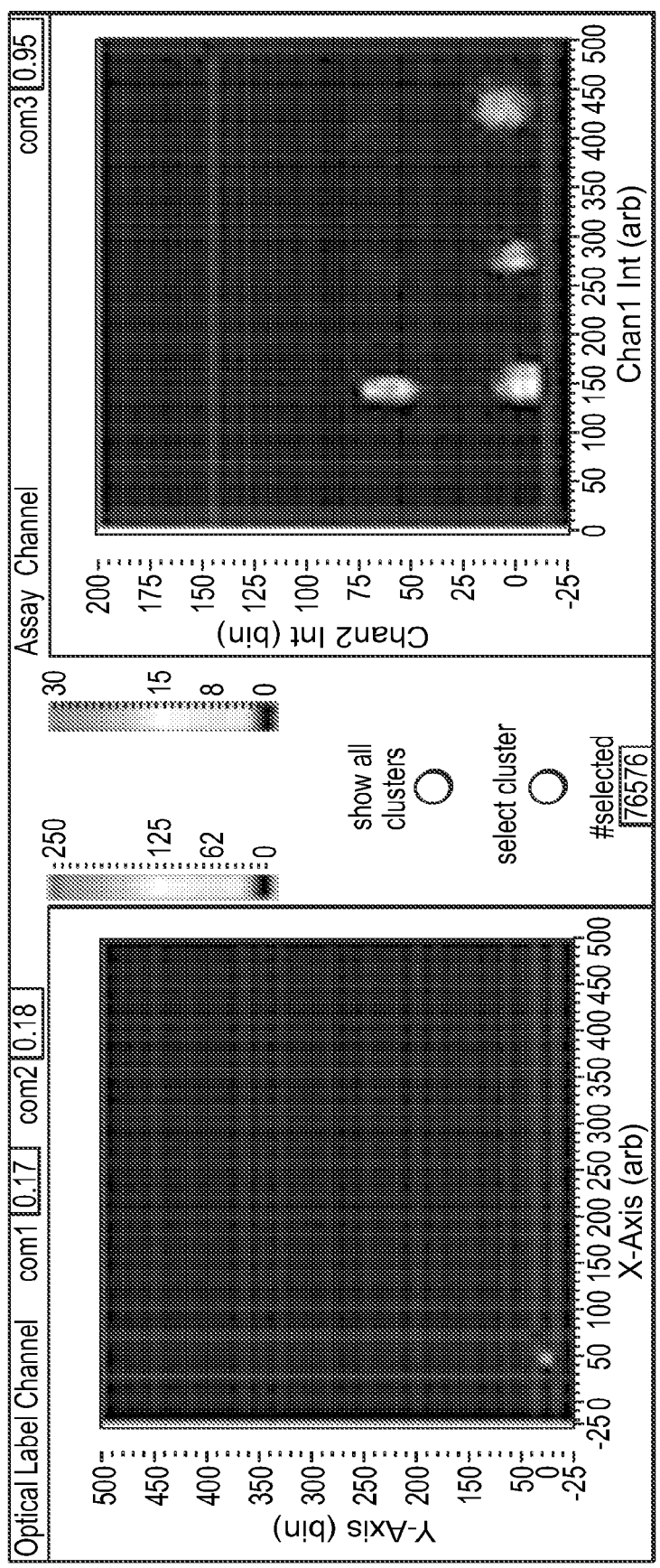
Figure 21H:
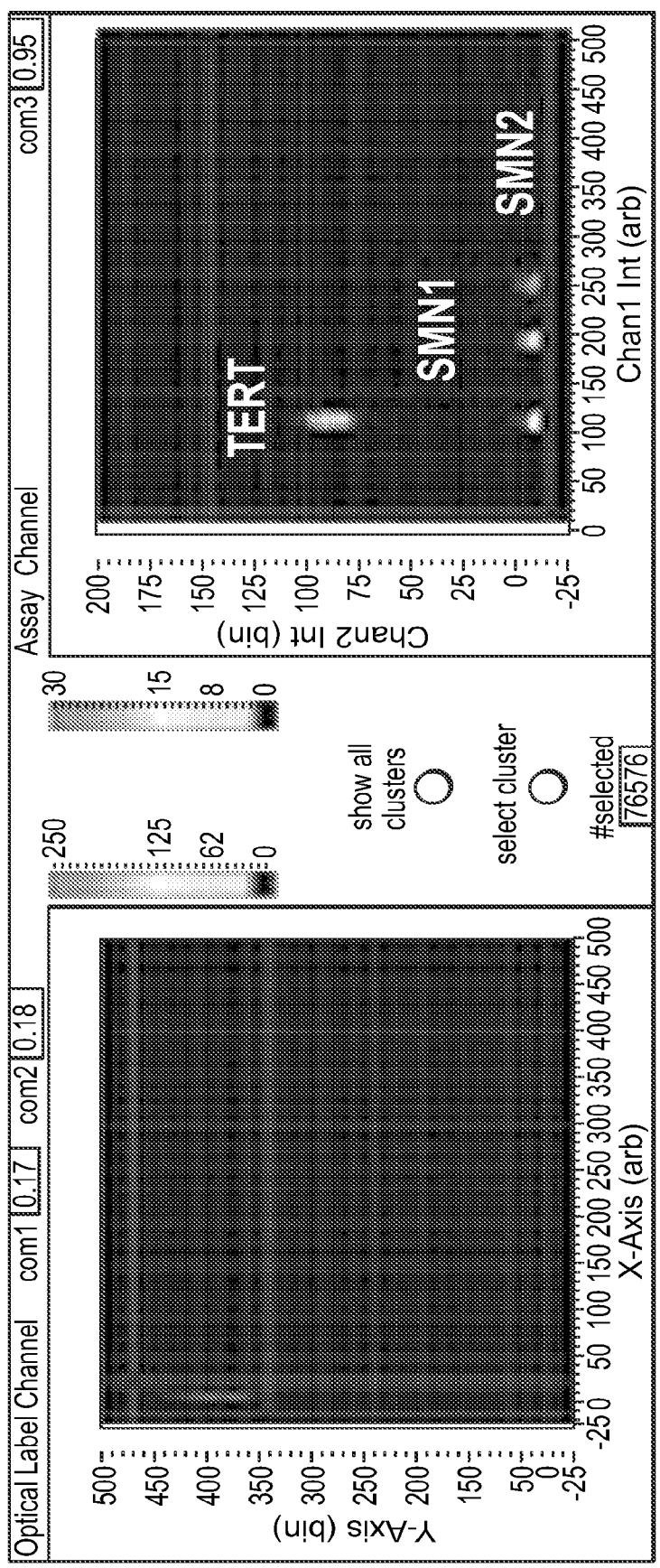
Figure 21I:
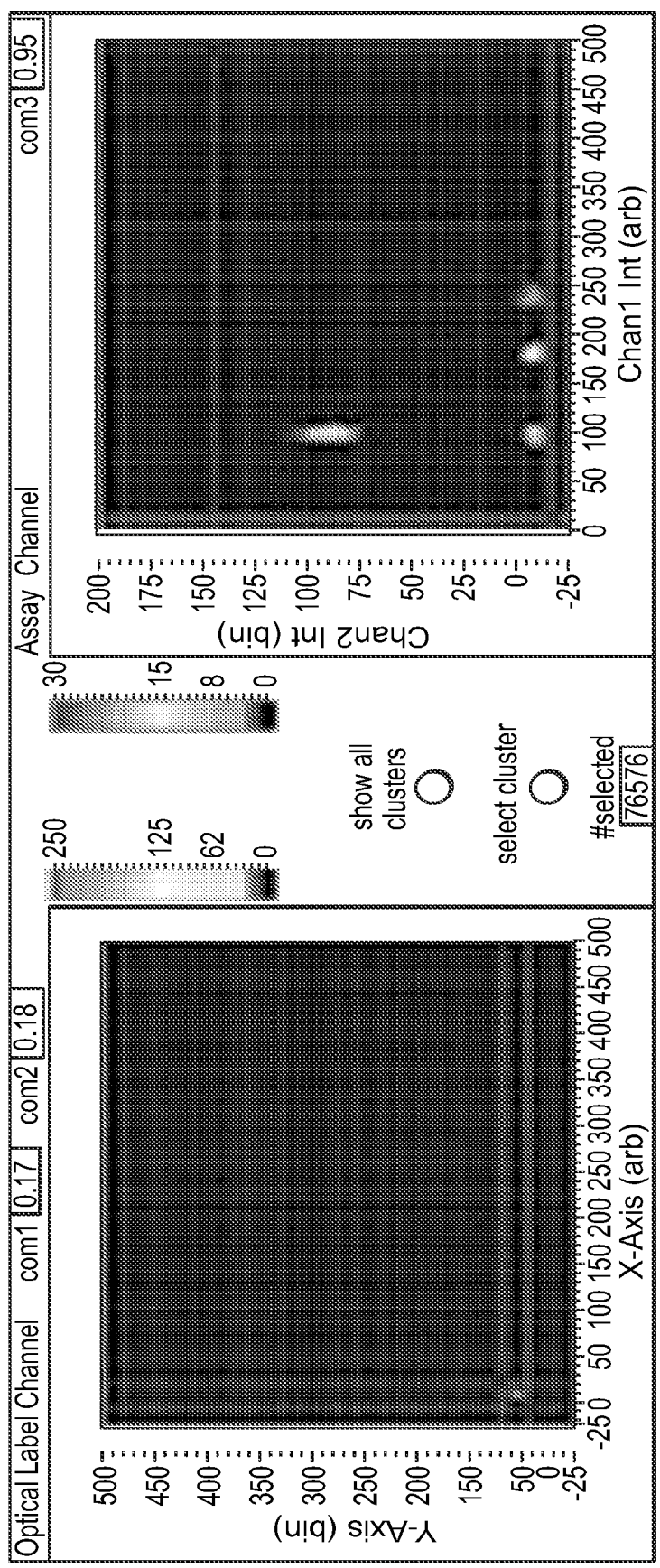
Figure 21J:
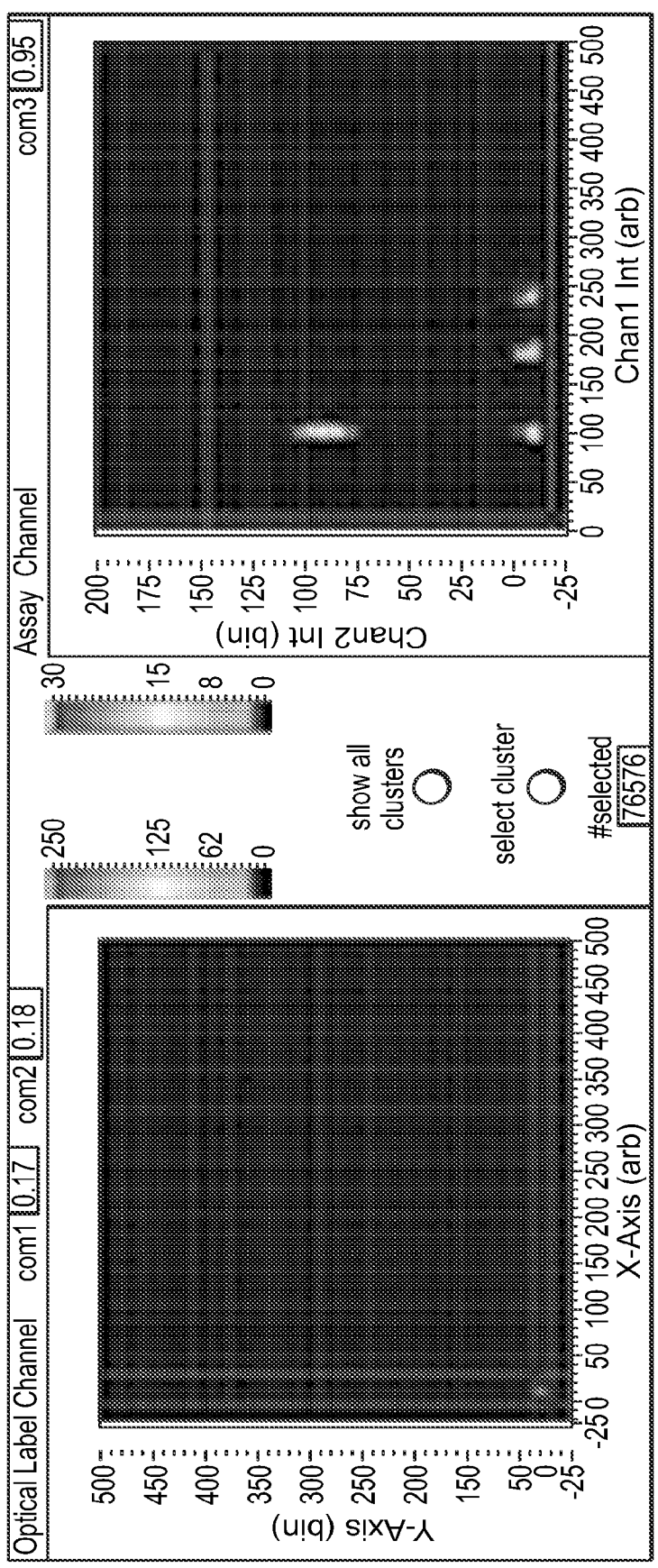

FIGS. 19A, B, and C show optical label selections for a different assay (TERT, c.5C in the SMN1 gene, and BCK-DHA (labeled E1a in the figure)). In each case four distinct clusters also appeared, and by the same methods of the invention above, accurate measurements of gene copy number were made for c.5C and BCKDHA, referenced to TERT, of 2.9±0.1 and 2.0±0.2 compared to 3 and 2, respectively. FIGS. 20A, B, and C show optical label selections for a third assay (TERT, c.88G in the SMN1 gene, and RNaseP, where RNaseP is a common reference gene). Accurate gene copy numbers of 2.1±0.1 were measured for both c.88G and RNaseP, referenced to TERT, compared to the expected value of 2.

In summary, the demonstration here shows use of nine different optical labels to enable independent measurement of three triplex assays in a single experiment. Although some of the optical labels encoded for redundant assays in this example (there were only three different assays despite having nine optical labels), the invention is not constrained to any particular formatting of assays and optical labels. Embodiments of the invention include formats where all of the assays are the same across all of the optical labels; where none of the assays are the same across all of the optical labels; where some of the assays are the same across all of the optical labels; where some of the assays have greater plexity than others across all of the optical labels; where all of the assays have the same plexity across all of the optical labels; and any other arrangements of assays across all of the optical labels are considered.

Although two different fluorophores were used to create the optical labels in this example, the invention is not constrained to any particular number of fluorophores comprising the optical labels. Embodiments of the invention include optical labels comprised of 1 fluorophore, or 2 fluorophores, or 3 fluorophores, or 4 fluorophores, or up to 10 fluorophores, or up to 20 fluorophores. Optical labels can also comprise more than 20 fluorophores.

Although solely triplex assays were used in the example demonstration here, the invention is not constrained to use of triplex assays with optical labels. Embodiments of the invention include plexities of the following amounts when used with optical labels: single plex, duplex, triplex, 4-plex, up to 10-plex, up to 20-plex, up to 50-plex, and up to 100-plex. Embodiments of the invention also include plexities exceeding 100 when used with optical labels.

Another method of the invention involves the use of droplet merging, instead of co-flow, for combining multiplexing with optical labels. A demonstration using droplet merging was performed with the same 3×3×3 assay as in the preceding example with co-flow. The assays (probes and primers) combined with their unique optical labels were first encapsulated into droplets along with the PCR master mix. Subsequently, according to methods of the invention described above, a library containing a mixture of droplets from all nine optically labeled assays was merged one-to-one with droplets containing template DNA from the same patient as in the preceding example. As another method of the invention, the droplet merge was performed using a lambda-injector style merge module, as described in U.S. Provisional Application, Ser. No. 61/441,985, incorporated by reference herein. Aside from the differences between co-flow and merge, the assays and experimental procedures were identical to those above for the co-flow experiment. FIG. 21 shows 2-D histograms of droplet fluorescence intensity for the optical labels and the assays that are similar to those in FIGS. 17-20. As in the case for co-flow, upon selection of droplets containing individual optical labels, the expected distinct clusters of droplets corresponding to each assay were clearly evident. Furthermore for each assay the measured gene copy number matched or very nearly matched the expected values within experimental uncertainty (See Table 1).

TABLE 1

Gene copy number measurements from the 3 × 3 × 3 assay.

| Gene or genotype | Measured copy number | Expected copy number |
|---|---|---|
| SMN1 | 1.98 ± 0.09 | 2 |
| SMN2 | 0.99 ± 0.04 | 1 |
| c.5C in SMN1 | 3.01 ± 0.06 | 3 |
| c.88G in SMN1 | 2.15 ± 0.08 | 2 |
| BCKDHA | 2.00 ± 0.05 | 2 |
| RNaseP | 2.11 ± 0.16 | 2 |

Although methods of the invention include using either microfluidics with co-flow or droplet merging, the invention is not limited in this regard. Any fluidic method capable of generating optically labeled droplets that also contain fluorogenic DNA hybridization probes are considered. For example, other embodiments well known in the art are mixing optical labels and assays in the macrofluidic environment before injection into a droplet generating chip; and mixing optical labels and assays thoroughly upstream from the droplet forming module in dedicated mixing modules, such as with a serpentine mixer.

Data Analysis

One method of the invention involves histogram-based data presentation and analysis for identifying and characterizing populations of statistically similar droplets that arise from unique probe signatures (color and intensity), and for discriminating one population of droplets from the others. Another method of the invention involves histogram-based data presentation and analysis for identifying and selecting populations of droplets based on unique signatures from optical labels. Examples of one and two-dimensional histograms have been provided for these methods, but the invention is not limited in this regard. As described above, it is anticipated that greater numbers of colors will be used for both multiplexing and for optical labels. Hence, embodiments of the invention include histograms of dimensionality greater than two, such as 3, or 4, or up to 10, or up to 20. Histograms of dimensionality greater than 20 are also incorporated into the invention.

Another method of the invention involves the selection of droplets within histograms, either for counting, or for assay selection as in the use of optical labels, or for any other purpose. Methods of the invention include selections by boundaries, either closed or unclosed, of any possible shape and dimension. Methods of the invention also include selections of droplets that exhibit fluorescence from single types of fluorophores, or from multiple types of fluorophores, such as arising from multiple probes against a common DNA target.

Polymerase Error Correction

For applications requiring very high sensitivity, such as searching for rare mutations amidst an abundance of wild-type DNA, false positive results can arise from errors from the DNA polymerase itself. For example, during one of the early thermal cycles the polymerase might synthesize the mutant strand of DNA from a wild-type template. This type of error is most likely to occur when the difference between the mutant and the wild-type is very small, such as single nucleotide polymorphism (SNP). In this method of the invention, each droplet contains only a single target nucleic acid, if any at all. In the preferred embodiment, this is accomplished under the conditions of terminal dilution. Droplets that contain amplification products that are a wild-type of the target are detected based on emission from the fluorophore that is released from the probe that hybridizes to the wild-type of the target. Droplets that contain the variant of the target are detected based on emission from the fluorophore that is released from the probe that hybridizes to the variant of the target. Since each droplet starts with only a single nucleic acid molecule, the resultant amplification products in each droplet are either homogeneous for the target or homogenous for the variant of the target.

However, certain droplets will contain a heterogeneous mixture of both target and target variant due to polymerase errors during the PCR reaction. Error rates in PCR vary according to the precise nucleic acid sequence, the thermostable enzyme used, and the in vitro conditions of DNA synthesis. For example, the error frequency (mutations per nucleotide per cycle) during PCR catalyzed by the thermostable *Thermus aquaticus* (Taq) DNA polymerase vary more than 10-fold, from $\sim 2\times10^4$ to $<1\times10^{-5}$. Eckert et al. (Genome Res. 1:17-24, 1991), the content of which is incorporated by reference herein in its entirety. Polymerase-mediated errors at a frequency of 1 mutation per 10,000 nucleotides per cycle are an important consideration for any PCR application that begins with a small amount of starting material (e.g., less than a total of 10,000 nucleotides of target DNA) or that focuses on individual DNA molecules in the final PCR population.

The proportion of DNA molecules that contain sequence changes is a function of the error rate per nucleotide per cycle, the number of amplification cycles and the starting population size. The population of altered DNA molecules arises during PCR from two sources: (1) new errors at each PCR cycle; and (2) amplification of DNA molecules containing errors from previous cycles. The formula $f=np/2$ describes the average mutation frequency (f) for PCR amplification as a function of the polymerase error rate per nucleotide per cycle (p) and the number of cycles (n), assuming that p is constant at each cycle. Due to the exponential nature of PCR, the occurrence of an early error can increase the final error frequency above the average described by $f=np/2$, because the variant DNA molecule will be amplified with each cycle, resulting in populations with a larger than average number of variants.

A polymerase error that converts a wild-type of the target to a variant of the target during an early round of amplification results in a heterogeneous population of target and target variant in a droplet, and may lead to a droplet being incorrectly identified as containing a variant of the target, i.e., a false positive. Such false positives greatly impact the validity and precision of digital PCR results.

Methods of the invention are able to detect which droplets contain a heterogeneous population of molecules and are able to exclude those droplets from analysis. As droplets containing amplified product flow in a channel through the detector module, the module is able to detect the fluorescent emission in each droplet. Droplets that produce only a single signal are classified as droplets that contain a homogeneous population of target. Since probes that hybridize to the wild-type of the target have a different fluorophore attached than probes that hybridize to a variant of the wild-type of the target, methods of the invention can classify each droplet as containing either a homogeneous population of amplicons of the target or a homogeneous population of amplicons of the variant of the target.

Droplets that produce two signals are classified as droplets that contain a heterogeneous population of molecules. Since each droplet started with at most a single target nucleic acid, a droplet that includes amplification products that are both amplicons of the target and amplicons of a variant of the target are droplets in which the variant of the target was produced by a polymerase error during the PCR reaction, most likely a polymerase error during an early cycle of the PCR reaction. Such droplets are detected and excluded from analysis.

Polarization Detection

As discussed, droplets containing amplified products may be detected by detecting the fluorescent emission of the detectable probe (such as a TaqMan probe) coupled to a target. TaqMan probes consist of a fluorescent molecule covalently attached to the 5'-end of the oligonucleotide probe and a quencher at the 3'-end. Several different fluorophores (e.g. 6-carboxyfluorescein, acronym: FAM, or tetrachlorofluorescein, acronym: TET) and quenchers (e.g. tetramethylrhodamine, acronym: TAMRA, or dihydrocyclopyrroloindole tripeptide minor groove binder, acronym: MGB) are available and suitable for use in methods of the invention. The quencher molecule quenches the fluorescence emitted by the fluorescent molecule when excited by, e.g., a PCR cycler light source via FRET (Fluorescence Resonance Energy Transfer). As long as the fluorescent molecule and the quencher are in proximity, quenching inhibits fluorescence signals. While the fluorescence signal is inhibited, intact probes still emit a background or dim fluorescent signal.

TaqMan probes are designed such that they anneal within a DNA region amplified by a specific set of primers. As the Taq polymerase extends the primer and synthesizes the nascent strand, the 5' to 3' exonuclease activity of the polymerase degrades the probe that has annealed to the template. Degradation of the probe releases the fluorescent molecule from it and breaks the close proximity to the quencher, thus relieving the quenching effect and allowing fluorescence of the fluorescent molecule. Hence, fluorescence detected in the real-time PCR thermal cycler is directly proportional to the fluorescent molecule released (cleaved) and the amount of DNA template present in the PCR.

However, for certain applications that include a large volume of probes within a droplet, the fluorescence of the released (cleaved) fluorescent molecule of the amplified product is hard to detect amid the dim background fluorescence of the large volume of intact probes. A low bright to dim ratio decreases the ability to successfully detect amplifiable product within a droplet by merely detecting the optical fluorescence of a droplet.

As an alternative to optical fluorescence detection, methods of the invention provide for detecting amplifiable product by analyzing the fluorescence polarization of fluorescent molecule (e.g., dyes and fluorophores) within a droplet. Using fluorescence polarization, a dye molecule attached to a probe can be distinguished from a dye molecule that is free floating in the droplet after cleavage. Prior to cleavage, a dye molecule intact with the quencher portion of a probe has a high degree of fluorescence polarization whereas a cleaved dye molecule has a low fluorescence polarization value.

Fluorescence polarization is based on the principle that, when temperature and viscosity of a solvent is held constant, the degree of fluorescence polarization detected when a fluorescent dye molecule is excited by polarized light depends on the molecular weight of the dye molecule. By monitoring the fluorescence polarization, one can detect significant changes in molecular weight of a dye molecule, which allows one to detect whether the dye molecule remains intact with the probe or free-floating due to cleavage. Detection of a free-floating dye molecule signifies amplifiable product, and enables detection of a corresponding target.

Light emitted from a fluorescent molecule becomes polarized when it is excited by polarized light at a certain wavelength. When the fluorescent molecule is in a medium, the molecule rotates. This rotation causes the observed fluorescence polarization to be proportional to the molecules rotational relaxation time. Rotational relaxation time correlates to the viscosity of the solvent, absolute temperature, molecular volume, and gas content, which is why a degree of fluorescence polarization is directly proportional to molecular weight when temperature and viscosity of a solvent is held constant. If a fluorescent molecule is large and has a high molecular weight (such as an intact probe having a fluorescent molecule coupled to a quencher probe), it slowly rotates within the solvent so that polarization of the fluorescent molecule is preserved. However, if a fluorescent molecule is small and has a low molecular weight (such a fluorescent molecule cleaved from a probe during amplification), it rotates quickly and loses polarity or becomes depolarized. Based on the difference in the degree of fluorescent polarization between cleaved and intact probes, fluorescence polarization can be used to detect amplifiable products in any assay that releases a fluorescent molecule during amplification of a target nucleic acid, e.g. standard 5' nuclease assay for determining mutational status in a nucleic acid. It is understood that several factors may be adjusted to increase the sensitivity of this technique. For example, the excitation state of the dye, the size of the initial probe, the size of the cleaved fluorescent molecule, and the fluorescence/polarization lifetime of the fluorescent molecule after excitation. Detecting nucleic acids with fluorescence polarization is described in more detail in Latif et al., Genome Re. 2001 11:436-440, the contents of which is incorporated by reference in its entirety.

Another consideration effecting polarization of a fluorescent molecule, either quenched or free-floating, is the fluorescence lifetime of the molecule. The fluorescence polarization measurements are based on an inverse relationship between the fluorescence lifetime of a fluorescent molecule and the molecular rotation of the molecule by itself and/or other molecules bound thereto (e.g. probe) attached thereto. If the fluorescence lifetime of a fluorescent molecule is greater than the rotation correlation of time the molecule(s) bound thereto, the molecule(s) randomize during emission and quickly become unpolarized. If the fluorescence lifetime of a fluorescent molecule is lesser than the rotational correlation of time to molecules bound thereto, the molecules remain aligned during emission and the emission remains polarized. As such, certain embodiments provide for optimizing use of the fluorescence lifetime of a molecule in order to optimize polarization detection. This includes selecting a fluorescent molecule and designing probes (e.g. quencher probe length or adding a weight-bearing molecule) to maximize polarization differences between quenched and free-floating fluorescent molecules based on the fluorescence lifetime of the molecules.

In certain embodiments, any moiety that changes the rotational velocity can be added to the probe. For, example, a weight-bearing molecule is attached to a quencher portion of a probe to increase the combined molecular weight of an intact probe. The higher molecular weight of an intact probe (i.e. quenched probe), the greater disparity between the polarizations of a fluorescent molecule still attached to the probe and a cleaved fluorescent molecule. This is because the added weight restricts motion of the intact probe, which better preserves the polarization of the fluorescent molecule. Examples of weight-bearing molecules suitable for increasing weight of an intact probe for motion reduction include, for example, attaching a random sequence to the '3 prime end of the intact probe or attaching a protein, bead, or other nanoparticle to the probe (via a random sequence, which allows access to template for PCR).

For detection of targets via fluorescent polarization in droplets, a laser is used to emit polarized light into a droplet containing a single template nucleic acid and subjected to an amplification process (such as PCR amplification). The laser will polarize fluorescent molecules of intact probes and free-floating fluorescent molecules that were cleaved during amplification. The wavelength of the polarized light used to excite the fluorescent molecules depends on the type of the fluorescent molecules utilized. Lasers suitable for polarizing the fluorescent molecules include, for example, lasers that emit any type of polarized light of certain wavelengths (such as a ring-laser). The emitted polarized light can include, for example, linear, elliptical, plane, circular polarized light. One or more detectors, such as a photomultiplier tubes, are used to detect the polarization of the intact and free-floating fluorescent molecules. Each detector is operably coupled to a polarizer for detection of the polarized light. A polarizer is an optical filter that passes light of a specific polarization and blocks waves of other polarizations. It can convert a beam of light of undefined or mixed polarization into a beam with well-defined polarization. The common types of polarizers are linear polarizers and circular polarizers. A polarizer may be chosen to correspond to the type of polarized light emitted from the laser.

Polarizers may be oriented parallel or perpendicular to the emitted polarized light (e.g. turning the polarizing filter so that its grid is perpendicular to a plane of emitted polarized light. In particular embodiments, a polarizing filter is placed cross (i.e. perpendicular) to the polarization excitation of the light source. The crossed polarizing filter blocks substantially more of the polarized light emitted from the quenched probes (having the fluorescent molecule intact) because the quenched probes rotate less and therefore maintain substantially the same polarization excitation of the light source. In contrast, the cross polarizing filter receives (i.e. allows light to pass through to the detector) emitted light from free-floating fluorescence molecules, which were cleaved from the probe) because those molecules are rotating more erratically and are more likely to emit polarized light that deviates from the polarization excitation of the light source. As a result, the crossed polarizing filter provides a better brightness-to-dimness ratio between the free-floating cleaved fluorescent molecules and the intact quenched probes. Therefore, signals pertinent to the detection of the target (cleaved signals) are more readily apparent.

Figure 30A:
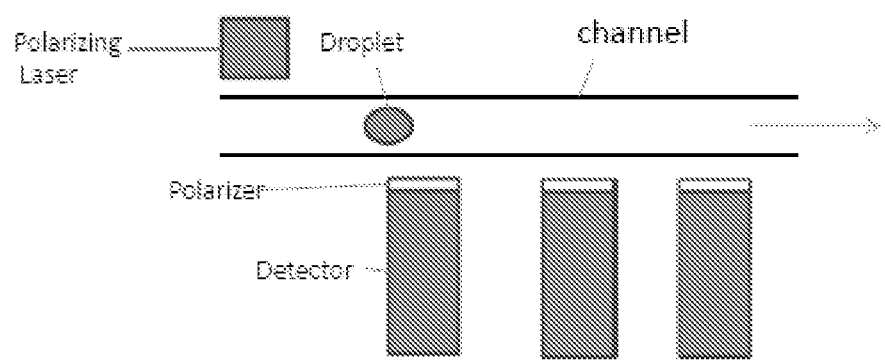
FIG. 30A exemplifies fluorescent polarization detectors placed adjacent to each other for tracking polarized light emitted from a droplet over time according to one embodiment.
Figure 30B:
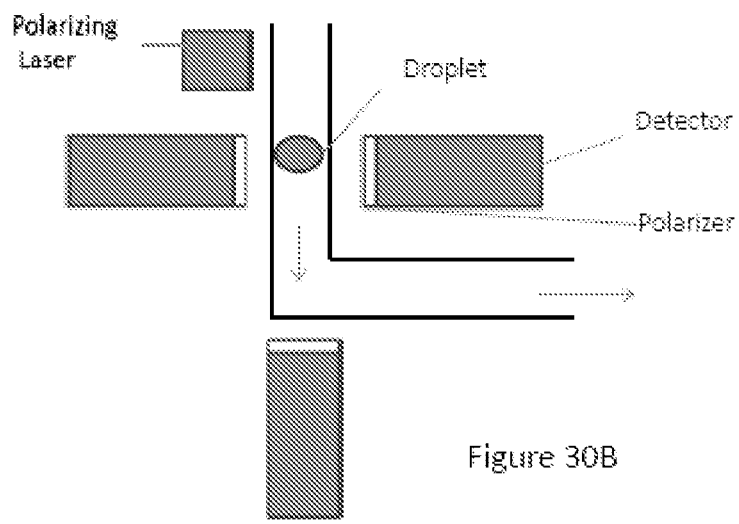
FIG. 30B exemplifies fluorescent polarization detectors arranged to simultaneously obtain polarized light emitted from a droplet according to one embodiment.

The configuration of the detectors also increases the specificity for detecting polarized light emitted from intact and free-floating fluorescent molecules. FIG. 30A depicts detectors lined up adjacently along the channel. With the detectors spatially-arranged in an adjacent configuration, the detectors can sense changes in polarization emitted from an excited droplet over a period of time as the droplet moves through the channel past the detectors. FIG. 30B illustrates a configuration where more than one detector is collecting polarized light emitted from a droplet at the same time. This increases the amount of signals being emitted by the fluorescent molecules that are detected at a certain time point, which leads to increased specificity of polarized light/signal emitted from the fluorescent molecules. In addition, the polarizers for the detectors may be the same or different. For example, one detector may have a polarizer crossed with the polarization excitation of the laser and another detector may have a parallel with the polarization excitation of the laser. This also increases the amount of data received.

Figure 31:
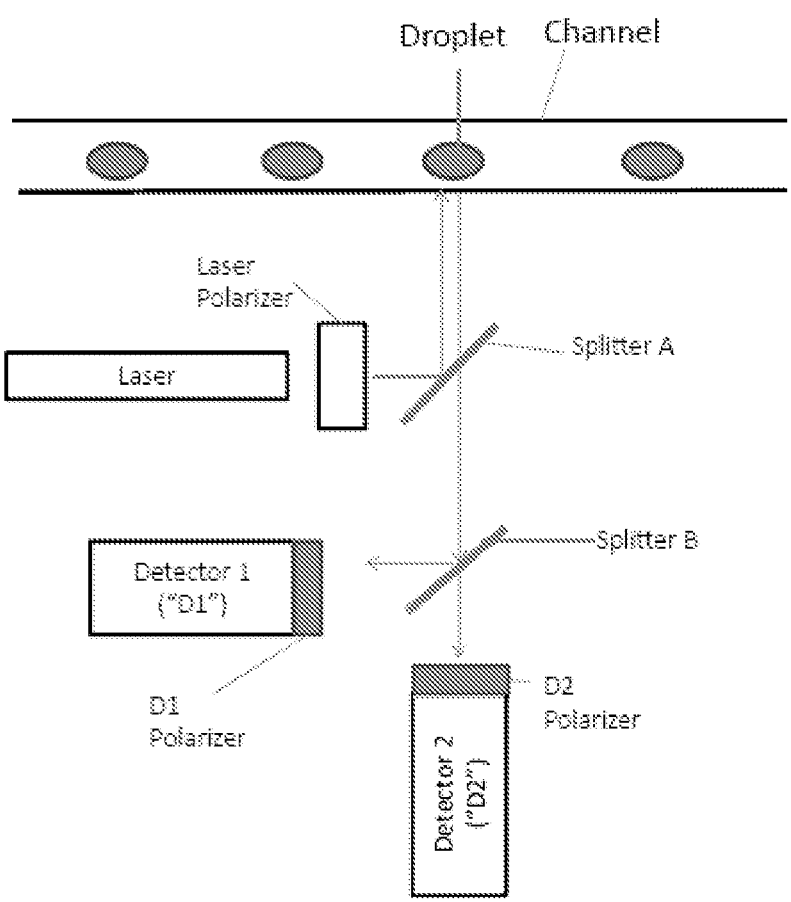
FIG. 31 depicts another configuration for detecting fluorescence polarization according to certain embodiments.

FIG. 31 depicts another configuration for detecting fluorescence polarization. As shown in FIG. 31, a laser transmits polarized light to a splitter A. Splitter A directs polarized light from the laser to the channel for energizing the droplet. Polarized light emitted from one or more fluorescent molecules in the droplet is then transmitted through splitter A to splitter B. Splitter B splits light into detector 1 coupled to polarizer 1 and detector 2 coupled to polarizer 2. Polarizers 1 and 2 may be the same or different.

FIGS. 32A and 32B illustrate yet another configuration for detecting fluorescence polarization. As shown in FIG. 32A, a laser transmits polarized light to a splitter C. Splitter C directs polarized light from the laser to the channel for energizing the droplet. Polarized light (P1+P2) emitted from one or more fluorescent molecules in the droplet is then transmitted through Splitter A to a polarizing beam splitter. P1 indicates emitted polarized light that is parallel to the polarization excitation of the laser and P2 indicates emitted polarized that is perpendicular to the polarization excitation of the laser. The polarizing beam splitter splits the emitted polarized light into two beams of differing linear polarization beams. The polarizing beam splitter is exemplified in FIG. 32B. As shown the polarizing beam splitter splits polarized light (P1 and P2) emitted from the droplet into separate beams. Each beam P1 and P2 is transferred into a detector having two different detection channels. Although, it is understood that two separate detectors may also be utilized. With the polarized beam splitter, polarized light emitted from the droplet having polarization P1 and P2 can be detected.

One or more filters (not shown in FIGS. 30A-32B), such as wavelength specific filters, can be utilized to prevent unwanted light from entering the detectors. It is also understood that the position of the laser can be adjusted in any one of the configurations depicted in FIGS. 30A-32B.

The detected signals can be compared to reference polarization values of the fluorescence probes when intact (i.e. quenched) or free floating in order to determine whether the fluorescence molecules are intact (negative reaction/amplification) or free-floating (positive reaction/amplification).

In the case of two or more probes having fluorescence molecules for different targets, semi-automated genotype assignments may be made by taking a ratio between normalized fluorescence polarization values of two or more different fluorescent molecules (e.g. DYE1 and DYE2). For example, a sample with a low DYE1/DYE2 ratio represents a homozygous allele 1 sample (cleaved DYE1 probe, intact DYE2 probe); a high DYE1/DYE2 ration represents a homozygous allele 2 sample (intact DYE1 probe, cleaved DYE2 probe); a DYE1/DYE2 ratio close to one represents a heterozygote if the absolute FP values of both dyes are low (both probes are cleaved); and indicating failed PCR when ratio is close to one but both dye values are high (both probes are intact).

The fluorescence polarization detection technique is not limited to TaqMan probes as discussed above, but may adapted for use with any other fluorogenic DNA hybridization probes, such as molecular beacons, Solaris probes, scorpion probes, and any other probes that function by sequence specific recognition of target DNA by hybridization and result in increased fluorescence on amplification of the target sequence.

The following example illustrates a preferred method of detecting polarized light emitted. Two reaction mixes were prepared: Group #1. 0.4 uM quenched (intact) SMN88G_FAM probe in 1× Genotyping mix and 0.5% tetronic; Group #2. 0.2 uM free-floating 6FAM in 1× Genotyping mix and 0.5% tetronic. The reactions were mixed and diluted into eight separate samples. Intact Group #1 and free-floating Group #2 were excited with a laser beam emitting plane polarized light. A first Detector and a second Detector were used to detect light emitted from the excited FAM molecules in both Group #1 and Group #2. The first Detector included a polarizer arranged perpendicular to the polarization excitation of the laser, and the second Detector included a polarizer arranged parallel to the polarization excitation of the laser. In addition, a third detector without a polarizer was also used to detect signals emitted from Group #1 and Group #2. Polarized light emitted from the excited FAM molecules in both Group #1 and Group #2 were detected. The below Table 4 shows the brightness-to-dimness ratio of Group #1 and Group #2 from the three detectors:

TABLE 4

| | Quenched | Free | Brightness-to-Dim Ratio |
|---|---|---|---|
| Detector 1: Parallel Polarizing Filter | 0.17 | 0.97 | 5.7 |
| Detector 2: Perpendicular Polarizing Filter | 0.13 | 0.91 | 7.0 |
| Detector 3: No Polarizing Filter | 0.42 | 2.57 | 6.1 |

As shown in Table 4, the brightness-to-dim ratio is improved when the polarizing filter is perpendicular (i.e. crossed) with the polarization excitement of the polarized laser source. A enhanced brightness-to-dim ratio with respect to quenched and free-floating fluorescent molecules allows one to focus on the signals relevant to the amplified product. That is, the detector having a polarizing filter crossed with the polarization excitement of the light source provides better signal return for the cleaved free-floating fluorescent molecules, and reduces signals received from the quenched probes that did not hybridize to the target.

Analysis

Analysis is then performed on the droplets. The analysis may be based on counting, i.e., determining a number of droplets that contain only wild-type target, and determining a number of droplets that contain only a variant of the target. Such methods are well known in the art. See, e.g., Lapidus et al. (U.S. Pat. Nos. 5,670,325 and 5,928,870) and Shuber et al. (U.S. Pat. Nos. 6,203,993 and 6,214,558), the content of each of which is incorporated by reference herein in its entirety.

Generally, the presence of droplets containing only variant is indicative of a disease, such as cancer. In certain embodiments, the variant is an allelic variant, such as an insertion, deletion, substitution, translocation, or single nucleotide polymorphism (SNP).

Biomarkers that are associated with cancer are known in the art. Biomarkers associated with development of breast cancer are shown in Erlander et al. (U.S. Pat. No. 7,504,214), Dai et al. (U.S. Pat. Nos. 7,514,209 and 7,171,311), Baker et al. (U.S. Pat. Nos. 7,056,674 and 7,081,340), Erlander et al. (US 2009/0092973). The contents of the patent application and each of these patents are incorporated by reference herein in their entirety. Biomarkers associated with development of cervical cancer are shown in Patel (U.S. Pat. No. 7,300,765), Pardee et al. (U.S. Pat. No. 7,153,700), Kim (U.S. Pat. No. 6,905,844), Roberts et al. (U.S. Pat. No. 6,316,208), Schlegel (US 2008/0113340), Kwok et al. (US 2008/0044828), Fisher et al. (US 2005/0260566), Sastry et al. (US 2005/0048467), Lai (US 2008/0311570) and Van Der Zee et al. (US 2009/0023137). Biomarkers associated with development of vaginal cancer are shown in Giordano (U.S. Pat. No. 5,840,506), Kruk (US 2008/0009005), Hellman et al. (Br J Cancer. 100(8):1303-1314, 2009). Biomarkers associated with development of brain cancers (e.g., glioma, cerebellum, medulloblastoma, astrocytoma, ependymoma, glioblastoma) are shown in D'Andrea (US 2009/0081237), Murphy et al. (US 2006/0269558), Gibson et al. (US 2006/0281089), and Zetter et al. (US 2006/0160762). Biomarkers associated with development of renal cancer are shown in Patel (U.S. Pat. No. 7,300,765), Soyupak et al. (U.S. Pat. No. 7,482,129), Sahin et al. (U.S. Pat. No. 7,527,933), Price et al. (U.S. Pat. No. 7,229,770), Raitano (U.S. Pat. No. 7,507,541), and Becker et al. (US 2007/0292869). Biomarkers associated with development of hepatic cancers (e.g., hepatocellular carcinoma) are shown in Home et al. (U.S. Pat. No. 6,974,667), Yuan et al. (U.S. Pat. No. 6,897,018), Hanausek-Walaszek et al. (U.S. Pat. No. 5,310,653), and Liew et al. (US 2005/0152908). Biomarkers associated with development of gastric, gastrointestinal, and/or esophageal cancers are shown in Chang et al. (U.S. Pat. No. 7,507,532), Bae et al. (U.S. Pat. No. 7,368,255), Muramatsu et al. (U.S. Pat. No. 7,090,983), Sahin et al. (U.S. Pat. No. 7,527,933), Chow et al. (US 2008/0138806), Waldman et al. (US 2005/0100895), Goldenring (US 2008/0057514), An et al. (US 2007/0259368), Guilford et al. (US 2007/0184439), Wirtz et al. (US 2004/0018525), Filella et al. (Acta Oncol. 33(7):747-751, 1994), Waldman et al. (U.S. Pat. No. 6,767,704), and Lipkin et al. (Cancer Research, 48:235-245, 1988). Biomarkers associated with development of ovarian cancer are shown in Podust et al. (U.S. Pat. No. 7,510,842), Wang (U.S. Pat. No. 7,348,142), O'Brien et al. (U.S. Pat. Nos. 7,291,462, 6,942,978, 6,316,213, 6,294,344, and 6,268,165), Ganetta (U.S. Pat. No. 7,078,180), Malinowski et al. (US 2009/0087849), Beyer et al. (US 2009/0081685), Fischer et al. (US 2009/0075307), Mansfield et al. (US 2009/0004687), Livingston et al. (US 2008/0286199), Farias-Eisner et al. (US 2008/0038754), Ahmed et al. (US 2007/0053896), Giordano (U.S. Pat. No. 5,840,506), and Tchagang et al. (Mol Cancer Ther, 7:27-37, 2008). Biomarkers associated with development of head-and-neck and thyroid cancers are shown in Sidransky et al. (U.S. Pat. No. 7,378,233), Skolnick et al. (U.S. Pat. No. 5,989,815), Budiman et al. (US 2009/0075265), Hasina et al. (Cancer Research, 63:555-559, 2003), Kebebew et al. (US 2008/0280302), and Ralhan (Mol Cell Proteomics, 7(6): 1162-1173, 2008). The contents of each of the articles, patents, and patent applications are incorporated by reference herein in their entirety. Biomarkers associated with development of colorectal cancers are shown in Raitano et al. (U.S. Pat. No. 7,507,541), Reinhard et al. (U.S. Pat. No. 7,501,244), Waldman et al. (U.S. Pat. No. 7,479,376); Schleyer et al. (U.S. Pat. No. 7,198,899); Reed (U.S. Pat. No. 7,163,801), Robbins et al. (U.S. Pat. No. 7,022,472), Mack et al. (U.S. Pat. No. 6,682,890), Tabiti et al. (U.S. Pat. No. 5,888,746), Budiman et al. (US 2009/0098542), Karl (US 2009/0075311), Arjol et al. (US 2008/0286801), Lee et al. (US 2008/0206756), Mori et al. (US 2008/0081333), Wang et al. (US 2008/0058432), Belacel et al. (US 2008/0050723), Stedronsky et al. (US 2008/0020940), An et al. (US 2006/0234254), Eveleigh et al. (US 2004/0146921), and Yeatman et al. (US 2006/0195269). Biomarkers associated with development of prostate cancer are shown in Sidransky (U.S. Pat. No. 7,524,633), Platica (U.S. Pat. No. 7,510,707), Salceda et al. (U.S. Pat. Nos. 7,432,064 and 7,364,862), Siegler et al. (U.S. Pat. No. 7,361,474), Wang (U.S. Pat. No. 7,348,142), Ali et al. (U.S. Pat. No. 7,326,529), Price et al. (U.S. Pat. No. 7,229,770), O'Brien et al. (U.S. Pat. No. 7,291,462), Golub et al. (U.S. Pat. No. 6,949,342), Ogden et al. (U.S. Pat. No. 6,841,350), An et al. (U.S. Pat. No. 6,171,796), Bergan et al. (US 2009/0124569), Bhowmick (US 2009/0017463), Srivastava et al. (US 2008/0269157), Chinnaiyan et al. (US 2008/0222741), Thaxton et al. (US 2008/0181850), Dahary et al. (US 2008/0014590), Diamandis et al. (US 2006/0269971), Rubin et al. (US 2006/0234259), Einstein et al. (US 2006/0115821), Paris et al. (US 2006/0110759), Condon-Cardo (US 2004/0053247), and Ritchie et al. (US 2009/0127454). Biomarkers associated with development of pancreatic cancer are shown in Sahin et al. (U.S. Pat. No. 7,527,933), Rataino et al. (U.S. Pat. No. 7,507,541), Schleyer et al. (U.S. Pat. No. 7,476,506), Domon et al. (U.S. Pat. No. 7,473,531), McCaffey et al. (U.S. Pat. No. 7,358,231), Price et al. (U.S. Pat. No. 7,229,770), Chan et al. (US 2005/0095611), Mitchl et al. (US 2006/0258841), and Faca et al. (PLoS Med 5(6):e123, 2008). Biomarkers associated with development of lung cancer are shown in Sahin et al. (U.S. Pat. No. 7,527,933), Hutteman (U.S. Pat. No. 7,473,530), Bae et al. (U.S. Pat. No. 7,368,255), Wang (U.S. Pat. No. 7,348,142), Nacht et al. (U.S. Pat. No. 7,332,590), Gure et al. (U.S. Pat. No. 7,314,721), Patel (U.S. Pat. No. 7,300,765), Price et al. (U.S. Pat. No. 7,229,770), O'Brien et al. (U.S. Pat. Nos. 7,291,462 and 6,316,213), Muramatsu et al. (U.S. Pat. No. 7,090,983), Carson et al. (U.S. Pat. No. 6,576,420), Giordano (U.S. Pat. No. 5,840,506), Guo (US 2009/0062144), Tsao et al. (US 2008/0176236), Nakamura et al. (US 2008/0050378), Raponi et al. (US 2006/0252057), Yip et al. (US 2006/0223127), Pollock et al. (US 2006/0046257), Moon et al. (US 2003/0224509), and Budiman et al. (US 2009/0098543). Biomarkers associated with development of skin cancer (e.g., basal cell carcinoma, squamous cell carcinoma, and melanoma) are shown in Roberts et al. (U.S. Pat. No. 6,316,208), Polsky (U.S. Pat. No. 7,442,507), Price et al. (U.S. Pat. No. 7,229,770), Genetta (U.S. Pat. No. 7,078,180), Carson et al. (U.S. Pat. No. 6,576,420), Moses et al. (US 2008/0286811), Moses et al. (US 2008/0268473), Dooley et al. (US 2003/0232356), Chang et al. (US 2008/0274908), Alani et al. (US 2008/0118462), Wang (US 2007/0154889), and Zetter et al. (US 2008/0064047). Biomarkers associated with development of multiple myeloma are shown in Coignet (U.S. Pat. No. 7,449,303), Shaughnessy et al. (U.S. Pat. No. 7,308,364), Seshi (U.S. Pat. No. 7,049,072), and Shaughnessy et al. (US 2008/0293578, US 2008/0234139, and US 2008/0234138). Biomarkers associated with development of leukemia are shown in Ando et al. (U.S. Pat. No. 7,479,371), Coignet (U.S. Pat. Nos. 7,479,370 and 7,449,303), Davi et al. (U.S. Pat. No. 7,416,851), Chiorazzi (U.S. Pat. No. 7,316,906), Seshi (U.S. Pat. No. 7,049,072), Van Baren et al. (U.S. Pat. No. 6,130,052), Taniguchi (U.S. Pat. No. 5,643,729), Insel et al. (US 2009/

0131353), and Van Bockstaele et al. (Blood Rev. 23(1):25-47, 2009). Biomarkers associated with development of lymphoma are shown in Ando et al. (U.S. Pat. No. 7,479,371), Levy et al. (U.S. Pat. No. 7,332,280), and Arnold (U.S. Pat. No. 5,858,655). Biomarkers associated with development of bladder cancer are shown in Price et al. (U.S. Pat. No. 7,229,770), Orntoft (U.S. Pat. No. 6,936,417), Haak-Frendscho et al. (U.S. Pat. No. 6,008,003), Feinstein et al. (U.S. Pat. No. 6,998,232), Elting et al. (US 2008/0311604), and Wewer et al. (2009/0029372). The content of each of the above references is incorporated by reference herein in its entirety.

Devices and methods described herein may be used to assess the quality of a sample to be analyzed for methylation. DNA methylation is a chemical modification of DNA performed by enzymes called methyltransferases, in which a methyl group (m) is added to certain cytosines (C) of DNA, to yield 5-methylcytosine. This non-mutational (epigenetic) process (mC) is a critical factor in gene expression regulation. See, e.g., J. G. Herman, Seminars in Cancer Biology, 9: 359-67, 1999. Research suggests genes with high levels of 5-methylcytosine in a promoter region are transcriptionally silent, which allows unchecked cell proliferation. Additionally, it is likely that there a correlation between gene transcription and undermethylation. Methylation patterns of DNA from cancer cells are significantly different from those of normal cells. Therefore, detection of methylation patterns in appropriately selected genes of cancer cells can lead to discrimination of cancer cells from normal (i.e., non-cancerous) cells, thereby providing an approach to early detection of cancer.

A common method for assessing methylation status, e.g., the presence of CpG islands, is methylation specific PCR, also known as MSP. In MSP a nucleic acid sample is treated with a methylation reactant, typically bisulfite, and then amplified in the presence of two sets of primers. One primer set is complimentary to sequences with converted Cs and the second primer set is complimentary to non-converted Cs. Using these two separate primer sets, both the methylated and unmethylated DNA can be simultaneously amplified, and the amplification products compared (e.g., sequenced) to determine methylation sites in a given sequence. The MSP method, and variations on the MSP method, are described in greater detail in U.S. Pat. Nos. 6,265,171, 6,331,393, 6,977,146, 7,186,512, and 7,229,759 all of which are incorporated by reference herein in their entireties.

In some instances, a bisulfite treatment to convert unmethylated Cs to Us degrades the sample, making the later amplification and sequencing steps of little value because the resulting sample is no longer contiguous in the region(s) of interest. Using the techniques described herein, it is possible to assess the post bisulfite treatment sample to determine the quality of the sample, for example the amount of contiguous DNA. Thus, a bisulfite treated sample can be partitioned into samples comprising nucleic acids of different lengths, primer pairs can be introduced along with appropriate probes, the nucleic acids amplified, and the make-up, e.g., the continuity of the nucleic acid sample can be determined. Because the sample may contain unmethylated Cs which are converted to Us as well as methylated Cs which are not converted to Us, it may be necessary to use additional primer sets which are complimentary to targets having Cs as well as primer sets complimentary to targets having Us.

In certain embodiments, methods of the invention may be used to monitor a patient for recurrence of a cancer. Since the patient has already been treated for the cancer, the genetic profile and particular mutation(s) associated with that patient's cancer are already known. Probes may be designed that specifically hybridize to the region of the nucleic acid that contains the mutation(s) that is indicative of the cancer for which the patient was previously treated. A patient's sample (e.g., pus, sputum, semen, urine, blood, saliva, stool, or cerebrospinal fluid) may then be analyzed as described above to determine whether the mutant allele(s) is detected in the sample, the presence of which being indicative of recurrence of the cancer.

Droplet Sorting

Methods of the invention may further include sorting the droplets based upon whether the droplets contain a homogeneous population of molecules or a heterogeneous population of molecules. A sorting module may be a junction of a channel where the flow of droplets can change direction to enter one or more other channels, e.g., a branch channel, depending on a signal received in connection with a droplet interrogation in the detection module. Typically, a sorting module is monitored and/or under the control of the detection module, and therefore a sorting module may correspond to the detection module. The sorting region is in communication with and is influenced by one or more sorting apparatuses.

A sorting apparatus includes techniques or control systems, e.g., dielectric, electric, electro-osmotic, (micro-) valve, etc. A control system can employ a variety of sorting techniques to change or direct the flow of molecules, cells, small molecules or particles into a predetermined branch channel. A branch channel is a channel that is in communication with a sorting region and a main channel. The main channel can communicate with two or more branch channels at the sorting module or branch point, forming, for example, a T-shape or a Y-shape. Other shapes and channel geometries may be used as desired. Typically, a branch channel receives droplets of interest as detected by the detection module and sorted at the sorting module. A branch channel can have an outlet module and/or terminate with a well or reservoir to allow collection or disposal (collection module or waste module, respectively) of the molecules, cells, small molecules or particles. Alternatively, a branch channel may be in communication with other channels to permit additional sorting.

A characteristic of a fluidic droplet may be sensed and/or determined in some fashion, for example, as described herein (e.g., fluorescence of the fluidic droplet may be determined), and, in response, an electric field may be applied or removed from the fluidic droplet to direct the fluidic droplet to a particular region (e.g. a channel). In certain embodiments, a fluidic droplet is sorted or steered by inducing a dipole in the uncharged fluidic droplet (which may be initially charged or uncharged), and sorting or steering the droplet using an applied electric field. The electric field may be an AC field, a DC field, etc. For example, a channel containing fluidic droplets and carrier fluid, divides into first and second channels at a branch point. Generally, the fluidic droplet is uncharged. After the branch point, a first electrode is positioned near the first channel, and a second electrode is positioned near the second channel. A third electrode is positioned near the branch point of the first and second channels. A dipole is then induced in the fluidic droplet using a combination of the electrodes. The combination of electrodes used determines which channel will receive the flowing droplet. Thus, by applying the proper electric field, the droplets can be directed to either the first or second channel as desired. Further description of droplet sorting is shown for example in Link et al. (U.S.

patent application numbers 2008/0014589, 2008/0003142, and 2010/0137163) and European publication number EP2047910 to Raindance Technologies Inc.

Based upon the detected signal at the detection module, droplets containing a heterogeneous population of molecules are sorted away from droplets that contain a homogeneous population of molecules. Droplets may be further sorted to separate droplets that contain a homogeneous population of amplicons of the target from droplets that contain a homogeneous population of amplicons of the variant of the target.

Threshold Detection

Since the advent of digital detection, many methods have been developed that are based on diagnosing a disease state based on a ratio of normal (wild-type) nucleic acid to abnormal (mutant) nucleic acid in a sample. Digital detection involves partitioning a sample so that individual target molecules within the sample are localized and concentrated within many separate regions. Analysis is then based on analyzing each partitioned portion. In order to achieve only a single target molecule per partition, a sample must be significantly diluted. In fact, most partitioned portions are empty, i.e., include no target molecule. That means that during analysis, significant amounts of time and resources are used to analyze empty partitioned portions.

Embodiments of the invention recognize that due to the disperse nature of partitioned portions, efficiency can be increased by not analyzing empty partitioned portions. Aspects of the invention are accomplished by setting a threshold level on a detector that is above an optical signal emitted by empty droplets (background), and recording an optical signal above the threshold level emitted by droplets that include amplified nucleic acid. Typically, millions of droplets are produced by systems of the invention, and at 1% loading, the probability that two signal producing droplets will be adjacent is less than 0.01%. Since not every single droplet is being analyzed in these methods of the invention, that means that droplets do not need to be mono-disperse within a channel. In fact, making a plurality of droplets past by the detector simultaneously decreases analysis time and saves on reagents.

Figure 27A:
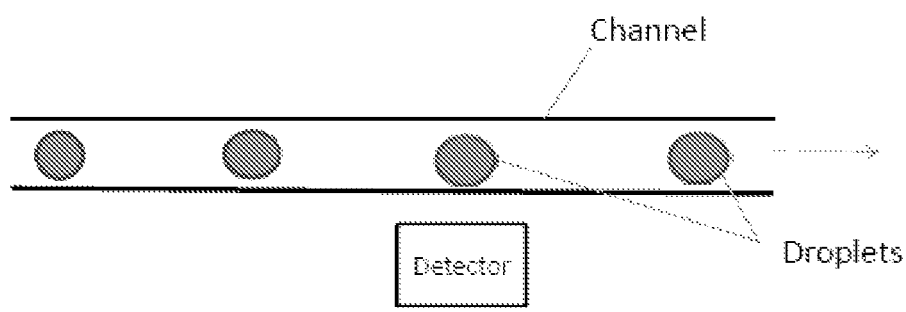
FIG. 27A depicts detection of droplets flowing single-file and spaced apart configuration through a channel.
Figure 27B:
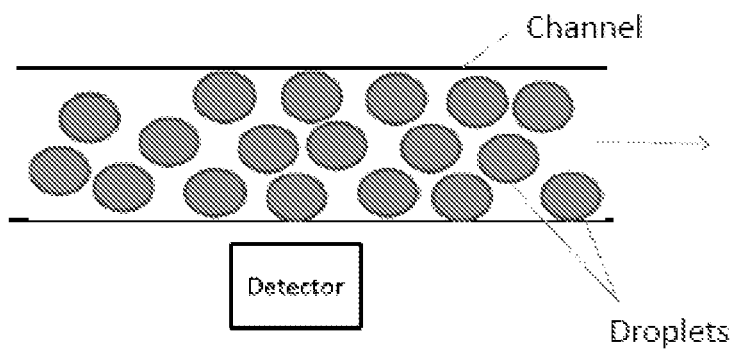
FIG. 27B depicts detection of droplets flowing in a non-single file configuration through a channel.
Figure 27C:
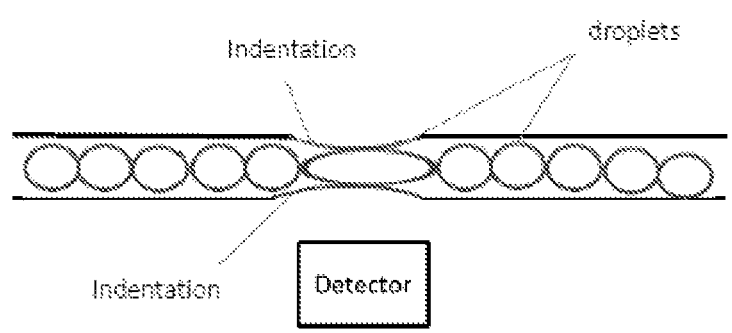
FIG. 27C depicts detection of droplets flowing past the detector which adjacent and in contact with each other.
Figure 28A:
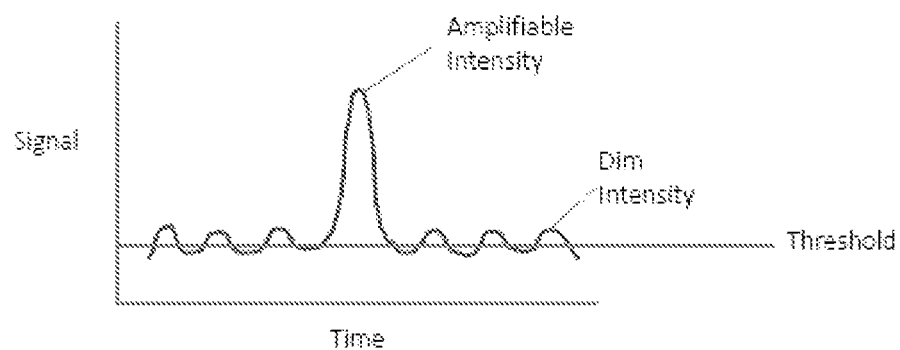
FIG. 28A depicts threshold detection of droplets flowing past a detector in a mono-dispersed configuration.

This is further explained with reference to FIGS. 27 and 28. According to one technique for detecting a target nucleic acid, a plurality of droplets is directed through a detection channel (or a detection portion of a channel) in a single-file and spaced manner. This technique is shown in FIG. 27A. As shown in FIG. 27A, mono-dispersed droplets (i.g. droplets of uniform volume) are flowed through a channel in a single-filed fashion, in which each droplet is spaced apart from another droplet and passed by the detector one at a time. The detector detects the signal intensity of each droplet to determine a number of droplets having amplifiable product and also detects empty droplets. Although FIG. 27A shows mono-dispersed droplets, the droplets may be non-mono-dispersed such that the droplets are not uniform in size/volume. As exemplified in FIG. 28A, droplets having amplifiable product have a signal intensity (amplifiable intensity) that is higher than the intensity of empty droplets (dim or background intensity). If the detector is set to detect a threshold intensity below the background intensity level, each droplet flowing through the droplet is counted. The detected intensity of each droplet is recorded and can be used for subsequent analysis. Differences in amplifiable intensity can be used to determine which molecule (reference or mutant) was amplified in the droplet.

Droplets having amplifiable intensity (e.g., due to amplified wild-type target (or other reference sequence) and amplified target mutant molecule) may be counted to determine a number Y of reference molecules and a number X of target mutant molecules within the sample. The number Y of reference molecules is compared to the number X of target mutant molecules to ascertain a ratio which reflects the biological sample. In certain embodiments, the ratio is indicative of a condition. The total droplet count, which includes both droplets with amplifiable product and non-amplifiable product, can be used for Poisson correction of the amplifiable products to determine the statistical significance of the ratio of the reference molecules and the target mutant molecules in the sample. Methods of comparing a number of reference molecules to a number of target mutant molecules in order to determine a clinical condition are described in more detail in U.S. Pat. No. 6,440,706, the entirety of which is incorporated by reference.

Using the single-file and spaced-apart technique, the detector collects a large volume of data because every droplet, including amplifiable signals and background signals, is collected. For analysis of large nucleic acid samples, the number of droplets for analysis can be in the millions. Another drawback of the single-file technique is the time it takes to flow droplets in a single file line past the detector so that each droplet can be separately analyzed. As such, an alternative technique for counting droplets that obtains significantly less data in a short time span while still obtaining clinically significant data is desirable.

Figure 28B:
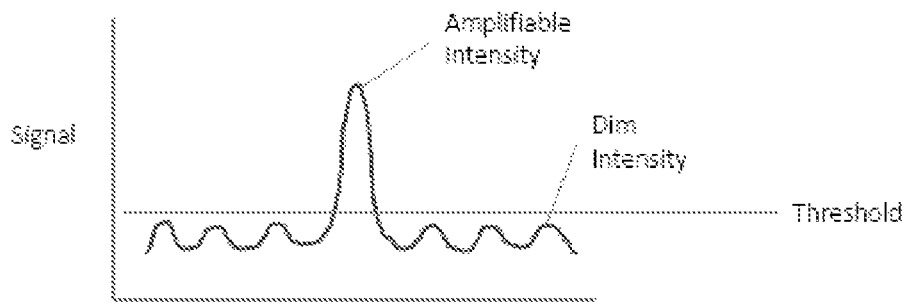
FIG. 28B depicts threshold detection of droplets flowing past a detector in a non-mono-dispersed configuration.

Methods of the invention provide an alternative technique for assessing droplets that minimize the data obtained by the detector and increase the quantity of droplets flowing through a channel (or portion thereof) that simultaneously pass by the detector. According to the alternative technique of the invention, the detector is set to detect signals at a threshold above the background (i.e. dim) intensity level (FIG. 28B). FIG. 28B illustrates the threshold level of the detector being above the background intensity level. In this manner, the detector only collects signals from droplets containing amplifiable products (reference nucleic acid or template nucleic acid) and empty droplets are processed as background signal. Since only droplets having amplifiable products are being detected, this technique does not require that the droplets pass by the detector in a mono-dispersed configuration because the probability that adjacent droplets will simultaneously pass by the detector is very low, i.e., less than 0.01% at 1% loading. In other words, two or more droplets may pass by the detector at the same time without affecting the results because statistically only one of the droplets is likely to contain an amplifiable product (thereby producing an amplifiable signal above the threshold). In the event that two or more droplets are within the detection field at the same time, the signals may be separately identifiable because the peaks of the signals will be shown separated in time. An added benefit of flowing the plurality of droplets pass the detector in a non single-filed and spaced-apart configuration is that less carrier fluid is needed to flow the same amount of droplets passed the detector. FIG. 27B illustrates a plurality of droplets passing the detector that are not in a single-filed and spaced apart configuration. Although the droplets shown in FIG. 27B are monodispersed (uniform volume), this technique may also be used with non mono-dispersed droplets.

In another alternative technique for assessing droplets, droplets are passed by the detector in a non-spaced apart manner in order to decrease the time it takes for the each droplet to pass by the detector. In this technique (shown in FIG. 27C), one or more droplets passing by the detector are in contact with each other without coalescing into a single droplet. This allows the detector to detect signals from more droplets over a period of time. In one embodiment, a neck formed from one or more indentations is placed in the channel above the detector to slow the pace of a droplet while it is within the detection field of the detector. As shown, the neck causes the droplet to elongate as it passes by the channel. In addition, the neck in FIG. 27C includes two indentations; however the same effect may be accomplished with only one indentation. This increases the detector's ability to separate signals from each droplet. In the event that two or more droplets are within the detection field at the same time, the signals may be separately identifiable because the peaks of the signals will be shown separated in time. In this technique, the detector may also be set to detect signals at a threshold above the background (i.e. dim) intensity level (as shown in FIG. 28B). While only one droplet is passed by the detector at a time using the necking technique, the high threshold significantly reduces the file size of the detected signals. With this technique, the droplets may be monodispersed or of non-uniform volume.

Because each droplet contains a single template molecule, each amplifiable intensity above background intensity that is recorded may be counted as one droplet (which represents, e.g., either a reference molecule or a target mutant molecule). This is true for detection methods shown in FIGS. 27B and 27C. Droplets having amplifiable intensity (e.g., due to amplified wild-type target (or other reference sequence) and amplified mutant target) may be counted to determine a number Y of reference molecules and a number X of target mutant molecules within the sample. Differences in amplifiable intensity can be used to determine which molecule (reference or mutant) was amplified in the droplet. The number Y of reference molecules is compared to the number of target mutant molecules to ascertain a ratio which reflects the biological sample. In certain embodiments, the ratio is indicative of a condition.

Release of Target from Droplet

Methods of the invention may further involve releasing amplified target molecules from the droplets for further analysis. Methods of releasing amplified target molecules from the droplets are shown in for example in Link et al. (U.S. patent application numbers 2008/0014589, 2008/0003142, and 2010/0137163) and European publication number EP2047910 to RainDance Technologies Inc.

In certain embodiments, sample droplets are allowed to cream to the top of the carrier fluid. By way of non-limiting example, the carrier fluid can include a perfluorocarbon oil that can have one or more stabilizing surfactants. The droplet rises to the top or separates from the carrier fluid by virtue of the density of the carrier fluid being greater than that of the aqueous phase that makes up the droplet. For example, the perfluorocarbon oil used in one embodiment of the methods of the invention is 1.8, compared to the density of the aqueous phase of the droplet, which is 1.0.

The creamed liquids are then placed onto a second carrier fluid which contains a de-stabilizing surfactant, such as a perfluorinated alcohol (e.g. 1H,1H,2H,2H-Perfluoro-1-octanol). The second carrier fluid can also be a perfluorocarbon oil. Upon mixing, the aqueous droplets begins to coalesce, and coalescence is completed by brief centrifugation at low speed (e.g., 1 minute at 2000 rpm in a microcentrifuge). The coalesced aqueous phase can now be removed and the further analyzed.

The released amplified material can also be subjected to further amplification by the use tailed primers and secondary PCR primers. In this embodiment the primers in the droplet contain an additional sequence or tail added onto the 5' end of the sequence specific portion of the primer. The sequences for the tailed regions are the same for each primer pair and are incorporated onto the 5' portion of the amplicons during PCR cycling. Once the amplicons are removed from the droplets, another set of PCR primers that can hybridize to the tail regions of the amplicons can be used to amplify the products through additional rounds of PCR. The secondary primers can exactly match the tailed region in length and sequence or can themselves contain additional sequence at the 5' ends of the tail portion of the primer. During the secondary PCR cycling these additional regions also become incorporated into the amplicons. These additional sequences can include, but are not limited to adaptor regions utilized by sequencing platforms for library preparation and sequencing, sequences used as a barcoding function for the identification of samples multiplexed into the same reaction, molecules for the separation of amplicons from the rest of the reaction materials such as biotin, digoxin, peptides, or antibodies and molecules such as fluorescent markers that can be used to identify the fragments.

In certain embodiments, the amplified target molecules are sequenced. In a particular embodiment, the sequencing is single-molecule sequencing-by-synthesis. Single-molecule sequencing is shown for example in Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Briefly, a single-stranded nucleic acid (e.g., DNA or cDNA) is hybridized to oligonucleotides attached to a surface of a flow cell. The single-stranded nucleic acids may be captured by methods known in the art, such as those shown in Lapidus (U.S. Pat. No. 7,666,593). The oligonucleotides may be covalently attached to the surface or various attachments other than covalent linking as known to those of ordinary skill in the art may be employed. Moreover, the attachment may be indirect, e.g., via the polymerases of the invention directly or indirectly attached to the surface. The surface may be planar or otherwise, and/or may be porous or non-porous, or any other type of surface known to those of ordinary skill to be suitable for attachment. The nucleic acid is then sequenced by imaging the polymerase-mediated addition of fluorescently-labeled nucleotides incorporated into the growing strand surface oligonucleotide, at single molecule resolution.

Determining the Nucleic Acid Make-Up of a Sample

Further aspects of the invention include methods for determining the nucleic acid make-up of a sample. Specifically, the method can determine the presence of a contiguous, intact nucleic acid, i.e., an unbroken chain of nucleotides, between two locations on the nucleic acid. Presence of a contiguous nucleic acid is determined via detection of both a first and second detectably labeled probe that hybridizes to a first and second location on the nucleic acid (e.g., a sequence, an oligomer, a polymer, a template, dsDNA). The detection of only one probe indicates a fragmented nucleic acid, in other words, a nucleic acid that is not contiguous through the entirety of the two aforementioned locations on the nucleic acid. In some embodiments, the method involves partitioning a sample comprising nucleic acid of different lengths into a plurality of partitioned portions, wherein each portion comprises, on average, a single nucleic acid molecule, introducing first and second primer pairs and first and second detectably labeled probes to the partitioned portions, wherein the first and second primer pairs are specific for first and second locations on the nucleic acid, the first and second locations being spaced apart from each other, and wherein the first probe hybridizes to the first location and the second probe hybridizes to the second location, amplifying the nucleic acid in the partitioned portions, the presence of signal from both probes indicating the presence of a nucleic acid that is contiguous between the first and second locations, and determining a nucleic acid make-up of the sample based upon results of the detecting step.

Specific methods for the partitioning, introducing, amplifying, and detecting steps have been presented throughout the present disclosure. Further detail on determination step is now presented. As mentioned above, determination of contiguous or intact nucleic acid involves detecting a first and second detectably labeled probe that hybridizes to a first and second location on a nucleic acid. The detection of only one probe indicates the presence of a fragment of the longer nucleic acid. In some embodiments, the determining step may involve comparing relative amounts of contiguous nucleic acid to relative amounts of non-contiguous nucleic acid. In other embodiments, the determining step involves comparing amount of contiguous nucleic acid or non-contiguous nucleic acid to a total amount of amino acid.

For sequencing and other extensive molecular biology studies, a sample comprising mostly intact nucleic acid is desirable and is conducive to accurate results. The presence of a relatively large population of nucleic acid fragments, i.e., non-contiguous nucleic acids, may indicate that a sample is not suitable for sequencing. Because sequencing is relatively expensive, knowing the make-up of the sample prior to testing is advantageous. This is especially so when the sample is an FFPE sample or some other form of preserved sample in which the nucleic acid of interest has degraded into fragments. In some embodiments, if less than 90% of the nucleic acid sample, e.g., less than 80% of the nucleic acid sample, e.g., less than 70% of the nucleic acid sample, e.g., less than 50% of the nucleic acid sample, e.g., less than 40% of the nucleic acid sample, e.g., less than 30% of the nucleic acid sample, e.g., less than 20% of the nucleic acid sample, e.g., less than 10% of the nucleic acid sample is fragmented, the nucleic acid sample is suitable for further sequencing. Accordingly, once the nucleic acid make-up of a sample is determined, a further step may involve sequencing the sample, enriching the sample, or sequencing the sample after enrichment. Furthermore, because the method of determining the nucleic acid make-up incorporates the dPCR methods described throughout the present disclosure, extremely small amounts of sample can be tested successfully. In some embodiments, the test sample may contain 50 ng or less of DNA or RNA.

Figure 23:
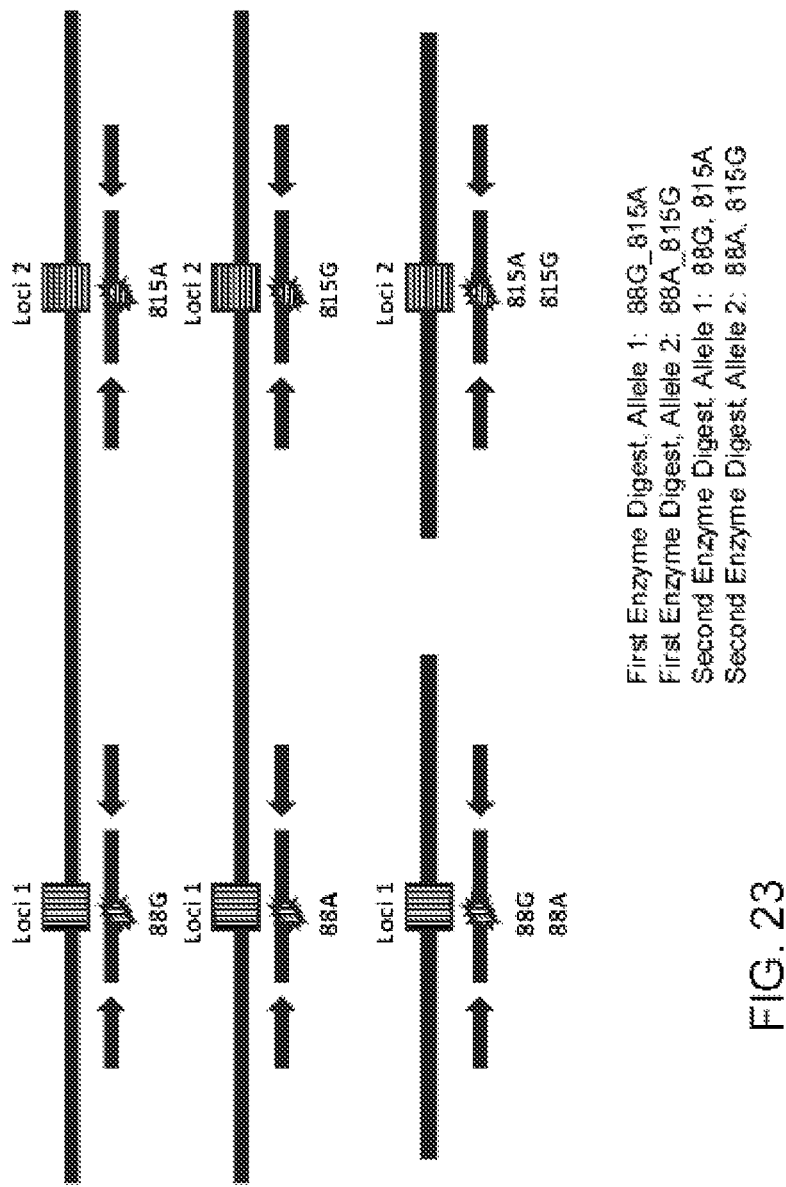
FIG. 23 is a schematic showing several loci of interest on a pair of alleles and fragments of those alleles resulting from enzymatic digestion.

A demonstration of concept in accordance with the invention is presented schematically in FIG. 23. Two alleles are presented: Allele 1, comprising genes 88G and 815A, and Allele 2, comprising genes 88A and 815G. Alleles 1 and 2 were digested with a first enzyme to produce a first nucleic acid containing 88G and 815A ("88G_815A") and a second nucleic acid containing 88A and 815G ("88A_815G"). A portion of these products were then subjected to a second digestion with a second enzyme to obtain four additional fragments, each containing only one gene of interest ("88G," "815A", "88A", and "815G"). Methods of performing enzymatic digestion as well as selecting the proper enzymes are well-known in the art. While enzymatic digestion was used in this example, other methods of fragmenting or shearing the nucleic acid prior to partitioning the samples can be used. Such means may include, for example, sonication, the use of commercially available shearing devices, such as a Covaris® shearing device, or other means known in the art. In this demonstration of concept, the fragmentation is performed to simulate the degradation of a nucleic acid that may naturally occur in a sample, such as a FFPE sample. In certain embodiments of the invention, however, the nucleic acid is fragmented prior to partitioning the sample.

The six nucleic acids were then partitioned into a plurality of partitioned portions, each portion containing on average, a single nucleic acid molecule. Partitioning may involve any methods known in the art, such as serial or terminal dilution. Partitioning may also involve the methods described in in the present disclosure, including forming droplets from a sample present in an aqueous fluid. Additional details on droplet formation have been described throughout the present disclosure.

As further shown in FIG. 23, a first and second primer pair and a first and second detectably labeled probe specific for the regions of interest were introduced to the partitioned portions. In this example, the probes were labeled with either VIC™ or FAM. Further detail on probe embodiments has been described throughout the present disclosure. The nucleic acid was then amplified and the amplicons detected through the hybridized probes.

Figure 24:
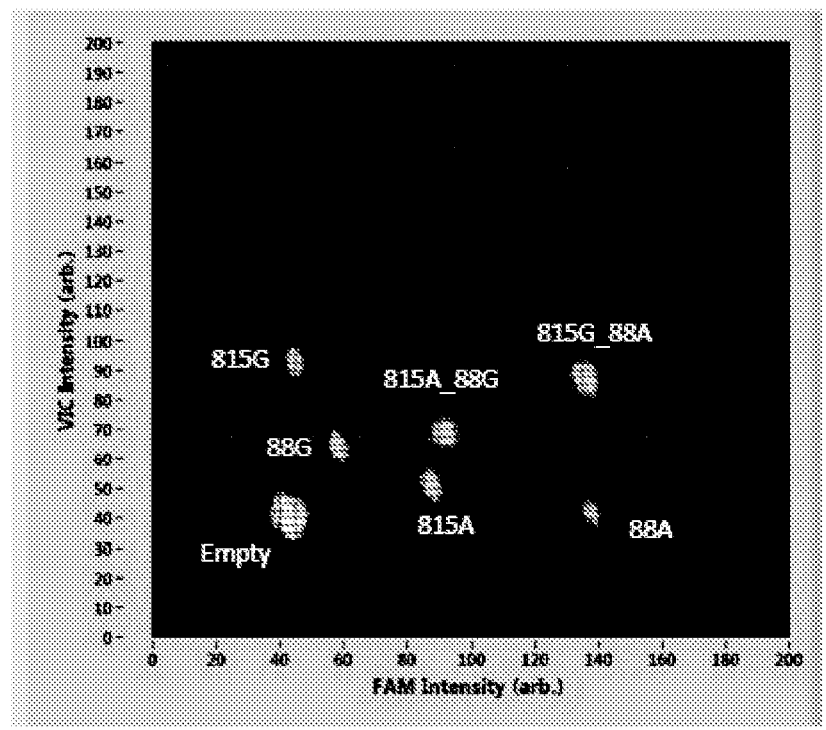
FIG. 24 depicts a multiplex dPCR assay to determine the nucleic acid make-up of a sample containing nucleic acids shown schematically in FIG. 23.

Sample data is presented in FIG. 24, which shows the six populations of nucleic acids along with the empty droplets as peaks on a graph. 815A_88 G and 815G_88A, oriented approximately along the diagonal axis, are the longer nucleic acids. 815G, 88G, 815A, and 88A, arranged primarily along the y-axis and x-axis, respectively, are the shorter fragments.

Accordingly, the invention encompasses a method for determining the nucleic acid make-up of a sample. The method can determine the presence of intact or contiguous nucleic acids, represented in this experiment by peaks corresponding to 815A_88 G and 815G_88A, as well as the presence of non-contiguous nucleic acids, represented by peaks corresponding to 815G, 88G, 815A, and 88A. In this example, the nucleic acid make-up can be assessed by looking at the number of counts in all the peaks. In a sample where the level of fragmentation is unknown, for example, in a FFPE sample, a prevalence of nucleic acid where only one probe has bound would indicate the presence of non-contiguous nucleic acid and sample degradation. In contrast, the prevalence of nucleic acid where both the first and second probe has bound would indicate the presence of a contiguous nucleic acid and a relatively more intact sample.

The methods described herein are not limited to the use of two probes, however. In some embodiments a plurality of probes are used to give additional information about the properties of nucleic acids in a sample. For example, three probes could be used wherein one probe was one color (e.g., VIC™), and two probes were another color (e.g., FAM). Differences in intensity or polarization make it possible to distinguish between the probes of the same color, as discussed previously. Analysis using such a method may make it possible to determine the presence of multiple different contiguous lengths of nucleic acid molecules.

While methods described herein can encompass the use of several primer pairs, methods in accordance with the invention also encompass the use of a single primer pair. In some embodiments, the method includes providing a fluid comprising the sample nucleic acid and a plurality of one or more primer pairs, wherein each primer pair has at least one unique related probe and is selected to be complementary to one or more sequences of known length. The method also includes partitioning the fluid into a plurality of partitions, wherein at least a first portion of the partitions comprise one molecule of the nucleic acid sample having sequences complementary to one or more of the primer pairs, and at least one related probe, and a second portion of the partitions comprise no molecules of the sample nucleic acid having sequences complementary to one or more of the primer pairs. The method further includes conducting a PCR reaction in the partitions, thereby changing a fluorescent property of the first portion of the partitions, detecting the fluorescent property of each partition, and determining the number of occurrences in the sample nucleic acid of one or more sequences of known length based on the detecting step. In some aspects of the invention, the method further includes comparing a first number of occurrences of a first sequence of known length to a second number of occurrences of a second sequence of a second known length.

Additional embodiments of the invention may also contemplate the use of a single primer pair as well as rely on something other than a probe for detecting the amplified sequence. In certain embodiments, the method comprises partitioning a sample comprising nucleic acid of different lengths into a plurality of partitioned portions, wherein each portion comprises, on average a single nucleic acid molecule. The method further includes introducing at least one primer pair, in which each primer of the pair is specific for a first and second location on the nucleic acid, the first and second locations being spaced apart from each other. The method further includes amplifying the nucleic acid in the partitioned portions, detecting the amplicons in the partitioned portions, and determining a nucleic acid make-up of the sample based on the results of the detecting step. In certain embodiments, the amplicons may be detected with a probe, for example, a fluorescently labeled probe. In other embodiments, the amplicon may be detected with a dye that intercalates within the nucleic acid. The invention also contemplates any other means of detecting nucleic acid sequences known in the art that do not interfere with the other steps described herein.

Figure 25:
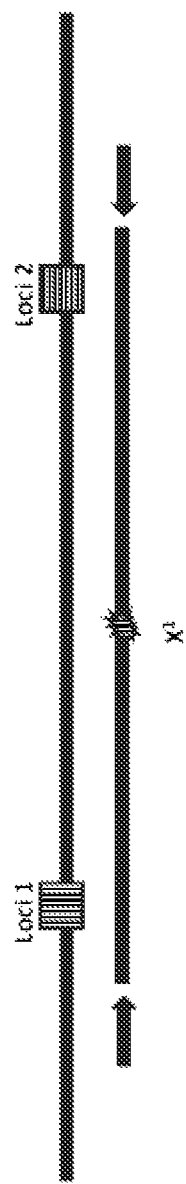
FIG. 25 is a schematic showing a nucleic acid and a pair of primers, each primer specific for a separate location on the nucleic acid, and probe specific for a region of interest on the nucleic acid.

A demonstration of concept using a single primer pair is shown in FIG. 25. Each primer within the primer pair is specific for a first and second location on the nucleic acid. The distance between the two primers for this sequence is known beforehand so that the resulting amplicons will be of a known length. The sequence between the primers is then amplified by PCR. In this particular demonstration of concept, the amplicons are detected via a fluorescent probe, specific for region $X^1$ on the nucleic acid sequence. As discussed above, other means of detection are encompassed by the invention.

Figure 26:
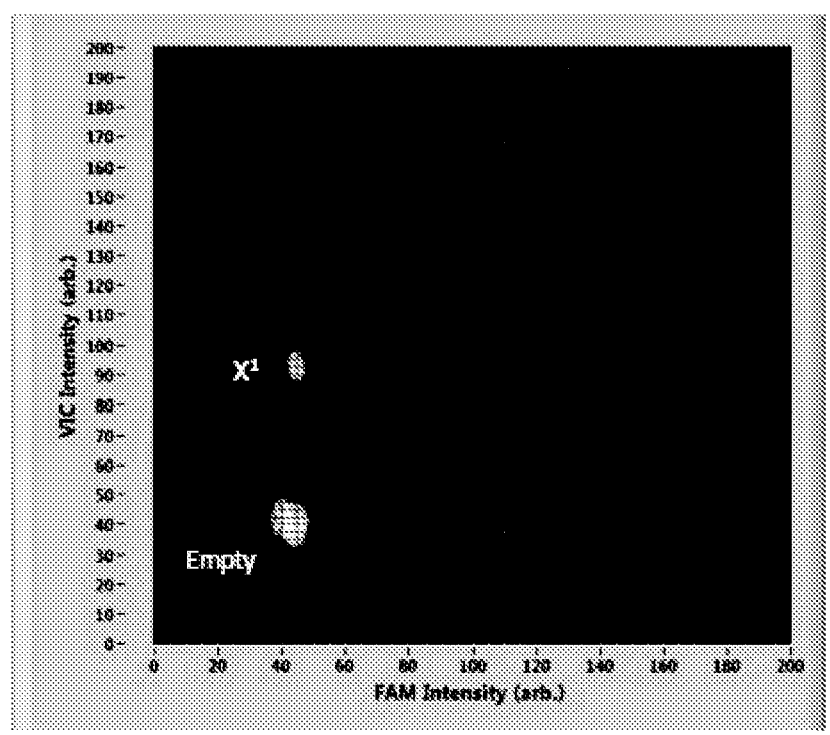
FIG. 26 depicts dPCR assay conducted with a single pair of primers and a nucleic acid shown schematically in FIG. 25.

Sample data is presented in FIG. 26, which shows as peaks, the hybridization of the fluorescent probe to the amplified sequences along with the empty wells, i.e, partitions containing no molecules of sample nucleic acid. The amplicons, as detected by the $X^1$ specific probe, appear primarily along the Y-axis. Accordingly, the method encompasses a method of analyzing a sample nucleic acid or determining the nucleic acid make-up of a sample with just one pair of primers. As in the earlier experiment, the nucleic acid make-up of the sample can be assessed by looking at the number of the counts in the peaks. In this case, by looking at the counts, one could determine the number of occurrences in the sample nucleic acid of a sequence of predetermined length. Accordingly, one could determine whether or not the sample was suitable for further testing based on the number of nucleic acids within the sample having the desired length.

Methods in accordance with the invention also encompass the analysis of cell-free nucleic acids. Collecting and assaying cell-free nucleic acids provides advantages over analysis of cellular nucleic acids in that anomalies, e.g., mutations, are easier to identify in the absence of massive quantities of normal nucleic acids. For example, circulating cell-free tumor DNA has been detected in the serum, plasma, and blood of cancer patients. Cell-free nucleic acids are versatile in that they can be analyzed to detect the presence of mutations, or epigenetic markers of a disease. Cell-free nucleic acids can also be used to identify the presence of foreign pathogens, e.g., a bacterial infection. In some embodiments, the biological sample can be blood, saliva, sputum, urine, semen, transvaginal fluid, cerebrospinal fluid, sweat, breast milk, breast fluid (e.g., breast nipple aspirate), stool, a cell or a tissue biopsy.

The methods of the invention can also be used to evaluate the quality of cell-free nucleic acids, for example cell-free DNA or RNA, which can be obtained from a biological sample. In some instances cell-free nucleic acid is greatly degraded, for example, because the nucleic acid was partially digested by normal metabolic processes in the body. The invention allows the cell-free nucleic acid to be evaluated for quality, e.g., continuity, prior to amplification and sequencing. Thus, a cell-free nucleic acid sample can be partitioned into samples comprising nucleic acids of different lengths, primer pairs can be introduced along with appropriate probes, the nucleic acids amplified, and the make-up, e.g., the continuity of the cell-free nucleic acid sample can be determined.

Primers for Maintaining the Representation of a Nucleic Acid Population for a Sequencing Reaction This aspect of the invention relates to maintaining the representation of a nucleic acid population for a sequencing reaction. Methods of the invention remove the biases associated with bulk amplification reactions by compartmentalizing a sample into a plurality of compartmentalized portions that include on a subset of the nucleic acids from each sample, preferably only a single nucleic acid from each sample. The amplification reaction is then conducted on the subset of nucleic acid in each compartmentalize portion, rather than conducting a bulk amplification reaction on all of the nucleic acid in a single vessel. In this manner, the over or under representation of any portion of the population of nucleic acids in the sample is avoided, and the resulting post-amplification nucleic acid population represents the true condition of the sample from which it was obtained. The amplicons from each compartmentalized portion are then pooled and are subjected to sequencing.

Compartmentalizing may involve diluting the sample such that it may be dispensed into different wells of a multi-well plate in a manner such that each well includes a subset of nucleic acids from the sample. In certain embodiments, each compartmentalized portion includes, on average, a single nucleic acid. Other exemplary compartmentalizing techniques are shown for example in, Griffiths et al. (U.S. Pat. No. 7,968,287) and Link et al. (U.S. patent application number 2008/0014589), the content of each of which is incorporated by reference herein in its entirety.

In certain embodiments, the compartmentalizing involves forming droplets and the compartmentalized portions are the droplets. An exemplary method involves for forming droplets involves flowing a stream of sample fluid including the amplicons such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets. The carrier fluid may be any fluid that is immiscible with the sample fluid. An exemplary carrier fluid is oil, particularly, a fluorinated oil. In certain embodiments, the carrier fluid includes a surfactant, such as a fluorosurfactant. The droplets may be flowed through channels.

In certain embodiments, the compartmentalized portions include loci specific primers and secondary primers that include an adaptor sequence and a barcode sequence. During the amplification reaction, the secondary primers interact with the loci specific primers such that each produced amplicon includes an adaptor sequence and a barcode sequence.

Any amplification reaction known in the art may be used with methods of the invention, such as PCR, LCR, rolling circle amplification, transcription-mediated amplification (TMA), strand-displacement amplification (SDA), NASBA, the use of allele-specific oligonucleotides (ASO), allele-specific amplification. In certain embodiments, the amplification method is PCR.

Sequencing may be by any method known in the art. Sequencing-by-synthesis is a common technique used in next generation procedures and works well with the instant invention. However, other sequencing methods can be used, including sequence-by-ligation, sequencing-by-hybridization; gel-based techniques and others. In general, sequencing involves hybridizing a primer to a template to form a template/primer duplex, contacting the duplex with a polymerase in the presence of a detectably-labeled nucleotides under conditions that permit the polymerase to add nucleotides to the primer in a template-dependent manner. Signal from the detectable label is then used as to identify the incorporated base and the steps are sequentially repeated in order to determine the linear order of nucleotides in the template. Exemplary detectable labels include radiolabels, florescent labels, enzymatic labels, etc. In particular embodiments, the detectable label may be an optically detectable label, such as a fluorescent label. Exemplary fluorescent labels include cyanine, rhodamine, fluorescien, coumarin, BODIPY, alexa, or conjugated multi-dyes.

Another aspect of the invention generally relates to sample preparation for multiplex next-generation sequencing applications, but is also applicable across a broad range of detection assays. In sequencing applications, a barcode oligonucleotide is attached to nucleic acid from a sample. The barcode oligonucleotide is unique to nucleic acid from each sample such that no two samples have the same barcoded oligonucleotides. The barcodes serve to map from a given molecule to nucleic acid from a particular sample. Once barcoded, libraries are pooled, optionally amplified, and finally sequenced.

Methods of the invention provide for sample preparation in which sample and all reagents necessary for an amplification reaction are mixed prior to droplet formation, including reagents necessary for attaching adaptor sequences and barcode sequences to the nucleic acids in the sample. Such a method dramatically reduces reagent costs, and preparation time. In certain embodiments, nucleic acid is mixed with loci specific primers and secondary primers that include an adaptor sequence and a barcode sequence. This mixture is partitioned into droplets such that each droplet includes a subset of the nucleic acid, loci specific primers, and secondary primers. In certain embodiments, each droplet includes, on average, a single nucleic acid. The nucleic acid in the droplet is then amplified to thereby produce amplicons in which each amplicon includes an adaptor sequence and a barcode sequence. The droplets are then pooled, the amplicons are released from the droplets, and the amplicons are then analyzed, for example, by sequencing.

In the methods described herein that include barcodes, the sequencing process consists of two reads, a read of the genomic region and a read of the barcode with the barcode read serving to allow the mapping of the genomic read to nucleic acid from a given sample.

Figure 29:
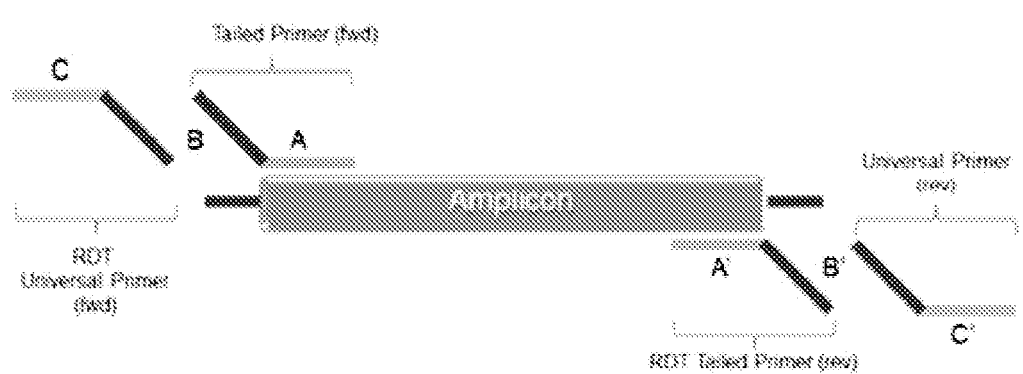
FIG. 29 is a schematic showing an amplification strategy that inserts sequence adaptors and barcodes onto amplicons.

In certain embodiments, methods of the invention utilize at least two sets of primers for maintain the representation of a nucleic acid population for a sequence reaction. In these embodiments, the at least two sets of primers include a loci specific set of primers and a secondary set of primers that interact with the loci specific primers. The loci specific primers include a tail, and the secondary primers include a portion that interacts with the tail of the loci specific primers and a second portion that includes an adaptor sequence and a barcode sequence. The two primer sets are shown in FIG. 29.

Any method known in the art may be used to insert the tails onto the loci specific primers and the secondary primers, for example, a ligase, a polymerase, Topo cloning (e.g., Invitrogen's topoisomerase vector cloning system using a topoisomerase enzyme), or chemical ligation or conjugation. The ligase may be any enzyme capable of ligating an oligonucleotide (RNA or DNA) to the primers. Suitable ligases include T4 DNA ligase and T4 RNA ligase (such ligases are available commercially, from New England Biolabs). Methods for using ligases are well known in the art. The polymerase may be any enzyme capable of adding nucleotides to the 3' and the 5' terminus of template nucleic acid molecules.

Exemplary methods for designing sets of barcode sequences and other methods for attaching barcode sequences are shown in U.S. Pat. Nos. 6,138,077; 6,352,828; 5,636,400; 6,172,214; 6,235,475; 7,393,665; 7,544,473; 5,846,719; 5,695,934; 5,604,097; 6,150,516; RE39,793; 7,537,897; 6,172,218; and 5,863,722, the content of each of which is incorporated by reference herein in its entirety.

The barcode sequence generally includes certain features that make the sequence useful in sequencing reactions. For example the barcode sequences can be designed to have minimal or no homopolymer regions, i.e., 2 or more of the same base in a row such as AA or CCC, within the barcode sequence. The barcode sequences can also be designed so that they do not overlap the target region to be sequence or contain a sequence that is identical to the target.

The barcode sequence is designed such that each sequence is correlated to a particular sample, allowing samples to be distinguished and validated. Methods of designing sets of barcode sequences is shown for example in Brenner et al. (U.S. Pat. No. 6,235,475), the contents of which are incorporated by reference herein in their entirety. In certain embodiments, the barcode sequences range from about 2 nucleotides to about 50; and preferably from about 4 to about 20 nucleotides. Since the barcode sequence is sequenced along with the template nucleic acid or may be sequenced in a separate read, the oligonucleotide length should be of minimal length so as to permit the longest read from the template nucleic acid attached. Generally, the barcode sequences are spaced from the template nucleic acid molecule by at least one base.

The secondary primer also includes an adaptor sequence, which is generally a homopolymer region, e.g., a region of poly(A) or poly(T), that can hybridize to a universal primer for the sequence reaction. Adaptor sequences are further described in Sabot et al. (U.S. patent application number 2009/0226975), Adessi et al. (U.S. Pat. No. 7,115,400), and Kawashima et al. (U.S. patent application number 2005/0100900), the content of each of which is incorporated by reference herein in its entirety. In certain embodiments, an "A" and a "B" adapter are introduced into each compartmentalized portion. The "A" adapter and "B" adapter sequences correspond to two surface-bound amplification primers on a flow cell used for amplification of the nucleic acids prior to sequencing, as is discussed in greater detail below.

The purpose of the two primer sets is such that during an amplification reaction, a sequence adaptor and a barcode sequence is added to each amplicon. As shown in FIG. 29, A and A' are a primer pair (forward and reverse) of loci specific primers. Each of A and A' includes a target sequence specific portion that hybridizes to the target site on the nucleic acid. A and A' also include a tailed portion, B and B'. The secondary primers include a universal portion of B and B' also, such that the B and B' portions of the loci specific primers and the secondary primers can hybridize with each other. The secondary primers also include a second portion, C and C'. C and C' include an adaptor sequence and a barcode sequence. The result of the amplification reaction using these loci specific primers and secondary primers is amplicons in which each amplicon includes an adaptor sequence and a barcode sequence. Accordingly, the amplicons are ready for sequencing without further sample preparation.

The sample is diluted such that each compartmentalized portion includes only a subset of the nucleic acid in the sample. In certain embodiments, each compartmentalized portion includes, on average, a single nucleic acid. Poisson statistics dictate the dilution requirements needed to insure that each compartment contains only a subset of the nucleic acid in the sample. In particular embodiments, the sample concentration should be dilute enough that most of the compartments contain no more than a single nucleic acid with only a small statistical chance that a compartment will contain two or more molecules. The parameters which govern this relationship are the volume of the compartment and the concentration of nucleic acid in the sample solution. The probability that a compartment will contain two or more nucleic acid ($NAT_{\leq 2}$) can be expressed as:

$$NAT_{\leq 2} = 1 - \{1 + [NAT] \times V\} \times e^{-(NAT) \times V}$$

where "[NAT]" is the concentration of nucleic acid in units of number of molecules per cubic micron ($\mu m^3$), and V is the volume of the compartment in units of $\mu m^3$. It will be appreciated that $NAT_{\leq 2}$ can be minimized by decreasing the concentration of nucleic acid in the sample solution.

In embodiments in which loci specific primers and secondary primers are pre-mixed with the sample prior to compartmentalizing the sample, the primers are provided in significantly excess the concentration of the nucleic acid in the sample, thereby ensuring that after sample dilution, every droplet will still receive a set of loci specific primers and secondary primers. One of skill in the art will readily be able to calculate the concentrations of primers needed to ensure that after dilution of the sample, each compartmentalized portion will receive a subset of nucleic acid from the sample and loci specific primers and secondary primers. This pre-mixture also includes reagents for the PCR reaction. Such reagents generally include Taq polymerase, deoxynucleotides of type A, C, G and T, magnesium chloride, all suspended within an aqueous buffer.

In embodiments in which the primers are pre-mixed with the sample, this step is not necessary. However, in certain embodiments, droplets containing nucleic acid are formed and primers are subsequently introduced to those droplets. In these embodiments, along with the primers, reagents for a PCR reaction are also introduced to the droplets. Such reagents generally include Taq polymerase, deoxynucleotides of type A, C, G and T, magnesium chloride, all suspended within an aqueous buffer.

An exemplary method of introducing primers and PCR reagents to a sample droplet is as follows. After formation of the sample droplet from the first sample fluid, the droplet is contacted with a flow of a second sample fluid stream, which contains the loci specific primers and the secondary primers. Contact between the droplet and the fluid stream results in a portion of the fluid stream integrating with the droplet to form a mixed droplet containing a nucleic acid, primers and PCR reagents.

Droplets of the first sample fluid flow through a first channel separated from each other by immiscible carrier fluid and suspended in the immiscible carrier fluid. The droplets are delivered to the merge area, i.e., junction of the first channel with the second channel, by a pressure-driven flow generated by a positive displacement pump. While droplet arrives at the merge area, a bolus of a second sample fluid is protruding from an opening of the second channel into the first channel. The intersection of the channels may be perpendicular. However, any angle that results in an intersection of the channels may be used, and methods of the invention are not limited to the orientation of the channels.

The bolus of the second sample fluid stream continues to increase in size due to pumping action of a positive displacement pump connected to the second channel, which outputs a steady stream of the second sample fluid into the merge area. The flowing droplet containing the first sample fluid eventually contacts the bolus of the second sample fluid that is protruding into the first channel. Contact between the two sample fluids results in a portion of the second sample fluid being segmented from the second sample fluid stream and joining with the first sample fluid droplet 201 to form a mixed droplet.

In order to achieve the merge of the first and second sample fluids, the interface separating the fluids must be ruptured. In certain embodiments, this rupture can be achieved through the application of an electric charge. In certain embodiments, the rupture will result from application of an electric field. In certain embodiments, the rupture will be achieved through non-electrical means, e.g. by hydrophobic/hydrophilic patterning of the surface contacting the fluids.

Description of applying electric charge to sample fluids is provided in Link et al. (U.S. patent application number 2007/0003442) and European Patent Number EP2004316 to Raindance Technologies Inc, the content of each of which is incorporated by reference herein in its entirety. Electric charge may be created in the first and second sample fluids within the carrier fluid using any suitable technique, for example, by placing the first and second sample fluids within an electric field (which may be AC, DC, etc.), and/or causing a reaction to occur that causes the first and second sample fluids to have an electric charge, for example, a chemical reaction, an ionic reaction, a photocatalyzed reaction, etc.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, tungsten, tin, cadmium, nickel, indium tin oxide ("ITO"), etc., as well as combinations thereof. In some cases, transparent or substantially transparent electrodes can be used.

The electric field facilitates rupture of the interface separating the second sample fluid and the droplet. Rupturing the interface facilitates merging of the bolus of the second sample fluid and the first sample fluid droplet. The forming mixed droplet continues to increase in size until it a portion of the second sample fluid breaks free or segments from the second sample fluid stream prior to arrival and merging of the next droplet containing the first sample fluid. The segmenting of the portion of the second sample fluid from the second sample fluid stream occurs as soon as the force due to the shear and/or elongational flow that is exerted on the forming mixed droplet by the immiscible carrier fluid overcomes the surface tension whose action is to keep the segmenting portion of the second sample fluid connected with the second sample fluid stream. The now fully formed mixed droplet continues to flow through the first channel.

In another technique involves droplet merging. The merging of droplets can be accomplished using, for example, one or more droplet merging techniques described for example in Link et al. (U.S. patent application numbers 2008/0014589, 2008/0003142, and 2010/0137163) and European publication number EP2047910 to Raindance Technologies Inc.

In embodiments involving merging of droplets, two droplet formation modules are used. A first droplet formation module produces the sample droplets that on average contain a single target nucleic acid. A second droplet formation module produces droplets that contain reagents for a PCR reaction. Such droplets generally include Taq polymerase, deoxynucleotides of type A, C, G and T, magnesium chloride, loci specific primers and secondary primers, all suspended within an aqueous buffer.

The droplet formation modules are arranged and controlled to produce an interdigitation of sample droplets and PCR reagent droplets flowing through a channel. Such an arrangement is described for example in Link et al. (U.S. patent application numbers 2008/0014589, 2008/0003142, and 2010/0137163) and European publication number EP2047910 to Raindance Technologies Inc.

A sample droplet is then caused to merge with a PCR reagent droplet, producing a droplet that includes Taq polymerase, deoxynucleotides of type A, C, G and T, magnesium chloride, loci specific primers, secondary primers, and the target nucleic acid. Droplets may be merged for example by: producing dielectrophoretic forces on the droplets using electric field gradients and then controlling the forces to cause the droplets to merge; producing droplets of different sizes that thus travel at different velocities, which causes the droplets to merge; and producing droplets having different viscosities that thus travel at different velocities, which causes the droplets to merge with each other. Each of those techniques is further described in Link et al. (U.S. patent application numbers 2008/0014589, 2008/0003142, and 2010/0137163) and European publication number EP2047910 to Raindance Technologies Inc. Further description of producing and controlling dielectrophoretic forces on droplets to cause the droplets to merge is described in Link et al. (U.S. patent application number 2007/0003442) and European Patent Number EP2004316 to Raindance Technologies Inc.

Once compartmentalized, an amplification reaction is conducted on the nucleic acids in the compartmentalized portions. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification and restriction fragments length polymorphism, transcription based amplification system, nucleic acid sequence-based amplification, rolling circle amplification, and hyper-branched rolling circle amplification.

Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of primers (oligonucleotides) to a DNA mixture containing a desired target sequence, followed by a precise sequence of thermal cycling. The present invention includes, but is not limited to, various PCR strategies as are known in the art, for example QPCR, multiplex PCR, assymetric PCR, nested PCR, hotstart PCR, touchdown PCR, assembly PCR, digital PCR, allele specific PCR, methylation specific PCR, reverse transcription PCR, helicase dependent PCR, inverse PCR, intersequence specific PCR, ligation mediated PCR, mini primer PCR, and solid phase PCR, emulsion PCR, and PCR as performed in a thermocycler, droplets, microfluidic reaction chambers, flow cells and other microfluidic devices.

Compartmentalized portions may be amplified using standard thermo cyclers and standard amplification protocols known in the art. See Sambrook et al., Molecular Cloning, 3rd edition, Cold Spring Harbor Laboratory Press, Cold Spring Harbor, N.Y., USA, 2001, the content of which is incorporated by reference herein in its entirety. In embodiments in which the compartmentalized portions are droplets, the droplets may be amplified in PCR tubes according to well know techniques or may be amplified as they are flowing through channels.

Methods for performing PCR in droplets are shown for example in Link et al. (U.S. patent application numbers 2008/0014589, 2008/0003142, and 2010/0137163), Anderson et al. (U.S. Pat. No. 7,041,481 and which reissued as U.S. Pat. No. RE41,780) and European publication number EP2047910 to Raindance Technologies Inc. The content of each of which is incorporated by reference herein in its entirety.

In certain embodiments, the droplets are flowed through a channel in a serpentine path between heating and cooling lines to amplify the nucleic acid in the droplet. The width and depth of the channel may be adjusted to set the residence time at each temperature, which can be controlled to anywhere between less than a second and minutes.

In certain embodiments, the three temperature zones are used for the amplification reaction. The three temperature zones are controlled to result in denaturation of double stranded nucleic acid (high temperature zone), annealing of primers (low temperature zones), and amplification of single stranded nucleic acid to produce double stranded nucleic acids (intermediate temperature zones). The temperatures within these zones fall within ranges well known in the art for conducting PCR reactions. See for example, Sambrook et al. (Molecular Cloning, A Laboratory Manual, $3^{rd}$ edition, Cold Spring Harbor Laboratory Press, Cold Spring Harbor, N.Y., 2001).

In certain embodiments, the three temperature zones are controlled to have temperatures as follows: 95° C. ($T_H$), 55° C. ($T_L$), 72° C. ($T_M$). The prepared sample droplets flow through the channel at a controlled rate. The sample droplets first pass the initial denaturation zone ($T_H$) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the high temperature zone, of approximately 95° C., where the sample is first separated into single stranded DNA in a process called denaturation. The sample then flows to the low temperature, of approximately 55° C., where the hybridization process takes place, during which the primers anneal to the complementary sequences of the sample. Finally, as the sample flows through the third medium temperature, of approximately 72° C., the polymerase process occurs when the primers are extended along the single strand of DNA with a thermostable enzyme.

The nucleic acids undergo the same thermal cycling and chemical reaction as the droplets passes through each thermal cycle as they flow through the channel. The total number of cycles in the device is easily altered by an extension of thermal zones. The sample undergoes the same thermal cycling and chemical reaction as it passes through N amplification cycles of the complete thermal device.

In other embodiments, the temperature zones are controlled to achieve two individual temperature zones for a PCR reaction. In certain embodiments, the two temperature zones are controlled to have temperatures as follows: 95° C. ($T_H$) and 60° C. ($T_L$). The sample droplet optionally flows through an initial preheat zone before entering thermal cycling. The preheat zone may be important for some chemistry for activation and also to ensure that double stranded nucleic acid in the droplets are fully denatured before the thermal cycling reaction begins. In an exemplary embodiment, the preheat dwell length results in approximately 10 minutes preheat of the droplets at the higher temperature.

The sample droplet continues into the high temperature zone, of approximately 95° C., where the sample is first separated into single stranded DNA in a process called denaturation. The sample then flows through the device to the low temperature zone, of approximately 60° C., where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing.

The amplification reaction produces numerous amplicons within each compartmentalized portion, and each amplicon now includes an adaptor sequence and a barcode sequence.

Methods of the invention may further involve pooling the compartmentalized portions and releasing the nucleic acid from the compartmentalized portions for further analysis. For well plate based methods, samples may simply be pooled into a single vessel. For droplet based embodiments, methods of releasing amplified target molecules from droplets are shown in for example in Link et al. (U.S. patent application numbers 2008/0014589, 2008/0003142, and 2010/0137163) and European publication number EP2047910 to Raindance Technologies Inc.

In certain embodiments, sample droplets are allowed to cream to the top of the carrier fluid. By way of non-limiting example, the carrier fluid can include a perfluorocarbon oil that can have one or more stabilizing surfactants. The droplet rises to the top or separates from the carrier fluid by virtue of the density of the carrier fluid being greater than that of the aqueous phase that makes up the droplet. For example, the perfluorocarbon oil used in one embodiment of the methods of the invention is 1.8, compared to the density of the aqueous phase of the droplet, which is 1.0.

The creamed liquids are then placed onto a second carrier fluid which contains a de-stabilizing surfactant, such as a perfluorinated alcohol (e.g. 1H,1H,2H,2H-Perfluoro-1-octanol). The second carrier fluid can also be a perfluorocarbon oil. Upon mixing, the aqueous droplets begins to coalesce, and coalescence is completed by brief centrifugation at low speed (e.g., 1 minute at 2000 rpm in a microcentrifuge). The coalesced aqueous phase can now be removed and the further analyzed.

In certain embodiments, the barcoded amplicons are then sequenced. Sequencing may be by any method known in the art.

Experimental Detail

What follows is experimental detail for the various experiments details above.

Primers and Probes

All TaqMan® primers and probes used here are listed in Table 2. Unless otherwise noted by reference in the table, the primers and probes were designed with the "Custom TaqMan® Assay Design Tool" from Applied Biosystems Inc. (ABI) and procured through ABI (Carlsbad, Calif.). Probes were labeled with 6-carboxyfluorescein (FAM, $\lambda_{ex}$ 494 nm \ $\lambda_{em}$ 494 nm) or VIC™ (from ABI, $\lambda_{ex}$ 538 nm \ $\lambda_{em}$ 554 nm).

TABLE 2

5'-exonuclease genotyping assay design. Assay conditions in column 5 are specific to the multiplexed SMA assay.

| Target | Assay | Primers (5' to 3') | Probe (5' to 3') | 5-plex assay conditions | Ref |
|---|---|---|---|---|---|
| SMN1 | Copy number | (f) AATGCTTTTTAA-CATCCATATAAAG CT (SEQ ID NO.: 1) (r) CCTTAATTTAAG-GAATGTGAGCACC (SEQ ID NO.: 2) | FAM-CAGGGTTTC*AGACAAA-MGBNFQ (SEQ ID NO.: 3) | 0.37x | Anhuf et al., 2003 |
| SMN2 | Copy number | (f) AATGCTTTTTAA-CATCCATATAAAG CT (SEQ ID NO.: 4) (r) CCTTAATTTAAG-GAATGTGAGCACC (SEQ ID NO.: 5) | FAM-TGATTTTGTCTA*AAA-CCC-MGBNFQ (SEQ ID NO.: 6) | 0.76x | Anhuf et al., 2003 |
| BCKDHA | Copy number | (f) CAACCTACTCTT-CTCAGACGTGTA (SEQ ID NO.: 7) (r) TCGAAGTGATCC-AGTGGGTAGTG (SEQ ID NO.: 8) | (FAM/VIC)-CAGGAGATGCCCG-CCCAGCTC-TAMRA (SEQ ID NO.: 9) | FAM: 0.18x VIC: 0.56x | DiMatteo et al., 2008 |
| c.815A>G | SNP | (f) TGCTGATGCTTT-GGGAAGTATGTTA (SEQ ID NO.: 10) (r) TGTCAGGAAAAG-ATGCTGAGTGATT (SEQ ID NO.: 12) | (A) (FAM/VIC)-CATGAGTGG-CTA*TCATAC-MGBNFQ (SEQ ID NO.: 11) (G) FAM-ATGAGTGGCTG*TC-ATAC-MGBNFQ (SEQ ID NO.: 13); VIC-CATGA-GTGGCTG*TCATAC-MGBNFQ (SEQ ID NO.: 14) | 0.9x  FAM: 0.9x VIC: 0.45x | |
| RNaseP | Copy number | Unknown | unknown | n/a | Standard product, 4403326, ABI |

References: D. Anhuf, T. Eggermann, S. Rudnik-Schöneborn and K. Zerres, *Hum Mutat.*, 2003, 22, 74-78; D. DiMatteo, S. Callahan and E. B. Kmiec, *Exp Cell Res.*, 2008, 15, 878-886.

Target DNA

For some genetic targets, BCKDHA and SMN2, plasmid DNA was synthesized (GeneArt, Regensburg, Germany) containing the sequence spanning between the primers (see Table 2) and cloned into the GeneArt standard vector (2.5 kb). The target fragment was released from the cloning vector by restriction digestion with SfiI to avoid any DNA supercoiling that might affect the assay. For simplicity, these gene fragments are called "plasmid DNA" throughout the text. A string of different gene fragments was also synthesized (GeneArt) and cloned into the GeneArt standard vector for demonstration of multiplexed reactions, called an "artificial chromosome" in the text. In this case, the fragments were separated from each other by restriction digestion at flanking EcoRV sites. Human DNA was obtained in already purified form from cell lines (See Table 3; Coriell, Camden, N.J.) and fragmented before use with a K7025-05 nebulizer following manufacturer's instructions (Invitrogen, Carlsbad, Calif.). DNA concentration was quantified by measuring absorbance at 260 nm on a Nanodrop 2000 spectrophotometer (Thermo Scientific, Wilmington, Del.).

TABLE 3

Map of patient numbers used in the text to Coriell cell lines.

| Patient number | Coriell cell line |
|---|---|
| 1 | NA14638 |
| 2 | NA14637 |
| 3 | NA14097 |
| 4 | NA14096 |
| 5 | NA14094 |
| 6 | NA14093 |
| 7 | NA14092 |
| 8 | NA14091 |
| 9 | NA14090 |
| 10 | NA13715 |
| 11 | NA13714 |
| 12 | NA13712 |
| 13 | NA13709 |
| 14 | NA13707 |
| 15 | NA13705 |
| SMA carrier | NA03814 |
| SMA 1 | NA03813 |
| SMA 2 | NA00232 |

TABLE 3-continued

Map of patient numbers used in the text to Coriell cell lines.

| Patient number | Coriell cell line |
|---|---|
| SMA 3 | NA09677 |
| SMA 4 | NA10684 |

Microfluidics

Microfluidic chips were manufactured by conventional soft lithography. Molding masters were fabricated by spin coating SU-8 negative photoresist (MicroChem Corp., Newton, Mass.) onto 6 inch silicon wafers and transferring the fluidic features from photomasks (CAD/Art Services, Bandon, Oreg.) by contact lithography with an OAI Hybralign Series 200 aligner (OAI, San Jose, Calif.). Chips contained channels with two depths: deep channels with low hydrodynamic resistance (100±10 urn) for transporting fluid from external ports to the functional regions of the chip, and shallow channels (20±1 urn) for droplet manipulation and detection. SU-8 photoresists 2100 and 2025 were used for deep and shallow channels respectively. Polydimethylsiloxane (PDMS) (Sylgard® 184, Dow Corning, Midland, Mich.) chips were molded from the negative masters within mold housings of custom design. Glass cover slides were permanently bonded to the fluidic side of the chips by surface activation in an AutoGlow™ oxygen plasma system (Glow Research, Phoenix, Ariz.) followed by immediate contact bonding. To create hydrophobic surfaces, the microfluidic channels were exposed for ~2 min to 1H,1H,2H,2H-perfluorodecyltrichlorosilane (Alfa Aesar, Ward Hill, Mass.) dissolved in FC-3283 (3M Specialty Materials, St. Paul, Minn.) prepared as a mixture of 18 g silane in 100 uL solvent.

Two different microfluidic devices were used, one for droplet generation and the other for fluorescence readout after thermal cycling. The droplet generation chip created an emulsion of uniformly sized aqueous droplets of template DNA and PCR master mix that were suspended in an inert fluorinated oil with an emulsion stabilizing surfactant, called "carrier oil" from this point forward (REB carrier oil; RainDance Technologies, Lexington, Mass.). Droplets were generated in a cross-shaped microfluidic intersection, or "nozzle". As shown in FIG. 3a, under typical operation the aqueous phase flowed into the nozzle from the right (160 uL/hr), joining flows of the carrier oil from the top and bottom (750 uL/hr of total oil), and producing 4 pL droplets at a rate of 11 kHz. The channel widths at the intersection measured 15 urn for the aqueous inlet, 12.5 for the oil inlets, and 15 urn widening to 40 urn at the outlet. Flow was driven by custom OEM pumps (IDEX Corporation, Northbrook, Ill.).

Approximately 25 uL of the PCR reaction mixture was collected as an emulsion from the droplet generation chip and thermally cycled in a DNA Engine (Bio-Rad, Hercules, Calif.). The reaction mixture contained 1× TaqMan® universal PCR master mix (Applied Biosystems, Carlsbad, Calif.), 0.2 mM dNTP (Takara Bio, Madison, Wis.), and various amounts of primer pairs and probes as described in the results. 1× assay concentration is defined as 0.2 µM probes with 0.9 µM primers. In all cases, when varied from the 1× concentration, the primers and probes were varied by the same amount. The cycler program included a 10 min hot start at 95° C., and 45 cycles of 15 s at 95° C. and 60 s at 60° C.

The droplets became concentrated during off-chip handling because the carrier oil is more dense than the aqueous phase and drained down from the emulsion. Hence the droplets were reinjected into the readout chip as a tightly packed emulsion that required dilution prior to readout to properly distinguish one droplet from another. A "spacer" nozzle similar to the droplet generation nozzle above was used to inject uniform plugs of extra carrier oil between droplets immediately before readout. As shown in FIG. 3b, the droplet entrance into the nozzle tapered down into a constriction about the size of an individual droplet forcing the droplets to enter the nozzle in single file and consequently at a stable rate. Opposed flow of the carrier oil from the top and bottom channels separated the droplets uniformly. The channel leaving the spacer nozzle increased in width along the direction of flow, and the droplets were interrogated by laser induced fluorescence at the location along the channel where the width was smaller than or equal to the droplet diameter (marked with an arrow in FIG. 3b). The nozzle dimensions were 15 um for the droplet entrance and exit, and 20 um for the oil lines.

Instrumentation

Fluorescence readout was performed by conventional epifluorescence microscopy with a custom microscope. A 20 mW, 488 nm laser source (Cyan; Picarro, Sunnyvale, Calif.) was expanded 2× and focused by the objective lens (20×/0.45 NA; Nikon, Japan) onto the microfluidic channel. Two band pass filters discriminated the fluorescence collected through the objective lens: 512/25 nm and 529/28 nm for FAM and VIC fluorophores respectively (Semrock, Rochester, N.Y.). Fluorescence was detected by two H5784-20 photomultipliers (Hamamatsu, Japan) and was typically recorded at a 200 kHz sampling rate with a USB-6259 data acquisition card (National Instruments, Austin, Tex.). The data traces were smoothed by a seven-point, second-order Savitzky-Golay algorithm before subsequent analysis. Concurrent with the fluorescence read out, the droplets were imaged through the same objective lens with backside illumination from an 850 nm LED (TSHG6200; Vishay Semiconductors, Shelton, Conn.), a short pass filter to separate the optical paths for fluorescence detection and imaging, and a Guppy CCD camera (Allied Vision Technologies, Newburyport, Mass.). Droplets were imaged with short illumination pulses (5-20 us) to avoid image streaking.

Data Analysis

Data was analyzed with custom LabView software (National Instruments, Austin, Tex.) that interpreted droplet events as contiguous bursts of fluorescence intensity above a threshold value. The signal-to-noise ratio was generally quite high and the signal levels were consistent from day to day, hence a fixed threshold value of 50 mV was used predominantly, otherwise the threshold was set by eye. The peak fluorescence intensity was recorded for each droplet event for both VIC and FAM fluorophores. Some coalescence of droplets did occur during thermal cycling, typically as isolated events between two intact droplets forming "doublets." Doublets and the rare larger coalesced events were easily filtered from the data set on based on the duration of the fluorescence burst.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A method of detecting a target nucleic acid molecule, the method comprising:
    providing a plurality of droplets, wherein one or more droplets comprise a target nucleic acid molecule and at least 99% of the droplets are empty;
    flowing the plurality of droplets through a microfluidic channel, wherein the plurality of droplets are not single-file within a portion of the channel; and
    flowing the plurality of droplets that are not single-file in the microfluidic channel past a detector in an overlapping configuration with respect to the detector, thereby detecting the one or more droplets comprising the target nucleic acid molecule.

2. The method of claim 1, wherein prior to the providing step, the method comprises forming the plurality of droplets.

3. The method of claim 1, wherein the plurality of droplets are aqueous droplets in an immiscible fluid.

4. The method of claim 3, wherein the immiscible fluid is oil.

5. The method of claim 3, wherein the oil comprises a surfactant.

6. The method of claim 5, wherein the surfactant is a fluorosurfactant.

7. The method of claim 4, wherein the oil is a fluorinated oil.

8. The method of claim 1, wherein the droplets are uniform in size.

9. The method of claim 1, wherein the droplets are non-uniform in size.

* * * * *